US012614614B2

(12) United States Patent
Nunez et al.

(10) Patent No.: US 12,614,614 B2
(45) Date of Patent: Apr. 28, 2026

(54) SYSTEMS, METHODS, AND APPARATUS TO PROVIDE LONGITUDINAL PATIENT DATA

(71) Applicant: ProSciento, Inc., San Diego, CA (US)

(72) Inventors: Maria Nunez, El Cajon, CA (US); Marcus Hompesch, San Diego, CA (US); Helge Guenther, Rancho Santa Margarita, CA (US); Will Santos, San Diego, CA (US); Zoe Molina, Denver, CO (US); Brian Mooney, Millstone Township, NJ (US)

(73) Assignee: ProSciento, Inc., San Diego, CA (US)

( * ) Notice: Subject to any disclaimer, the term of this patent is extended or adjusted under 35 U.S.C. 154(b) by 0 days.

(21) Appl. No.: 18/649,504

(22) Filed: Apr. 29, 2024

(65) Prior Publication Data

US 2024/0339184 A1      Oct. 10, 2024

Related U.S. Application Data

(63) Continuation of application No. PCT/US2024/023604, filed on Apr. 8, 2024.

(Continued)

(51) Int. Cl.
| | |
|---|---|
| *G16H 10/20* | (2018.01) |
| *G16H 10/60* | (2018.01) |

(Continued)

(52) U.S. Cl.
CPC ............. *G16H 10/20* (2018.01); *G16H 10/60* (2018.01); *G16H 20/10* (2018.01); *G16H 70/00* (2018.01); *G16H 70/20* (2018.01); *G16H 80/00* (2018.01)

(58) Field of Classification Search
CPC ........ G16H 10/20; G16H 10/60; G16H 20/10; G16H 70/00; G16H 70/20; G16H 80/00; G16H 40/67

(Continued)

(56) References Cited

U.S. PATENT DOCUMENTS

| | | |
|---|---|---|
| 6,556,999 B1 | 4/2003 | Kloos et al. |
| 7,401,028 B2 | 7/2008 | Deakter |

(Continued)

FOREIGN PATENT DOCUMENTS

| | | |
|---|---|---|
| JP | 2004530223 A | 9/2004 |
| WO | 2015144931 A1 | 10/2015 |

(Continued)

OTHER PUBLICATIONS

"International Application Serial No. PCT/US2024/023604, International Search Report and Written Opinion mailed Sep. 17, 2024", ProSciento, Inc., 30 pages.

(Continued)

*Primary Examiner* — Joy Chng
(74) *Attorney, Agent, or Firm* — GTC Law Group PC & Affiliates

(57) ABSTRACT

A patient portal system may include a patient database module to interpret a patient profile value and a clinical database module to interpret a clinical study description. The patient database module may also interpret patient clinical data in response to the patient profile value and the clinical study description, and include at least a portion of the patient clinical data as longitudinal data of a patient corresponding to the patient profile value. The system may also include a patient interface module to implement a patient engagement interface and to interpret a patient medical event value in response to patient interactions with the patient engagement interface. The patient database may also adjust the longitudinal data in response to the patient medical event value.

20 Claims, 66 Drawing Sheets

Related U.S. Application Data

(60) Provisional application No. 63/457,535, filed on Apr. 6, 2023, provisional application No. 63/600,488, filed on Nov. 17, 2023.

(51) Int. Cl.

| | | |
|---|---|---|
| *G16H 20/10* | (2018.01) | |
| *G16H 70/00* | (2018.01) | |
| *G16H 70/20* | (2018.01) | |
| *G16H 80/00* | (2018.01) | |

(58) Field of Classification Search

USPC ........................................................ 705/2–3

See application file for complete search history.

(56) References Cited

U.S. PATENT DOCUMENTS

| | | | | |
|---|---|---|---|---|
| 10,937,527 | B2 | 3/2021 | Klein et al. | |
| 11,102,304 | B1* | 8/2021 | Jain ......................... | H04L 67/12 |
| 11,664,099 | B1 | 5/2023 | Jain et al. | |
| 2003/0163488 | A1 | 8/2003 | Kloos et al. | |
| 2011/0301982 | A1 | 12/2011 | Green et al. | |
| 2013/0282405 | A1 | 10/2013 | Van Zon et al. | |
| 2013/0346090 | A1* | 12/2013 | Brincat .................. | G16H 70/60 |
| | | | | 705/2 |
| 2014/0310015 | A1 | 10/2014 | Goldner | |
| 2014/0337052 | A1 | 11/2014 | Pellini et al. | |
| 2015/0347599 | A1 | 12/2015 | Mcmains et al. | |
| 2016/0012182 | A1* | 1/2016 | Golay .................... | G16H 40/20 |
| | | | | 705/3 |
| 2016/0125171 | A1 | 5/2016 | Finken et al. | |
| 2016/0210427 | A1 | 7/2016 | Mynhier et al. | |
| 2016/0300039 | A1 | 10/2016 | Burgio | |
| 2016/0317077 | A1* | 11/2016 | Sillay .................... | A61B 5/1101 |
| 2016/0357944 | A1 | 12/2016 | Iyer et al. | |
| 2017/0206338 | A1 | 7/2017 | Burgio | |
| 2017/0228501 | A1 | 8/2017 | Turner et al. | |
| 2018/0075205 | A1 | 3/2018 | Moturu et al. | |
| 2018/0151252 | A1 | 5/2018 | Iyer et al. | |
| 2018/0181716 | A1 | 6/2018 | Mander et al. | |
| 2019/0066822 | A1* | 2/2019 | Ramaci .................. | G16H 80/00 |
| 2019/0206519 | A1 | 7/2019 | Eteminan et al. | |
| 2020/0211680 | A1* | 7/2020 | Sablinski ............... | G16H 20/00 |
| 2020/0410614 | A1 | 12/2020 | Bonageri et al. | |
| 2021/0257065 | A1 | 8/2021 | Mander et al. | |
| 2021/0319898 | A1 | 10/2021 | Kapoor et al. | |
| 2021/0375459 | A1 | 12/2021 | Longmire et al. | |
| 2022/0051773 | A1* | 2/2022 | Appelbaum ........... | G16H 10/40 |
| 2022/0084633 | A1 | 3/2022 | Das et al. | |
| 2022/0181012 | A1 | 6/2022 | Skelton et al. | |
| 2023/0035208 | A1 | 2/2023 | Akin | |
| 2023/0040463 | A1 | 2/2023 | SjÖlin et al. | |
| 2023/0051982 | A1 | 2/2023 | Sasidharan et al. | |
| 2023/0127453 | A1 | 4/2023 | Agrawal et al. | |
| 2023/0187042 | A1 | 6/2023 | Vogt et al. | |
| 2024/0339180 | A1 | 10/2024 | Hompesch et al. | |
| 2024/0339181 | A1 | 10/2024 | Hompesch et al. | |
| 2024/0339182 | A1 | 10/2024 | Hompesch et al. | |
| 2024/0339183 | A1 | 10/2024 | Hompesch et al. | |
| 2025/0299828 | A1 | 9/2025 | Chaganti et al. | |

FOREIGN PATENT DOCUMENTS

| | | | | |
|---|---|---|---|---|
| WO | WO-2015179484 A1 * | 11/2015 | ............. | G16H 10/60 |
| WO | 2024211901 A2 | 10/2024 | | |

OTHER PUBLICATIONS

"International Application Serial No. PCT/US2024/023604, Invitation to Pay Additional Fees and, Where Applicable, Protest Fee mailed Jun. 26, 2024", ProsCiento, Inc., 2 pages.

\* cited by examiner

1000

Begin

Interpret a patient profile value    1002

Interpret a clinical study description    1004

Implement a patient clinical study interface in response to the patient profile value and the clinical study description    1006

End

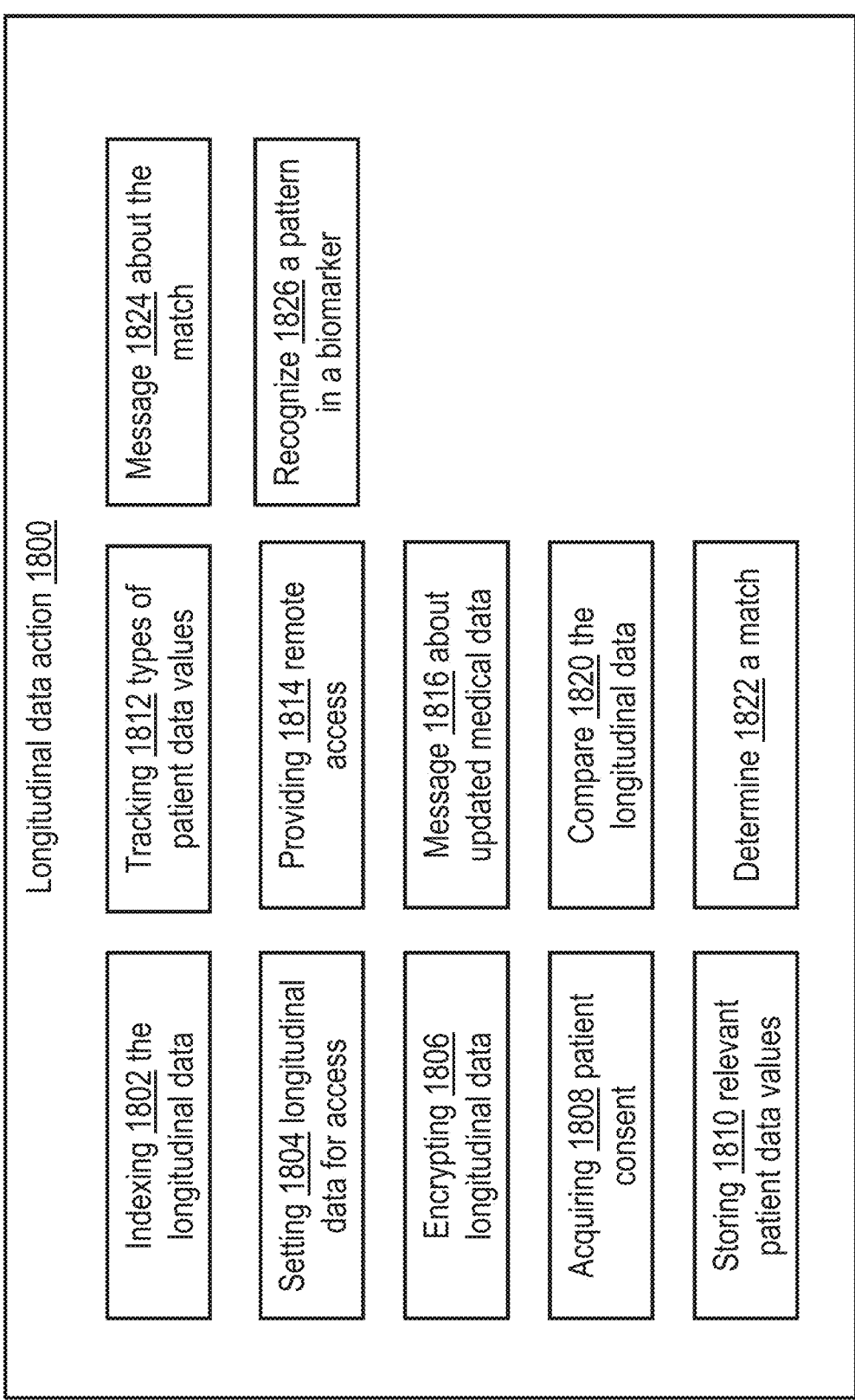

Longitudinal data action 1800

Indexing 1802 the longitudinal data

Tracking 1812 types of patient data values

Message 1824 about the match

Setting 1804 longitudinal data for access

Providing 1814 remote access

Recognize 1826 a pattern in a biomarker

Encrypting 1806 longitudinal data

Message 1816 about updated medical data

Acquiring 1808 patient consent

Compare 1820 the longitudinal data

Storing 1810 relevant patient data values

Determine 1822 a match

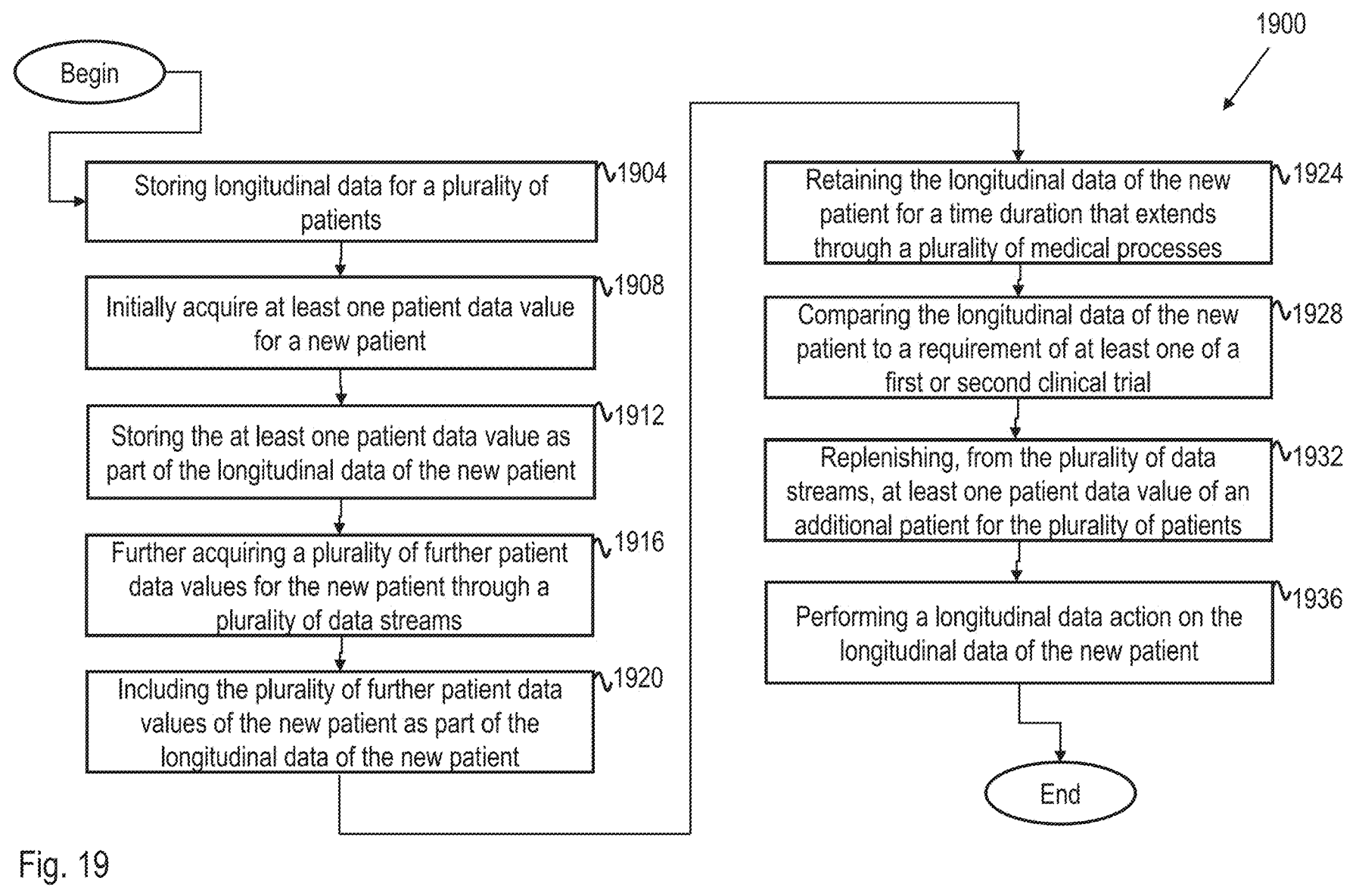

1924 — Retaining the longitudinal data of the new patient for a time duration that extends through a plurality of medical processes 1928 — Comparing the longitudinal data of the new patient to a requirement of at least one of a first or second clinical trial 1932 — Replenishing, from the plurality of data streams, at least one patient data value of an additional patient for the plurality of patients 1936 — Performing a longitudinal data action on the longitudinal data of the new patient End Begin 1904 — Storing longitudinal data for a plurality of patients 1908 — Initially acquire at least one patient data value for a new patient 1912 — Storing the at least one patient data value as part of the longitudinal data of the new patient 1916 — Further acquiring a plurality of further patient data values for the new patient through a plurality of data streams 1920 — Including the plurality of further patient data values of the new patient as part of the longitudinal data of the new patient

Fig. 19

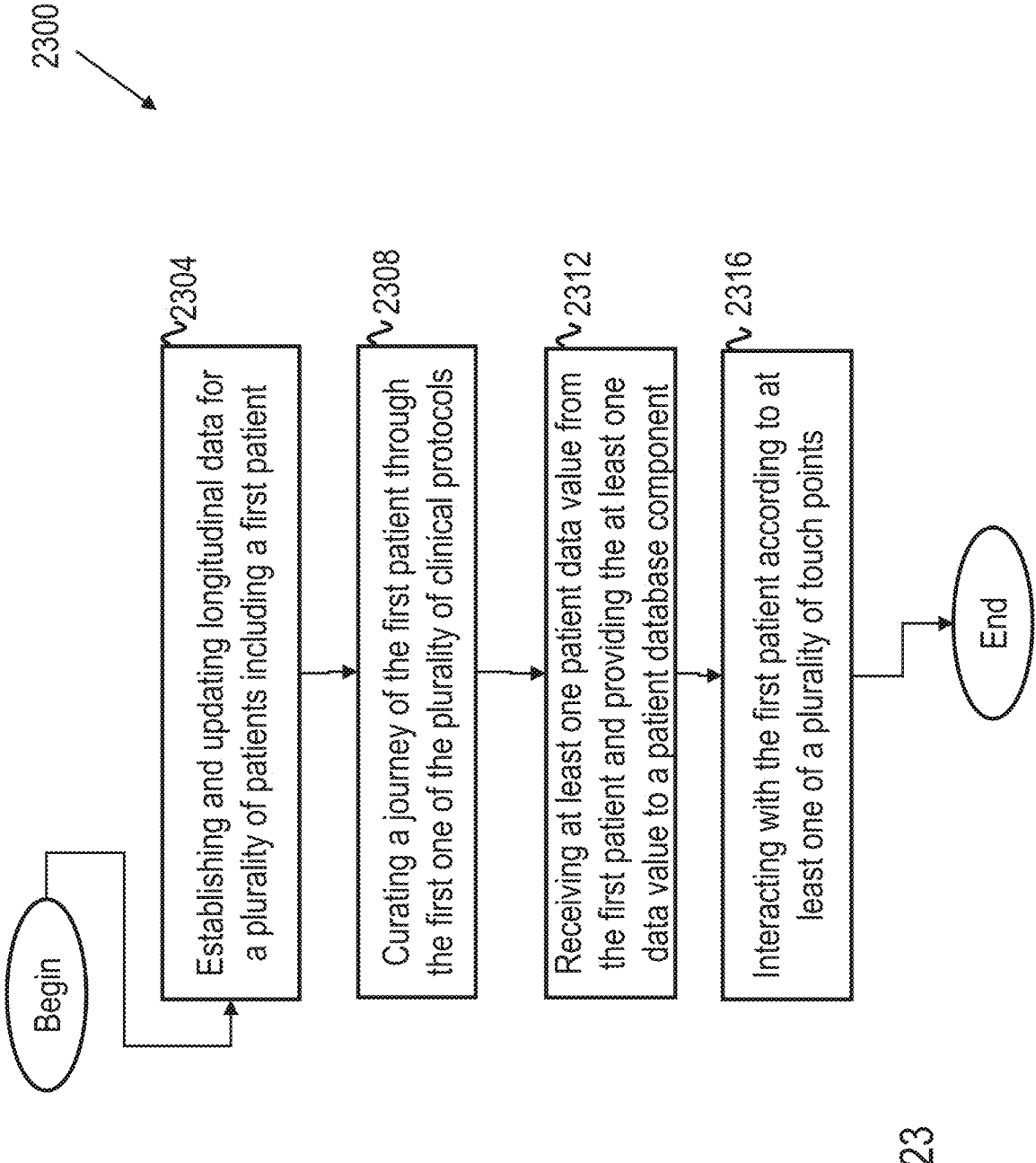

2300

2304 Establishing and updating longitudinal data for a plurality of patients including a first patient 2308 Curating a journey of the first patient through the first one of the plurality of clinical protocols 2312 Receiving at least one patient data value from the first patient and providing the at least one data value to a patient database component 2316 Interacting with the first patient according to at least one of a plurality of touch points Begin End

Begin

Determine pre-completion information in response to, e.g., longitudinal data and/or patient profile value(s) — 5102

Pre-complete value(s) of a questionnaire, survey, and/or enrollment documents — 5104

End

6400

Begin

Interpret a patient profile value    6402

Determine patient outcome improvement value    6404

Provide patient engagement communication    6406

End

6500

6402

Interpret a patient profile value

6404

Determine patient outcome improvement value

6406

Provide patient engagement communication

6502

Operate a machine learning model to iteratively improve determining the patient outcome improvement value Begin End

SYSTEMS, METHODS, AND APPARATUS TO PROVIDE LONGITUDINAL PATIENT DATA

CROSS-REFERENCE TO RELATED APPLICATIONS

The present application is a continuation of, and claims priority to, PCT Patent Application Serial No. PCT/US2024/023604, filed 8 Apr. 2024, and entitled "SYSTEM, METHOD, AND APPARATUS FOR PATIENT ACCESS AND ENGAGEMENT AND INTEGRATED SOCIAL HEALTH NETWORK".

PCT Patent Application Serial No. PCT/US2024/023604 claims the benefit of U.S. Provisional Patent Application No. 63/457,535, filed on 6 Apr. 2023, entitled "SYSTEM, METHOD, AND APPARATUS FOR PATIENT ACCESS AND ENGAGEMENT", and U.S. Provisional Patent Application No. 63/600,488, filed on 17 Nov. 2023, entitled "SYSTEM, METHOD, AND APPARATUS FOR PATIENT ACCESS AND ENGAGEMENT AND INTEGRATED SOCIAL HEALTH NETWORK".

Each of the foregoing applications is incorporated herein by reference in the entirety for all purposes.

SUMMARY

Aspects and embodiments of the present disclosure provide for a number of benefits and improvements over previously known systems for engaging patients, participating in clinical trials, and coordinating medical information.

Embodiments herein include technical features that result in a number of improvements to patient care, connecting patients with clinical trials, medical treatments, giving patients control over their medical information and course of treatments, and promoting better outcomes for patients generally. Further, embodiments herein include technical features that improve the operations of computing devices that support and/or embody portions of the systems, portals, platforms, modules, components, or other embodiments of the present disclosure, including reducing processing cycles required to perform operations, reducing memory utilization including intermediate memory utilized for operations, and network communication resources to support operations herein. Additionally, embodiments herein reduce a number of operations required, windows, menus, or applications that need to be navigated to perform operations herein. Further, embodiments herein enhance the security of sensitive information, giving patients control and visibility of their health related information, and other information that is utilized to support operations of the systems, portals, platforms, modules, components, or other embodiments of the present disclosure.

For example, embodiments herein utilizing a patient database to store longitudinal data for patients, including storing ongoing patient data, communications with the patient over time and across events, and/or between different systems, platforms, portals, or the like, are leveraged to support various embodiments throughout the present disclosure, and where present provide technical features that realize various improvements to computing devices—for example providing a lever for various features to target operations to specific patients, reducing the time and processing cycles to search through a larger set of patients and/or prospective patients, and providing an efficient data source for improvement operations over time that allow for more limited and effective decisions to find relevant patients, provide for efficient scheduling and patient contact operations. Further, the utilization of the longitudinal data, and implementation of longitudinal data operations, support data security for the patient, and control of patient's information by the patient.

In another example, embodiments of the present disclosure to build a patient journey utilizing various systems herein support the organization of data and patient communications, utilizing communications to target patients for specific communications such as clinical trial education and outreach, contacting patients only at appropriate times relevant to their situation, providing multiple contact possibilities that can be tailored to the contact points that are relevant and effective for the particular patient.

In another example, the utilization of modular components to build systems, portals, platforms, or other embodiments is a technical feature that supports various improvements herein, including improvements to the operations of computing devices. For example, the modular components allow for experts in other areas apart from computer programming to effectively implement patient contact and outreach communications, enhancing the efficiency of computer operations as the systems, portals, platforms, and the like can be built to achieve better patient outcomes, focus on the contact points that are relevant to specific patients, and reduce the search space of patients for matching to clinical trials, providing educational materials about medical concepts, or the like. Further, the ability of appropriate experts to focus on operational aspects of embodiments herein allows certain improvement features, for example expert systems, machine learning models, or the like, to more rapidly converge on efficient and effective procedures, match settings, and the like, allowing those embodiments to reduce resource usage by converging on improved operations more quickly. Further, the utilization of modular components allows the overall system, platform, or portal, to operate more efficiently, effectively, and securely, as the system is more amenable to updating components to later and/or improved versions of those components.

In another example, embodiments herein to utilize and support a clinical study interface allows for the patient to access relevant clinical studies with fewer navigation operations, and provides a framework to efficiently target communications to enroll users. Further, the utilization of a customizable dashboard allows the patient control over their data, enrollment operations, efficiently update on the progress of workflows, and increase confidence that communications are from a proper source—increasing both the actual security of the patient and their information, and making the workflows more efficient. In certain embodiments, utilization of a clinical invitation communication provides for additional or alternative support for the improvements listed foregoing for the clinical study interface and customizable dashboard.

Embodiments herein to perform clinical enrollment operations and clinical screening operations are technical features that improve the operations of computing devices, for example by reducing processing cycles and network communications utilized to solicit and enroll patients for clinical studies, and by ensuring that screening and enrollment information are completed completely, correctly, and redundancy of data entry is reduced. Further, features of the clinical enrollment operations and clinical screening operations provide for reduced navigation of menus, enhanced security by giving the user a consistent interface for data entry and by providing consistent sourcing of messages for that patient.

Embodiments herein to perform clinical matching operations, including utilization of a clinical matching communication, allows for a reduction of computing resources by focusing on patients that are relevant to clinical studies, as well as improving patient outcomes by focusing efforts of both the patients and clinical study groups on clinical trials that are likely to be successful in terms of enrollment and execution of the study. Further, the matching operations may be leveraged by other systems, portals, platforms, or other embodiments, improving the efficiency of those operations and reducing the convergence time for determining successful and effective communication methods, and responding more quickly to changes in the patient preferences or situation over time. Additionally, the utilization of patient groups for enrollment operations significantly reduces computing resources, communications, navigation operations, and the like to develop, solicit, and/or enroll groups of patients sufficient to support clinical studies.

Embodiments herein to utilize patient engagement communications that are informed by patient outcome improvement values improve the utilization of computing resources, focusing patient communications, educational support efforts, and touch points, on aspects that are likely to be beneficial to the goals and medical outcomes of the patient. The utilization of patient outcome improvement values further supports more rapid convergence to effective communication techniques, matching operations, storage and utilization of data that is likely to be effective in assisting the patient, and allowing for the reduction of data and/or communications that are not likely to be effective.

Embodiments herein including a patient centered social platform include technical features that improve the operations of a computing device, for example providing an efficient communication lever to reach multiple relevant patients with a single communication cycle, and providing tools to rapidly connect patients into communities, and/or to connect patients or patient communities with advocacy groups. Such features further improve patient security by promoting patients to learn more quickly about health related aspects relevant to that user, giving them better information to utilize the control and visibility of their information that is otherwise provided by platforms, systems, portals, and other embodiments throughout. Additionally, tools are provided that allow patients to receive information, and create or connect groups, with a reduced number of operations, navigation events, and the like.

Any improvements, benefits, or the like, as set forth foregoing, are non-limiting examples. Any particular benefit may be present in certain embodiments, and not present in another embodiment. Further, additional benefits and/or improvements may be relevant to listed embodiments, or other embodiments.

BRIEF DESCRIPTION OF THE DRAWINGS

FIG. 18 illustrates longitudinal data actions according to example embodiments.

FIG. 19 illustrates a method of operating a patient database system according to example embodiments.

FIG. 23 illustrates a method for providing a patient engagement platform for a plurality of clinical protocols according to example embodiments.

DETAILED DESCRIPTION

Figure 1:
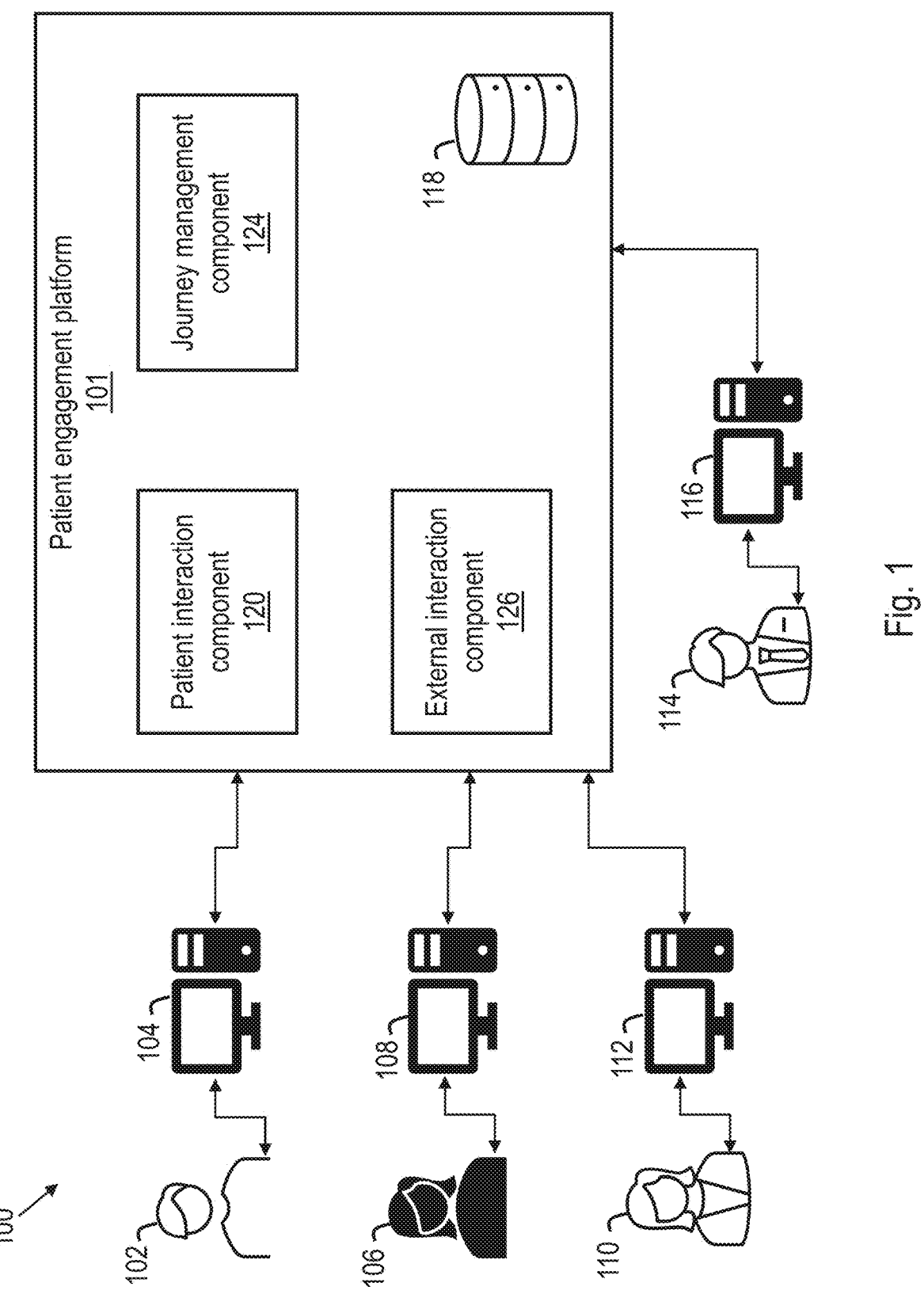
FIG. 1 depicts an illustrative patient engagement platform according to example embodiments.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles disclosed herein as would normally occur to one skilled in the art to which this disclosure pertains.

Referencing FIG. 1, an example system 100 includes a patient engagement platform 101, configured to perform patient support operations for embodiments as set forth throughout the present disclosure. The example patient engagement platform 101 supports a number of features set forth throughout the present disclosure, including without limitation operations for any procedure or method described herein, and/or any operations performed by a component, circuit, controller, module, computing device, or the like.

An example patient engagement platform 101 builds, maintains, updates, provides backup support, and manages the lifecycle (e.g., deletion dates, redundancy management, prioritization of data, and/or location of data—for example between fast retrieval and slow retrieval locations) of a data store 118. The example data store 118 stores patient information, for example patient demographic data, biometric data, medical records information (e.g., medications, labs, factual data assessments, etc.), patient preferences, patient provider relationships, patient behavioral data, biomarkers, medical conditions, geographic information, occupational information, and/or patient related data from external data sources, such as social media, proprietary databases, public records, or the like. In certain embodiments, patient information on the data store 118 allows for the patient engagement platform 101 to provide a number of support operations for the patient, for example and without limitation: matching the patient to relevant clinical studies (or clinical trials); providing notifications to the patient related to procedures, medications, activities to be performed (e.g., abstaining from eating or drinking before a procedure, performing an at-home test or check, etc.), and/or general health related information that may be relevant to the patient; tracking patient interactions with the platform (e.g., logins, searches, messages, etc.) and/or supported procedures or studies (e.g., tracking patient enrollment in a study, tracking patient behavior with regard to the study, accepting input from the patient or a provider related to the procedure or study, etc.); ensuring medication compatibility (e.g., allergies, interactions, side effect profiles for the patient and/or associated medications, etc., for example to ensure that new medications are compatible, the patient is a good fit for a study, procedure, or medication program, etc.); facilitating relevant information sharing between distinct providers; providing the patient with a convenient access point for their own historical information; providing the patient with recommendations (e.g., medications, tests, procedures, exercise or diet routines, and/or clinical studies).

An example patient engagement platform 101 operates as a data warehouse, and provides a framework for a patient to access, monitor, and control their health care over time. For example, the data store 118 may include medical lab data, medical records, biometric data (e.g., from wearables, mobile app inputs, etc.), behavioral data (e.g., socioeconomic data, cultural data, financial data, quality of life data, and/or genotyping), long term storage of various (or all) data elements. An example patient engagement platform 101 includes study results relevant to the patient and/or generated by patient participation in studies, whether those studies were engaged by the patient on the platform 101 or separate from the platform 101. Operations of the platform 101, including operations using the data store 118, allow for engagement of the patient with their own health care activity, and inform the patient on planned or pending medical treatments. Operations of the platform 101 facilitate improved prediction and/or scientific analysis for study design and/or analysis of study outcomes, and for designing new and/or improving existing medical treatments.

Operations on the platform to utilize behavioral data, and/or behavioral algorithms to determine behavioral data from any data available on the platform, can be utilized to individualize and/or influence individual engagements with a patient—for example to determine the why and when of each individual engagement with a patient, and/or absence of an engagement (e.g., when an engagement was expected and/or otherwise recommended). Such operations can identify gaps in care for patients, for example patients with metabolic disease, and merge the study of patient individual behaviors with predictive analytics and/or artificial intelligence (AI) to produce actionable recommendations, prompts that encourage behavior changes, and/or to determine or adjust engagement schemes that are likely to influence patient behavior in a positive manner and/or with higher success rates. Such operations contribute to helping patients manage disease, treatments, and/or increase their quality of life.

The example data store 118 is depicted as a single data store on a single device, but the data store 118 may be distributed, placed on one or more cloud servers, and/or be segregated (e.g., based on geography, privacy protection level, age of data, clinical study status of patients, etc.) either physically or logically (e.g., with separate portions of the data in the data store 118 available to different users based on permissions level, role, identity of the accessing user, etc.). In certain embodiments, the data store 118 is a unified data store 118, for example a data store 118 accessible in the entirety by the patient engagement platform 101, even where individual components or users may have access to only relevant portions of the data store 118. In certain embodiments, the patient engagement platform 101 is capable to access the entire data store 118, even where one or more distinct components of the patient engagement platform 101 are only able to access a relevant portion of the data store 118. In certain embodiments, portions of the data store 118 are accessible only to components "internal" to the platform, for example meta-data related to patients, clinicians, or other users, and/or determined values from the data that are utilized to facilitate certain aspects described herein (e.g., patient classification information, patient-study compatibility determinations and/or analysis, patient behavioral information, etc.). In certain embodiments, aspects herein include the platform directly, and may further include access to the unified data store 118. Even where an embodiment does not include a component having access to the unified data store 118, many such embodiments are enhanced by the platform capable to access the unified data store 118. A number of operations, systems, and platform examples set forth throughout the present disclosure are enhanced by the data store 118 as set forth herein, for example: operations to customize a patient interface; operations to assist the patient in completing a study; operations to determine patient-study compatibility and/or suitability; operations to adjust permissions to data and/or patient information; and/or operations to support longitudinal studies, including changing the longitudinal study plan after the clinical study is commenced or completed.

Certain aspects of the present disclosure reference a clinician and/or a study group. These terms should be understood broadly. A clinician, as used herein, can reference any entity related to a clinical treatment and/or a particular clinical study. For example, a clinician may be a doctor or medical professional involved in activities to execute the study. An example clinician may include a third party or entity involved to perform an aspect of a study, including for example recruiting of patients, scheduling study activities, administering study related paperwork, ensuring data storage and security and/or accessing relevant data on the data store 118, or the like. In certain embodiments, a clinician may reference a site utilized by the person involved that is performing the study related actions described. A study group, as utilized herein, can reference any entity involved in the planning, updating, and/or execution of a clinical study or trial. In certain embodiments, a clinician and a study group may be the same person, entity, site, or the like. The utilization of various terms in a particular context is for clarity of the description, and not limiting to the disclosure herein.

An example patient engagement platform 101 facilitates finding appropriate patients for a clinical study, where the patients are determined to have, or be likely to have, relevant medical conditions, and where the patients are otherwise compatible (e.g., based on allergies, prior medication history, demographic aspects, geographic location, etc.) with the clinical study. In certain embodiments, the patient engagement platform 101 further determines patient compatibility according to one or more behavioral aspects such as: patient medication compliance (e.g., does the patient take medications on schedule); patient appointment compliance (e.g., does the patient attend appointments on time); and/or patient behavioral compliance (e.g., does the patient attend to sleep schedules, dietary recommendations, exercise recommendations, etc.). It can be seen that the determination of appropriate patients, including patient compatibility, may depend upon the criteria of the study, and further upon the specific information for the patient. For example, a study that requires a strict routine may not be compatible with a patient having low medication or behavioral compliance, regardless of the match between a patient medical condition and the medical target for the clinical study. In certain embodiments, the compliance for the patient may be dependent upon certain factors, such as communication methods to the patient (e.g., email, text, phone call, and/or instant messaging), that can be determined according to patient behavioral information in the data store 118, for example determining that a patient is compatible for a study with modifications, and/or with a particular implementation scheme that can otherwise be supported by the patient engagement platform 101.

An example patient engagement platform 101 further supports the patient journey for a clinical study (e.g., the entire lifecycle of the patient interaction, from finding the compatibility match, through enrollment, execution, follow-up, and/or longitudinal study aspects). Example operations to support the patient journey through the clinical study include one or more operations, without limitation, such as: connecting the patient and the study group; enrollment of the patient in the study; execution of aspects of the study, such as medications, at-home testing, provider visits, and data capture throughout; execution of follow-up actions, such as follow-up provider visits, additional testing, data tracking, implementing surveys or questionnaires, and/or providing information (e.g., study results, patient outcomes, etc.) to the patient from the study group; and/or long term activity to support longitudinal study aspects, such as patient status updates, additional provider visits, implementing surveys or questionnaires, and/or facilitating communications between the patient and the study group (e.g., where years after the fact, it may be otherwise difficult to find the patient, for the patient to remember the study and/or what happened during or after the study, and/or for the patient to reliably determine that follow-up communications are legitimate, etc.).

An example patient engagement platform 101 is provided as a modular system, with components, circuits, controllers, or the like, that are provided to perform specific aspects of operations herein, allowing for an entity that implements a patient engagement platform 101 and/or that accesses a patient engagement platform 101 for certain features can readily configure the patient engagement platform 101 to perform the desired functions. In certain embodiments, modular aspects of the patient engagement platform 101 are implemented as low-code modules, proprietary modules, or a combination of these. An example patient engagement platform 101 is built utilizing Salesforce modular components, customized to implement operations as set forth herein. In certain embodiments, one or more components herein may be implemented using an CRM (customer relationship management) tools, including with customization, and/or with adding full coded additional features, and/or may be implemented in a fully coded environment. In certain embodiments, utilization of a tool may facilitate quickly building certain ordinary aspects, such as implementing user interfaces, data storage, data sharing, completion of forms, providing notifications, or the like. The benefits of the present disclosure are realized, without limitation, in the selection of the content and implementation for these aspects, the selected connections between entities, the selection of notification triggers, methods, and/or content, and the decision making aspects (e.g., including determining which decisions to make, and the criteria to make those decisions) set forth herein.

An example patient engagement platform 101 includes providing a customizable user interface to a user, for example a patient, that is specific for the patient in question. For example, the layout of the interface may include prominent positioning for information that is important to that patient (e.g., available studies, immediate notifications or actions to be taken, progress in a current study or treatment regiment, etc.), include information based on actual data related to the patient, and/or include information related to recent changes related to the patient (e.g., beginning or ending participation in a study, a change in stage of a study, a change in medication, a change in diagnosis, a recent procedure and/or provider visit, etc.). In certain embodiments, the customizable user interface may be based on one or more of: preferences provided by the patient, permissions provided by the patient, usage history of the patient with the patient engagement platform 101, medical history of the patient (e.g., medications taken, procedures performed, active diagnoses, etc.), demographic information of the patient, and/or behavioral information (e.g., which menus or locations are typically accessed, which interface types the user interacts with most frequently, whether the user tends to type information, or select information from menus, whether the user takes advantage of auto-fill suggestions, etc.). In certain embodiments, customization of the user interface can include one or more aspects such as: where interface items are positioned (location, order, orientation, etc.); size, orientation, and/or aspect ratio of interface elements; which elements appear on a landing page, which elements appear in a deeper menu or page, and/or which elements appear or are omitted; units and/or scaling for graphical elements; presentation of written elements (e.g., font, size, formatting, utilization of abbreviations, length of words or sentences utilized, etc.); utilization of accessibility aspects (e.g., audible elements, high visibility presentation, simplification of menus, automation selections, etc.). In certain embodiments, the customized user interface may be adjusted based on which studies, medications, treatments, appointments, or the like are active for the patient (e.g., a customized interface to show stages of a study, current progress, next activities, etc.; a customized interface that highlights medication schedules for a complex and/or stringent medication regime; a customized interface that highlights behavioral activity, such as fasting, eating, or sleeping, related to a study, an upcoming treatment, a recently completed procedure, etc.).

An example patient engagement platform 101 includes providing data to or from the data store 118 to support longitudinal patient data for a clinical study(ies). For example, patient data may be tagged based on completion of a particular clinical study, facilitating access to the relevant data over a period of years (or other relevant period) after the study is completed. In certain embodiments, the study group (e.g., the clinician and/or related entity that performed the study) can access the relevant data through a clinician interface with the patient engagement platform 101. Depending upon the data needed, the clinician can automatically get the relevant data, for example patient outcomes, long-term progress, etc., which may be anonymized, aggregated, grouped according to selected criteria (e.g., by dosage, placebo, control group, etc.), or otherwise processed according to the requirements of the study and/or applicable privacy considerations. In certain embodiments, the clinician can implement a request for the data through the patient engagement platform 101, for example by selecting a Request Data interface element, whereupon the patient engagement platform 101 communicates a request to relevant patient(s) for permissions to provide the data to the clinician. In certain embodiments, the permissions may be provided earlier, for example when the patient enrolls in the study, but the patient engagement platform 101 can be configured in any manner, including changing the permissions scheme (e.g., to conform to an updated privacy law). The patient engagement platform 101 and data store 118 allow for the clinician and/or study group to readily access detailed longitudinal data, enhancing clinical study implementation, makes it easy to capture detailed data about the patients—such as medications, long-term health outcomes, further treatments, etc., makes it easy to contact patients even after an extended period (for example facilitating follow-up research beyond what was originally planned for the study), gives patients confidence that a requesting party for longitudinal data is a legitimate requestor, and helps patients immediately understand which element (e.g., study, treatment, procedure, etc.) is related to any requested data. Accordingly, the patient engagement platform 101 supports longitudinal data for deeper analysis, meta-analysis, long term outcomes for a study, improved security of data, reduced time for requesting and receiving data, and/or reduced time for finding and following up with patients. In certain embodiments, a study group may wish to contact patients for any reason, for example to suggest a further study, request certain tests or procedures, and/or to provide notifications related to the earlier study, and the patient engagement platform 101 provides a mechanism for this to be completed. In certain embodiments, it may be desirable to keep the patient anonymous with regard to the study group, and the patient engagement platform 101 provides a full functioning implementation (e.g., including support for longitudinal data, follow-up tests or procedures, and/or notifications to the patient) even where patient anonymity is preserved.

An example patient engagement platform 101 provides a patient specific interface to facilitate patient engagement with a clinical study, for example to help the patient successfully participate in the study. In certain embodiments, the patient engagement platform 101 provides a status indicator to the patient—for example whether the patient is enrolled, on a waitlist, actively participating in the study, and/or the progress or stage of the patient in the study. In certain embodiments, the patient engagement platform 101 provides an overview of the study, for example with a dashboard indicating steps to be completed, which steps are already completed, and/or the next activities to be performed as a part of the study. In certain embodiments, the patient engagement platform 101 provides the patient with convenient access to study information, such as how long the study is expected to take, activities the patient will be expected to perform, and/or information about how the patient's information is going to be collected and/or used as a part of the study. In certain embodiments, the patient interface is configured to support the study implementation, including with a messaging section, notification section, or the like, and/or including selections to automatically schedule appointments, medication pickup or delivery, access to activity charts (e.g., daily schedule, dietary guidelines, exercise routines, etc.) related to the study. In certain embodiments, the patient engagement platform 101 utilizes elements outside of the interface, for example by providing messages of upcoming appointments and/or reminders for patient actions. In certain embodiments, a message and/or notification to the patient may include a link (e.g., an automatic link to schedule an appointment, and/or a link to the user interface on the patient engagement platform 101) allowing the patient to immediately respond to the notification without having to navigate to other windows, applications, menus, or the like.

An example patient engagement platform 101 provides a clinician (and/or study group) interface to facilitate recruiting, enrollment, implementation, and/or analysis of clinical studies. Such operations provide a convenient way for a clinician to find a suitable patient group for a clinical study, for example by providing a number of compatible patients (e.g., patients having medical conditions, demographics, and/or any other criteria required for the clinical study) to the clinician. In certain embodiments, the patient engagement platform 101 determines whether patients are suitable for the study, for example by analyzing soft criteria for the study, such as geographic location, number of participants (e.g., where the number may be flexible within a range, above a threshold, etc.), a group aspect of participants (e.g., to ensure that the group of patients that is "suitable" reflects a proper designed mix for a population), and/or that the group is not skewed or biased in an undesirable manner (e.g., unacceptably clustered within an otherwise acceptable range, etc.). The description herein setting forth some aspects of patient matching as "compatible" vs. "suitable" is for clarity of the description, including using some aspects as a threshold (e.g., must be met) and some aspects as a flexible range (e.g., may be close, and/or can be met in consideration of the entire group). A given aspect, for example geographic location or demographics, may be a compatibility aspect in certain embodiments of a platform and/or for certain operations on the platform, and a suitability aspect in other embodiments of a platform and/or for other certain operations on the platform. One of skill in the art, having the benefit of the present disclosure, can readily determine whether a given patient-clinical study matching aspect should be utilized as a compatibility aspect or a suitability aspect. Certain considerations for which aspects are to be utilized for patient-clinical study matching, and whether those aspects are compatibility (e.g., must have) or suitability (e.g., should have, must be sufficiently close, and/or must be reflected in some group or aggregated value) include, without limitation: the medical requirements for the clinical study; the available support infrastructure for the clinical study; the patient activities performed in the study (e.g., in-person visits, video calls, medication regimens, etc.); the number of patients planned for the study; which variables the study is determining and/or controlling; and/or the behavioral sensitivity of the study (e.g., medication must be taken at the same time every day, versus one shot received at the beginning of the study). In certain embodiments, compatibility and/or suitability criteria may be adjusted during enrollment operations, for example as patients enroll in the study, the compatibility and/or suitability criteria may be adjusted, for example to ensure that a representative group for a target population is achieved.

The example patient engagement platform 101 includes interface elements allowing the clinician to request a number of patients for a study, to enter patient criteria for the study, and/or to enter population criteria for the study. In certain embodiments, the population criteria for the study may indicate a minimum number of acceptable patients, a distribution constraint for the overall group (e.g., target averages, clustering/anti-clustering descriptions, minimums/maximums (e.g., per bucket for a bucketed distribution, based on geography, etc.), and/or any other descriptions for the target composition of the group. In certain embodiments, the patient engagement platform 101 includes interface elements allowing the clinician to enter: a description of the study, including potentially separate descriptions for separate audiences (e.g., a regulator description, a health care provider description, and/or a participating patient description); a description of medications, dosages, dosing schedules, etc. relevant to the study; a description of patient activities (e.g., diet guidelines, sleep guidelines, exercise guidelines, provider visits, documentation events, video calls or check-ins, etc.) to be performed as a part of the study; and/or a description of patient information that will be collected and/or utilized (e.g., which may further include how long the information will be retained, whether the information will be identifiable or anonymous, and/or any other information that is desirable to communicate, required by regulation, according to industry standards, and/or according to internal policies, such as a policy of a provider of the patient engagement platform 101 and/or a policy of the study group). In certain embodiments, one or more aspects of information about the study may be provided later (e.g., during enrollment operations for the study), and/or may be amended (e.g., potentially with notifications to patients, and/or with a subsequent update to the patient-clinical study matching, including removing no-longer compatible/suitable patients, and/or inviting additional patients to either replace removed patients and/or to complete or reinstate a representative group based on the amendments to the study information).

An example patient engagement platform 101 is configured to perform matching between clinical studies, and/or planned clinical studies, and patients and/or perspective patients. Example embodiments facilitate finding and/or enrolling patients in clinical studies, determining contact points, communications, advertisements, and/or social media engagements that are likely to discover sufficient patient and/or prospective patient pools to support a clinical study, to ensure that patients are well suited for a clinical study that will be beneficial for the patient, and that the patients are likely to be able to complete successfully. Example embodiments include determining patient contact locations (e.g., the types of outreach that will be likely to reach the patients, such as advertising platforms, social media platforms, direct communications, blog or discussion post locations, web site content, etc.) and/or determining patient contact content (e.g., the content of advertisements, communications, etc., that are likely to successfully educate and engage patients for clinical studies). In certain embodiments, patients that are discovered and/or matched to clinical studies may be patients already having a presence on the patient engagement platform 101, for example having an account on the platform, preferences indicated on the platform, medical records stored on and/or accessible to the platform, and/or having participated in one or more previous clinical studies. Patients already having a presence on the platform may be more likely to be matched to a clinical study that is particularly suitable for that patient, but various benefits and improvements herein are also applicable to patients or prospective patients that are discovered before having a presence on the patient engagement platform 101. Such patients may be reached, and/or brought into the corpus of patients considered for matches, utilizing any method and/or data associated with, and/or available to, the patient engagement platform 101, for example through publicly available information, monitoring of social media, through contacts with the patient engagement platform 101 (e.g., users registering for notifications, or other interactions that are of a lower engagement level than a full registered user with a platform account), users as a part of a group where the group leader provides for a contact to the user (e.g., a social group, a health related group, an employer created group, an industry related group, etc.), and/or through proprietary information (e.g., access to a proprietary database, relationship partner, etc., where users are available, for example, based on user provided permissions).

In certain embodiments, matching patients and/or prospective patients to clinical studies and/or planned clinical studies may be based on matching users (e.g., patients or prospective patients) to clinical studies based on medical conditions of the user (e.g., based on direct knowledge, such as user information on the data store 118, and/or based on inferred knowledge, for example based on search data, publicly available posts, or the like, that may provide an indication that the user may have a medical condition), compatibility of the user with medications of the clinical study (e.g., based on allergies, confounding medical conditions, interactions with other medications taken by the user, etc.), compatibility of the user with activities performed as a part of the study (e.g., time availability, schedule compatibility, demographic compatibility, and/or a distribution of properties among a group of patients for the study, including the impact of adding the user to the group), behavioral compatibility of the user with activities performed as a part of the study (e.g., based on estimated, observed, and/or historical behavior of the user, for example with regard to compliance with patient visits, medication regimens, sleep behavior, diet behavior, etc.), and/or geographic compatibility of the user with the study (e.g., ensuring the user will have access to study resources, aspects of geographic locations that affect the study (e.g., pollen in the area, environmental exposure profiles in the area, laws and/or regulations associated with the area, and/or ensuring that a sufficient number of patients from a given area are available—such as to sufficiently control for environmental factors, to justify resource provision to an area, to ensure proximity to related medical care providers, or the like). In certain embodiments, any aspect of the matching information for the patient to a study may include inferred information, estimated information, and/or direct information available through observation, medical records, and/or any user information on the data store 118. In certain embodiments, matching decisions may be updated periodically and/or based on events, such as changes in a medical status of the user, adjustments to inferred and/or estimated information about the user, changes in the clinical study, changes in a group constituency for the study (e.g., based on acceptance and/or decline events by other users). In certain embodiments, matching decisions may be utilized to provide direct communications for patients, for example by providing a direct invitation to apply to a study, providing contact information to apply to a study, and/or providing information about a study that may be of interest to the patient. In certain embodiments, matching decisions may be utilized to provide communications to a study group, for example by providing contact information to potential patients (e.g., which may be direct contact information, and/or allow for anonymized contacts), and/or by providing analytics to allow the study group to make decisions (e.g., an indication of the number of participants available, likely to join, and/or distribution descriptions of the potential participants, for example geographic distributions, medical distributions, contact-type distributions (e.g., 35% of the group would participate virtually, with 65% participating through in-person visits, etc.), likely number of participants expected to successfully complete the study, or the like). In certain embodiments, a clinician interface is implemented to allow clinicians to approve outreach to patients, to open or close a study, to change characteristics (e.g., medication, behaviors such as diet and/or sleep schedules, visit plans, etc.) of the study, and/or to view enrollment status of patients. In certain embodiments, the patient engagement platform 101 is configured to replenish patient lists—for example a list of prospective patients, additional patients for a study (e.g., where some patients may have dropped out, and the criteria of the study allow for replacement patients to enroll, and/or where the study is adjusted on the fly, for example to expand the number of patients involved in the study).

An example patient engagement platform 101 is configured to perform patient intake and/or patient pre-screening operations for clinical studies. In certain embodiments, operations for patient intake and/or patient pre-screening are performed in relation to patients that have enrolled with the patient engagement platform 101, and interfaces may be provided through a web portal, interactive web page, mobile application, proprietary program (e.g., a desktop and/or laptop application installed on a computer), and/or with messaging associated with the patient engagement platform 101, for example through a platform based messaging application, a messaging function within the platform interface, and/or with platform messages pushed out beyond the platform (e.g., texts, e-mails, automated calls, and/or a messaging application) to provide various notifications, confirmations, and/or links to activities for the user. In certain embodiments, one or more operations for patient intake and/or patient pre-screening are performed off-platform (e.g., prior to the user agreeing to join the study and/or the platform), and one or more operations are performed on-platform (e.g., after enrollment in the study, after an invitation for the user to join the platform, etc.).

In certain embodiments, pre-screening operations may include aspects such as determining any information relating to the compatibility of the user with the study as set forth throughout the present disclosure. In certain embodiments, pre-screening operations may include operations to confirm and/or update any relevant information, such as determining (e.g., through a query, survey, or direct message to the user, to a medical provider of the user, etc.) the actual value of an estimated or inferred aspect of the patient information, to validate available information (e.g., getting confirmation of a medical condition from a relevant medical provider, confirming the patient address or geographical location, etc.), to get higher resolution information (e.g., variations of a medical condition, specific location information, specific demographic information, behavioral information, etc.), and/or to get information from the user that is not known. Any pre-screening information may be utilized to determine whether to provide the patient with a formal invitation to a study, to confirm that the patient is compatible with the study, to update the characteristics of a group (e.g., to ensure the group distribution is compatible with the study), to determine supplemental information that would be helpful to the patient, to ensure that the patient provides appropriate permissions, or the like. In certain embodiments, pre-screening operations provide for a number of benefits, for example: allowing for real time updates of a study enrollment status and/or group characteristics; ensuring that all relevant criteria are checked and considered in study analysis immediately as obtained; providing an interface to communicate pre-study testing, including allowing for scheduling such tests, confirming the tests are complete, and integrating pre-study testing data into the platform; providing frictionless transitions for the patient between pre-study, study, and post-study interactions; and providing for a single location for the patient to access health information and study information, updated throughout the progress of the study and beyond. In certain embodiments, the availability of medical records, study data, patient preferences and/or permissions, clinician data, patient interaction history, and the like, improve operations of the patient engagement platform 101, reduce the cost to enroll patients with relevant clinical studies, improve enrollment and successful participation rates of patients with relevant clinical studies, improve information available to patients after studies are completed, and/or improve the ability of clinicians to reach out to patients during the study, after the study is completed, to follow up on the study, and/or to engage with patients for future contacts—for example to reach out to patients for a subsequent clinical study.

An example patient engagement platform 101 provides for patient engagement operations throughout the life cycle of a clinical study—for example providing visibility between patients and clinical studies (e.g., allowing patients to see which studies might be helpful for their conditions, and/or allowing study groups to reach out to patients with relevant conditions), enrolling patients with relevant studies, performing pre-screening and initial engagement operations (e.g., initial testing, entry of baseline medical information, etc.), and/or performing study execution engagement (e.g., ensuring ongoing tests, study behaviors such as procedures, visits, regimens for diet, exercise, and/or medication, performing study conclusion actions such as data entry, testing, etc., and/or after-study engagement such as follow-up visits, surveys, testing, results determination, etc.). Patient engagement operations by the patient engagement platform 101 include multi-point access, for example contacting patients via phone, messages (e.g., text messages, messaging application, on-platform messaging, etc.), texts, or the like. Contact to patients may be automated, in-person, and/or may be facilitated in an anonymous manner (e.g., allowing the study group to reach out to patients, including specific patients, patients having specific conditions, patients at specific stages in study execution, and/or patients of certain classifications—such as patients taking a specific medication, regimen, part of a control group, etc., without the study group needing the specific contact information for the patients, or having to contact the patients directly which may compromise the study itself, where anonymous engagement may preserve the patient's privacy as much as possible, and/or to promote study trial integrity, for example avoiding group communications or thinking about participation in specific trials and introducing potential bias). The patient data, available to the patient engagement platform 101, may be utilized to push data to the patient that may be of particular interest to the patient—for example information that may be specific to the patient's medical situation (e.g., allergies, medication interactions, specific to the medication or procedures relevant to the patient from the study, etc.), specific to the treatment regiment and/or stage of the study for that patient, and/or information developed based on what has been learned from the study, whether that information is developed during the study and/or after the study. In certain embodiments, engagement with the patient can be "gamified"—for example providing benefits or bonuses to the patient for completing study activities, responding to communications, completing visitations, confirming behaviors performed for the study, or the like. In certain embodiments, incentives for the patient can be targeted to the specific patient, for example determining incentives that are especially likely to make the patient respond (e.g., based on classification of the patient, and response profiles of similarly classified patients), and/or providing incentives for activities that the patient might be less likely to complete (e.g., based on classification of the patient, and activity profiles of similarly classified patients). Example patient classifications include any patient classifications set forth throughout the present disclosure, including at least: preferred communication avenues, preferred communication times, activity types (e.g., medication regimen, dietary regimen, exercise regimen, visitation types and/or activities such as test types), preferred response times (e.g., providing communications with sufficient advance notice for the patient, providing relevant deadlines for the patient, etc.), and the like. In certain embodiments, the patient classification may be based on any similarity criteria to other patients (e.g., based on demographics, occupation, indicated preferences, etc.) and/or based on behavioral information gathered from the patient specifically (e.g., based on response times for different communication avenues, and/or adherence to activities such as visitations, test completion, data entry, etc.). In certain embodiments, the patient classification may be updated on an ongoing basis, with the responses and engagement operations of the patient engagement platform 101 adjusting over time to the patient's updated classification, for example as the system learns more about the specific changes, and/or as the patient's actual behavior evolves.

An example patient engagement platform 101 matches patients to clinical studies, which can help patients find relevant studies, and/or help study groups find relevant patients for a study. In certain embodiments, a study may be planned as a prospective study, where the patient engagement platform 101 provides information that is utilized to determine whether to proceed with the study, and/or to modify the study (e.g., activities to be performed as a part of the study, intended size of the study, etc.) based on the available patient pool for the study. Operations to match patients with studies, and/or prospective studies, provide for a number of benefits, such as: ensuring patients get visibility to studies that would be helpful to them; ensuring that patients spend the time and effort to engage with studies that they are likely to be able to participate in fully; configuring resources around the study based on the likelihood that a sufficient group of patients will enroll and complete the study; and/or configure aspects of the study to promote successful completion of patient activities and/or overall useful completion of the study. In certain embodiments, patients can be ranked against the study goals and activities to prioritize a group of patients that will be likely to be able to complete the study and provide for sufficient information to be generated for the goals of the study. In certain embodiments, triage operations of the patient engagement platform 101 as part of the patient-study matching can ensure that the group of patients that will be most helped by the study, and/or that have the most urgent need for the study, can be performed to prioritize enrollment and execution of the study for maximum overall benefit to patients and for the study. Example operations for the patient engagement platform 101 to match patients include behavioral modeling for patients to determine whether they will be able to, and/or are likely to, complete the operations required for the study, and thereby be a successful participant in the study. An example patient engagement platform 101 allows patients to self-select trial opportunities, and/or self-screen for potential trial opportunities, for example by allowing the patient to perform any further testing, completion of surveys, confirming information, and/or comparing medical conditions (e.g., allowing the medical records of the patient to be scanned for elements relevant to the study, without exposing that information for any other purpose and/or in a manner that could be used to match medical information with the patient). Accordingly, by the time the patient requests to enroll in a particular study, the patient can develop some certainty that they are a good candidate for the study, and are likely to be accepted for the study.

The following description referencing the figures set forth certain embodiments of the present disclosure that embody and/or implement certain aspects of a patient engagement platform 101. The examples in the figures may be utilized, in whole or part, to perform any operations set forth herein.

Referencing FIG. 1, an example system 100 includes a patient engagement platform 101 having a number of components configured to perform operations of the patient engagement platform 101. The example components are depicted on the patient engagement platform 101, but may additionally or alternatively be positioned, in whole or part, on a separate device from the patient engagement platform 101, on a web server, on a user device (e.g., 104, 108, 112), and/or may be positioned on separate devices at separate times and/or depending upon which operations are being performed. In the example of FIG. 1, example user devices 104, 108, 112 are provided that are accessed by different users—for example a patient user 102, a clinician user 106 (e.g., a user associated with a study group, for example someone creating a clinical study, considering whether to create a study, and/or a third party supporter engaging the patient engagement platform 101 on behalf of a study group), a medical provider user 110 (e.g., a health care provider that may or may not be associated with a study group or the patient, for example: a health care provider performing tests, examinations, providing medication, etc., for example as a part of activities performed as a part of the study; a primary care provider for the patient, for example that may suggest studies to the patient, monitor patient participation in a study, and/or to keep visibility of the patient study participation and/or results; and/or a medical provider providing medical records of the patient, with the knowledge and/or approval of the patient, to the patient engagement platform 101), and/or any supporting user 114 (e.g., a user supporting scheduling for patients, delivery of medications, confirmation of visit completions, providing technical support for patients or other users, etc.). The example users 102, 106, 110, 114 are non-limiting examples, and any user engaging with the patient engagement platform 101 for any purpose or operations set forth herein, is contemplated herein. The example devices 104, 108, 112, 116 are non-limiting examples, and the specific device 104, 108, 112 utilized by a user at any given time may be varied—for example the patient user 102 may access the patient engagement platform 101 using a laptop, desktop, mobile device, etc., and may access the patient engagement platform 101 using distinct devices at different times and/or for different operations.

The example patient engagement platform 101 includes a patient interaction component 120, for example providing interfaces to the patient device 104, sending messages to the patient, receiving information from the patient, and/or receiving information automatically from the patient (e.g., a patient using a wearable device that transmits certain information to the platform, such as patient biometric information, sleep information, exercise information, or the like). In certain embodiments, any interactions of the patient engagement platform 101 with the patient may be provided by the patient interaction component 120, be commanded by the patient interaction component 120, and/or be monitored by the patient interaction component 120.

The example patient engagement platform 101 includes an external interaction component 126, for example providing interfaces to other devices such as clinician devices, medical provider devices, accessing external databases, and/or any other devices to perform operations set forth throughout the present disclosure.

The example patient engagement platform 101 includes a journey management component 124, which performs any supporting operations to curate the patient journey with the patient engagement platform 101, for example determining the timing of notifications, communications, etc., determining patient medical information and/or matching operations to clinical studies, determining patient behavioral information and/or matching operations to clinical studies, determining patient classification information (e.g., for matching to studies, configuring communications, configuring notifications, determining follow-up activities, etc.), and/or providing communication access between study groups and patients (e.g., before a study, during the study, after the study, and/or providing for anonymized communication avenues). An example operation to determine the patient behavioral information includes storing relevant patient information on the data store 118, and applying behavioral science methods to that information to determine the behavioral information. Example relevant patient information for determining the behavioral information include any patient information as set forth throughout the present disclosure, and including at least aspects such as: patient lifestyle information (e.g., diet, exercise, sleep patterns, etc.) determined from mobile applications, wearable devices, and/or patient entered information (e.g., from surveys, tracking applications, journal applications, etc.); patient medical information (e.g., lab results, information tracked from a wearable device such as heart rate information or the like, and/or behavioral information as indicated in medical records); patient activity that may indicate behavioral characteristics of the patient (e.g., locations, travel patterns, time-of-day considerations for these, etc.); and/or any other information available to the platform 101 that may be utilized to determine patient behavioral information (e.g., mood indications from text posted by the patient, clusters or patterns of information that may be determined, for example by an AI component, to relate to and/or indicate certain behavioral aspects of the patient, and/or historical performance of the patient—for example responding to communications, requesting particular aspects of information, and/ or attending to medication regimes, medical provider visits, etc.). The journey management component 124 performs operations to match patients, to ensure patient efforts are likely to be beneficial and effective for the patients, to ensure that clinical study development efforts are likely to be successful and effective for finding a patient pool, and/or to enable longitudinal study aspects, for example allowing patients and study groups to maintain contact over a long period of time.

Figure 2:
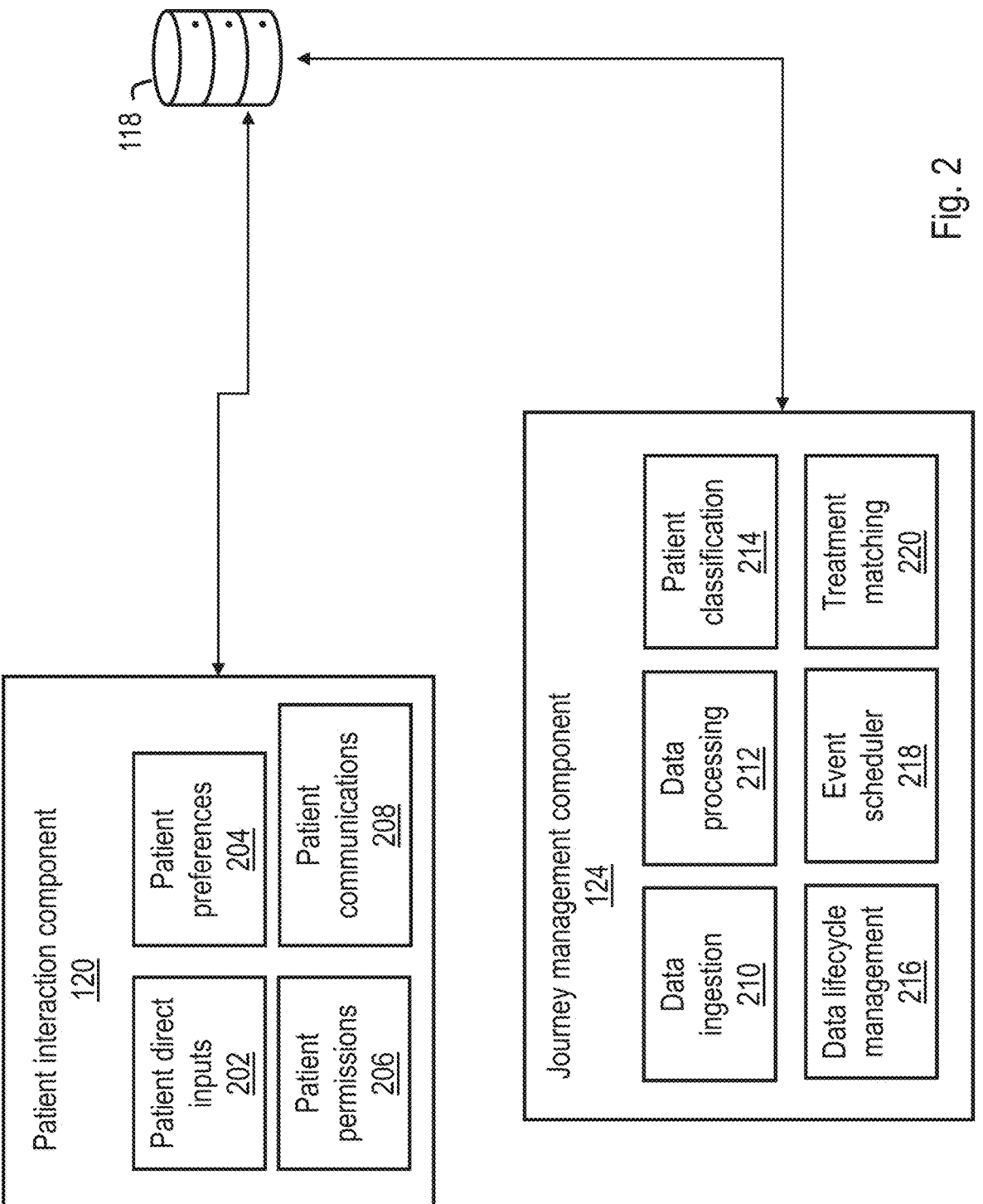
FIG. 2 depicts aspects of an illustrative patient engagement platform according to example embodiments.

Referencing FIG. 2, an example patient interaction component 120 includes sub-components for patient direct inputs 202, capturing patient preferences 204 (e.g., directly input preferences and/or inferred preferences), patient permissions 206 (e.g., including maintaining a record of permissions, appropriately refreshing permissions, and/or requesting permissions as needed on an ongoing basis, and/or further including providing a single place for patients to review, confirm, and/or change permissions as needed), and/or patient communications 208. An example journey management component 124 includes sub-components for data ingestion 210 (e.g., through direct communications with the patient, access to publicly available information for the patient, acquisition of medical records for the patient, etc.), data processing 212 (e.g., normalizing and/or adjusting data into a standardized format, determining classifications or patterns from the data, and/or making any other determinations from the data according to aspects of the present disclosure), patient classification 214 (e.g., storing any classifications related to the patient, and/or storing any data utilized in such determinations, for example to allow for re-classification periodically and/or in real time), data lifecycle management 216 (e.g., determining how long to retain data, enforcing data retention protocols, enforcing patient permission values, determining whether to store data in high-speed short term memory and/or lower-speed long term memory, etc.), an event scheduler 218 (e.g., scheduling events associated with a particular study, and/or more general medical support scheduling such as tests, follow-up events, indicated tests according to the ongoing medical status of the patient, etc., and which can include helping a patient to find appropriate medical providers, and/or adjusting scheduling according to the patient's behavioral information such as preferred timing, notification avenues, etc.), and/or a treatment matching 220 component (e.g., determining whether available clinical studies, new tests or treatments, etc. would be a good fit for the patient, medically, behaviorally, according to patient classifications, etc.).

Figure 3:
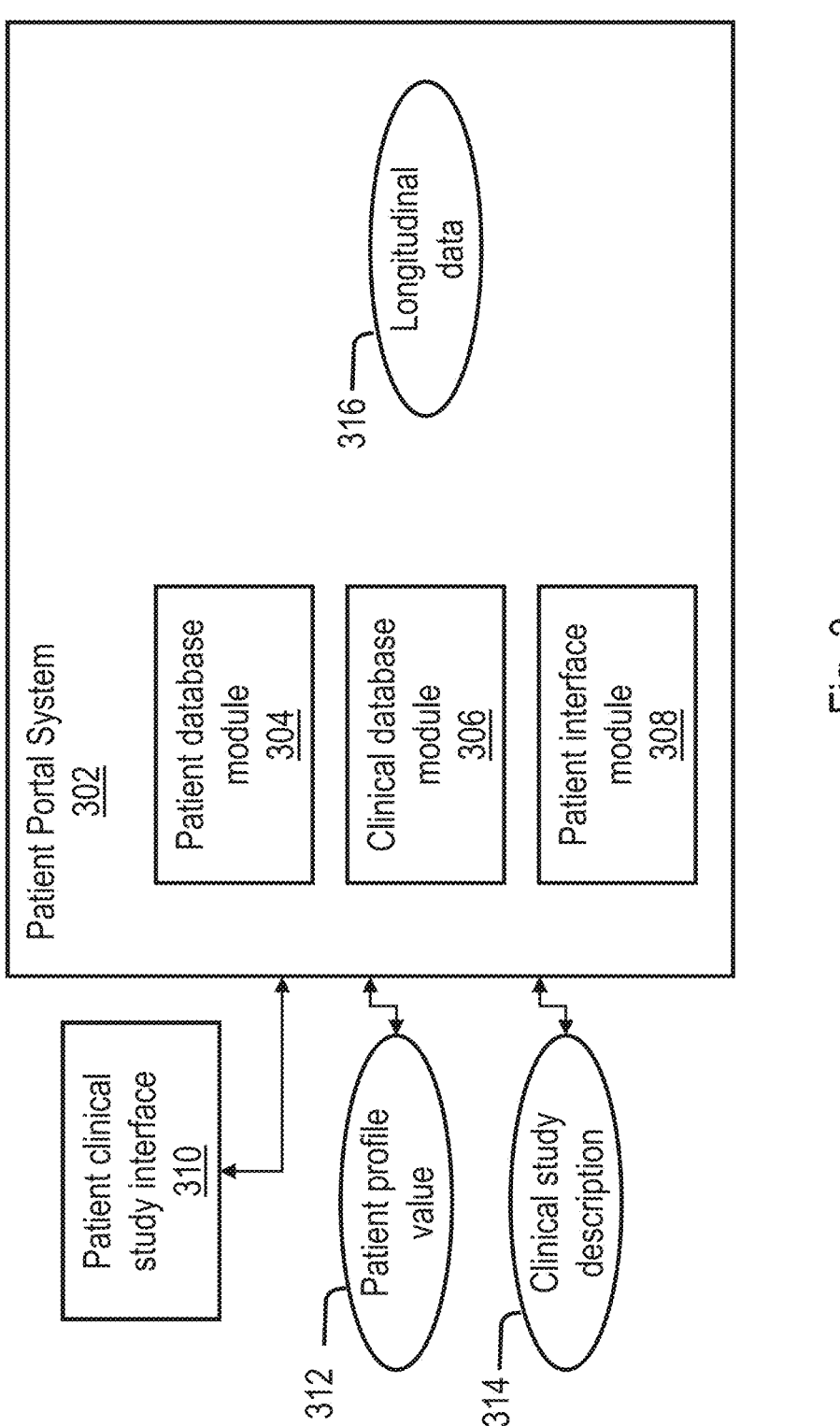
FIG. 3 depicts an illustrative patient portal system according to example embodiments.

Referencing FIG. 3, an example patient portal system is schematically depicted to assist patients in finding appropriate clinical studies, and facilitating engagement, screening, enrollment, and/or performance of activities related to clinical studies. The example system includes a patient database module 304 configured to interpret a patient profile value 312, a clinical database module 306 configured to interpret a clinical study description 314, and a patient interface module 308 configured to implement a patient clinical study interface 310 in response to the patient profile value 312 and the clinical study description 314. In certain embodiments, the patient profile value 312 includes information for a patient, such as an identifier, patient name, patient demographic information, and/or may further include information such as medical conditions, likely or suspected medical conditions, symptoms, or other information that can be utilized to determine whether the patient is a good candidate for particular clinical studies, and/or whether the patient is potentially a candidate for clinical studies. In certain embodiments, the clinical study description 314 includes information about one or more clinical studies, including information provided by a provider of the clinical study, including information such as relevant medical conditions, demographic information, geographic information, a target number of individuals planned for the study, or the like. The example clinical database module 306 determines whether the patient is a good candidate for a study, and/or whether the patient is a potential candidate for the study, in response to a comparison of aspects of the relevant clinical study description 314 and the patient profile value 312. The example patient interface module 308 provides a relevant communication to the patient in response to determining the patient is a possible candidate for the study, which may be provided by any patient touch point or communication method as set forth throughout the present disclosure, including without limitation by providing a text message, an on-platform message, providing a message to a social media feed of the patient, or the like, connecting the patient with the potential to participate in the clinical study and/or to connect with the provider of the clinical study. In certain embodiments, the patient interface module 308 provides the patient a communication on the patient clinical study interface 310 to allow the patient to begin enrollment in the study, to perform pre-screening operations for the study, to provide further information to determine if the patient is a good candidate for the study, and/or to allow the patient to request or access further information about the study so the patient can determine if the study is a good fit for them. In certain embodiments, the clinical database module 306 further determines if the patient is a candidate for the study in response to patient aspects that may not be directly medically related, for example to configure the size of the patient group for the study is within the practical limits to conduct the study (e.g., a large enough group for statistical significance, and/or a small enough group to be properly accommodated for the study), to determine whether the patient is in a particular geographic region, within a specified range of relevant facilities such as medical providers or laboratories equipped to support aspects of the study, or the like. In certain embodiments, the example patient database module 304 includes at least a portion of the patient clinical data as longitudinal data 316 of a patient corresponding to the patient profile value 312.

Figure 4:
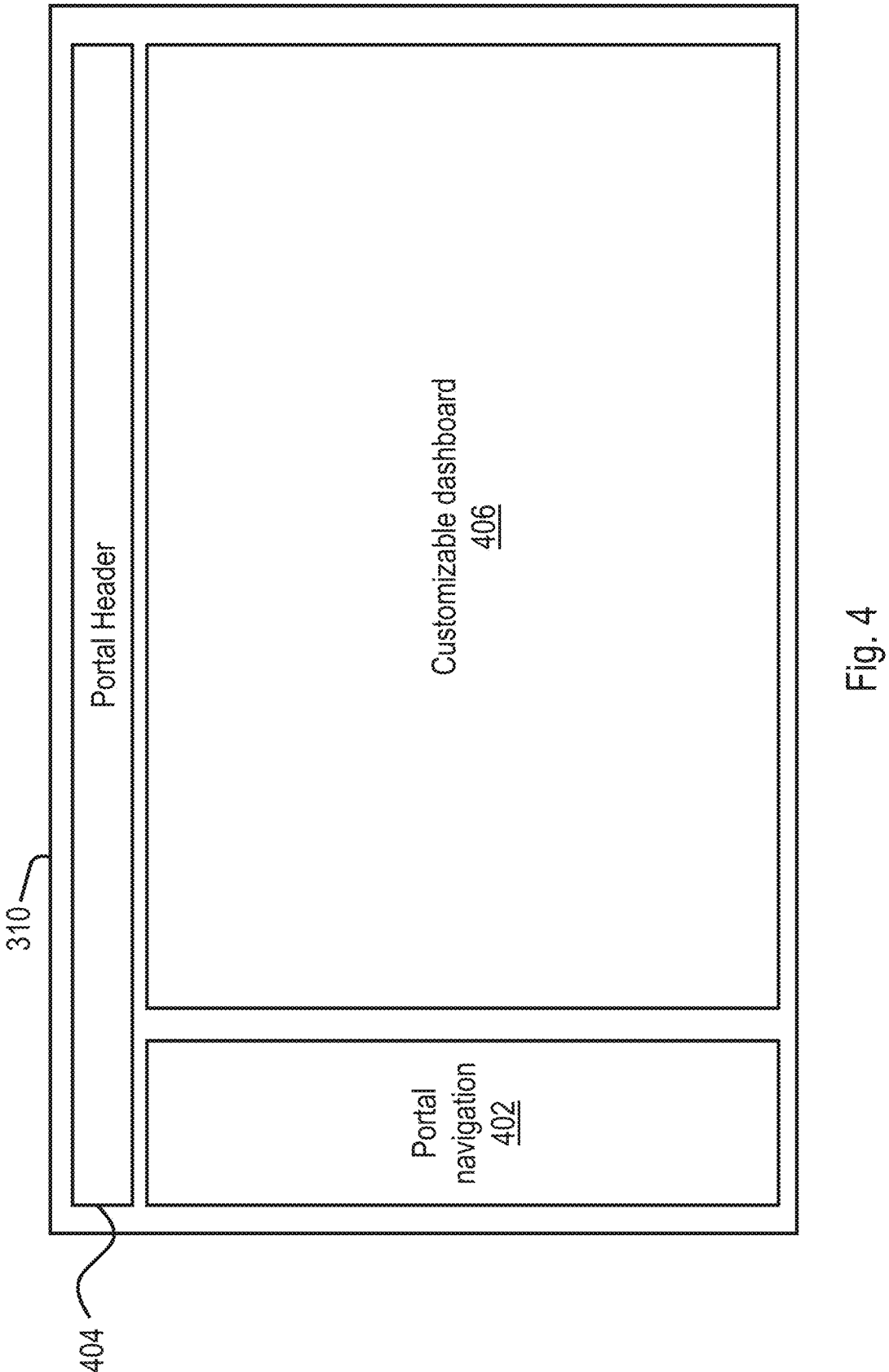
FIG. 4 depicts an illustrative patient clinical study interface according to example embodiments.

Referencing FIG. 4, an example patient interface module 308 provides a customizable dashboard 406 on the interface 310, for example to provide the patient with information to track relevant medical information, procedures, or treatments, to easily access communication avenues such as on-platform messaging and/or social media access, to communicate with medical providers, clinical study groups, advocacy groups, or the like. The example interface 310 includes, as a non-limiting example, a portal navigation 402 section that may include menus, navigation links, or the like, to provide convenient navigation on the platform, portal, system, or the like, for example to access educational content, social media content, scheduling, and/or any other features of a platform, portal, or system as set forth throughout the present disclosure. The example interface 310 further includes, as a non-limiting example, portal header 404 information, for example allowing the patient to confirm that they are on the platform, which section they are currently accessing, or the like.

Figure 5:
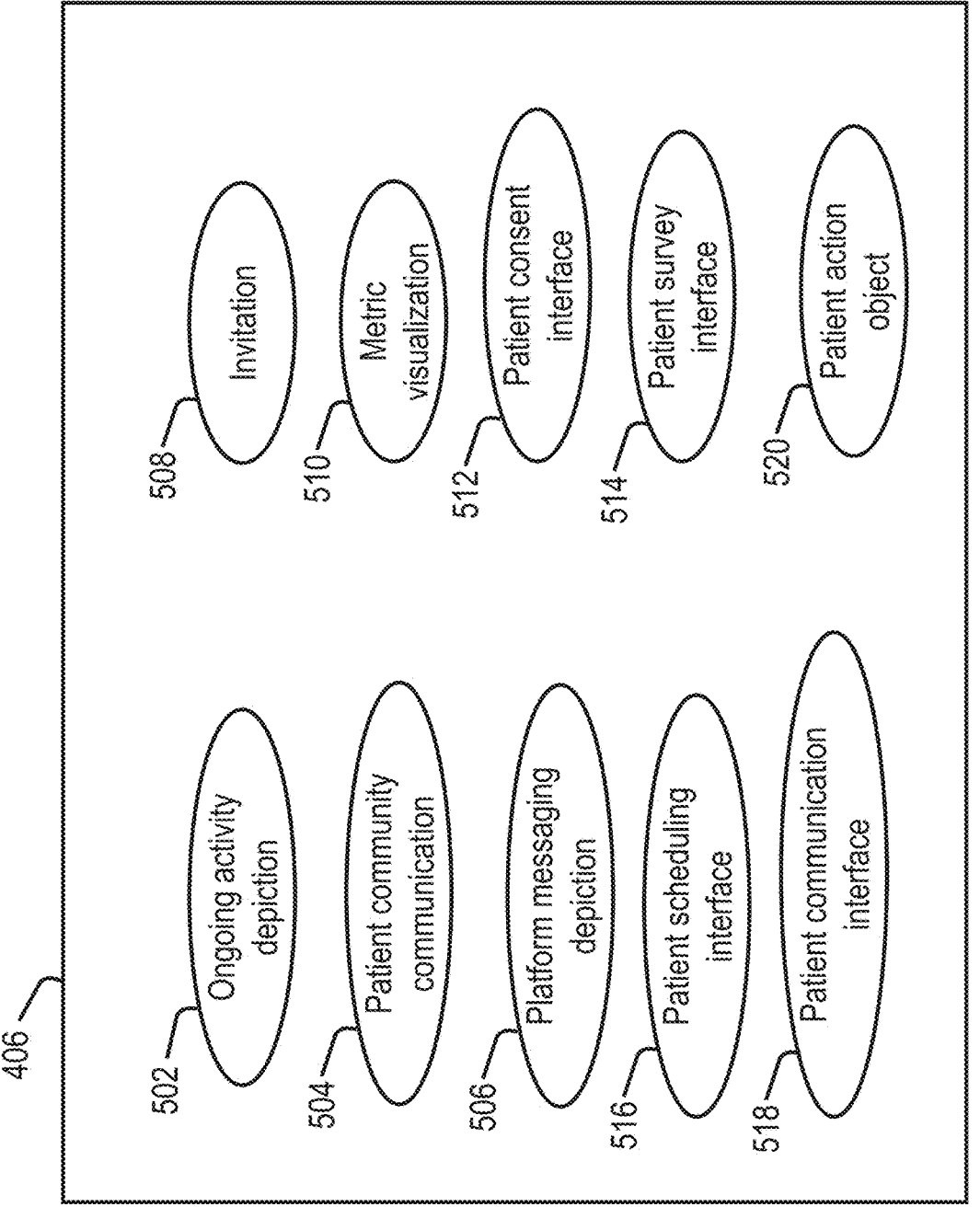
FIG. 5 depicts example elements of a customizable dashboard according to example embodiments.
Figure 9:
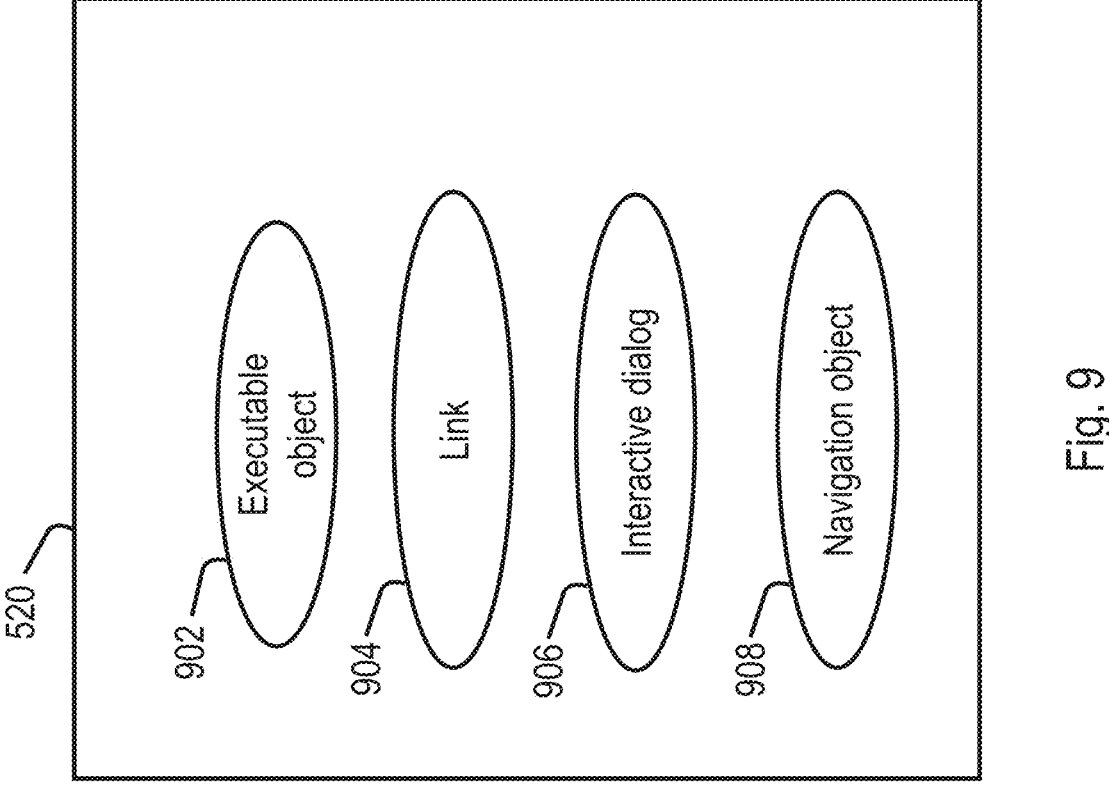
FIG. 9 depicts example elements of a patient action object according to example embodiments.

Referencing FIG. 5, example and non-limiting aspects that may be provided on the customizable dashboard 406 are depicted schematically. An example customizable dashboard 406 includes one or more aspects such as: an ongoing activity depiction 502 (e.g., studies, treatments, medications, social media activity, and/or any other type of activity related to the platform/portal/system and/or medical activity for the patient); a patient community communication 504 (e.g., communications relevant to a patient community on a social media platform that the patient is a member of, and/or has indicated an interest in, notifications relevant to such patient communities, or the like); a platform messaging depiction 506 (e.g., an indicator of unread messages, important messages, requested messages, message responses, or the like); an invitation 508 (e.g., an invitation to enroll in a clinical study, an invitation to perform pre-screening for a clinical study, an invitation to a patient community, an invitation to receive educational materials for example related to particular medical conditions, or the like); a metric visualization 510 (e.g., a metric related to the patient, such as tracking a medical treatment, health progress, or the like, a metric related to the platform such as communication responses, patient community attendance, or the like, and/or any metric related to the platform and/or medical information of the patient); a patient consent interface 512 (e.g., utilized to prompt a patient to complete a consent form, to confirm a change in terms and conditions and/or management of patient health information, or the like, which may be utilized to facilitate ensuring that the patient has consented to utilization of their information, to reduce enrollment times for clinical studies and/or medical treatments, and/or to provide the patient with a convenient and prominent method to confirm how their information is being utilized); a patient survey interface 514 (e.g., a survey for feedback from the patient, for example in response to a clinical study, medical treatment, related to a patient community and/or advocacy group; and/or utilized to provide a survey to the patient to develop further information about the patient and/or perform pre-screening to determine whether the patient is a good candidate for a particular clinical study, medical treatment, or the like); a patient scheduling interface 516 (e.g., for the patient to schedule procedures utilized during enrollment and/or execution of a clinical study, to schedule a particular medical procedure, and/or to schedule any communication, treatment, or procedure with any stakeholder having access to the platform/portal/system that includes and/or is in communication with the patient portal system 302); and/or a patient communication interface 518 (e.g., allowing the patient a convenient interface to access incoming communications and/or provide outgoing communications with clinical study groups, medical providers, insurers, patient communities, advocacy groups, other patients, and/or any stakeholder having access to the platform/portal/system that includes and/or is in communication with the patient portal system 302). An example customizable dashboard 406 includes a patient action object 520 providing a lever for the patient clinical study interface 310 to be utilized to facilitate actions by the patient on the patient portal system 302, including any patient activity as set forth throughout the present disclosure. Referencing FIG. 9, an example patient action object 520 may include an executable object 902 of any type (e.g., a button, check box, slider bar, etc., allowing the user to perform an action by clicking on it, checking or clearing the box, adjusting the slider setting, or the like). The example executable object 902 may be utilized to perform enrollment operations, seek additional information, confirm or decline requests, adjust metrics depicted on the dashboard 406, or the like). An example patient action object 520 includes a link 904 (e.g., within a message, directly on the dashboard, or the like, for example to navigate to relevant portions of the platform/portal/system, to contact stakeholders, to connect with patient communities and/or advocacy groups, and/or to a selected website, etc.). An example patient action object 520 includes an interactive dialog 906 (e.g., a pop-up dialog window, a guided dialog, for example to clarify information from the patient and/or to allow the patient to seek information or clarification, or the like). An example patient action object 520 includes a navigation object 908, for example a menu, navigation pane, or the like, allowing the patient to rapidly navigate to an area of interest within the platform/portal/system, and/or to any elements such as those described in relation to the link 904.

Figure 7:
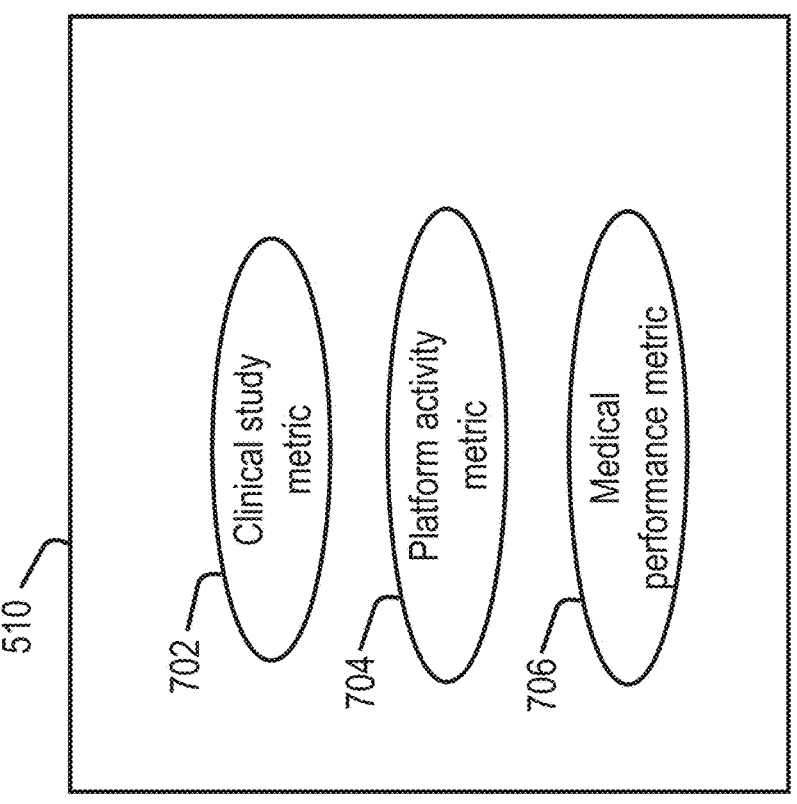
FIG. 7 depicts example elements of an invitation according to example embodiments.
Figure 6:
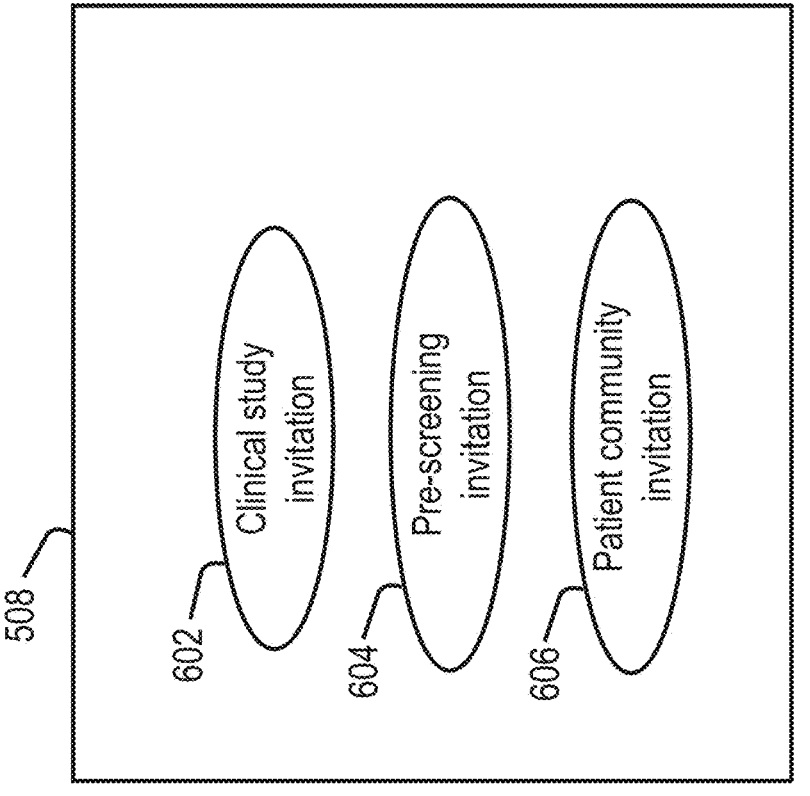
FIG. 6 depicts example elements of a metric visualization according to example embodiments.
Figure 8:
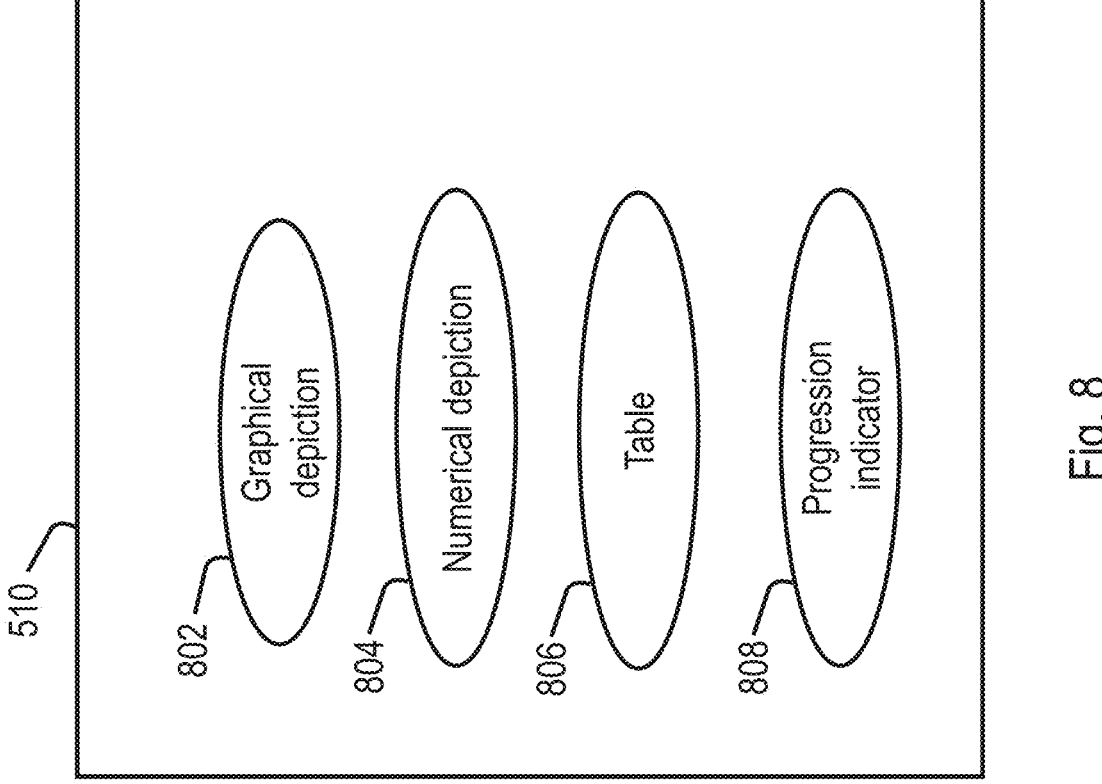
FIG. 8 depicts example elements of a metric visualization according to example embodiments.

Referencing FIG. 6, example and non-limiting invitations 508 include one or more of: a clinical study invitation 602, a pre-screening invitation 604, and/or a patient community invitation 606. Referencing FIG. 7, example and non-limiting metric visualizations 510 include one or more of: a clinical study metric 702 (e.g., progress in a clinical study enrollment and/or execution, available clinical studies, predicted fitness for a clinical study, or the like); a platform activity metric 704 (e.g., any activity on the platform, such as patient community participation, available relevant patient communities, communication activity, available advocacy groups, behavior performance and/or tracking, or the like); and/or a medical performance metric 706 (e.g., progress for a treatment, upcoming treatment events, upcoming medical events, or the like). Referencing FIG. 8, example and non-limiting metric visualizations 510 include one or more of: a graphical depiction 802 (e.g., tracking a metric over time, a graphical progress indication, a chart, etc.); a numerical depiction 804 (e.g., a prominently displayed number relevant to a metric relevant to the patient or patient journey, such as a health indicator, communication indicator, progress indicator, etc.); a table 806 (e.g., a table depicting metric information over time, depicting a number of metrics grouped into a table, etc.); and/or a progression indicator 808 (e.g., a filling color bar, pie chart, speedometer depiction, or the like indicating a progress, for example toward a medical goal of the patient, performance over the course of a treatment or study, or the like).

Without limitation to any other aspect of the present disclosure, a stakeholder as utilized herein, for example a stakeholder of any platform/portal/system herein, includes: a patient; a patient community member; a clinical study team; a medical provider; a scheduling assistant; a laboratory; a clinical study provider; a pharmaceutical provider; an advocacy group; and/or an advocacy group member.

Figure 10:
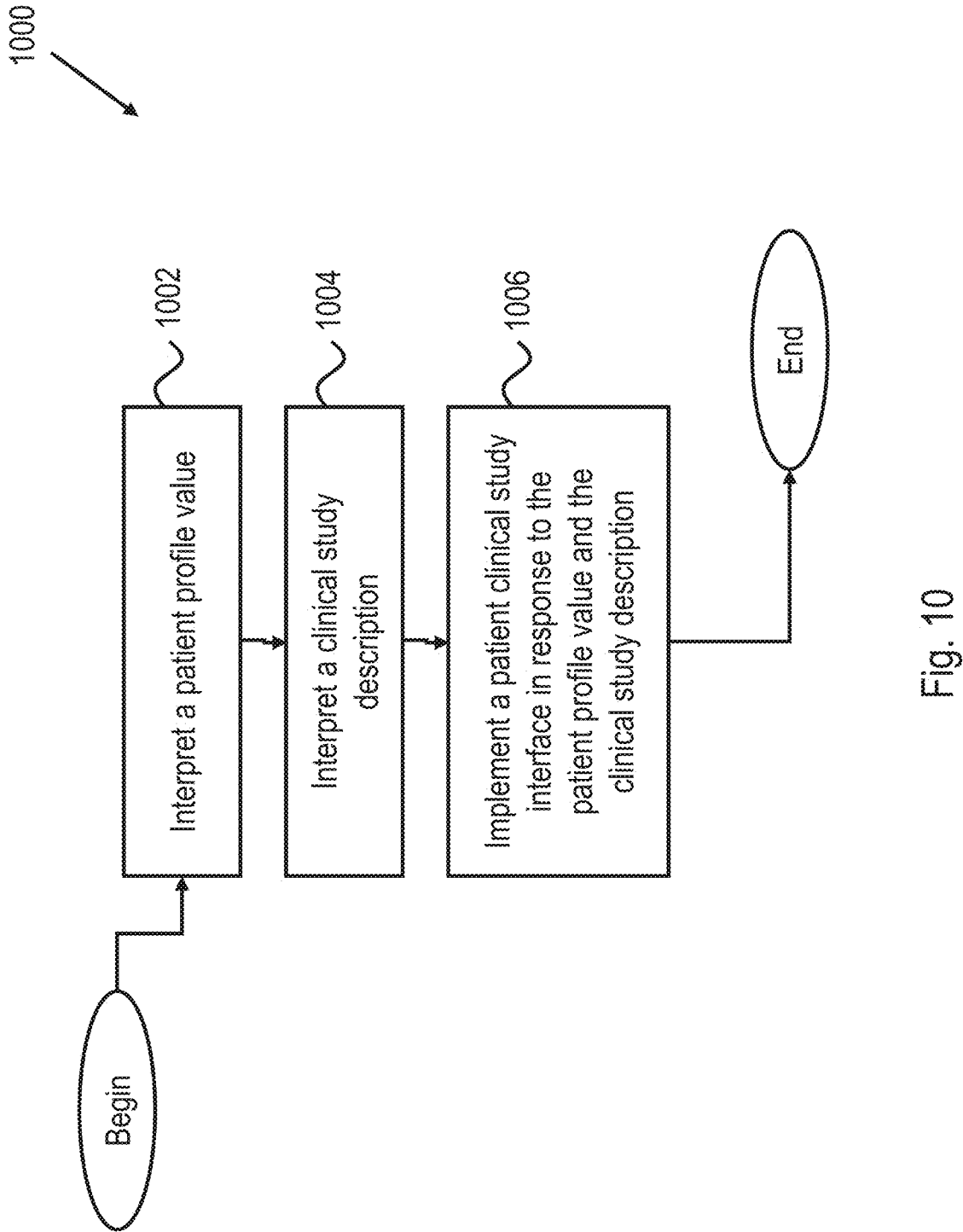
FIG. 10 depicts an example procedure to implement a clinical study interface.
Figure 11:
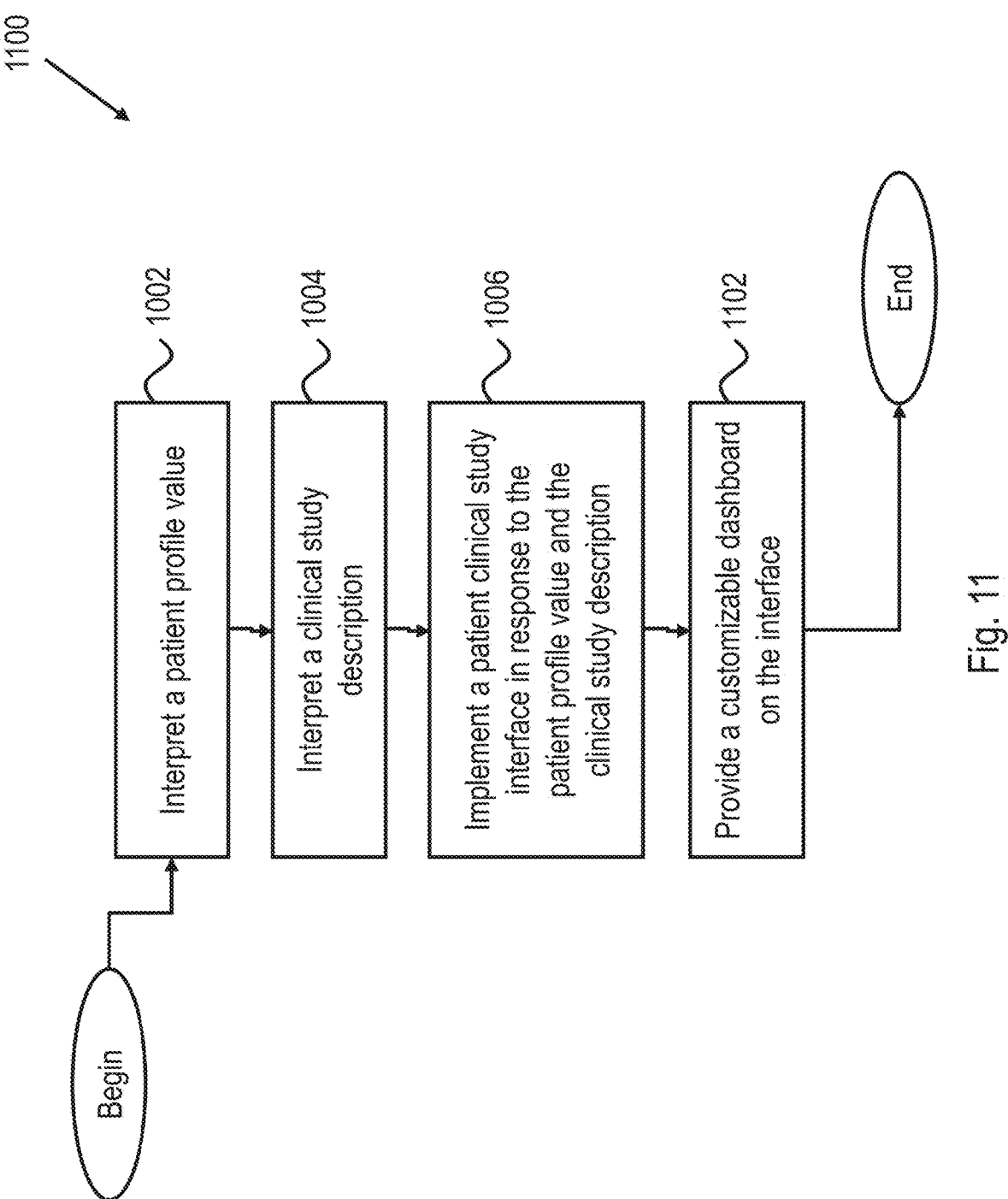
FIG. 11 depicts an example procedure to provide a customizable dashboard.

Referencing FIG. 10, an example procedure 1000 for implementing a patient portal system, and/or assisting patients in finding appropriate clinical studies, and facilitating engagement, screening, enrollment, and/or performance of activities related to clinical studies, is schematically depicted. The example procedure 1000 includes an operation 1002 to interpret a patient profile value, an operation 1004 to interpret a clinical study description, and an operation 1006 to implement a patient clinical study interface in response to the patient profile value and the clinical study description. Referencing FIG. 11, an example procedure 1100 further includes, in addition to the procedure 1000, an operation 1102 to provide a customizable dashboard on the patient clinical study interface.

Figure 12:
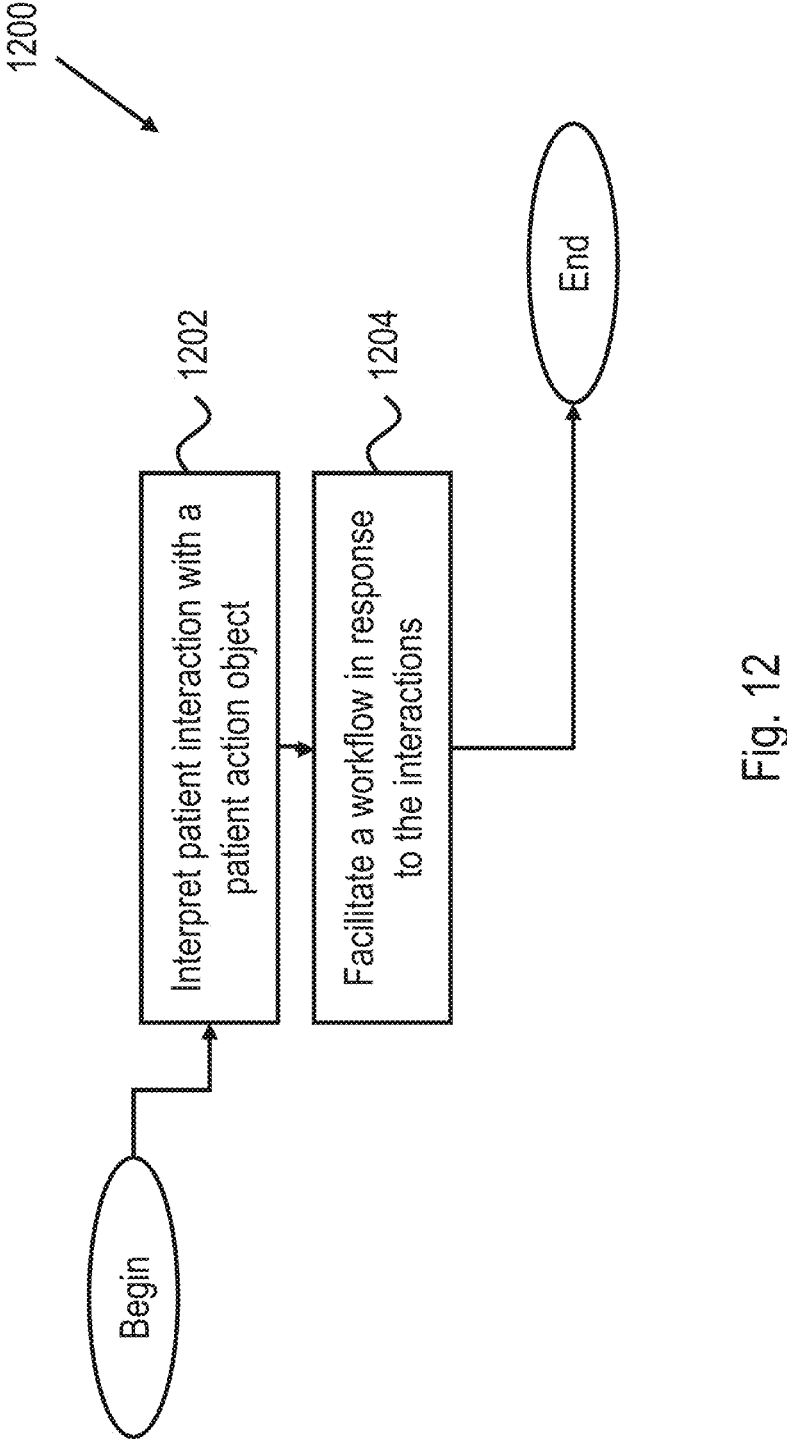
FIG. 12 depicts an example procedure to facilitate a workflow.
Figure 13:
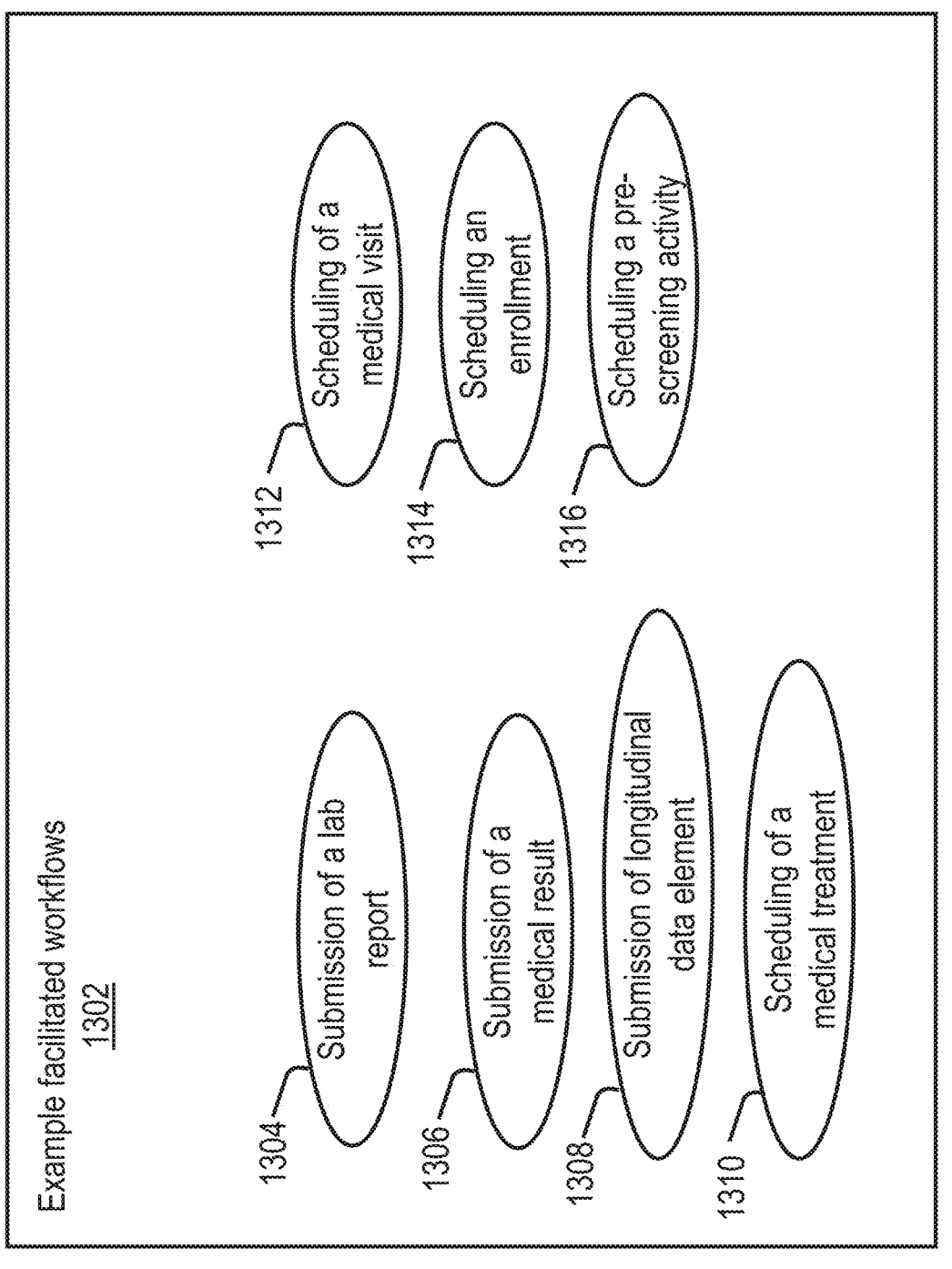
FIG. 13 depicts example facilitated workflows.

Referencing FIG. 12, an example procedure 1200 for responding to patient interactions with a patient action object includes an operation 1202 to interpret a patient interaction with the patient action object, and an operation 1204 to facilitate a workflow in response to the patient interactions. Referencing FIG. 13, example and non-limiting workflows 1302, for example as facilitated by procedure 1200, include one or more operations such as: an operation 1304 to submit a lab report (e.g., to be entered as longitudinal data for the patient, to be provided for a clinical study during screening, enrollment, and/or execution, and/or to be provided to a medical provider); an operation 1306 to submit a medical result; an operation 1308 to submit a longitudinal data element (e.g., allowing the patient to quickly provide selected information to a stakeholder on a platform/portal/system); an operation 1310 to schedule a medical treatment; an operation 1312 to schedule a medical visit; an operation 1314 to schedule and enrollment; and/or an operation 1316 to schedule a pre-screening activity (e.g., a survey, lab test, medical procedure, etc.).

Figure 31:
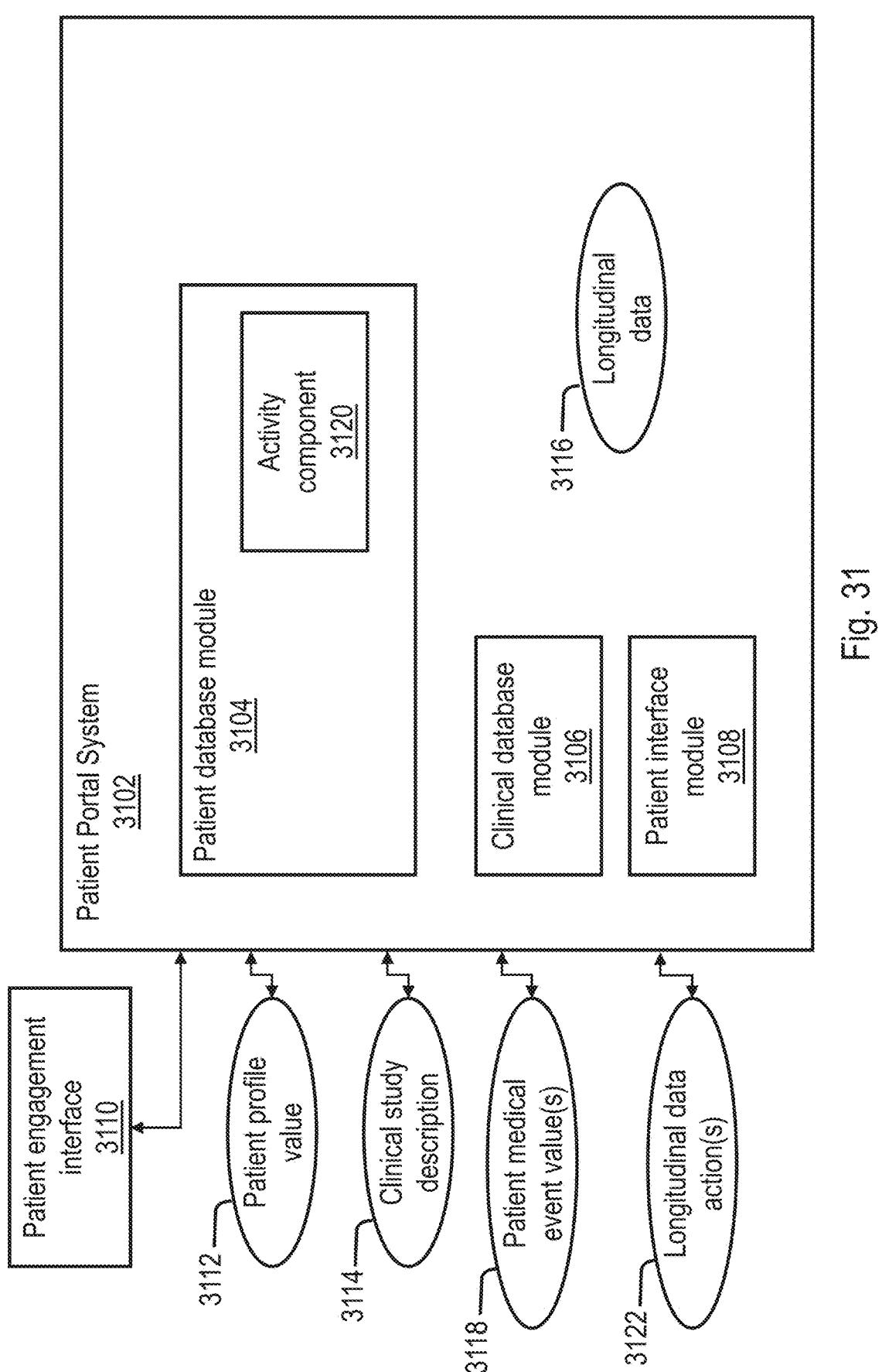
FIG. 31 depicts an example patient portal system.

Referencing FIG. 31, an example system for providing, curating, maintaining, and/or updating longitudinal data for patients enrolled with a platform/portal/system as set forth herein is schematically depicted, and/or for making the longitudinal data available to any platform/portal/system as set forth throughout the present disclosure, and/or to perform and/or support longitudinal data actions, is schematically depicted. The example system includes a patient portal system 3102 having a patient database module 3104 configured to interpret a patient profile value 3112, and a clinical database module 3106 that interprets a clinical study description 3114. The example patient database module 3104 interprets patient clinical data in response to the patient profile value and the clinical study description. The patient clinical data can include data related to pre-screening, enrollment, and/or execution of a clinical study, for example data from communications with the patient, comparisons between the patient profile value 3112 and the clinical study description 3114, and/or data from lab results, medical procedures, medical treatments, clinical procedures, and/or clinical treatments related to the clinical study. In certain embodiments, the patient clinical data can include administrative information, such as whether the patient is a candidate for a clinical study, whether the clinical study has been communicated to the patient, or the like. The example patient database module 3104 includes at least a portion of the patient clinical data as longitudinal data 3116 of a patient corresponding to the patient profile value 3112. The example patient portal system 3102 includes a patient interface module 3108 configured to implement a patient engagement interface 3110, to interpret a patient medical event value 3118 in response to patient interactions with the patient engagement interface 3110, and the patient database module 3104 adjusts the longitudinal data 3116 in response to the patient medical event value 3118. For example, the patient medical event value 3118 may include any value related to communications, enrollment, pre-screening, execution, and/or tracking of a clinical study, where the longitudinal data 3116 adjustment includes a representation of the patient medical event value 3118 (e.g., confirming the occurrence of the event, and/or capturing all or a portion of substantive information from the event, metadata related to the event, and/or other information derived from or determined in response to the event). In certain embodiments, the patient database module 3104 may include an activity component 3120 for performing one or more longitudinal data actions 3122 as described herein.

Figure 32:
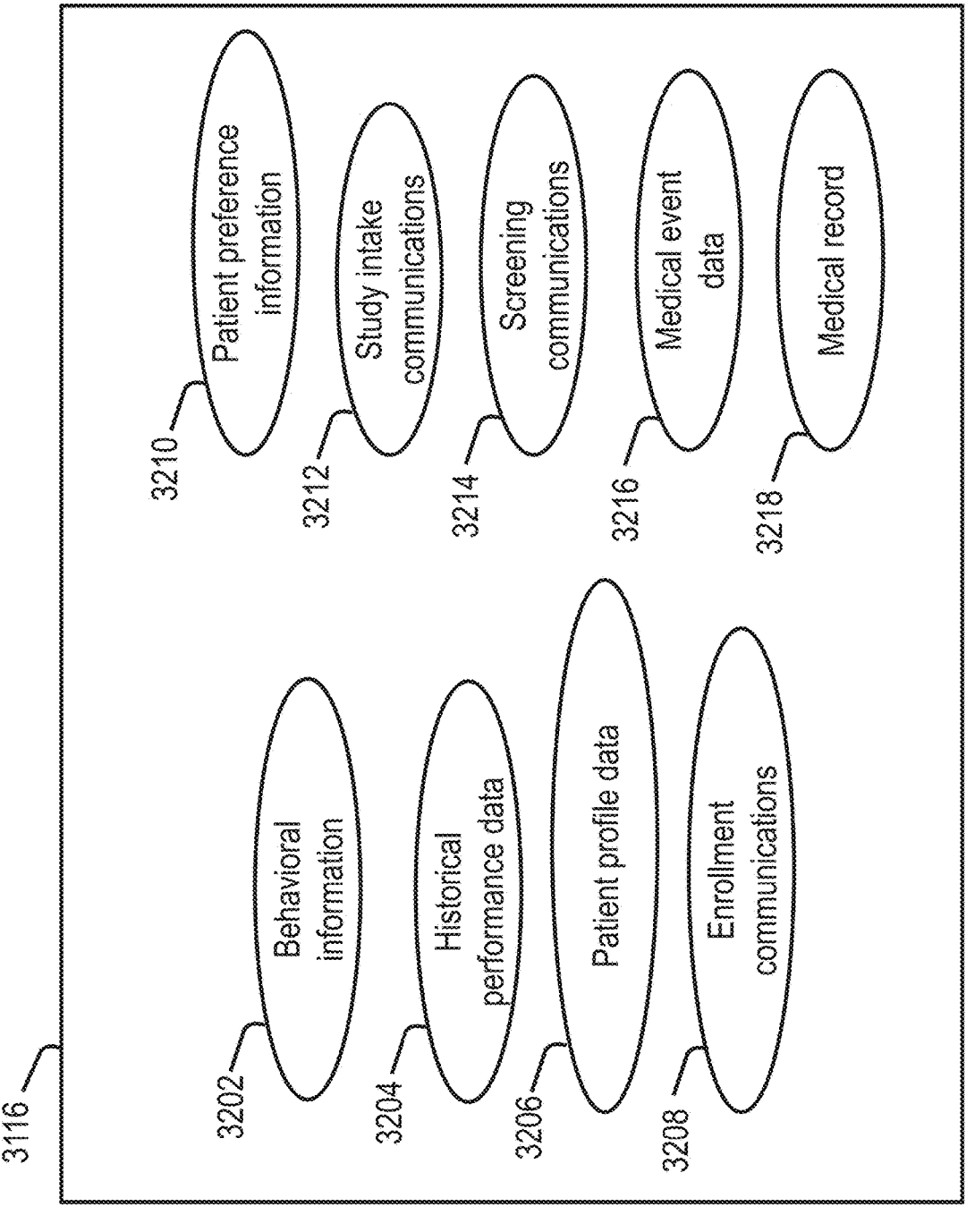
FIG. 32 depicts illustrative longitudinal data.
Figure 33:
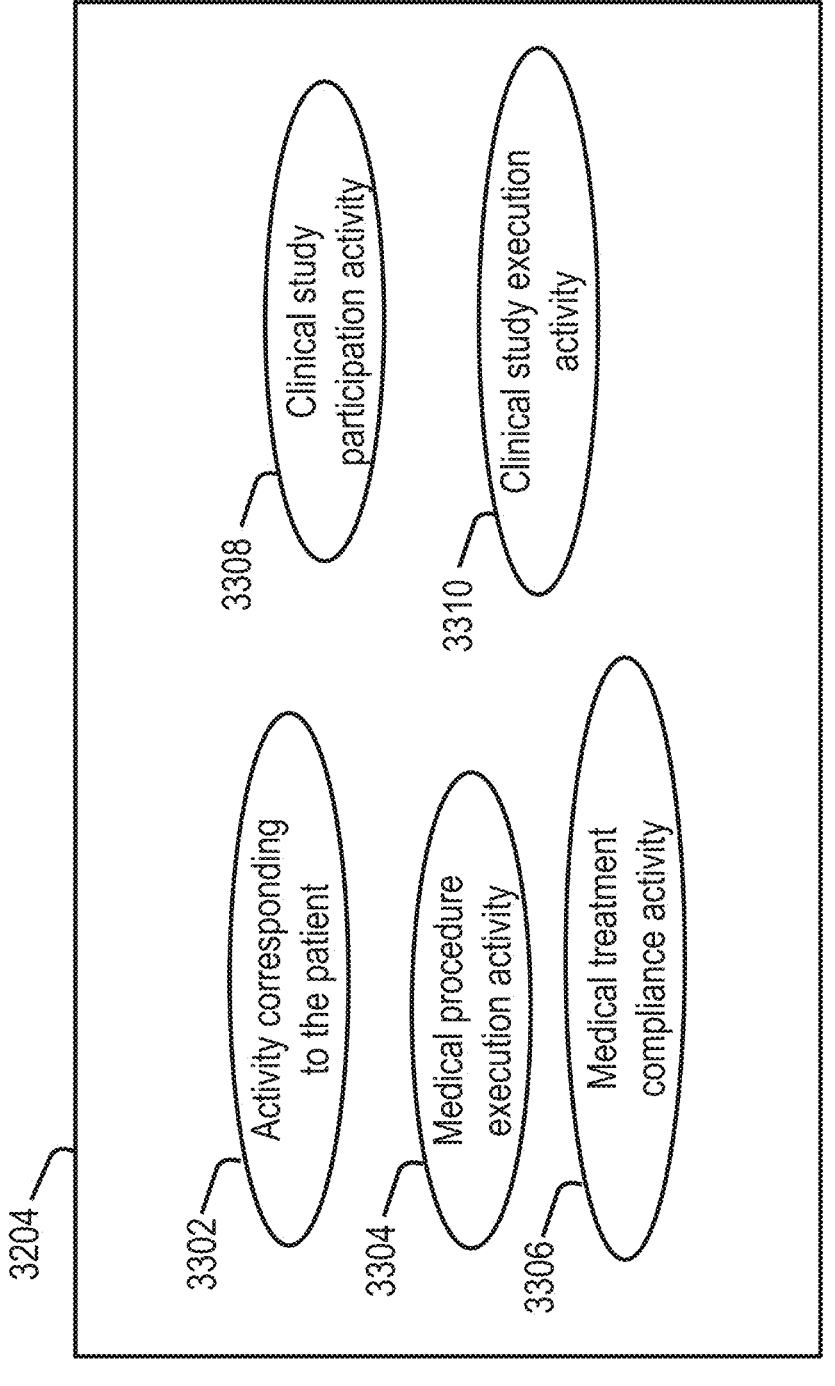
FIG. 33 depicts illustrative historical performance data.

Referencing FIG. 32, non-limiting examples of longitudinal data 3116 are schematically depicted, including one or more aspects such as: behavioral information 3202 (e.g., information that instructs applicability of the patient for particular clinical studies, behavioral information related to medical conditions, treatments, and/or procedures, patient communication preferences and habits, patient compliance with procedures, treatments, and medication regimens, etc.);

historical performance data 3204 (e.g., patient communication patterns and/or communications relating to clinical trials, medical procedures, scheduling, and/or social media interactions; medical procedures and/or events; clinical trial interactions at any phase; etc.); patient profile data 3206; enrollment communications 3208 (e.g., including communication methods and timing, content, acceptance or declining of offered clinical trials, etc.); patient preference information 3210 (e.g., preferences, express or inferred, on any platform/portal/system, for any patient community, etc.); study intake communications 3212 (e.g., communications from or to the patient relating to offered clinical studies); screening communications 3214 (e.g., communications from or to the patient relating to pre-screening and/or screening for clinical studies); medical event data 3216; and/or medical records 3218 and/or portions thereof. Referencing FIG. 33, non-limiting examples of historical performance data 3204 are schematically depicted, including one or more aspects such as: activity 3302 of, or corresponding to, the patient on at least one of: a patient engagement platform, the patient portal system, or a patient centered social platform; activity 3302 of, or corresponding to, the patient on a patient data system; medical procedure execution activity 3304; medical treatment compliance activity 3306; clinical study execution activity 3310; and/or clinical study participation activity 3308. Example longitudinal data 3116 includes patient profile data 3206 from at least one of a patient engagement platform, the patient portal system, and/or a patient centered social platform. Example longitudinal data 3116 includes patient preference information 3210 from at least one of: a patient engagement platform, the patient portal system, and/or a patient centered social platform.

In some aspects, the techniques described herein relate to a system, wherein the patient database module further includes an activity component configured to perform a longitudinal data action on the longitudinal data of CV1 and the relevant descriptions]

Figure 16:
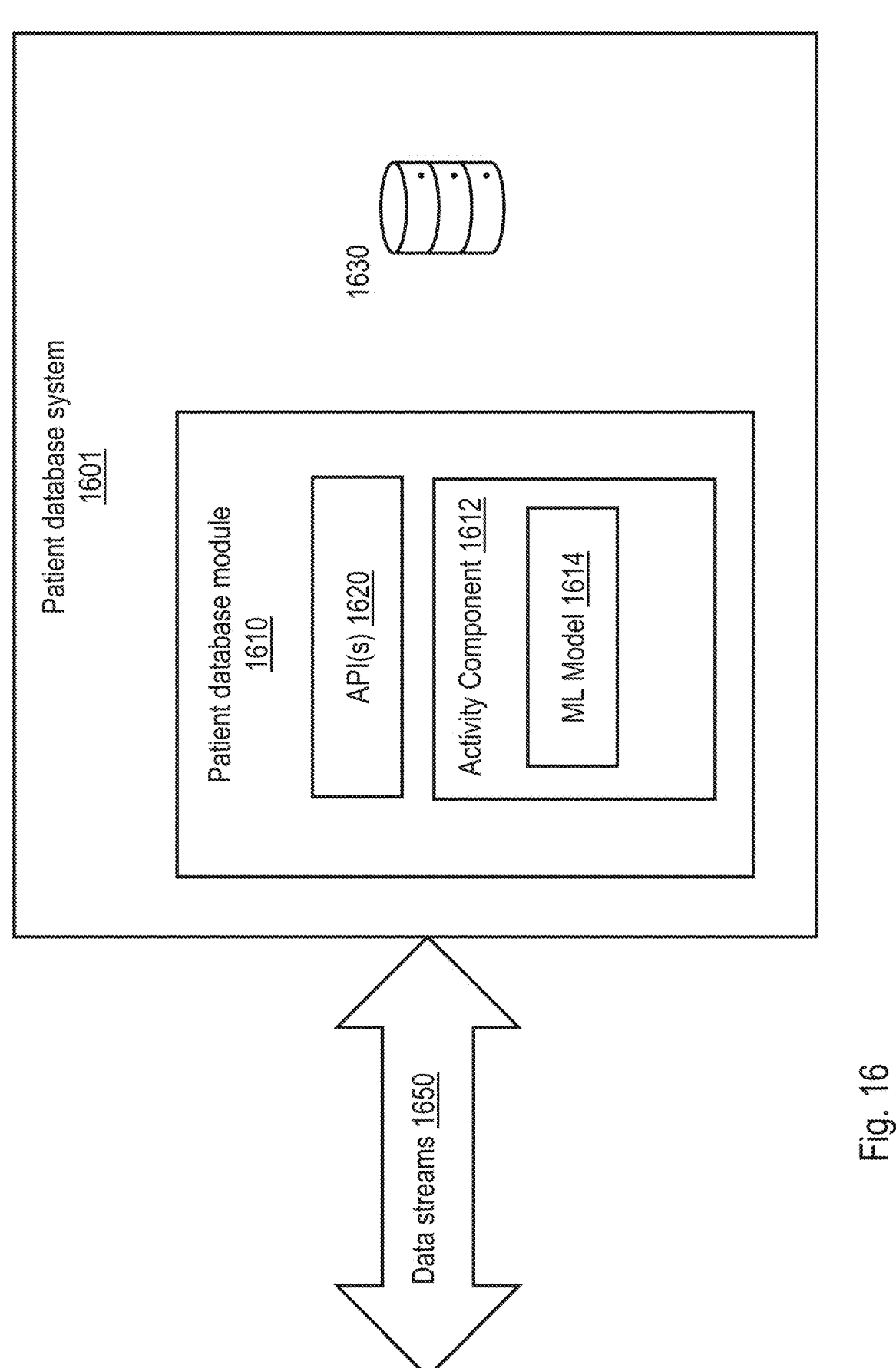
FIG. 16 illustrates a patient database system and data streams according to example embodiments.

With reference to FIG. 16, an example patient database system 1601 according to example embodiments may include modules such as a patient database module 1610 and a patient database 1630. In some examples, the patient database system 1601 itself may be one or more modular components. In some examples, the patient database 1630 may include any type and number of storage medium(s) 1632 for the storage of data as described herein, which in example embodiments may be at least one non-transitory computer-readable storage medium, and may, for example, at least one of a CD-ROM, DVD, memory, hard disk, flash drive, RAM, ROM, cache and the like.

In some embodiments, the storage medium(s) 1632 may include a plurality of different storage mediums. For example, the different storage mediums may include storage mediums having different writing and/or reading speeds, in geographically distinct locations (e.g., to comply with government regulations or to be proximate to other modular components of the systems as described herein), different levels and/or manners of protection (e.g., relating to a physical location, encryption technique(s), or otherwise), and/or other attributes that may be apparent to one skilled in the art upon reading this disclosure. In some examples, the different storage mediums may include a cloud database. Thus, for example, the patient database 1630 may include one or more cloud databases as the one or more storage medium(s) 1632.

In example embodiments, the patient database 1630 may be configured to store longitudinal data 1700 for a plurality of patients in the storage medium(s) 1632, such as the at least one non-transitory computer-readable storage medium. For example, the patient database 1630 may be configured to store longitudinal data 1700 of a new patient in the storage medium(s) 1632.

In example embodiments, the new patient may be an exemplary one of the plurality of patients, and it should be understood that while example embodiments may be described with reference to the new patient, the description may apply to any patient.

In some embodiments, the longitudinal data 1700 of the plurality of patients may include patient information of some or all of the plurality of patients. For example, for any one of the plurality of patients, the longitudinal data 1700 may include patient information such as at least one of a patient medical record, a patient communication, patient laboratory data, a patient data assessment, a patient medical condition, a patient medication, a patient biomarker, patient demographic data, patient biometric data, select information from patent medical records (e.g., medications, labs, factual data assessments, etc.), patient preferences, patient provider relationships, patient behavioral data, geographic information, occupational information, and/or patient related data from external data sources, such as social media, proprietary databases, public records, or the like. However, embodiments are not limited thereto, and other patient information may be included as may be understood based upon this disclosure.

In some embodiments, the patient database system 1601 (e.g., the patient database module 1610) may be configured to build, maintain, update, provide backup support, and manage the lifecycle (e.g., deletion dates, redundancy management, prioritization of data, and/or location of data such as the longitudinal data 1700—for example, between fast retrieval and slow retrieval locations) of data in the patient database 1630.

In FIG. 16, the example patient database 1630 is depicted as a single data store on a single device, but the patient database 1630 may be distributed, placed on one or more cloud servers, and/or be segregated (e.g., based on geography, privacy protection level, age of data, clinical study status of patients, etc.) either physically or logically (e.g., with separate portions of the data (e.g., the longitudinal data) in the patient database 1630 available to different users based on permissions level, role, identity of the accessing user, etc.). In certain embodiments, the patient database 1630 is a unified patient database 1630, for example a patient database 1630 accessible in the entirety by a patient engagement platform as may be described herein, even though individual components, users, or other entities may have access to only relevant portions of the patient database 1630, as may be provided by the patent database module 1610 or other component of patient database system 1601.

For example, in certain embodiments, a patient engagement platform as an aggregated collection of its modular components (see, e.g., FIG. 20 and corresponding description) may be capable of accessing the entire patient database 1630, though one or more distinct components of the patient engagement platform may only be able to access portions of the patient database 1630 that are relevant to that component's function(s). In this way, the patent database system 1601 may compartmentalize the patient data (e.g., the longitudinal data 1700) into buckets that are effectively provided to components of the platform on a "need to know" basis.

For example, in certain embodiments, portions of the patient database 1630 are accessible only to components "internal" to the platform, for example meta-data related to patients, clinicians, or other users, and/or determined values from the data that are utilized to facilitate certain aspects described herein (e.g., patient classification information, patient-study compatibility determinations and/or analysis, patient behavioral information, etc.). In certain embodiments, aspects herein include the platform directly, and may further include access to the unified patient database 1630. Even where an embodiment does not include a component having access to the unified patient database 1630, many such embodiments are enhanced by a platform capable to access the unified patient database 1630. A number of operations, systems, and platform examples set forth throughout the present disclosure are enhanced by the patient database 1630 as set forth herein, for example: operations to customize a patient interface; operations to assist the patient in completing a study (e.g., as part of a journey); operations to determine patient-study compatibility and/or suitability; operations to adjust permissions to data and/or patient information; and/or operations to support longitudinal studies, including changing the longitudinal study plan after the clinical study is commenced or completed.

In example embodiments, the patient database 1630 may store longitudinal data 1700 of a patient such as the new patient such that it is searchable and/or indexable for access by the patient database module 1610 without regard to a specific clinical trial and/or entity (although as described herein, the patient database module 1610 may control access to various distinct components). Additionally, as described herein, elements of the longitudinal data 1700 of the plurality of patients (including the new patient) may be updated (e.g., refreshed) as the patient database 1630 receives new data for those elements, such as from one or more of a plurality of data streams 1650. In some embodiments, the patient database module 1610 may verify the veracity and/or timing of the new data relative to the stored data it would replace before updating the storage with the new data.

In some embodiments, a patient database system 1601 may include providing (e.g., via patient database module 1610) data to or from the patient database 1630 to support longitudinal patient data 1700 for a clinical study(ies). For example, patient data, e.g. as stored as longitudinal data 1700, may be tagged based on completion of a particular clinical study (which may also be referred to as a clinical trial or a clinical protocol herein), facilitating access to the relevant data over a period of years (or other relevant period) after the study is completed. In certain embodiments, the study group (e.g., the clinician and/or related entity that performed the study) may access the relevant data through a clinician interface with a patient engagement platform as described herein. Depending upon the data needed, the clinician may automatically obtain the relevant data, for example patient outcomes, long-term progress, etc., which may be anonymized, aggregated, grouped according to selected criteria (e.g., by dosage, placebo, control group, etc.), or otherwise processed according to the requirements of the study and/or applicable privacy considerations by the patient database system 1601 such as the patient database module 1610. In certain embodiments, the clinician may implement a request for the data through the patient database system 1601, for example by selecting a "request data" interface element, whereupon the patient database system 1601 communicates a request to relevant patient(s) for permissions to provide the data to the clinician. In certain embodiments, the permissions may be provided earlier, for example when the patient enrolls in the study, but the patient database system 1601 can be configured in any manner, including changing the permissions scheme (e.g., to conform to an updated privacy law). The patient database module 1610 and patient database 1630 may allow for the clinician and/or study group to readily access detailed longitudinal data 1700, enhancing clinical study implementation, making it easy to capture detailed data about the patients—such as medications, long-term health outcomes, further treatments, etc., making it easy to contact patients even after an extended period (for example facilitating follow-up research beyond what was originally planned for the study), giving patients confidence that a requesting party for longitudinal data 1700 is a legitimate requestor, and helping patients immediately understand which element (e.g., study, treatment, procedure, etc.) is related to any requested data. Accordingly, the patient database system 1601 supports longitudinal data 1700 for deeper analysis, meta-analysis, long term outcomes for a study, improved security of data, reduced time for requesting and receiving data, and/or reduced time for finding and following up with patients. In certain embodiments, a study group may wish to contact patients for any reason, for example to suggest a further study, request certain tests or procedures, and/or to provide notifications related to the earlier study, and the patient database system 1601 provides a mechanism for this to be completed, for example, via the ability to quickly obtain patients that may be a match for the further study and/or who participated in the earlier study. In certain embodiments, it may be desirable to keep the patient anonymous with regard to the study group, and the patient database system 1601 may provide a full functioning implementation (e.g., including support for longitudinal data 1700, follow-up tests or procedures, and/or notifications to the patient) even where patient anonymity is preserved, such as by anonymizing all personally identifiable information before providing data to the study group.

In example embodiments, the patient database module 1610 may be configured to initially acquire at least one patient data value for the new patient of the plurality of patients and store the at least one patient data value as part of the longitudinal data 1700 of the new patient. For example, the at least one patient data value that is initially acquired may be from a patient engagement platform that interacts with the new patient, an electronic medical record of a healthcare provider, or other source, such from another one of the plurality of data streams 1650. In some examples, the at least one patient data value may include at least one of a name or a contact information of the new patient and may be provided from a data stream 1650. For example, the at least one patient data value may be received from social media, an electronic medical record, or a healthcare provider, and may be included as part of a plurality of patient data values for different patients that have been provided in accordance with the consent of the different patients. For example, the patient database module 1610 may be provided with the names and/or contact information of the different patients, including the new patient, having a first condition, a first biomarker, a first lab result, an expressed interest in a certain type of clinical trial, a phenotype, a geographic location, etc. In some examples, the at least one patient data value (such as a first condition) may be used as part of a recruitment and/or prescreening process of patients for potential participation in a clinical trial. In some embodiments, as described in further detail herein, the patient database system 1601 may automatically match (e.g., as requested by a clinical trial) any new patient data stored to the patient database 1630 to the needs of one or more clinical trials. In some examples, this automatic matching may be per request of the one or more clinical trials as part of a recruiting and/or prescreening process undertaken by the patient engagement platform for the one or more clinical trials.

In some embodiments, the patient database module 1610 may be further configured to establish a new patient record of a plurality of patient records 1640 corresponding to the plurality of patients upon receipt of the at least one patient data value for the new patient. While establishing the new patient record may include storing the new patient record having the at least one patient data value as part of the longitudinal data 1700 of the new patient, the new patient record (and indeed, any or all of the plurality of patient records 1640(1) to 1640(n)) may be stored such that the respective information contained in each patient record 1640(1) to 1640(n) (where 'n' is the total number of patients for which there are records) (including the initial and further patient data values described further herein) is organized per patient—e.g., it is attributable to that patient and indexed in the patient database 1630 accordingly.

Thus, for example, while the patient data values may be provided as longitudinal data 1700 in accordance with the meaning described herein, some or all of the patient data values may also be distinguished by the patient database module 1610 as pertaining to the patient record 1640 of that patient. In an example, by organizing the longitudinal data 1700 into individual patient records 1640, a complete patient record of the patient may be quickly provided from the patient database 1630 to a healthcare provider or other requester by the patient database module 1610 per the healthcare provider's request and per the patient's prior or concurrent real-time consent. Thus, the healthcare provider or other requester may quickly obtain a complete picture of the patient's record that is not a fragmented or partial view, as it may be if it were derived solely from any one source such as a single electronic medical record.

Additionally, in example embodiments, the patient database module 1610 may acquire a plurality of further patient data values for the new patient through the plurality of data streams 1650, and these plurality of further patient data values may be included as part of the longitudinal data 1700 of the new patient and, as described above, part of the patient's record 1640. Thus, the longitudinal data 1700 of the new patient may include a plurality of patient data values including, for example, the various patient data described herein, which may represent different types 1701 of longitudinal patient data (e.g., age, zip code, condition, medication(s), etc.). In some embodiments, the patient database module may be configured to automatically update the longitudinal data 1700 of the new patient upon receipt of a new patient data value for the first patient.

In some embodiments, the initial and/or further patient data values may be standardized into standardized data 1710 before storing such data values as longitudinal data 1700 of the patient. For example, with reference to FIG. 17, each of the patient records 1640(1) to 1640(n) may include respective standardized data 1710(1) to 1710(n), and the respective longitudinal patient data 1700(1) to 1700(n) may be included in that standardized data. In some examples, the data may be standardized according to data type.

As one example, received patient data values (as may be received by data streams 1650) may contain non-standard information such as handwritten notes by a clinician, which may be converted to standard text by optical character recognition and/or otherwise formatted so that the data values are in accordance with the formatting of other longitudinal data of the same type. However, the non-standardized data 1720(1) to 1720(n) may still be stored as part of the patients' records in the patient database 1630, such as for future reference by the patient engagement platform or to be provided as part of a patient's complete record to, e.g., a requester such as a healthcare provider or clinical trial.

In some embodiments, the patient database module 1610 may acquire at least one of the plurality of further patient data values via the one or more data streams 1650. For example, in some examples, at least some of the further patient data values for the new patient acquired through the plurality of data streams 1650 may be from an encounter of the new patient with a healthcare provider. For example, the healthcare provider may enter patient data into the healthcare provider's electronic medical record of the patient, which may be automatically forwarded or otherwise received by the patient database system 1601 and stored therein. Such data may be communicated electrically between, e.g., the patient database system 1601 and an external database storing the electronic health record, and such communication may be in accordance with any applicable government and/or industry standards and patient consent.

In some embodiments, the patient database module 1610 may acquire at least one of the plurality of further patient data values for the new patient from a patient engagement platform via, for example, the one or more data streams 1650. In an example, the patient engagement platform may include a social media platform.

In some embodiments, the patient database module 1610 may acquire at least one of the further patient data values from a laboratory result. For example, the laboratory result may be received by one or more application programming interfaces (APIs) 1620 of the patient database module 1610, and may be communicated electronically from the laboratory to the one or more APIs 1620 over a network. In an example, the at least one of the further patient data values may include a biomarker of the patient or an imaging result of the patient.

Indeed, in example embodiments, the one or more APIs 1620 of the patient database module 1610 are not limited to communications with a laboratory but may be used for any of the electronic communications described with reference to the patient database module 1610, patient database 1630 and/or the patient database system 1601 that may be external to the patient database system 1601, such as from one or more of the data streams 1650, which may interface with the one or more APIs 1620.

In some embodiments, the patient database module 1610 may be configured to receive a query from an external entity, such as a healthcare provider or clinical trial entity. The query may include a criteria, such as a request for patients with a certain condition, having a certain demographic, a certain phenotype, a certain geographic location, that have expressed their interest in a clinical trial, etc. The patient database module 1610 may respond by providing a selection of the longitudinal data 1700 of the plurality of patients from the patient database 1630 according to the criteria. For example, the patient database module 1610 may provide the selection to the requesting external entity. In some embodiments, the patient database module 1610 may anonymize the selection of longitudinal data before responding to the request by transmitting it to the external entity. For example, the patient database module 1610 may remove any and/or all personally identifiable information from the selection of longitudinal data. By providing the selection of longitudinal data 1700 to the requesting entity according to the criteria, the entity may evaluate a suitability of one or more of the plurality of patients for participating in a clinical trial and instruct that further action be taken by the platform, such as initiating a marketing or prescreening touch point by a journey management component 2014 as discussed elsewhere herein.

In some embodiments, such as when the patient database module 1610 has received a query from an external entity, such as a healthcare provider, for longitudinal data 1700 of one or more patients, only a subset of the longitudinal data may be provided to the external entity in accordance with that entity's access to the data—e.g., in accordance with patient consent and any applicable government regulations. Thus, only a subset of the longitudinal data may be accessible to an external entity such as a healthcare provider.

In example embodiments, the patient database 1630 may retain the longitudinal data 1700 of the new patient for a time duration that extends through a plurality of medical processes, where the medical processes have different time periods. For example, the medical processes may have time periods that overlap, or their time periods may encompass entirely different time ranges. Medical processes may include clinical trials/protocols/studies as described herein. For example, the plurality of medical processes may include a first clinical trial and a second clinical trial, and the first and second clinical trials may have the different time periods. In some examples, the different time periods may correspond to a length of a clinical trial for a particular patient, such as a patient's journey from start to completion of the clinical trial. Thus, for example, the patient database 1630 may retain the longitudinal data 1700 of the new patient before, during, and/or after their participation in one or more clinical trials.

In example embodiments, the patient database module 1610 may be configured to compare the longitudinal data 1700 of a patient—for example, the new patient—to a requirement of at least one of the first clinical trial or the second clinical trial. For example, the longitudinal data of the patient may indicate that the new patient may be a match for participation in the first clinical trial or the second clinical trial, such as by comparison to one or more requirements of the clinical trials. Likewise, the patient database module 1610 may be configured to match all or a subset of the plurality of patients to a plurality of clinical trials including the first clinical trial and the second clinical trial using the longitudinal data 1700 of the plurality of patients. Various patient data used for this comparison is described elsewhere herein, but may include patient data such as a certain condition, a geographic location, demographic information, phenotype, medications, etc.

In some examples, the longitudinal data 1700 of the new patient may include the geographic information of the new patient, such as a geographic location and/or a geographic radius in which the new patient is willing to travel for a clinical trial, and the patient database module 1610 may be further configured to match the new patient to the plurality of clinical trials (e.g., including at least one of the first or second clinical trial) using the longitudinal data 1700 including the geographical information. For example, the matching may include matching the geographic location and/or radius of the first patient to respective clinical sites (e.g., locations) of the first clinical trial and/or second clinical trial.

In some examples, the first or second clinical trial may require participants to have a certain condition, correspond to a certain demographic, reside in a certain geographic location, etc. In some embodiments, the requirements of a clinical trial may be stored locally to the patient database system 1601 for comparison with the longitudinal data of the plurality of patients, such as in patient database 1630. This may provide an advantage in that patient data (which may be required to be handled in accordance with government regulations and/or industry standards) is kept local to the system 1601 while the patient database module 1610 matches patients to clinical trials. By handling the patient data locally, the system 1601 may remain in compliance with any applicable government regulations and/or industry standards. Additionally, by storing the requirements of the clinical trial(s) locally, the patient database system 1601 may provide a technical advantage of performing matches more quickly (e.g., in real time) than if clinical trial requirements had to be obtained externally over a network, or if patient data had to be provided externally over a network for comparison by the clinical trial entity itself.

Meanwhile, the patient database module 1610 may indicate to the patient and/or clinical trial entity that the patient is a match for the clinical trial. For example, the patient database module 1610 may provide the patient's name and contact info to the clinical trial upon the patient's consent, as well as any other patient data that the clinical trial entity may use to determine whether the patient is a fit for the clinical trial. However, example embodiments herein may provide a platform for connecting the patient to clinical trial matches without a need for direct communications between the patient and clinical trial entity at the prescreening stage, thereby enhancing patient trust in the clinical trial process via a platform with which they are already familiar and promoting their willingness to engage in the clinical trial.

In some embodiments, the patient database module 1610 may be further configured to acquire, during a journey of the new patient through participation in at least one of the first clinical trial or the second clinical trial, additional patient data values for the new patient. For example, some of these additional patient data values may be received during various touch points with the patient along their clinical trial journey, and may be from one or more of the data streams 1650. The patient database module 1610 may include the additional patient data values in the plurality of patient data values of the longitudinal data of the new patient.

Indeed, in some embodiments, the new participant may participate in the first clinical trial, and the longitudinal data of the new patient may include data collected after the first clinical trial such that the patient database system 1601 may provide a long-term health outcome of the first clinical trial. For example, the data collected after the first clinical trial may include answers to follow-up questions, results of follow-up clinical visits, etc., and other data collected from post-trial touch points.

In some examples, the longitudinal data 1700 of the new patient may include data collected during a prescreening of the new patient for the first clinical trial, such as from a prescreening touch point or other pre-trial touch points. For example, the initially acquired at least one patient data value may be collected during the prescreening, and the longitudinal data 1700 of the new patient that is compared to a requirement of the first and/or second clinical trial may include this initially acquired at least one patient data value collected during the prescreening.

Additionally, the longitudinal data 1700 may include data collected during a participation of the new patient in the first clinical trial, such as via the one or more data streams 1650, and/or data collected after the new patient completes the first clinical trial.

In example embodiments, the patient database module 1610 may use data from the plurality of data streams 1650 to replenish the patient database 1630 with at least one patient data value of an additional patient for the plurality of patients. The at least one patient data value of the additional patient may be stored as longitudinal data 1700 of the additional patient. For example, from the plurality of data streams 1650, the patient database module may acquire a name and contact information (e.g., email, phone number, etc.) of a person (an additional patient) who may be considered for participation in one or more clinical trials. Other data about the additional patient may also be received, such as medical and/or demographic information. Thus, the patient database system 1601 may continually replenish the patient database 1630 with additional data values of an additional patient, or, indeed, a plurality of additional patients, and such additional patient data values may be stored as longitudinal data 1700 of the respective additional patients. The patient database system 1601 may make use of the longitudinal data 1700 of the additional patients akin to its use of the longitudinal data 1700 of the new patient (e.g., for corresponding to possible clinical trials).

In some embodiments, at least some of the plurality of patient data values of the longitudinal data (such as for the first patient) may comply with one or more applicable government regulations and/or industry standards. For example, the first patient and/or patient database 1630 may reside in a particular state of the United States, and the storage of such longitudinal data pertaining thereto may comply with any applicable local, state, and federal government regulations.

In example embodiments, the patient database module 1610 may include an activity component 1612 configured to perform a longitudinal data action 1800 on the longitudinal data 1700 of the new patient.

With reference to FIG. 18, in some embodiments, the longitudinal data action 1800 may include indexing 1802 the longitudinal data 1700 of the new patient to be searchable without regard to a clinical trial. For example, the longitudinal data 1700 of the new patient may be indexed along with longitudinal data of others of the plurality of patients according to their longitudinal patient data types 1701 (e.g., corresponding to the various types of patient data discussed herein).

In some embodiments, the longitudinal data action 1800 may include setting 1804 some (but not necessarily all) of the longitudinal data 1700 for access by a stakeholder. For example, the stakeholder may include a healthcare provider (e.g., a physician), clinical researchers or scientists, pharmaceutical or biotechnical companies, healthcare institutions and organizations, or community and patient advocacy groups. In an example, the patient database module 1610 may determine whether each piece of longitudinal data 1700 should be accessible to a stakeholder based on its longitudinal patient data type 1701 and/or patient record 1640 and/or pertinent information about the patient, such as their geographic location.

In some embodiments, the longitudinal data action 1800 may include encrypting 1806 some (but not necessarily all) of the longitudinal data in accordance with at least one applicable government regulation or industry standard.

In some embodiments, the longitudinal data action 1800 may include acquiring 1808 a consent of the new patient to store at least some of the longitudinal data 1700 of the new patient. For example, the consent may be acquired after the at least some of the longitudinal data 1700 is already stored in order to comply with a new government regulation.

In some embodiments, the longitudinal data action 1800 may include storing 1810 patient data values that are or may be relevant to matching a patient to a plurality of clinical trials in a higher-speed memory of, e.g., the patient database 1630, than patient data values that are not relevant. For example, the patient data values that are relevant may include a geographic location of the patient and/or a geographic radius in which the patient is willing to travel to participate in a clinical trial. The patient data values that are relevant may also include conditions of interest to one or more clinical trials for which the patient database system 1601 is aware and/or serving, and/or demographic information that is frequently requested as part of the prescreening process for clinical trials.

In some embodiments, the longitudinal data action 1800 may include tracking 1812, from the longitudinal data 1700 of at least some of the plurality of patients, which types of patient data values (e.g., which longitudinal data types 1701, see FIG. 17) are more likely to be used for matching patients to clinical trials. This tracking might be based on prior clinical trials. The longitudinal data action 1800 may further include storing the types of patient data values more likely to be used (e.g., accessed, retrieved, updated, etc.) in a higher-speed memory. For example, patient data values of more frequently used longitudinal data types 1701 are stored in a higher-speed memory, while other patient data values are stored in a lower-speed memory.

Figure 17:
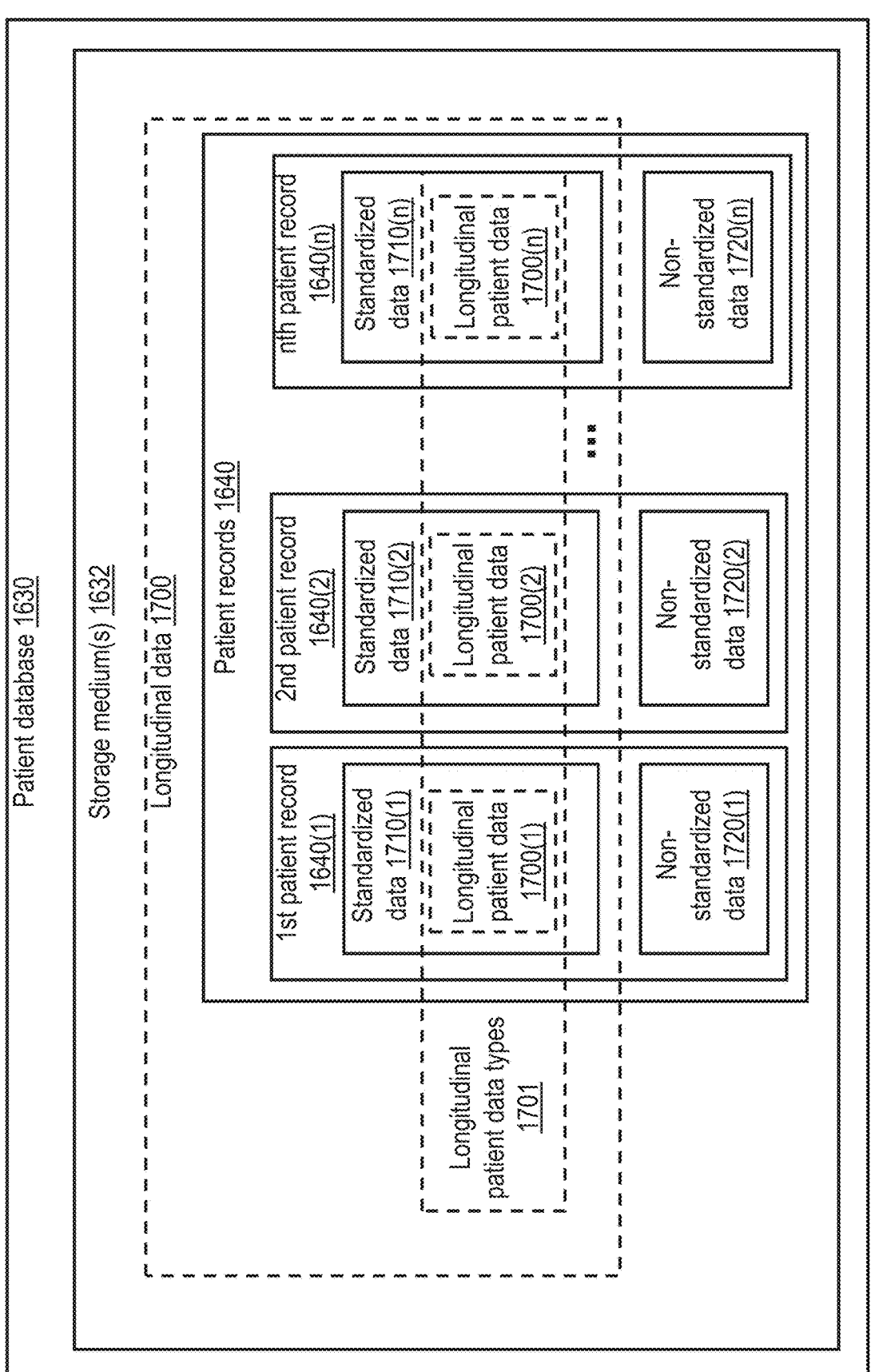
FIG. 17 illustrates a patient database and stored content therein according to example embodiments.

In some embodiment, as illustrated in FIG. 17, the patient database module may store the plurality of patient data values of the longitudinal data 1700 of the new patient in a standardized format as standardized data 1710 in the patient database 1630, while non-standardized data 1720 may not be stored as part of the longitudinal data 1700 but may nevertheless be stored as part of a patient's record 1640 in the patient database 1630. At least one of the plurality of patient data values of the longitudinal data 1700 of the new patient may include medical data.

Meanwhile, with reference to FIG. 16, the plurality of data streams 1650 may communicate with the patient database module 1610 over at least one network such as a computer network (e.g., the Internet). At least some of the plurality of data streams 1650 may interface with the patient database system 1601 through at least one API 1620, which may be included in the patient database module 1610 and/or in another component of the patient database system 1601. With reference to FIG. 18, the longitudinal data action 1800 performed by the activity component 1612 may include providing 1814 remote access to healthcare providers (or other stakeholders) over the at least one computer network so that, for example, any one of the healthcare providers may update the medical data to which the healthcare providers have access in real time through a graphical user interface. For example, a healthcare provider may be able to update a patient's medical data (e.g., in the form of patient data values) pertaining to data values that originated from that healthcare provider, or for which the healthcare provider is otherwise authorized to update.

In some embodiments, the patient database system 1601 may include at least one API 1620 that provides a bidirectional interface for access, and the providing the remote access to the healthcare providers may be via the at least one API 1620. Additionally and/or alternatively, in some embodiments, the remote access may be provided to the healthcare providers via a clinical research system.

One or more of the healthcare providers may provide the updated medical data in a non-standardized format dependent on the hardware or software platform used by the one of the healthcare providers. For example, the healthcare provider may enter the medical data into the graphical user interface in real time, either through typing, handwriting, pictures, etc. As discussed herein, the patient database module 1610 may convert these various non-standardized forms of input into a standardized format (e.g., using optical character recognition), which may be consistent (e.g., standardized) with the manner of storing other patient data values of the same type in the longitudinal data 1700. Thus, the patient database module 1610 may then store the standardized updated medical data in the longitudinal data 1700 of the new patient in the patient database 1630.

Furthermore, the patient database module 1610 may (e.g., as a longitudinal data action 1800) automatically generate a message 1816 containing the updated medical data whenever updated medical data has been stored, and may transmit the message to any number of entities over the network (e.g., the computer network such as the Internet) in real time so that the entities have immediate notification of the updated medical data. For example, the patient database module 1610 may transmit the message to the new patient in real time.

Additionally, the patient database module 1610 may be configured to automatically compare 1820 the longitudinal data of the new patient to a requirement of at least one of the first clinical trial or the second clinical trial in real time upon (e.g., whenever) the activity component stores the standardized updated medical data as part of the longitudinal data 1700 of the new patient. For example, as discussed herein, the patient database module 1610 may have already acquired or otherwise be aware of a requirement of the first or second clinical trial (e.g., a required condition of the patient, a required demographic of the patient, etc.) and stored such a requirement in the patient database 1630. Thus, the patient database module 1610 may be triggered to automatically compare 1820 new longitudinal data 1700 (e.g., when the activity component stores the standardized updated medical data) to the stored requirements of the clinical trials, such as the first or second clinical trial.

Furthermore, based on the automatic comparison 1820 of the longitudinal data of the new patient to the requirement, the patient database module 1610 such as activity component 1612 may be configured to determine 1822 a match of the new patient to at least one of the first clinical trial or the second clinical trial. Any time the patient database module 1610 determines a match of the new patient to a clinical trial such as the first or second clinical trials, the patient database module 1610 may automatically generate another message 1824 containing information about the match, and may transmit this message to the new patient over the network (e.g., a computer network such as the Internet) in real time. Thus, the new patient may have real time access to information regarding their match to the clinical trial, such as the first clinical trial or the second clinical trial. In one example, the patient database module 1610 may automatically generate a message containing the match (e.g., information about the match) whenever the match is determined and transmit this message to the new patient in real time so the patient has immediate notification of the match. The message may furthermore contain a link or other manner of providing more information about the match and the clinical trial.

In some embodiments, at least one of the plurality of further patient data values included in the longitudinal data of the new patient may be received from a laboratory via an application programming interface (API) 1620 of the patient database module 1610, and the at least one of the plurality of further patient data values may include a biomarker. However, embodiments are not limited thereto, and in some embodiments, at least one of the plurality of further patient data values may be received (e.g., via at least one of the one or more APIs 1620) from a data stream 1650, such as a clinical research system, an electronic medical record, a wearable or other device, etc. The longitudinal data action 1800 may include using a machine learning (ML) model 1614 to recognize 1826 a pattern in the at least one of the plurality of further patient data values, such as in the biomarker (or, as another example, in an imaging result or other patient measurement). Comparing the longitudinal data 1700 of the new patient to a requirement of at least one of the first clinical trial or the second clinical trial may include comparing the recognized pattern (e.g., in the biomarker) to match the patient to at least one of the first clinical trial or the second clinical trial.

The patient database module 1610 may train the ML model 1614 on a training data set (e.g., including prior biomarkers and patterns recognized therein), and the activity component 1612 may provide the at least one of the plurality of further patient data values (e.g., including the biomarker) as an input to the ML model 1614. In some examples, the ML model 1614 may include one or more neural networks that are trained on the training data set.

In some embodiments, the patient database system 1601 may host all communication and patient medical information in the patient database 1630. Additionally, the patient database system 1601, such as the patient database module 1610, may automatically communicate projected and actual visits to other modular components of the platform, such as a clinical trial management system, and may automatically communicate with components that embody, e.g. a call center.

With reference to FIG. 19, a method 1900 according to example embodiments may include storing 1904 longitudinal data for a plurality of patients in a non-transitory computer-readable storage medium of a patient database. The patient database may include the non-transitory computer-readable storage medium and may be included with a patient database module as part of a patient database system.

The method 1900 according to example embodiments may further include initially acquiring 1908 at least one patient data value for a new patient of the plurality of patients, storing 1912 the at least one patient data value as part of the longitudinal data of the new patient, further acquiring 1916 a plurality of further patient data values for the new patient through a plurality of data streams, and including 1920 the plurality of further patient data values for the new patient as part of the longitudinal data of the new patient, such that the longitudinal data of the new patient includes a plurality of patient data values.

The method 1900 according to example embodiments may further include retaining 1924 the longitudinal data of the new patient for a time duration that extends through a plurality of medical processes, where the medical processes have different time periods, comparing 1928 the longitudinal data of the new patient to a requirement of at least one of a first clinical trial or a second clinical trial, and replenishing 1932, from the plurality of data streams, at least one patient data value of an additional patient for the plurality of patients. The at least one patient data value of the additional patient may be stored as longitudinal data of the additional patient. Further, the method 1900 according to example embodiments may include performing 1936 a longitudinal data action on the longitudinal data of the new patient. The longitudinal data action may be performed by an activity component of the patient database module.

In the example method 1900 according to some embodiments, the plurality of medical processes include the first clinical trial and the second clinical trial, which may have the different periods. Furthermore, at least some of the plurality of patient data values of the longitudinal data of the first patient may comply with an industry standard.

In some embodiments, the method 1900 may further include establishing a new patient record of a plurality of patient records corresponding to the plurality of patients upon receipt of the at least one patient data value for the new patient, which may include storing the new patient record having the at least one patient data value as part of the longitudinal data of the new patient.

In some embodiments, the method 1900 may further include the longitudinal data action including indexing the longitudinal data of the new patient to be searchable without regard to a clinical trial.

In some embodiments, the method 1900 may further include the longitudinal data action including setting some of the longitudinal data for access by a stakeholder including at least one of a healthcare provider, a clinical researcher, a clinical scientist, a pharmaceutical company, a biotechnical company, a healthcare institution or other healthcare organization, a community group, or a patient advocacy group.

In some embodiments, the method 1900 may further include the longitudinal data action including encrypting some of the longitudinal data in accordance with at least one government regulation.

In some embodiments, the method 1900 may further include the longitudinal data action including acquiring a consent of the new patient to store at least some of the longitudinal data of the new patient.

In some embodiments, the method 1900 may further include the longitudinal data action including storing patient data values that are relevant to matching a patient to a plurality of clinical trials in a higher-speed memory, where the patient data values that are relevant may include a geographic location of the patient.

In some embodiments, the method 1900 may further include the longitudinal data action including tracking, from the longitudinal data of at least some of the plurality of patients, which types of patient data values are more likely to be used for matching patients to clinical trials, and storing the types of patient data values more likely to be used in a higher-speed memory.

In some embodiments, the method 1900 may further include the patient database module storing the plurality of patient data values of the longitudinal data of the new patient in a standardized format in the patient database, where at least one of the plurality of patient data values of the longitudinal data of the new patient includes medical data, the plurality of data streams communicating with the patient database module over at least one computer network, and the longitudinal data action performed by the activity component including providing remote access to healthcare providers over the at least one computer network for any one of healthcare providers to update the medical data to which the healthcare providers have access in real time through a graphical user interface, where the one of the healthcare providers provides the updated medical data in a non-standardized format dependent on the hardware or software platform used by the one of the healthcare providers, converting the non-standardized updated medical data into the standardized format, storing the standardized updated medical data in the longitudinal data of the new patient in the patient database, automatically generating a message containing the updated medical data whenever updated medical data has been stored, and transmitting the message to the new patient over the computer network in real time such that the new patient has immediate notification of the updated medical data.

In some embodiments, the method 1900 may further include the patient database module automatically comparing the longitudinal data of the new patient to a requirement of at least one of the first clinical trial or the second clinical trial in real time upon the activity component storing the standardized updated medical data as part of the longitudinal data of the new patient.

In some embodiments, the method 1900 may further include the patient database module determining a match of the new patient to at least one of the first clinical trial or the second clinical trial based on the automatic comparison of the longitudinal data, automatically generating another message containing information regarding the match whenever the match of the new patient to at least one of the first clinical trial or the second clinical trial is determined, and transmitting the another message to the new patient over the computer network in real time such that the new patient has real time access to information regarding the match of the new patient to at least one of the first clinical trial or the second clinical trial.

In some embodiments, the method 1900 may further include the patient database module storing the plurality of patient data values of the longitudinal data of the new patient in a standardized format in the patient database, where at least one of the plurality of patient data values of the longitudinal data of the new patient includes medical data, the plurality of data streams communicating with the patient database module over at least one computer network, and the longitudinal data action including providing remote access to healthcare providers over the at least one computer network for any one of the healthcare providers to update the medical data to which the any one healthcare provider has access in real time through a graphical user interface, where the any one healthcare provider provides the updated medical data in a non-standardized format dependent on the hardware and/or software platform used by the any one healthcare provider, converting the non-standardized updated medical data into the standardized format, storing the standardized updated medical data in the longitudinal data of the new patient in the patient database, where the patient database module automatically compares the longitudinal data of the new patient to a requirement of at least one of the first clinical trial or the second clinical trial in real time whenever the activity component stores the standardized updated medical data in the longitudinal data of the new patient, and determines therefrom a match of the new patient to at least one of the first clinical trial or the second clinical trial, automatically generating a message containing the match whenever the match is determined, and transmitting the message to the new patient over the computer network in real time such that the new patient has immediate notification of the match.

In some embodiments, the method 1900 may further include the patient database system including at least one application programming interface (API) providing a bidirectional interface for user access, and the providing remote access to the healthcare providers is via the at least one API.

In some embodiments, the method 1900 may further include the remote access being provided to the healthcare providers via a clinical research system.

In some embodiments, the method 1900 may further include receiving at least one of the plurality of further patient data values included in the longitudinal data of the new patient from a laboratory via an application programming interface (API) of the patient database module, where the at least one of the plurality of further patient data values includes a biomarker, and the longitudinal data action includes using a machine learning model to recognize a pattern in the biomarker, and comparing the longitudinal data of the new patient to a requirement of at least one of the first clinical trial or the second clinical trial includes comparing the recognized pattern in the biomarker to match the patient to at least one of the first clinical trial or the second clinical trial.

In some embodiments, the method 1900 may further include training the machine learning model on a training data set including prior biomarkers and patterns recognized therein, and the activity component providing the biomarker as an input to the machine learning model.

In some embodiments, the method 1900 may further include the patient database module acquiring, during a journey of the new patient through participation in at least one of the first clinical trial or the second clinical trial, additional patient data values for the new patient and including the additional patient data values in the plurality of patient data values of the longitudinal data of the new patient.

In some embodiments, the method 1900 may further include the patient database module continually replenishing the patient database with additional patient data values of a plurality of additional patients, where the additional patient data values are stored as longitudinal data of the respective additional patients.

In some embodiments, the method 1900 may further include the patient database module matching the plurality of patients to a plurality of clinical trials including the first clinical trial and the second clinical trial using the longitudinal data of the plurality of patients.

In some embodiments, the method 1900 may further include the longitudinal data of the new patient including a geographic location, and the patient database module matching the new patient to a plurality of clinical trials including at least one of the first clinical trial or the second clinical trial using the longitudinal data of the first patient, where the matching the new patient includes matching the geographical location of the first patient to a clinical site of the at least one of the first clinical trial or the second clinical trial.

In some embodiments, the method 1900 may further include at least some of the further patient data values for the new patient being acquired through the plurality of data streams from an encounter of the new patient with a healthcare provider.

In some embodiments, the method 1900 may further include the further acquiring including acquiring at least one of the further patient data values via at least one application programming interface (API) from at least one of the data streams including at least one of: a patient engagement platform, a clinical research system, a laboratory result from a laboratory system, where the at least one of the further patient data values includes a biomarker of the patient, an imaging result from an imaging system, a healthcare system electronic medical record (EMR), or a wearable device.

In some embodiments, the method 1900 may further include the initial acquiring including receiving the at least one patient data value from a patient engagement platform interface that interacts with the new patient.

In some embodiments, the method 1900 may further include the initial acquiring including receiving the at least one patient data value from an electronic medical record of a healthcare provider.

In some embodiments, the method 1900 may further include the at least one patient data value being at least one of a name or a contact information of the new patient and being included in a plurality of patient data values for different patients from the healthcare provider.

In some embodiments, the method 1900 may further include the electronic medical record indicating that the new patient has a first condition.

In some embodiments, the method 1900 may further include the condition being type 2 diabetes.

In some embodiments, the method 1900 may further include the patient database including a cloud database.

In some embodiments, the method 1900 may further include the longitudinal data of the plurality of patients including at least one of a patient medical record, a patient communication, patient laboratory data, a patient data assessment, a patient medical condition, a patient medication, or a patient biomarker.

In some embodiments, the method 1900 may further include the patient database module, in response to a query, providing a selection of longitudinal data of the plurality of patients aggregated according to a criteria specified in the query.

In some embodiments, the method 1900 may further include the patient database module anonymizing the selection of longitudinal data.

In some embodiments, the method 1900 may further include the new patient participating in the first clinical trial, and the longitudinal data of the new patient including data collected after the first clinical trial such that the patent database module is configured to provide a long-term health outcome of the first clinical trial.

In some embodiments, the method 1900 may further include the longitudinal data of the new patient including data collected during a prescreening of the new patient for the first clinical trial, data collected during a participation of the new patient in the first clinical trial, and data collected after the new patient completes the first clinical trial.

In some embodiments, the method 1900 may further include the patient database module automatically update the longitudinal data of the new patient upon receipt of a new patient data value for the first patient.

In some embodiments, the method 1900 may further include only a subset of the longitudinal data being accessible to a healthcare provider.

In some embodiments, the method 1900 according to example embodiments may be performed by the patient database system 1601 including the patient database module 1610 and patient database 1630. In some embodiments, the method 1900 according to example embodiments may be stored as instructions on at least one non-transitory computer-readable storage medium that is executable by at least one processor.

Figure 20:
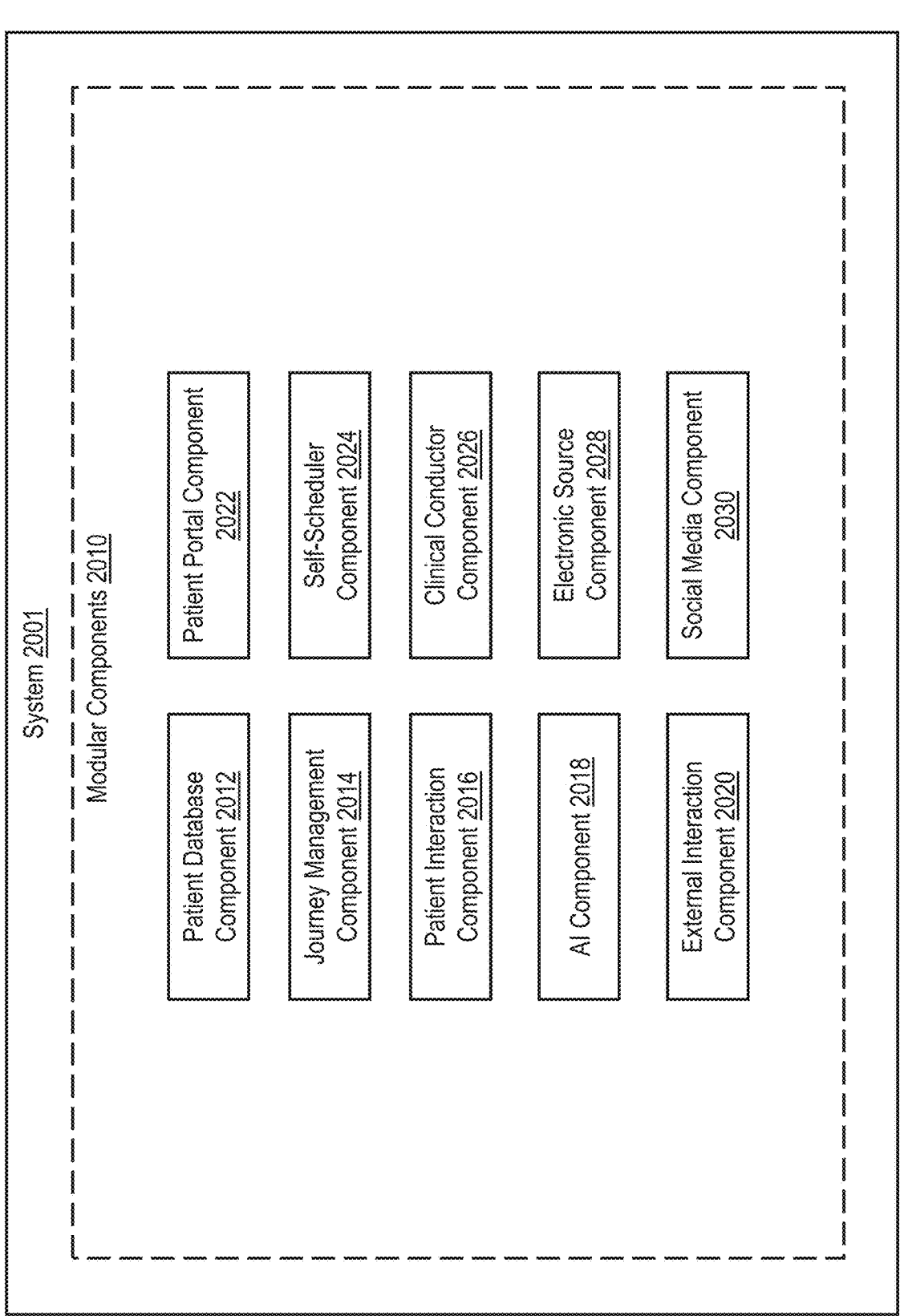
FIG. 20 illustrates a system to provide a patient engagement platform including a plurality of modular components according to example embodiments.

With reference to FIG. 20, a system 2001 to provide, e.g., a patient engagement platform for a plurality of clinical protocols (which may also be referred to herein as studies or trials) according to example embodiments may include a plurality of modular components 2010. Some or all of the plurality of modular components 2010 may be configured to interface with each other over a network such as the Internet. The implementation examples mention a few specific implementation details for clarity of the present description, such as a few specific modular components 2010 of the system 2001, but are not limiting to embodiments herein.

System 2001, which may be a modular system, may be provided with the modular components 2010 including, for example, components, circuits, controllers, or the like, that are provided to perform specific aspects of operations herein, allowing for an entity that implements a patient engagement platform and/or that accesses a patient engagement platform for certain features to readily configure the patient engagement platform to perform the desired functions. In certain embodiments, modular aspects of the patient engagement platform are implemented as low-code modules, proprietary modules, or a combination of these. An example patient engagement platform may be built utilizing Salesforce modular components, customized to implement operations as set forth herein. In certain embodiments, one or more components herein may be implemented using an CRM (customer relationship management) tool, including with customization, and/or with adding full coded additional features, and/or may be implemented in a fully coded environment. In certain embodiments, utilization of a tool may facilitate quickly building certain ordinary aspects, such as implementing user interfaces, data storage, data sharing, completion of forms, providing notifications, or the like. The benefits of the present disclosure are realized, without limitation, in the selection of the content and implementation for these aspects, the selected connections between entities, the selection of notification triggers, methods, and/or content, and the decision making aspects (e.g., including determining which decisions to make, and the criteria to make those decisions) set forth herein.

While the example modular components 2010 are depicted together in the system 2001, they may be additionally or alternatively be positioned, in whole or part, on a separate device from the patient engagement platform 101, on a web server, on a user device, and/or may be positioned on separate devices at separate times and/or depending upon which operations are being performed, and communicate with each other over a network such as the Internet.

In example embodiments, the plurality of modular components 2010 may include, for example, a patient database component 2012, a journey management component 2014, and/or a patient interaction component 2016. Also, at least some of the plurality of modular components 2010 may be configured to perform a modular component operation 2100.

In example embodiments, the patient database component 2012 may be configured to establish and update longitudinal data 1700 for a plurality of patients including a first patient. In some embodiments, the patient database component 2012 may correspond to all or portions of the patient database system 1601 as described herein. As described herein, the longitudinal data 1700 for the first patient may include a plurality of patient data values, and the patient database component 2012 may store the longitudinal data for a time duration longer than a first one of the plurality of clinical protocols. In some embodiments, the patient database component 2012 may match the first patient to the first one of the plurality of clinical protocols based on at least some of the longitudinal data of the first patient.

In some embodiments, with reference to FIG. 2, an example patient interaction component 120 may include sub-components for patient direct inputs 202, capturing patient preferences 204 (e.g., directly input preferences and/or inferred preferences), patient permissions 206 (e.g., including maintaining a record of permissions, appropriately refreshing permissions, and/or requesting permissions as needed on an ongoing basis, and/or further including providing a single place for patients to review, confirm, and/or change permissions as needed), and/or patient communications 208.

In example embodiments, the journey management component 2014 may be configured to curate a journey of the first patient through the first one of the plurality of clinical protocols. The journey may include a plurality of touch points between the system 2001 and the first patient.

Indeed, in some embodiments, the journey management component 2014 may perform any supporting operations to curate a patient journey with the patient engagement platform, as described herein. For example, the journey management component 2014 may include determining the timing of notifications, communications, etc., determining patient medical information and/or matching operations to clinical studies, determining patient behavioral information and/or matching operations to clinical studies, determining patient classification information (e.g., for matching to studies, configuring communications, configuring notifications, determining follow-up activities, etc.), and/or providing communication access between study groups and patients (e.g., before a study, during the study, after the study, and/or providing for anonymized communication avenues). An example operation to determine the patient behavioral information includes storing relevant patient information in the patient database component 2012, and applying behavioral science methods to that information to determine the behavioral information. Example relevant patient information for determining the behavioral information include any patient information as set forth throughout the present disclosure, and including at least aspects such as: patient lifestyle information (e.g., diet, exercise, sleep patterns, etc.) determined from mobile applications, wearable devices, and/or patient entered information (e.g., from surveys, tracking applications, journal applications, etc.); patient medical information (e.g., lab results, information tracked from a wearable device such as heart rate information or the like, and/or behavioral information as indicated in medical records); patient activity that may indicate behavioral characteristics of the patient (e.g., locations, travel patterns, time-of-day considerations for these, etc.); and/or any other information available to the platform 101 that may be utilized to determine patient behavioral information (e.g., mood indications from text posted by the patient, clusters or patterns of information that may be determined, for example by an AI component, to relate to and/or indicate certain behavioral aspects of the patient, and/or historical performance of the patient—for example responding to communications, requesting particular aspects of information, and/or attending to medication regimes, medical provider visits, etc.). The journey management component 2014 may perform operations to match patients, to ensure patient efforts are likely to be beneficial and effective for the patients, to ensure that clinical study development efforts are likely to be successful and effective for finding a patient pool, and/or to enable longitudinal study aspects, for example allowing patients and study groups to maintain contact over a long period of time.

In some embodiments, with reference to FIG. 2, an example journey management component 124 includes sub-components for data ingestion 210 (e.g., through direct communications with the patient, access to publicly available information for the patient, acquisition of medical records for the patient, etc.), data processing 212 (e.g., normalizing and/or adjusting data into a standardized format, determining classifications or patterns from the data, and/or making any other determinations from the data according to aspects of the present disclosure), patient classification 214 (e.g., storing any classifications related to the patient, and/or storing any data utilized in such determinations, for example to allow for re-classification periodically and/or in real time), data lifecycle management 216

(e.g., determining how long to retain data, enforcing data retention protocols, enforcing patient permission values, determining whether to store data in high-speed short term memory and/or lower-speed long term memory, etc.), an event scheduler 218 (e.g., scheduling events associated with a particular study, and/or more general medical support scheduling such as tests, follow-up events, indicated tests according to the ongoing medical status of the patient, etc., and which can include helping a patient to find appropriate medical providers, and/or adjusting scheduling according to the patient's behavioral information such as preferred timing, notification avenues, etc.), and/or a treatment matching component 220 (e.g., determining whether available clinical studies, new tests or treatments, etc. would be a good fit for the patient, medically, behaviorally, according to patient classifications, etc.).

In example embodiments, the patient interaction component 2016 may be configured to receive at least one patient data value from the first patient and provide the at least one data value to the patient database component 2012. The patient database component 2012 may include the at least one data value in the plurality of patient data values of the longitudinal data 1700 of the first patient and may interact with the first patient according to at least one of the plurality of touch points curated by the journey management component 2014.

In some embodiments, the patient interaction component 2016 may, for example, include providing interfaces to a patient device, sending messages to a patient, receiving information from the patient, and/or receiving information automatically from the patient (e.g., a patient using a wearable device that transmits certain information to the platform, such as patient biometric information, sleep information, exercise information, or the like). In certain embodiments, any interactions of the patient engagement platform with the patient may be provided by the patient interaction component 2016, be commanded by the patient interaction component 2016, and/or be monitored by the patient interaction component 2016.

In some embodiments, the plurality of modular components 2010 may include an example patient database component 2012 that includes aspects to support the creation and implementation of, e.g., the patient database 1630, an example journey management component 2014 that may establish communications with the patient (e.g., via one or more touch points as described herein), and ensure those communications support the patient activity and are useful for the patient, and an example patient interaction component 2016 that may include, for example, an SMS platform that supports messaging with the patient, and a call center workspace that supports voice interactions with the patient, and includes manual call support, automated call support, and patient initiated call support. A call center using Amazon Connect may be provided as a non-limiting example, but any type of call center support and/or implementation may be utilized. In some embodiments, the SMS platform and call center workspace may be separate modular components 2010.

In some embodiments, the example patient database component 2012 may automatically establish new patient records and update existing patient records, host all communication and patient medical information, automatically communicate projected and actual visits to a clinical trial management system, and automatically communicate with the patient interaction component 2016, such as including a call center.

In some embodiments, the example journey management component 2014 may automatically launch and push out patient nurturing content. Additionally, the journey management component 2014 may, in response to a specific phenotype advertisement, automatically push a patient into an appropriate nurturing journey. Also, for patients with, e.g., existing patient records and/or longitudinal data in the patient database component 2012, the journey management component 2014 may query the patient database component 2012 for phenotype and base the journey thereon.

In some embodiments, the example patient interaction component 2016 may, for example, provide global texting features, provide SMS messaging to groups for call-to actions, reminders, etc., automatically initiate contact via SMS, and provide integrated communication between clinical trial sites, patients, and updates to the patient database component 2012 including, e.g., a patient database 1630. Additionally, the example patient interaction component 2016 may provide an automated call center workflow system, automatically match existing patient inbound/outbound calls to medical records for distribution to a phone system, automatically recognize an advertisement to which a patient is responding and then communicate to the phone system for a call center agent distribution, provide a recruitment dashboard for call center patient outcomes, track recruitment productivity, track the interaction of patients, and communicate with the patient database component 2012 to store data as appropriate. Also, the example patient interaction component 2016 may provide a telephony platform that provides software for voice and data multichannel ("omnichannel") communication, create connections for calls, provide an automatic agent queueing to appropriate resources for actions, perform automatic calls, recognize call failures, log all contact attempts and outcomes, and provide one-to-one agent/patient SMS texts, in, e.g., a dashboard for real time appointment confirmation, instructions, visit details, etc. While the example patient interaction component 2016 may, in one example, be one component, embodiments are not limited thereto, and in some embodiments, the functionalities of the example patient interaction component 2016 may be distributed among a plurality of separate modular components 2010.

In some embodiments, the plurality of modular components 2010 may include an example patient portal component 2022 that supports patient interactions with the patient engagement platform 101, a self-scheduler component 2024 that provides assisted scheduling support for the patient (e.g., to generate calendar invites/reservations for the patient), a clinical conductor component 2026 (or clinical trial management system) that supports execution of clinical studies (e.g., communicates projected and actual visits into a database, houses study-specific documents, and provides management for patient stipends), and an electronic source ("eSource") component 2028 that supports integration between clinicians, patients, and other platform aspects. Additional potential components may be utilized in certain embodiments, for example to support behavioral determination for the patient, engagement support with the patient to ensure compliance, and/or personalization of engagement with the patient.

In some embodiments, an example patient portal component 2022 may be a patient access portal that provides patient access to medical information (e.g., study-specific lab results) using a unique user ID and/or login, and that facilitates direct communication to a study team. In some embodiments, a patient's ability to access the patient portal may be dependent on the requirements indicated by a study, patient phenotype, etc. In some embodiments, an example patient portal component may be embodied in whole or in part by the patient interaction component 2016.

In some embodiments, an example eSource component 2028 may include a clinical resource system and may be external to, e.g., the system 2001 and/or the other modular components 2010. For example, the example eSource component may be operated by a different entity than the system 2001 and modular components 2010 therein. The example eSource component 2028 may provide an integrated electronic source, electronic regulatory, clinical trial management system, and stipend platform. The example eSource component 2028 may provide the ability to automatically push study-specific content, such as appointment reminders. In some examples, the example eSource component 2028 may be dependent upon patient appointments being scheduled in the platform.

In some embodiments, the example system 1601 may be referenced as a platform such as an omnichannel technology platform. In certain embodiments, the platform may utilize and/or integrate previously known solutions for some aspects of the platform (e.g., as at least some of the plurality of modular components 2010), and/or may utilize and/or integrate customized versions of previously known solutions for one or more aspects. In certain embodiments, previously known and/or customized versions of solutions may be utilized for operations in regard to: recruitment (e.g., patients or other stakeholders to the platform, and/or to specific features on the platform, clinical trials, treatments, etc.); telehealth (e.g., communications to facilitate and/or implement distance based health care functions); concierge (e.g., providing scheduling or other services for patients); data/stats (e.g., to support analytics functions of the platform and/or for stakeholders); devices; and/or trial management supported by the platform. An example platform is configured for compliance based on the actual features on the platform, including for example IT compliance, HIPAA compliance, CCPA/CPRA compliance, and/or GDPR compliance. The example platform includes security, data segregation, process controls, and/or other features to promote compliance and/or embody compliant tools as a part of the platform. In certain embodiments, the platform provides for convenient compliance confirmation, reporting, or the like.

Figure 14:
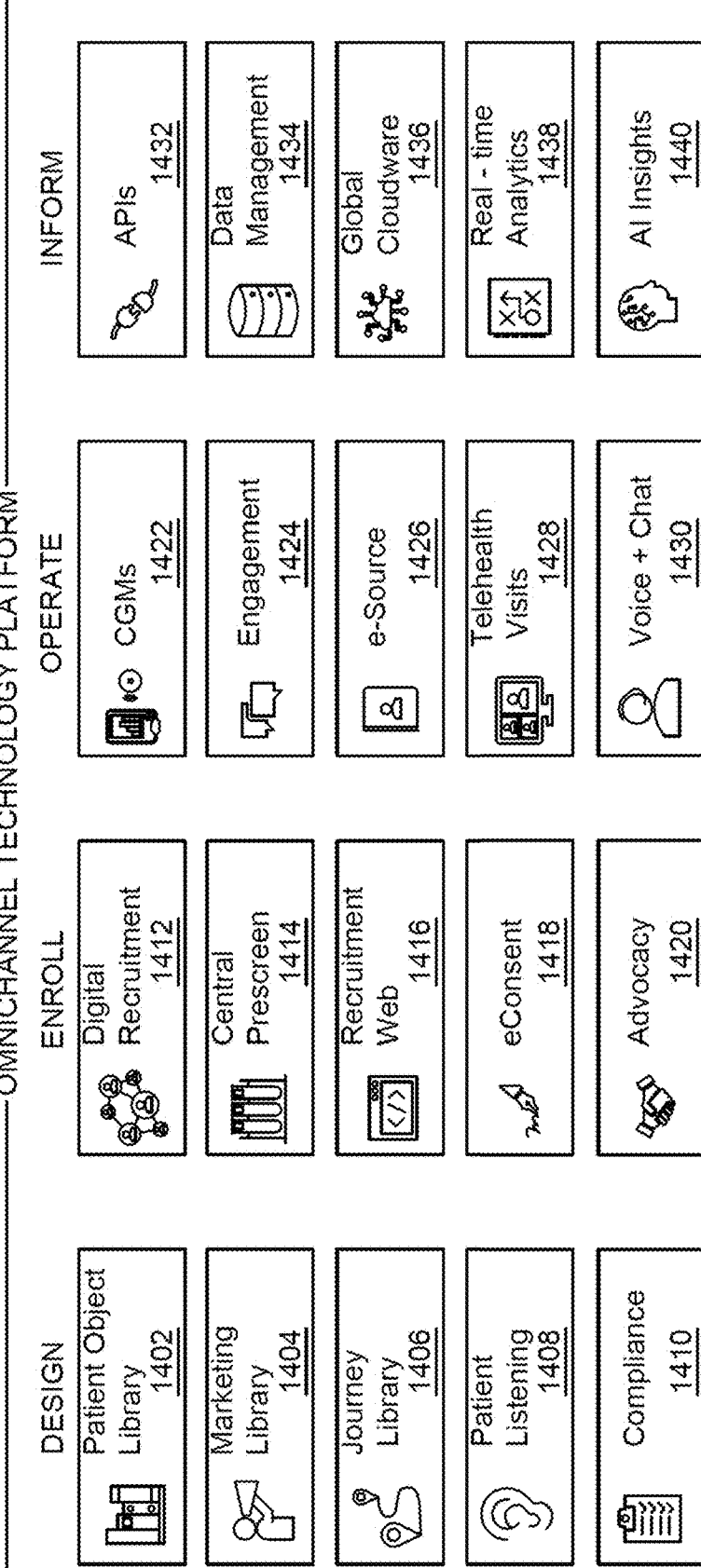
FIG. 14 schematically depicts an organization of an example platform.

In some embodiments, with reference to FIG. 14, the plurality of modular components 2010 may include components related to design, such as a patient object library 1402, a marketing library 1404, a journey library 1406, patient listening 1408, and compliance 1410. In some embodiments, the plurality of modular components 2010 may include components related to enrollment, such as digital recruitment 1412, central prescreening 1414, recruitment web 1416, electronic consent 1418, and advocacy 1420 components. In some embodiments, the plurality of modular components 2010 may include components related to operations, such as continuous glucose monitoring 1422, patient engagement 1424, electronic sources 1426 such as a clinical research system, telehealth visits 1428, and voice and chat functionalities 1430. In some embodiments, the plurality of modular components 2010 may include components related to information, such as APIs 1432, data management 1434, global cloudware 1436, real-time analytics 1438, and AI insights 1440. Some or all of these components may be embodied in whole or in part by the plurality of modular components 2010 described herein.

Figure 21:
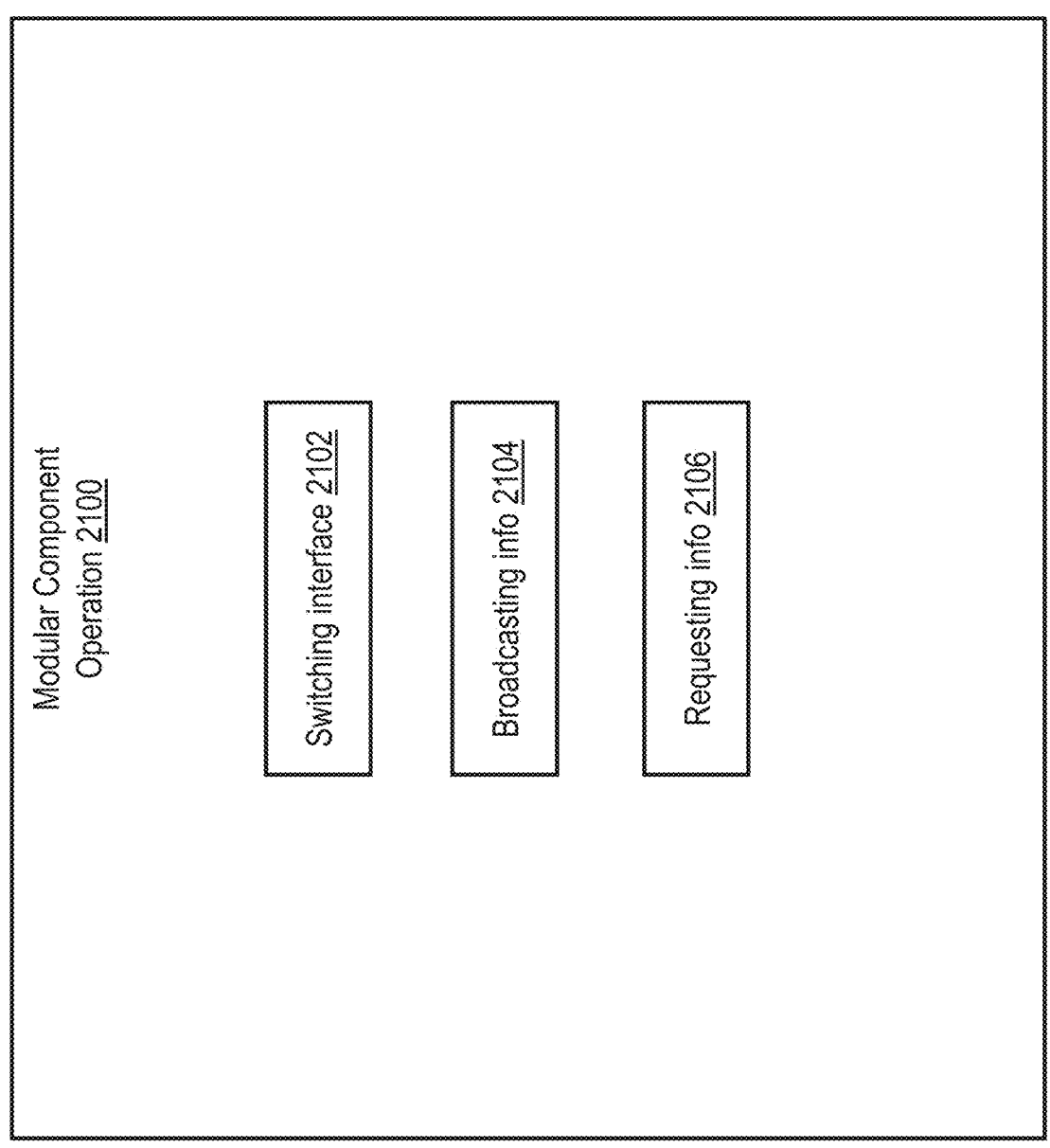
FIG. 21 illustrates modular component operations according to example embodiments.

With reference to FIG. 21, the modular component operation 2100 may include switching 2102 from interfacing with a first modular component to interfacing with a second modular component. For example, in some embodiments, the second modular component may replace the first modular component in a swapping operation. In an example, an operator of the system 2001 may reconfigure the system 2001 to utilize the second modular component in place of the first. Indeed, in some of the embodiments, at least one of the plurality of modular components may be configured to be swappable with different modular components. For example, the first modular component may be configured to have inputs and/or outputs corresponding to those of the second modular component, and/or vice versa.

In another example, the modular component operation 2100 may include a certain modular component broadcasting 2104 to other modular components information regarding the certain component. For example, the certain component's configuration may have changed, in which case it will broadcast its new configuration to other components so that they may know of the changes and how to interact. Or, for example, if the certain modular component is newly installed in the system 2001, the modular component may broadcast information including its presence and functions—which, in some embodiments, may trigger the switching 2102 in one or more other modular components as discussed above.

In another example, the modular component operation 2100 may include a certain modular component requesting 2106 information from the other modular components with which it is connected, such as their functions and interfaces. For example, a modular component may request information from another modular component that has newly been installed in the system 2001. In some examples, this may cause the modular component to switch 2102 its interface as discussed above, and/or otherwise change its configuration to interact with the new modular component.

Figure 22:
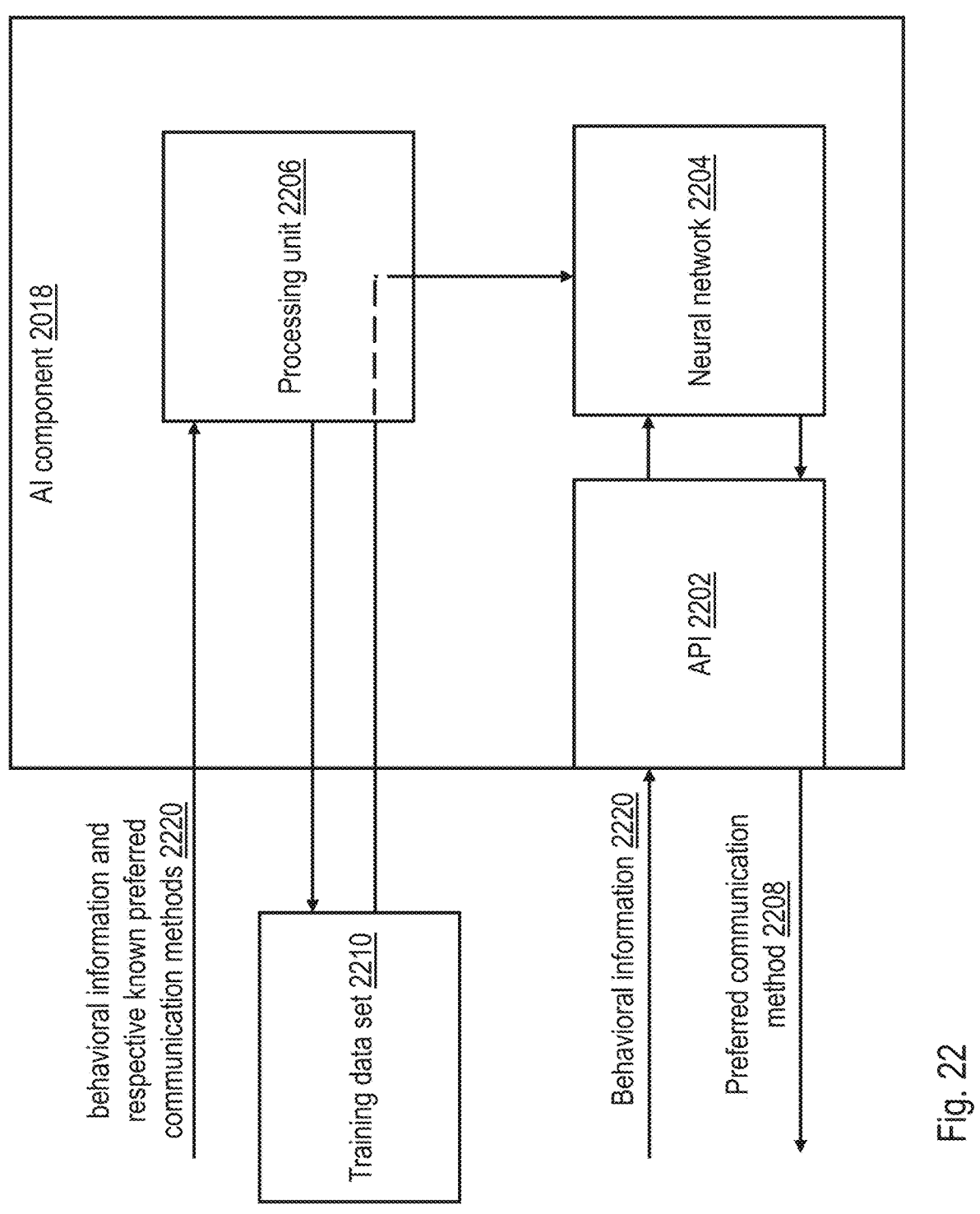
FIG. 22 illustrates an artificial intelligence component and its interface with other modular components according to example embodiments.
Figure 24:
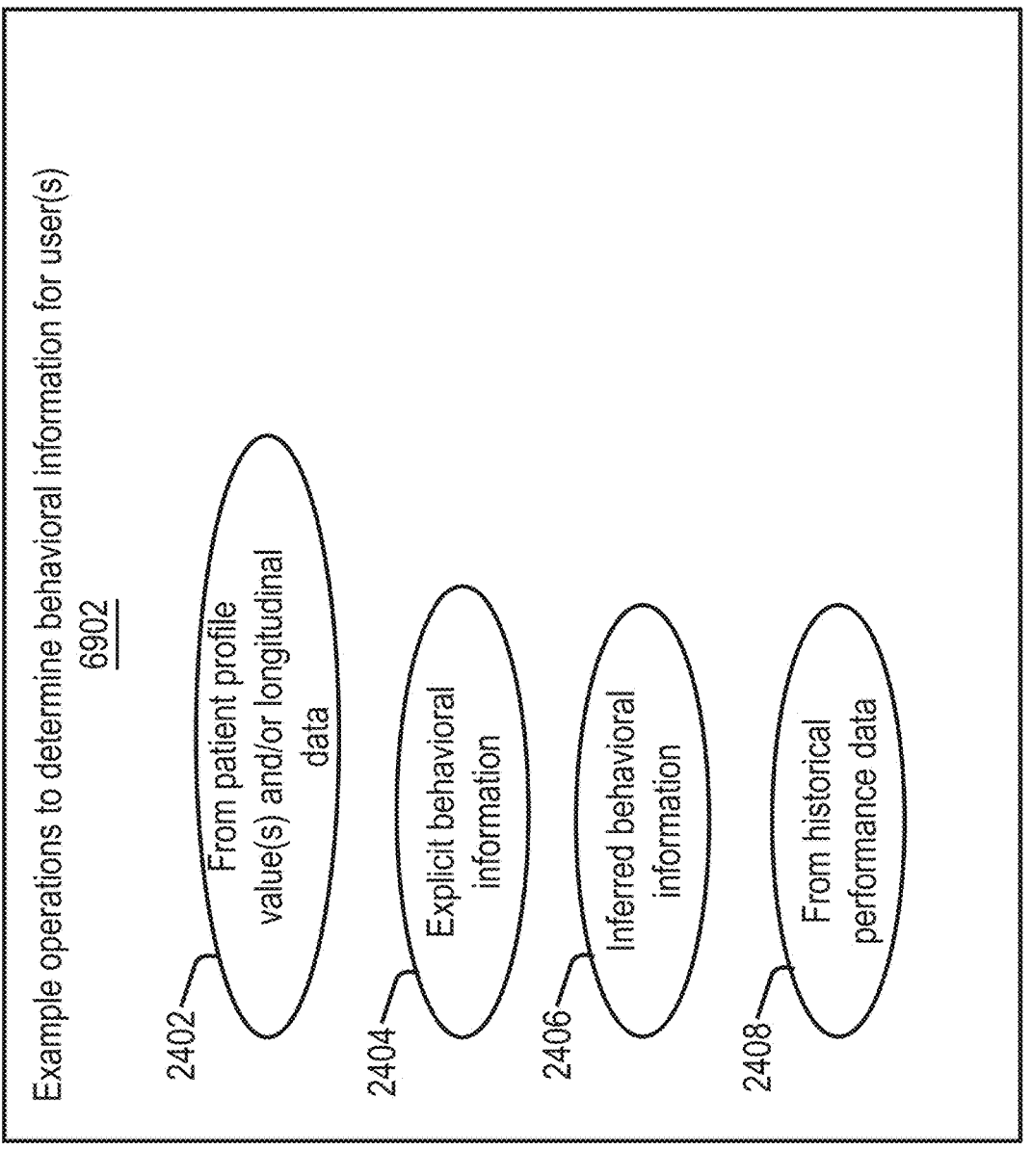
FIG. 24 depicts example operations to determine user behavioral information.

In some embodiments, with reference to FIG. 22, which illustrates an artificial intelligence (AI) component 2018 and its interface with the plurality of other modular components 2010 of system 2001, the AI component 2018 may include at least one neural network 2204. However, embodiments are not limited thereto, and in some embodiments, some or all of the AI component (e.g., including one or more neural networks) may be external to the system 2001. For example, some or all portions of the AI component may be provided in one or more cloud devices.

With reference to FIG. 22, the AI component 2018 may be configured to receive, through a first AI component application programming interface (API) 2202, behavioral information 2220 on the first patient from interactions of the first patient with the plurality of touch points provide the behavioral information as an input to the neural network 2204 (which may be a part of the AI component 2018 or may be external). Further, the AI component 2018 may be configured to obtain, as an output from the neural network 2204, an indication of at least one preferred communication method 2208 of the first patient, and to output, through the first AI component API 2202 or a different API, this indication of the at least one preferred communication method 2208 of the first patient (either directly from the neural network 2204 or as interpreted by one or more other components of the AI component 2018). For example, the at least one preferred communication method may be output to one or more other modular components 2010 of the system 2001, for example, to aid such modular components 2010 in determining how to contact the first patient.

In some embodiments, the AI component 2018 may be configured to maintain a training data set 2210 for training the neural network 2204. The training data set 2210 may be stored local to the AI component 2018, in the patient database component 2012, and/or externally, such as in a cloud database external to system 2001. The training data set 2210 may include prior behavioral information and known preferred communication methods of at least some of the plurality of patients. In some embodiments, the AI component 2018 (e.g., via processing unit 2206, which may include one or more processors configured to execute computer-readable instructions) may update the training data set 2210 as new behavioral information and respective known preferred communication methods 2230 of patients is obtained, and the AI component 2018 may thereby iteratively train the neural network 2204 on the training data set 2210.

In some embodiments, the AI component 2018 may receive feedback data indicating an effectiveness of the at least one preferred communication method of the first patient. The AI component 2018 (e.g., processing unit 2206) may interpret the effectiveness of the at least one preferred communication method of the first patient as a known preferred communication method of the first patient. Thus, the AI component 2018 may add, as added data, the behavioral information of the first patient and the known preferred communication method of the first patient to the training data set 2210—e.g., to the prior behavioral information and known preferred communication methods of at least some of the plurality of patients. The AI component 2018 may further iteratively train the neural network on the training data set 2210 including the added data. Thus, the AI component 2018 may effectively provide a feedback loop for further training the neural network 2204 based on the determined effectiveness of its output.

In some embodiments, the patient interaction component 2016 may be further configured to receive, via the first AI component API 2202 or a different API of the AI component, the indication of the at least one preferred communication method 2208 of the first patient. The at least one preferred communication method 2208 of the first patient may include any of a variety of communication methods, such as short message service (SMS) (e.g., text messages), phone calls, email, smartphone app notifications, a certain visual display, etc. The patient interaction component 2016 may contact the first patient using at least the at least one preferred communication method 2208 of the first patient.

In an example, the at least one preferred communication method 2208 may include SMS, and for at least one of the plurality of touch points, the patient interaction component 2016 may contact the first patient using SMS based on the at least one preferred communication method 2208 of the first patient including SMS.

In another example, the at least one preferred communication method may include a certain visual display, and for at least one of the plurality of touch points, the patient interaction component 2016 may contact the first patient using the certain visual display. For example, the first patient may prefer (e.g., through the patient's own indication or as learned by the AI component 2018) that communications from the system 2001 be displayed in a certain area or in another certain manner of, for example, a visually-displayed patient engagement platform and/or social media, and/or that communications from the system 2001 only be visually displayed when specifically requested by the first patient.

In some embodiments, the AI component 2018 may be included as part of the patient interaction component 2016. For example, the AI component 2018 may be included as part of a same modular component 2010 as the patient interaction component 2016.

In some embodiments, at least one of the plurality of modular components 2010 of the system 2001 may be swappable with a different modular component such that the other plurality of modular components 2010 interface with the different modular component over the network such as the Internet. For example, the at least one of the plurality of modular components 2010 may be configured such that its inputs, outputs, and/or functionalities appear identical to the other plurality of modular components 2010, such that swapping out the at least one of the plurality of modular components 2010 is transparent to the other plurality of modular components 2010.

For example, the different modular component swapped in to replace the at least one of the plurality of modular components 2010 may be a low-code module and may be customized via a low-code environment. Thus, an operator of the system 2001 that wishes to change operations of the one of the plurality of modular components, which may be customizable only via code or another mechanism with which the operator is not proficient, may replace the one of the plurality of modular components with this different modular component and customize it (e.g., its operations) via the low-code environment. Such an example is just one of many advantages resulting from the swappability of the modular components 2010. For example, one modular component may have better functions than another for a given application, may provide more recent technological advances leading to increased efficiencies in processing and/or power, may replace a component that is no longer being actively maintained by a vendor, may provide a smaller footprint (in cost, computational need, etc.), may provide a function that is newly needed by the system 2001, or may provide other advantages that may be apparent to one skilled in the art upon reading this disclosure.

With reference to FIG. 20, in some embodiments, the patient interaction component 2016 may include a plurality of patient interaction components. These plurality of patient interaction components may each include a modular component 2010 of system 2001, and thus, some, each, or any of the plurality of patient interaction components may be swappable with a different component. In an example, one of the patient interaction components 2016 may include (e.g., provide over a network) a social media platform as may be described elsewhere herein. However, embodiments are not limited thereto, and in some examples, a social media component 2030 providing a social media platform may be provided as a modular component 2010 separate from a patient interaction component 2016.

In some embodiments, the plurality of components 2010 may include an external interaction component 2020 including an interface for at least one external device. For example, the external interaction component 2020 may include functionalities for interacting with the at least one external device, including receiving and transmitting communications such as patient data. In an example, the interface of the external interaction component 2020 may include one or more APIs. Meanwhile, the at least one external device may include data streams as described herein, such as, for example, a device accessed by at least one of a medical provider, an external database, a medical laboratory, or a wearable device, and the external interaction component 2020 may receive data from a data stream 1650 including the at least one external device. In some embodiments, the external interaction component 2020 may include providing interfaces to other devices such as clinician devices, medical provider devices, accessing external databases, and/or any other devices to perform operations set forth throughout the present disclosure.

In some examples, the at least one external device is a wearable device of the first patient, and the wearable device of the first patient may provide data about the first patient in real time. For example, the external device such as the wearable device may provide data about the first patient to the external interaction component 2020 (or other modular component 2010 of the system 2001) in real time, and the external interaction component 2020 or other modular component 2010 may receive the real time data of the first patient and route it over a network to one or more other modular components 2010 of the system 2001 based, for example, on the configuration or other settings of the external interaction component 2020. In an example, the wearable device may include a continuous glucose monitor that monitors a blood glucose of the first patient and provides information regarding the monitored blood glucose to the external interaction component 2020 as the data in real time.

In some embodiments, the external interaction component 2020 may be configured to interact with (e.g., via an API) at least one of a social media platform, a website, a clinical trial management system, a call center application, an electronic source component, or a health database, which may be considered data streams. In an example, the external interaction component 2020 may be configured to interact with the electronic source component, which may include clinical protocol-level assessment data of the first patient captured electronically. In some embodiments, the external interaction component 2020 may be configured to automatically feed the clinical protocol-level assessment data of the first patient to the patient database component 2012.

In some embodiments, the patient database component 2012 may be configured to receive data regarding the first patient from the other plurality of modular components 2010 and to standardize the data regarding the first patient before storing the data regarding the first patient as part of the longitudinal data of the first patient, as discussed in more detail with reference to the patient database system 1601. Indeed, the patient database system 1601 may be embodied, in whole or in part, by the patient database component 2012.

Figure 27:
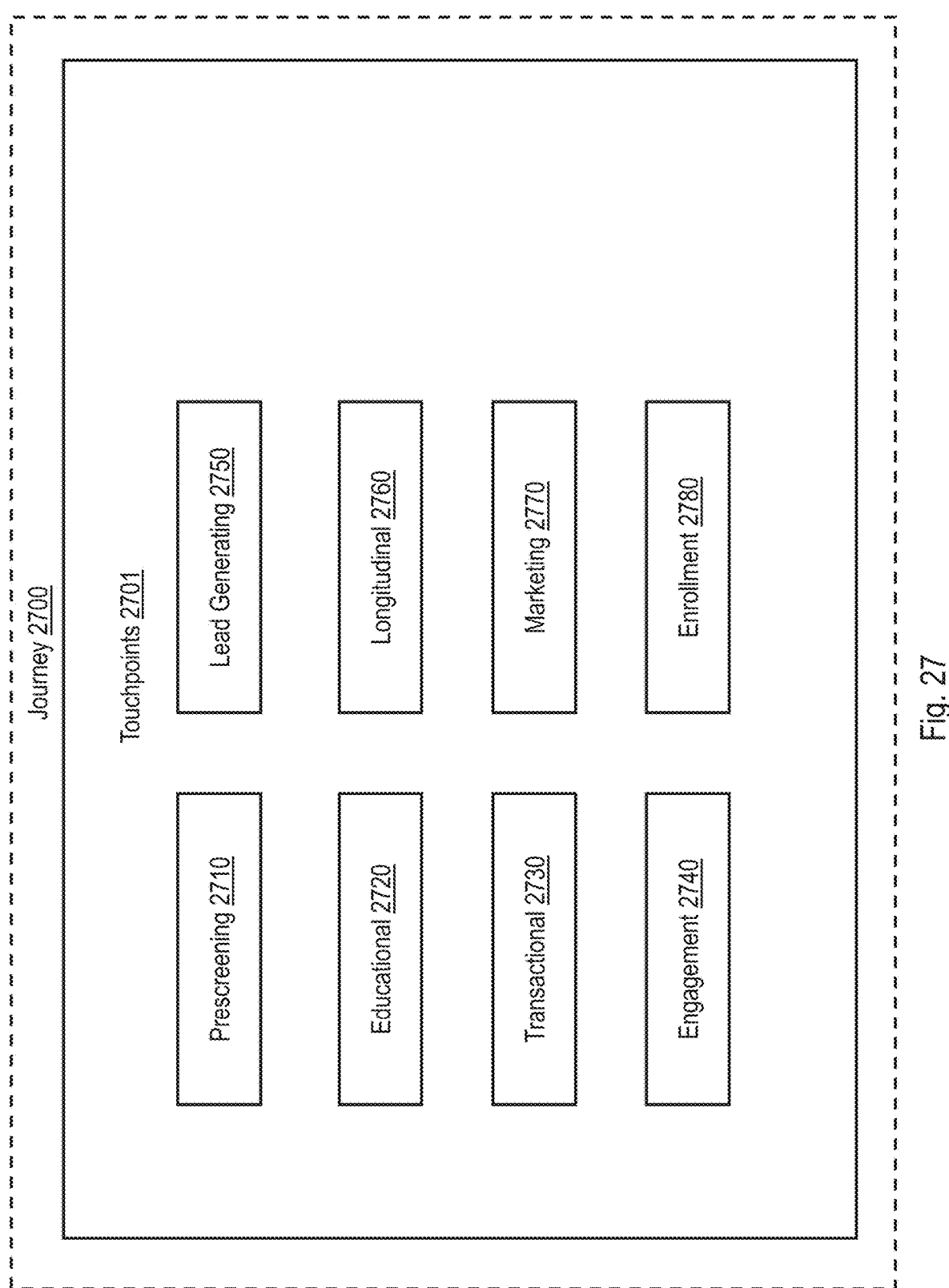
FIG. 27 illustrates a journey including touch points according to example embodiments.

In some embodiments, the journey management component 2014 may be configured to discern at least one clinical protocol-level touch point of the plurality of touch points for the first patient from the captured clinical protocol-level assessment data of the first patient. And, as discussed herein, the journey management component 2014 may be responsible for the journey 2700 (see FIG. 27) of a patient through at least a first clinical protocol, including generation and management of the touch points.

In some embodiments, the patient interaction component 2016 may be configured to collect a plurality of patient interaction values of the first patient and to classify the first patient therefrom. Further, the patient interaction component 2016 may provide this classification to the journey management component 2014, which may be configured to curate the journey including at least some of the plurality of touch points based on the classification of the first patient by the patient interaction component 2016.

In some embodiments, the plurality of touch points include, for example, touch points 2701 described with reference to a journey 2700. For example, the plurality of touch points 2701 may include at least one prescreening touch point including a touch point to acquire one or more data values of the patient during a prescreening process for the first clinical protocol, at least one educational touch point including a touch point to provide the patient with information for the first clinical protocol, at least one transactional touch point including a touch point to remind the patient of an upcoming clinical visit for the first clinical protocol, and at least one engagement touch point including a touch point to encourage interaction of the patient with the platform.

In some embodiments, the modular component operation 2100 may include interfacing with a new modular component, where the new modular component is at least one of added to the plurality of modular components or swapped with one of the plurality of modular components.

In some embodiments, the modular components 2010 of system 2001 may include any other building block functionalities of the system 2001 that are customized to perform specific functions as part of the framework of the system 2001. Thus, these modular components 2010 may be considered the "building blocks" of improvements provided by the system 2001. While the modular components 2010 have been described with the conceptual boundaries described and illustrated herein, the different modular components may be combined or separated depending on the underlying hardware and/or software capabilities of the system 2001.

With reference to FIG. 23, a method 2300 for providing a patient engagement platform for a plurality of clinical protocols according to example embodiments may include establishing and updating 2304 longitudinal data for a plurality of patients including a first patient, where the longitudinal data for the first patient includes a plurality of patient data values, and where the patient database component stores the longitudinal data for a time duration longer than a first one of the plurality of clinical protocols. The method 2300 may further include curating 2308 a journey of the first patient through the first one of the plurality of clinical protocols, where the journey includes a plurality of touch points between the system and the first patient. The method 2300 may also include receiving 2312 at least one patient data value from the first patient and providing the at least one data value to the patient database component, where the patient database component includes the at least one data value in the plurality of patient data values of the longitudinal data of the first patient. The method 2300 may additional include interacting 2316 with the first patient according to at least one of the plurality of touch points, where at least some of the plurality of modular components are configured to perform a modular component operation.

In some embodiments, the method 2300 further includes switching from interfacing with a first modular component to interfacing with a second modular component.

In some embodiments, the method 2300 further includes the second modular component replacing the first modular component in a swapping operation.

In some embodiments, the method 2300 further includes at least one of the plurality of modular components being swappable with a different modular component.

In some embodiments, the method 2300 further includes receiving, through a first AI component application programming interface (API), behavioral information on the first patient from interactions of the first patient with the plurality of touch points, providing the behavioral information as an input to the neural network, obtaining, as an output from the neural network, an indication of at least one preferred communication method of the first patient, outputting, through the first AI component API or a different API, the indication of the at least one preferred communication method of the first patient, maintaining a training data set including prior behavioral information and known preferred communication methods of at least some of the plurality of patients, and iteratively training the neural network on the training data set.

In some embodiments, the method 2300 further includes the AI component receiving feedback data indicating an effectiveness of the at least one preferred communication method of the first patient, interpreting the effectiveness of the at least one preferred communication method of the first patient as a known preferred communication method of the first patient, adding, as added data, the behavioral information of the first patient and the known preferred communication method of the first patient to the training data set, and further iteratively training the neural network on the training data set including the added data.

In some embodiments, the method 2300 further includes the patient interaction component receiving, via the first AI component API or a different API of the AI component, the indication of the at least one preferred communication method of the first patient, where the at least one preferred communication method of the first patient includes short message service (SMS), and for at least one of the plurality of touch points, contacting the first patient using SMS based on the at least one preferred communication method of the first patient including SMS.

In some embodiments, the method 2300 further includes the patient interaction component receiving, via the first AI component API or a different API of the AI component, the indication of the at least one preferred communication method of the first patient, where the at least one preferred communication method of the first patient includes a certain visual display, and for at least one of the plurality of touch points, contacting the first patient using the certain visual display.

In some embodiments, the method 2300 further includes including the AI component in the patient interaction component.

In some embodiments, the method 2300 further includes at least one of the plurality of modular components being swappable with a different modular component such that the other plurality of modular components interface with the different modular component over the network.

In some embodiments, the method 2300 further includes the different modular component being a low-code module and being configured to be customizable via a low-code environment.

In some embodiments, the method 2300 further includes the patient interaction component including a plurality of patient interaction components, where one of the patient interaction components includes a social media platform.

In some embodiments, the method 2300 further includes the patient database component matching the first patient to the first one of the plurality of clinical protocols based on at least some of the longitudinal data of the first patient.

In some embodiments, the method 2300 further includes an external interaction component including an interface for at least one external device.

In some embodiments, the method 2300 further includes the interface including an application programming interface (API) and the at least one external device including a device accessed by at least one of a medical provider, an external database, or a medical laboratory.

In some embodiments, the method 2300 further includes the external interaction component receiving data from a data stream including the at least one external device.

In some embodiments, the method 2300 further includes at least one external device being a wearable device of the first patient, and the wearable device of the first patient providing data about the first patient in real time.

In some embodiments, the method 2300 further includes the wearable device including a continuous glucose monitor monitoring a blood glucose of the first patient and providing information regarding the monitored blood glucose to the external interaction component as the data in real time.

In some embodiments, the method 2300 further includes an external interaction component interacting with at least one of a social media platform, a website, a clinical trial management system, a call center application, an electronic source component, or a health database.

In some embodiments, the method 2300 further includes the external interaction component interacting with the electronic source component, and the electronic source component including clinical protocol-level assessment data of the first patient captured electronically.

In some embodiments, the method 2300 further includes the journey management component discerning at least one clinical protocol-level touch point of the plurality of touch points for the first patient from the captured clinical protocol-level assessment data of the first patient.

In some embodiments, the method 2300 further includes the external interaction component automatically feeding the clinical protocol-level assessment data of the first patient to the patient database component.

In some embodiments, the method 2300 further includes the patient database component receiving data regarding the first patient from the other plurality of modular components and standardizing the data regarding the first patient before storing the data regarding the first patient as part of the longitudinal data of the first patient.

In some embodiments, the method 2300 further includes the patient interaction component collecting a plurality of patient interaction values of the first patient and classifying the first patient therefrom, and the journey management component curating the journey including at least some of the plurality of touch points based on the classification of the first patient by the patient interaction component.

In some embodiments, the method 2300 further includes at least one prescreening touch point including a touch point acquiring one or more data values of the patient during a prescreening process for the first clinical protocol, at least one educational touch point including a touch point providing the patient with information for the first clinical protocol, at least one transactional touch point including a touch point reminding the patient of an upcoming clinical visit for the first clinical protocol, and at least one engagement touch point including a touch point encouraging interaction of the patient with the platform.

In some embodiments, the method 2300 further includes the modular component operation interfacing with a new modular component, where the new modular component is at least one of added to the plurality of modular components or swapped with one of the plurality of modular components.

In some embodiments, the method 2300 according to example embodiments may be performed by a plurality of modular components 2010 configured to interface with each other over a network. In some embodiments, the method 2300 according to example embodiments may be stored as instructions on at least one non-transitory computer-readable storage medium that is executable by at least one processor.

Figure 26:
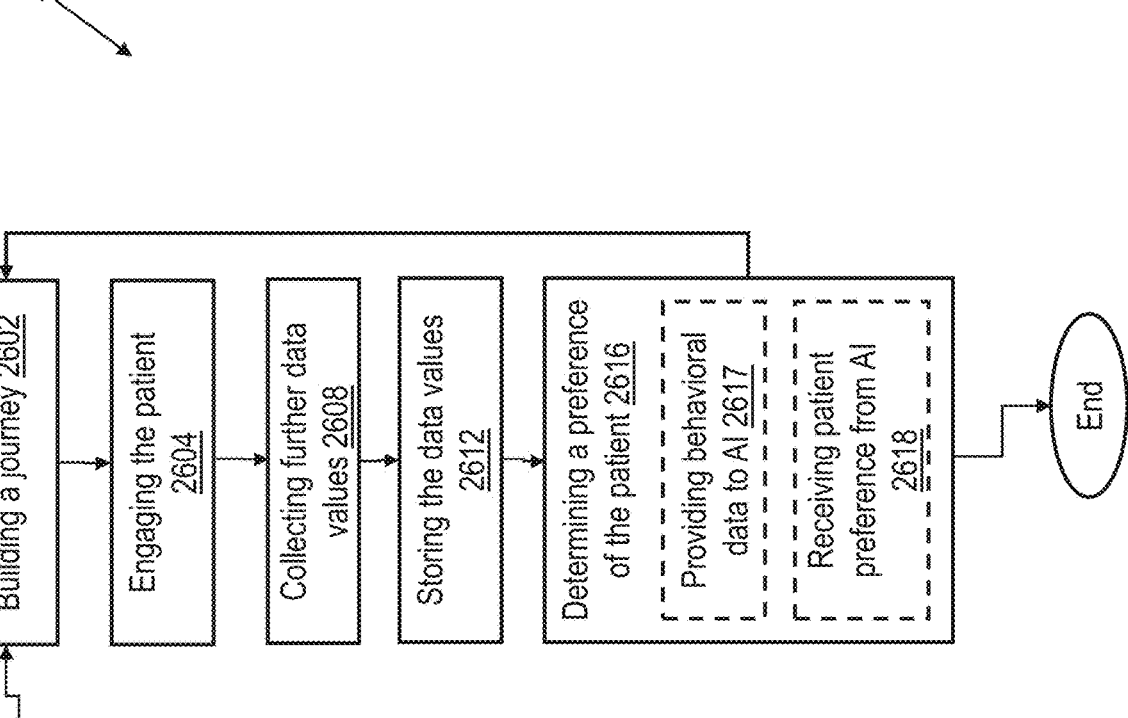
FIG. 26 illustrates an example method of implementing a patient journey according to example embodiments.

With reference to FIG. 26, an example method 2600 according to example embodiments may include building 2602, via an electronic platform (e.g., via one or more of the modular components 2010 of a system 2001 as described by example herein, such as journey management component 2014), a journey 2700 of a patient through at least a first clinical protocol. The journey 2700 may include a plurality of touch points 2701, as shown by example categories in FIG. 27, and some, each, or all of the plurality of touch points 2701 may include an electronic interaction with the patient. In example embodiments, touch points such as but not limited to those illustrated in FIG. 27, e.g., the prescreening 2710, enrollment 2780, educational 2720, transactional 2730, engagement 2740, lead generating 2750, longitudinal 2760, and marketing 2770 touchpoints may be provided by the journey 2700 as different categories of the plurality of touch points 2701. These touch points 2701 are provided by example only, and embodiments are not limited thereto. Other categories of touch points may exist, and/or a touch point 2701 may fall into more than one category.

In example embodiments, the touch points 2701 of a journey 2700 may support a patient before (e.g., "pre-trial"), during ("trial"), and after ("post-trial") the duration of a clinical protocol. For example, the touch points 2701 may include the entire lifecycle of the patient interaction, from finding the compatibility match, through enrollment, execution, follow-up, and/or longitudinal study aspects.

In example embodiments, the method 2600 may include engaging 2604 the patient in real time with the plurality of touch points 2701 via a plurality of communication channels. The plurality of touch points 2701 may include, for example, at least one prescreening touch point 2710 such as a touch point to acquire one or more data values of the patient during a prescreening process for the first clinical protocol. The plurality of touchpoints 2701 may also include at least one educational touch point 2720 including a touch point to provide the patient with information for the first clinical protocol, at least one transactional touch point 2730 including a touch point to remind the patient of an upcoming clinical visit for the first clinical protocol, and at least one engagement touch point 2740 including a touch point to encourage interaction of the patient with the platform.

In example embodiments, the method 2600 may further include collecting 2608, through at least some of the plurality of touch points 2701, further data values of the patient including medical information of the patient and behavioral information of the patient, and storing 2612 the data values of the patient as longitudinal data 1700 of the patient. As described with reference to example embodiments herein, the longitudinal data 1700 of the patient may be stored for a time duration that extends after the first clinical protocol is completed by the patient.

In example embodiments, the method 2600 may further include determining 2616, using the behavioral information of the patient, a preference of the patient for a specific one of the plurality of communication channels. Based on determining the preference of the patient for the specific one of the plurality of communication channels, the patient may be engaged via the specific one of the plurality of communication channels for at least one of the plurality of touch points 2701. Thus, the determining 2616 may provide feedback to the engaging 2604 step for selection of one or more communication channels with which to engage the patient.

In some embodiments, determining 2616, using the behavioral information of the patient, the preference of the patient for the specific one of the plurality of communication channels may include providing 2617 the behavioral information of the patient as an input to an artificial intelligence (AI) model and receiving 2618 the preference of the patient as an output from the AI model. In some embodiments, the AI model is trained on training data including behavioral information and communication channel preferences of a plurality of previous patients. In some embodiments, the plurality of communication channels may include at least one or at least two of short messaging service (SMS), a smartphone application, a social media platform and/or patient engagement platform, email, a wearable device, telephone calling, etc., and/or other channels such as illustrated and/or described with reference to FIG. 61.

In some embodiments, the plurality of touch points 2701 may further include a prescreening touch point 2710 for a second clinical protocol, and the prescreening touch point 2710 for the second clinical protocol may include acquiring one or more additional data values of the patient during a prescreening process for the second clinical protocol.

In some embodiments, the at least one educational touch point 2720 may include at least one of providing the patient with information about the first clinical trial (e.g., via a video or other media), providing the patient with a newsletter, providing the patient with other information to generally educate them about the trial, their condition, health tips, etc. Providing the patient with the video may, for example, include generating an animation for the video. Of course, educational touch points 2720 are not limited thereto, and may include any manner of providing educational information to the patient as described herein.

In some embodiments, the at least one engagement touch point 2720 may include a gamification of information related to the first clinical protocol or other manners of piquing the patient's interest. For example, the gamification may include a quiz in the form of a game to both encourage the player's participation in the platform and educate them. Indeed, in some examples, a touch point may be categorized as both an engagement touch point 2720 and an educational touch point 2720, since educating the patient about aspects related to the clinical protocol may, in some instances, be an inherent part of engaging the patient's interest.

In some embodiments, the plurality of touch points 2701 may further include a lead generating touch point 2750, including, prior to the prescreening touch point, generating a lead for possible patients for the first clinical protocol. For example, the leads may be generated through a social media platform, or through other manners described herein, and the possible patients may include the first patient.

In some embodiments, at least one of the plurality of communication channels may include a social media platform, and the method 2600 may include engaging 2604 the patient in real time with at least one of the plurality of touch points 2701 via the social media platform. For example, engaging 2604 the patient via the social media platform may be based on the determining 2616 that the social media platform is a communication preference of the patient.

In some embodiments, the plurality of touch points 2701 may further include at least one touch point after the first clinical trial to emphasize an importance of engaging in clinical protocols. Indeed, in some embodiments, the plurality of touch points 2701 may include a longitudinal touch point 2760, which may include this at least one touch point after the first clinical trial. The longitudinal touch point(s) 2760 may be structured to encourage engagement of the patient with the patient engagement platform and, e.g., nurture goodwill towards the platform and the clinical protocols provided therefrom. In this way, the longitudinal touch point(s) 2760 may promote engagement of the patient that is longitudinal—e.g., existing apart from any one clinical protocol. By retaining patient engagement beyond a specific protocol, the patient engagement platform may encourage the patient's interest in other clinical protocols and willingness to participate in the same.

In some embodiments, at least one of the plurality of touch points 2701 may be triggered via a trigger event from at least one of the communication channels. For example, upon sending the patient an SMS text confirming an upcoming appointment, an educational touch point 2720 may be triggered to provide the patient with details regarding what to expect at the appointment. As another example, in some embodiments, at least one of the plurality of touch points 2701 may be triggered via a trigger event from the data streams as described herein. For example, upon the patient database component 2012 receiving a new laboratory result from a clinical laboratory, a transactional touch point 2730 may be triggered to inform the patient about the new result.

In some embodiments, the plurality of touch points 2701 may further include a marketing touch point 2770. The marketing touch point(s) 2770 may be provided to the patient prior to at least one prescreening touch point 2710. In some examples, such a marketing touch point may be provided, for example, via an ad on social media, such as may be provided by the patient engagement platform. The marketing touch point(s) 2770 may provide marketing outreach to possible patients (including the patient) for one or more clinical protocols, such as the first clinical protocol, and may promote the possible patients to engage in a prescreening process.

In some embodiments, the at least one transactional touch point 2730 may include further touch points that may pertain to participation of the patient in the first clinical protocol. For example, in addition to the touch point to remind the patient of an upcoming clinical visit for the first clinical protocol, the transactional touch points 2730 may include touch points to indicate the progress of the patient through the first clinical protocol, to inform the patient of results from clinical visits, etc. In some examples, the transactional touch points 2730 may be considered clinical protocol touch points in that they relate to aspects of the patient's journey through the clinical protocol.

In some embodiments, the example method 2600 may include example operations to support the patient journey through the clinical study including one or more operations (e.g., touch points 2701), some of which are described above, but without limitation: connecting the patient and the study group (e.g., as a marketing touch point 2770); enrollment of the patient in the study (e.g., as an enrollment touch point 2780); execution of aspects of the study (e.g., as transactional touch points 2730), such as medications, at-home testing, provider visits, and data capture throughout; execution of follow-up actions (e.g., as transactional touch points 2730), such as follow-up provider visits, additional testing, data tracking, implementing surveys or questionnaires, and/or providing information (e.g., study results, patient outcomes, etc.) to the patient from the study group (e.g., as educational touch points 2720); and/or long term activity to support longitudinal study aspects (e.g., longitudinal touch points 2760), such as patient status updates, additional provider visits, implementing surveys or questionnaires, and/or facilitating communications between the patient and the study group (e.g., where years after the fact, it may be otherwise difficult to find the patient, for the patient to remember the study and/or what happened during or after the study, and/or for the patient to reliably determine that follow-up communications are legitimate, etc.).

Figure 15:
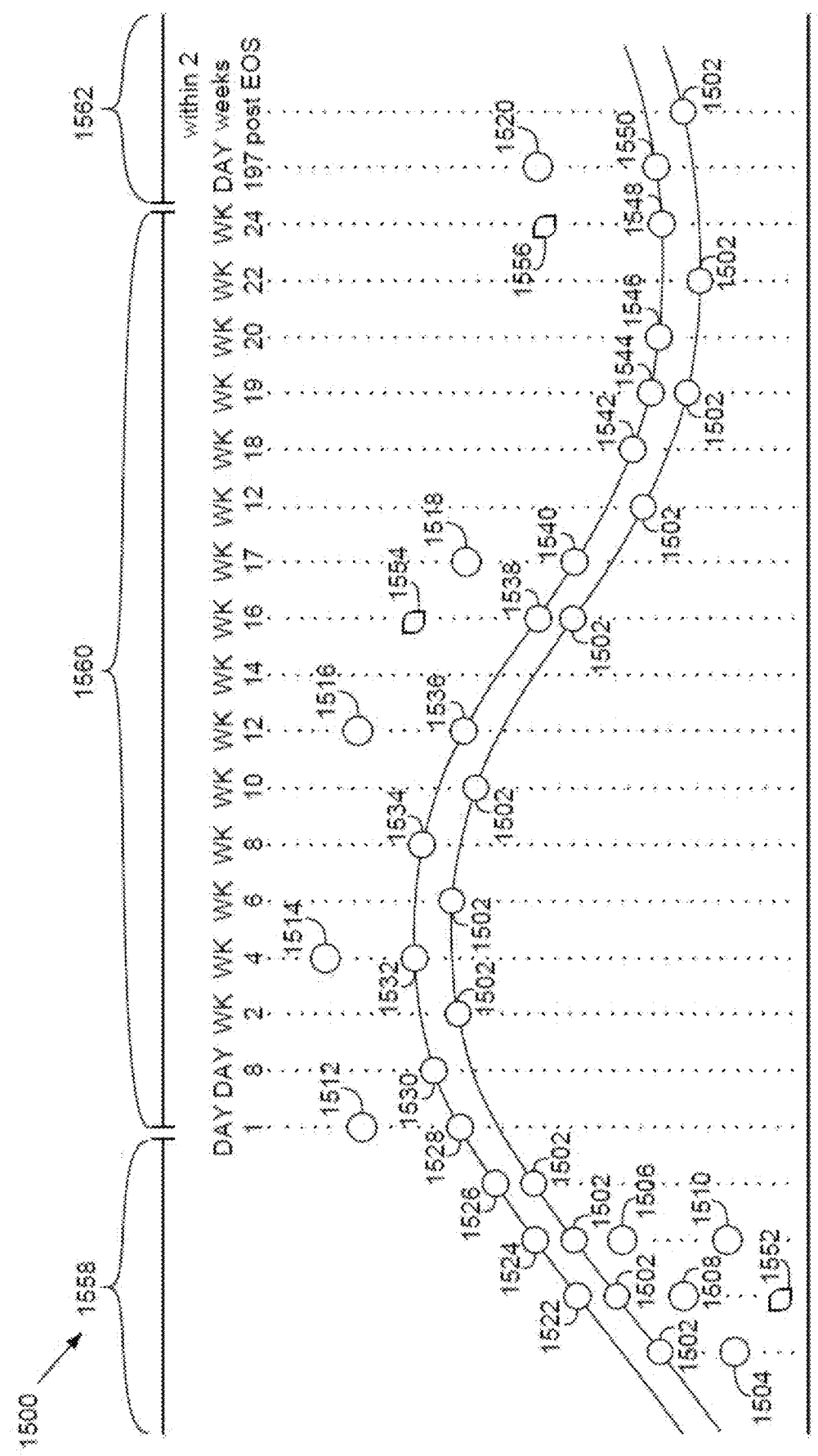
FIG. 15 schematically depicts an example patient journey.

With reference to FIG. 15, a non-limiting example of a patient journey 1500 and interactions with the platform over time is schematically depicted. As illustrated in FIG. 15, in addition to the categorizations of journey touch points 2701 described with reference to FIG. 27, journey touch points 2701 may also be categorized by pre-trial period 1558, trial period 1560, and post-trial period 1562. As shown in FIG. 15, journey touch points may coincide or otherwise be timed according to clinical visits 1522, 1524, 1526, 1528, 1530, 1532, 1534, 1536, 1538, 1540, 1542, 1544, 1546, 1548, and 1550, and/or according to other journey touch points such as concierge check-ins 1502. In certain embodiments, touch points may be utilized to maintain patient contact or appreciation, for example touch points 1552, 1554, 1556 may be scheduled times to send an appreciation kit or communication. For example, concierge check-ins 1502 may be categorized as transactional touch points 2730 and may keep the patient engagement platform in touch with the patient through, for example, assisting with scheduling, appointment reminders, and checking in the patient for a trial visit.

In an example, with reference to FIG. 15, touch points during a pre-trial period 1558 may include a prescreening touch point 1504 that greets the patient via one or more of the communication channels and provides information about the trial, a prescreening touch point 1508 that informs the patient via one of the communication channels that their results are in, a prescreening touch point 1506 that informs the patient via one or more of the communication channels of how to collect their A1C blood test and return it to the trial, which may be accompanied by a prescreening touch point 1510 that provides the patient with a procedure video. Of course, it should be understood that some of these pre-trial touchpoints may fall under various categories as described with reference to FIG. 27. For example, touch point 1510 providing the procedure video may also be an educational touch point 2720.

Furthermore, touch points during a trial period 1560 may include an educational touch point 1512 providing the patient with, e.g., information regarding nutrition management via one or more communication channels, an educational touch point 1514 providing the patient with, e.g., information about risks of developing a condition due to, e.g., diabetes via one or more communication channels, an educational touch point 1516 providing the patient with, e.g., information about diabetes management via one or more communication channels, and an educational touch point 1518 providing the patient with, e.g., information about the importance of portion control via one or more communication channels.

Additionally, touch points during a post-trial period 1562 may include a touch point 1520 that informs the patient of why their participation matters through one or more communication channels. Such a touch point may be categorized as both a marketing touch point 2770 and an educational touch point 2720. Additionally, as will be understood by one of ordinary skill upon review of this disclosure, some of the touch points described herein (such as touch point 1520) may also be categorized as nurturing touch points, as they enhance the good will and trust of the patient towards the platform and encourage further participation in the platform and trials referenced therethrough.

Figure 30:
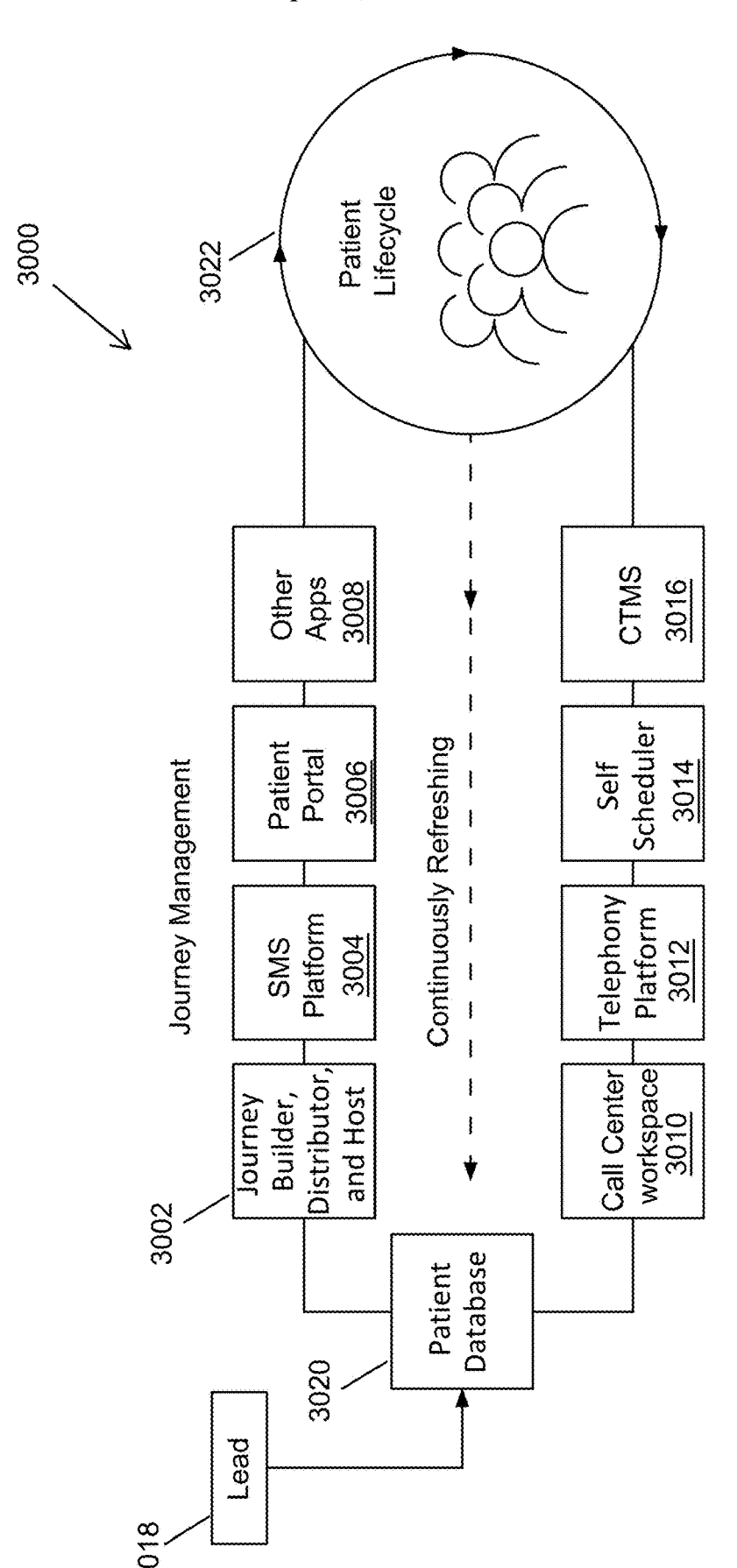
FIG. 30 depicts an example workflow and patient life-cycle managed by a platform.

Referencing FIG. 30, example operational flows for a patient engagement platform 101 are schematically depicted. The example of FIG. 30 includes a journey management flow including a journey builder operation (top flow) (e.g., as may be provided by a journey management component 2014) utilizing a messaging platform to perform patient engagement operations (e.g., using, and providing a patient portal that allows the patient to access the platform on-demand. The example of FIG. 30 includes a protocol lifecycle management flow that provides access to a call center, a telephony platform, and a self-scheduler, allowing the patient to access the platform to engage for help, support, scheduling, or the like. In the example of FIG. 30, the patient database 1630 may be utilized to support operations specific to the patient, and is refreshed over time to ensure that the patient portal, scheduling assistance, and the like, are configured for the patient over time as the patient is better understood by the patient engagement platform, and/or as the patient changes over time.

In some embodiments, the method 2600 according to example embodiments may be performed by a plurality of modular components 2010 configured to interface with each other over a network, including, for example, a journey management component 2014. In some embodiments, the method 2600 according to example embodiments may be stored as instructions on at least one non-transitory computer-readable storage medium that is executable by at least one processor.

Referencing FIG. 30, an example system 3000 to support operational flows (e.g., Journey Management, Protocol Lifecycle Management, and Continuously Refreshing) for a patient engagement platform 101 is schematically depicted. The example of FIG. 30 includes a journey management flow including a journey builder 3002 that manages a patient lifecycle 3022 (e.g., managing touch points of a patient journey), utilizing a messaging platform 3004 to perform patient engagement operations and exchange communications with the patient, and providing a patient portal 3006 that allows the patient to access the platform on-demand and to perform various operations as set forth herein by portal systems, possibly in combination with other applications 3008. The example of FIG. 30 includes a protocol lifecycle management flow that provides access to a call center 3010, a telephony platform 3012, a self-scheduler 3014 (e.g., allowing the patient to request or respond to various scheduling operations described therein), and a clinical trial management system (CTMS) 3016, which gathers clinical trial descriptions, allowing the patient to access the platform to engage for help, support, scheduling, or the like. In the example of FIG. 30, the patient database 3020 is utilized to support operations specific to the patient, and is refreshed over time to ensure that the patient portal, scheduling assistance, and the like, are configured for the patient over time as the patient is better understood by the patient engagement platform 101, and/or as the patient changes over time. The patient interacts with the example system 3000 as the LEAD 3018. The example system 3000 is a non-limiting example, and the system 3000 and/or components thereof may be embodied as, included with, and/or may include, all or a part of any other systems, portals, platforms, modules, components, or the like as set forth throughout the present disclosure.

Figure 34:
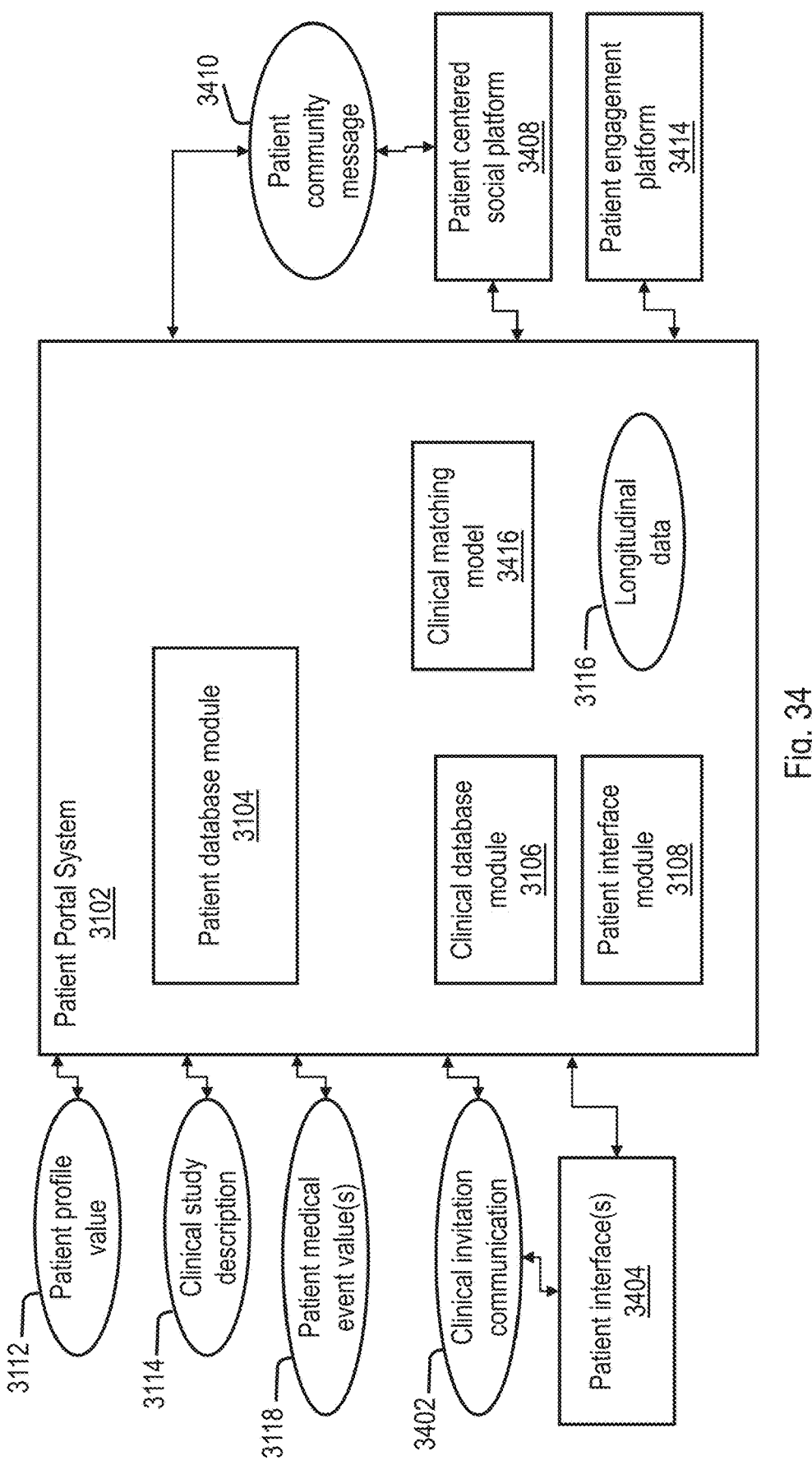
FIG. 34 depicts an example patient portal system.

Referencing FIG. 34, an example system for facilitating patient interactions to find relevant clinical studies, determine compatibility for clinical studies, and/or to access information about clinical studies is schematically depicted. The example system includes a patient portal system 3102 includes a patient database module 3104 configured to interpret a patient profile value 3112, a clinical database module 3106 configured to interpret a number of clinical study descriptions 3114, and a patient interface module 3108 configured to provide a clinical invitation communication 3402 to a patient (e.g., by implementing a patient interface 3404, and/or according to any other communications or messaging as set forth throughout the present disclosure) (where the patient may be, for example, a prospective patient or a present patient), in response to the patient profile value 3112 and one or more of the plurality of clinical study descriptions 3114.

A number of aspects of the present disclosure reference users of a platform, portal, system, or other embodiments as a patient. A patient, as utilized herein, should be understood broadly. Without limitation to any other aspect of the present disclosure, a patient includes any user that is seeking medical treatment, relevant clinical studies, and/or accessing any embodiments herein for medical information. A patient contemplates a person seeking or receiving medical treatment and/or participation in a clinical study, that may be prospectively seeking or receiving medical treatment and/or participation in a clinical study, and/or that accesses embodiments herein for other purposes such as for information and/or future preparation.

A number of aspects of the present disclosure reference interfaces of various types and directed to various parties (e.g., patients, users, stakeholders, or the like). Any such interfaces may be embodied according to any interfaces as set forth throughout the present disclosure, including, for example, a web page or portal, a web application, a mobile application, a platform according to any embodiment, and/or as communications directly to a user device (e.g., text messages, phone calls, e-mails, etc.), depictions on any of the foregoing (e.g., as a dashboard, graphical user interface, web page layout, notifications within any of these, a messaging service within any of these, etc.). In certain embodiments, an interface may be implemented in different ways depending upon the operations being performed, the time of day, the calendar date, the user device by which the user is accessing the system/portal/platform, and/or combinations of these at a given time or for a given operation. The terminology of the interface should be understood broadly. In certain embodiments, specific references to types of interfaces may be made to non-limiting illustrative examples of these to illustrate aspects of the present disclosure.

An example system 3102 includes the patient interface module 3108 implementing a patient outreach interface (e.g., as one of the patient interfaces 3404), and provides the clinical invitation communication 3402 to the patient on the patient outreach interface. In certain embodiments, the patient outreach interface may be a marketing interface, for example utilized to reach out to potential patients that are not presently enrolled with the system 3102, and/or that are not active on the system 3102. An example patient interface module 3108 is further configured to implement a patient messaging interface (e.g., as one of the patient interfaces 3404), and to provide the clinical invitation communication 3402 to the patient on the patient messaging interface. An example patient interface module 3108 provides the clinical invitation communication 3402 as a patient community message 3410, for example providing the clinical invitation communication 3402 to the patient as a user on a patient centered social platform 3408 (e.g., reference FIGS. 66-68, 24-25, 28-29 and the related description). An example patient interface module 3108 provides the clinical invitation communication 3402 to the patient by exercising a call center workflow (e.g., reference FIG. 30 and the related description, for example by providing an automated call with the clinical invitation communication 3402, and/or by providing the clinical invitation communication 3402 to the patient communicatively coupled through a human call center operator).

An example system 3102 includes a clinical matching model 3416 configured to match the patient to at least one clinical trial in response to the patient profile value 3112 and one or more clinical study descriptions 3114, and where the patient interface module 3108 is further configured to provide the clinical invitation communication in response to the match. In certain embodiments, the clinical matching model 3416 may operate a rules based expert system to determine the match, and/or may operate an artificial intelligence and/or machine learning component to perform the match (e.g., matching based on patient information that tends to result in a good fit for the clinical study, that results in successful enrollment, and/or that results in successful participation in and/or execution of the clinical study). In certain embodiments, the match may be made according to relevant medical conditions and/or suspected medical conditions of the patient, availability of the patient for the study (e.g., according to geography, time constraints, allergies, confounding medical conditions, or the like), limitations of the study (e.g., capacity of the study for number of patients, location of relevant study resources and/or study procedure locations, etc.). Without limitation to any other aspect of the present disclosure, patient-study matching operations may be performed, in whole or part, by embodiments set forth in FIGS. 52-58 and the related description.

An example patient interface module 3108 monitors interactions of the patient on the patient interface 3404, and updates the patient profile value 3112 in response to the monitored interactions. For example, monitored interactions may determine relevant conditions of the patient for suitability in other clinical studies, patient preferences and/or response performance for various communication aspects (e.g., communication method, language selection, time of day, targeted communication interface, etc.), patient interest in the study, etc.

Figure 35:
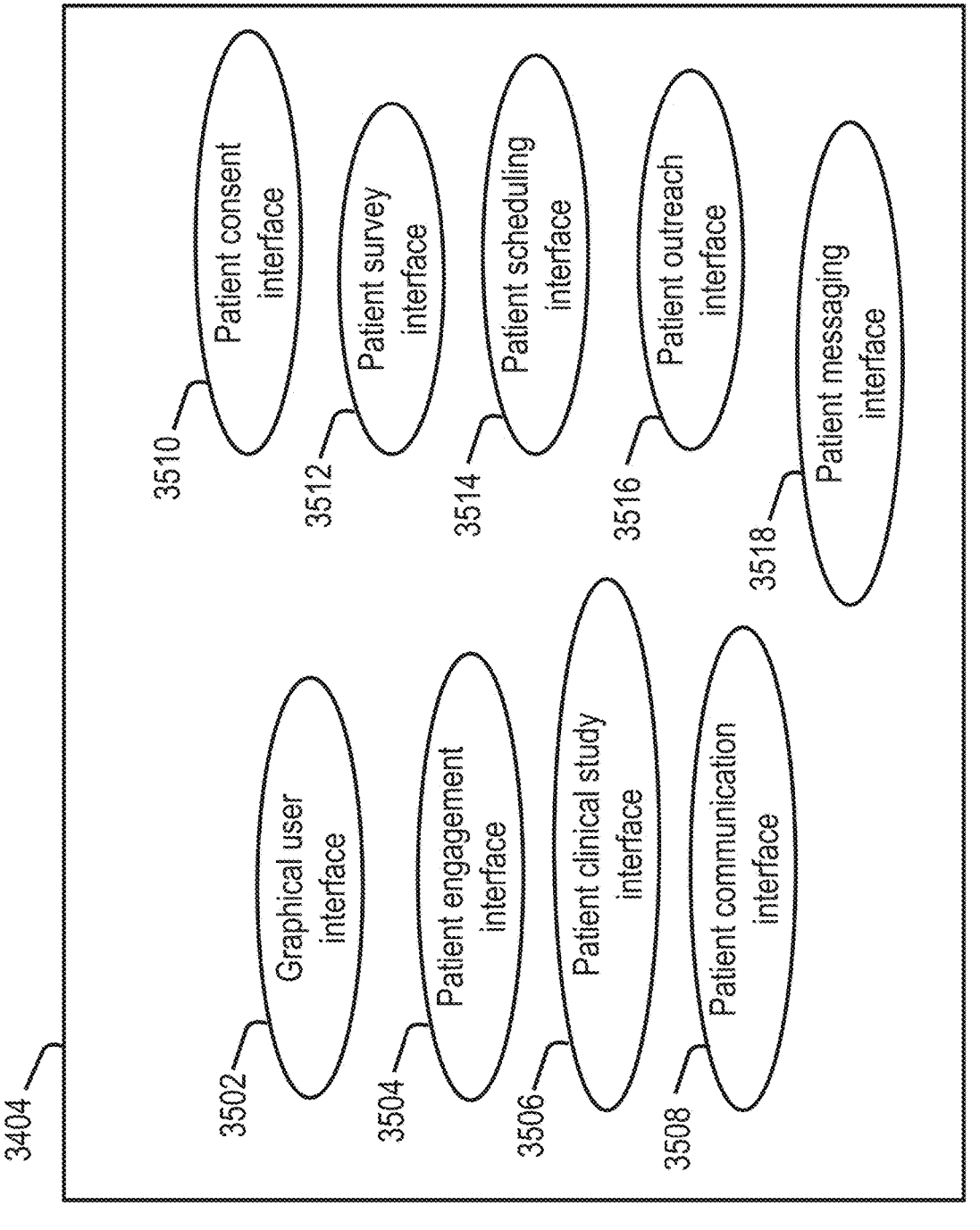
FIG. 35 depicts example elements of an illustrative patient interface.

Referencing FIG. 35, example and non-limiting patient interfaces 3404 are schematically depicted. The example interfaces 3404 include one or more of: a graphical user interface 3502 (e.g., provided on any platform, portal, system, etc. as set forth herein); a patient engagement interface 3504; a patient clinical study interface 3506; a patient communication interface 3508; a patient consent interface 3510 (e.g., exercising an interface to ensure patient awareness and consent, for example to utilize or share patient information); a patient survey interface 3512 (e.g., providing an interface for a patient to complete and submit a survey, for example to determine interest and/or suitability in a specific clinical study and/or a prospective clinical study); a patient scheduling interface 3514 (e.g., utilized to facilitate patient scheduling for any contacts, procedures, tests, etc., for example screening procedures and/or enrollment procedures for a clinical study); a patient outreach interface 3516; and/or a patient messaging interface 3518 (e.g., messaging to a patient for any embodiments herein, including direct messaging, messaging through any portal, application, system, platform, or the like as set forth throughout the present disclosure). An example patient database module 3104 provides at least a portion of the patient profile value 3112 to a patient engagement platform 3414 (e.g., as described herein), for example where the patient profile value 3112 includes information for a new patient, and/or new information for an existing patient, and/or according to information developed through monitored communications on the patient interface 3404, information submitted during screening or enrollment operations, or the like. In certain embodiments, the patient profile value 3112 may be added to, or replace previous information, for any patient profile value as set forth throughout the present disclosure, and/or for any longitudinal data 3116 corresponding to the patient.

Figure 36:
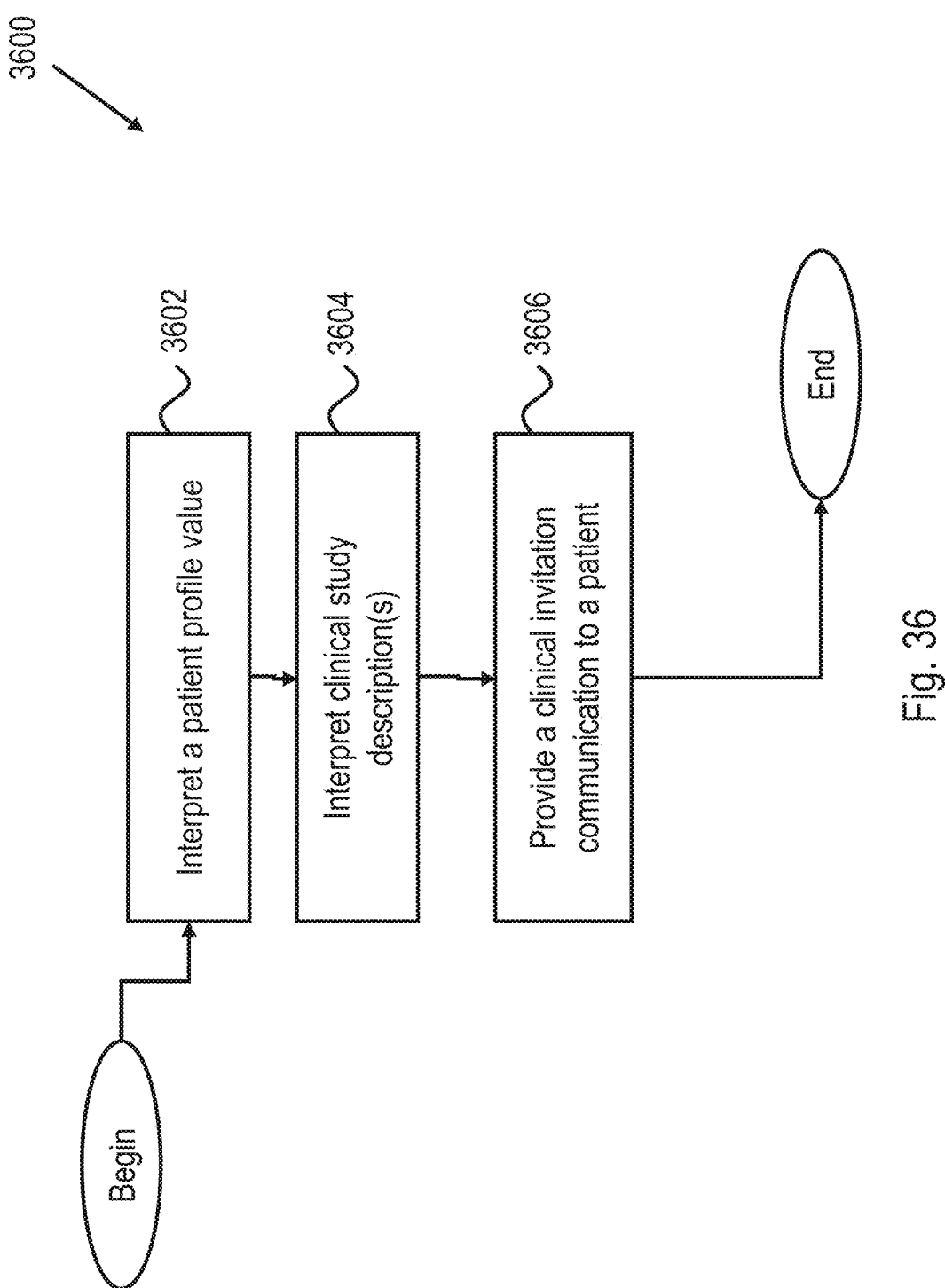
FIG. 36 depicts an example procedure for providing a clinical invitation communication.
Figures 37, 38:
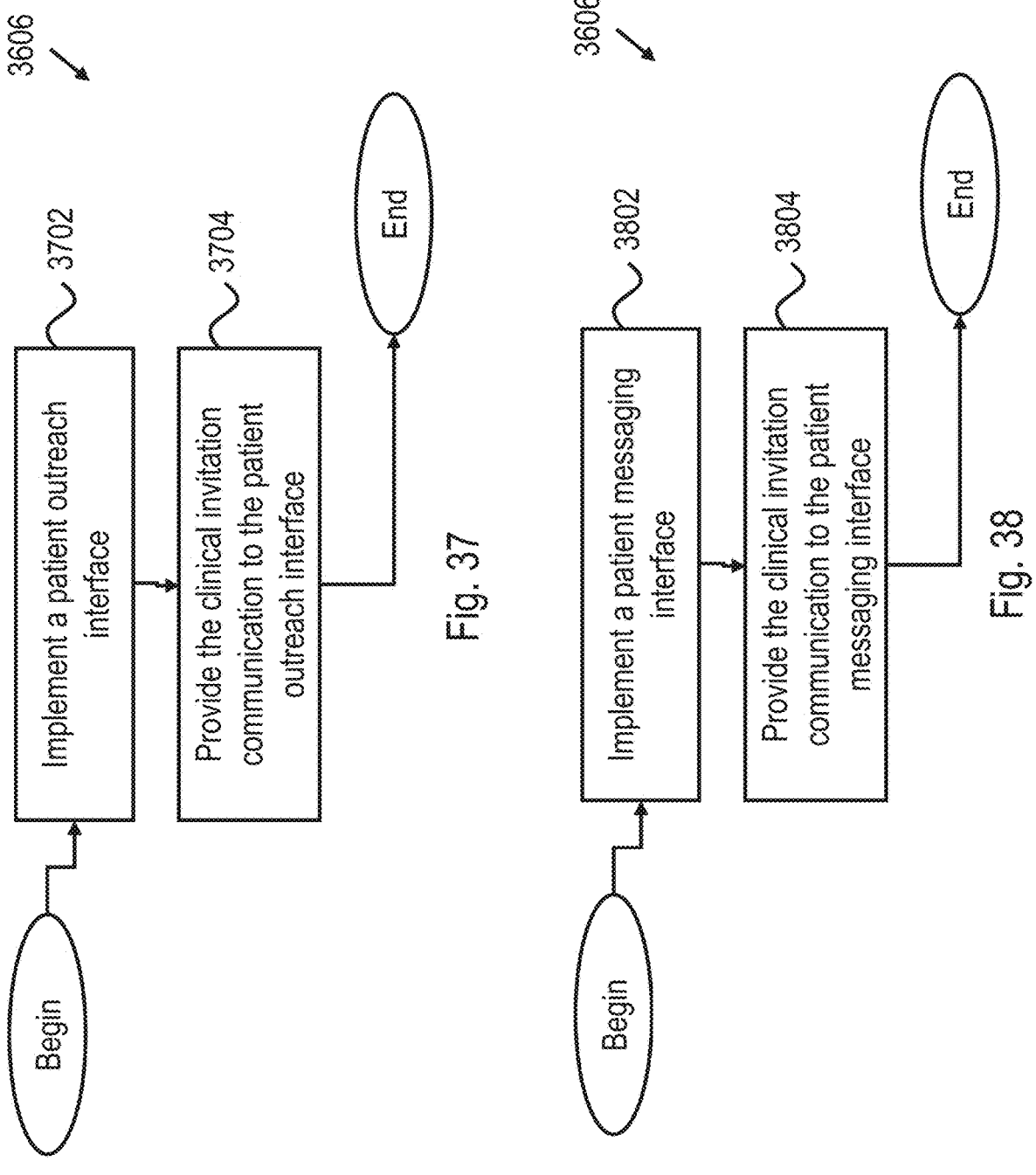
FIG. 37 depicts an example procedure for providing a clinical invitation communication.
FIG. 38 depicts an example procedure for providing a clinical invitation communication.

Referencing FIG. 36, an example procedure 3600 for facilitating patient interactions to find relevant clinical studies, determine compatibility for clinical studies, and/or to access information about clinical studies is schematically depicted. The example procedure 3600 include an operation 3602 to interpret a patient profile value, an operation 3604 to interpret a clinical study description, and an operation 3606 to provide a clinical invitation communication to a patient corresponding to the patient profile value. Referencing FIG. 37, an example operation 3606 to provide a clinical invitation communication includes an operation 3702 to implement a patient outreach interface, and an operation 3704 to provide the clinical invitation communication to the patient outreach interface. Referencing FIG. 38, an example operation 3606 includes an operation 3802 to implement a patient messaging interface, and an operation 3804 to provide the clinical invitation communication to the patient messaging interface.

Figure 39:
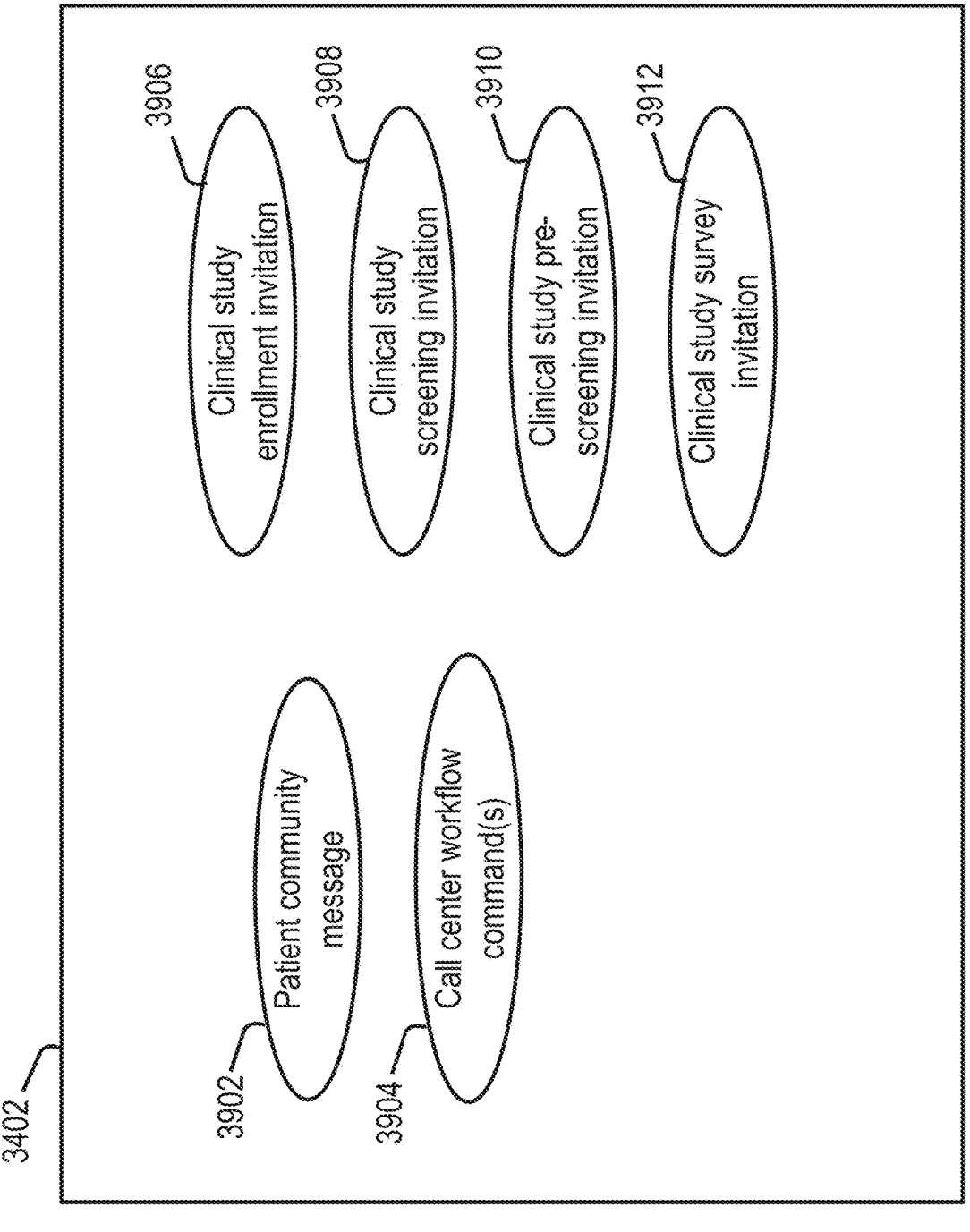
FIG. 39 depicts illustrative clinical invitation communications.

Referencing FIG. 39, example and non-limiting clinical invitation communications 3402 are schematically depicted. The example clinical invitation communications 3402 include one or more of: a patient community message 3902 (e.g., providing an invitation to a clinical study to a patient community on a patient centered social platform, for example where the patient community is focused on an aspect of interest for the clinical study); a call center workflow command 3904 (e.g., an automated communication, such as exercising an API to implement an automated call, and/or a command to a human operated call center, for example including call timing, call number to be utilized, dialog to be utilized, answers to common questions related to the clinical study, etc.); a clinical study enrollment invitation 3906 (e.g., providing a communication inviting the patient to enroll in a clinical study, and/or further including an action object allowing the patient to conveniently begin the enrollment process); a clinical study screening invitation 3908 (e.g., providing a communication inviting the patient to commence screening operations for a clinical study, and/or further including a survey, preliminary questions, information about the study, and/or an action object allowing the patient to conveniently begin the screening process); a clinical study pre-screening invitation 3910 (e.g., providing a communication inviting the patient to commence pre-screening operations, providing highly effective gating or selecting criteria for the user, or the like, which may be similar to a clinical study screening invitation 3908); and/or a clinical study survey invitation 3912 (e.g., providing a communication that directs the user to a survey, and/or that embodies the survey, for example to determine if the patient is a good fit for a clinical study, is interested in the clinical study, and/or is otherwise a potential subject that may benefit from the clinical study.

Figure 40:
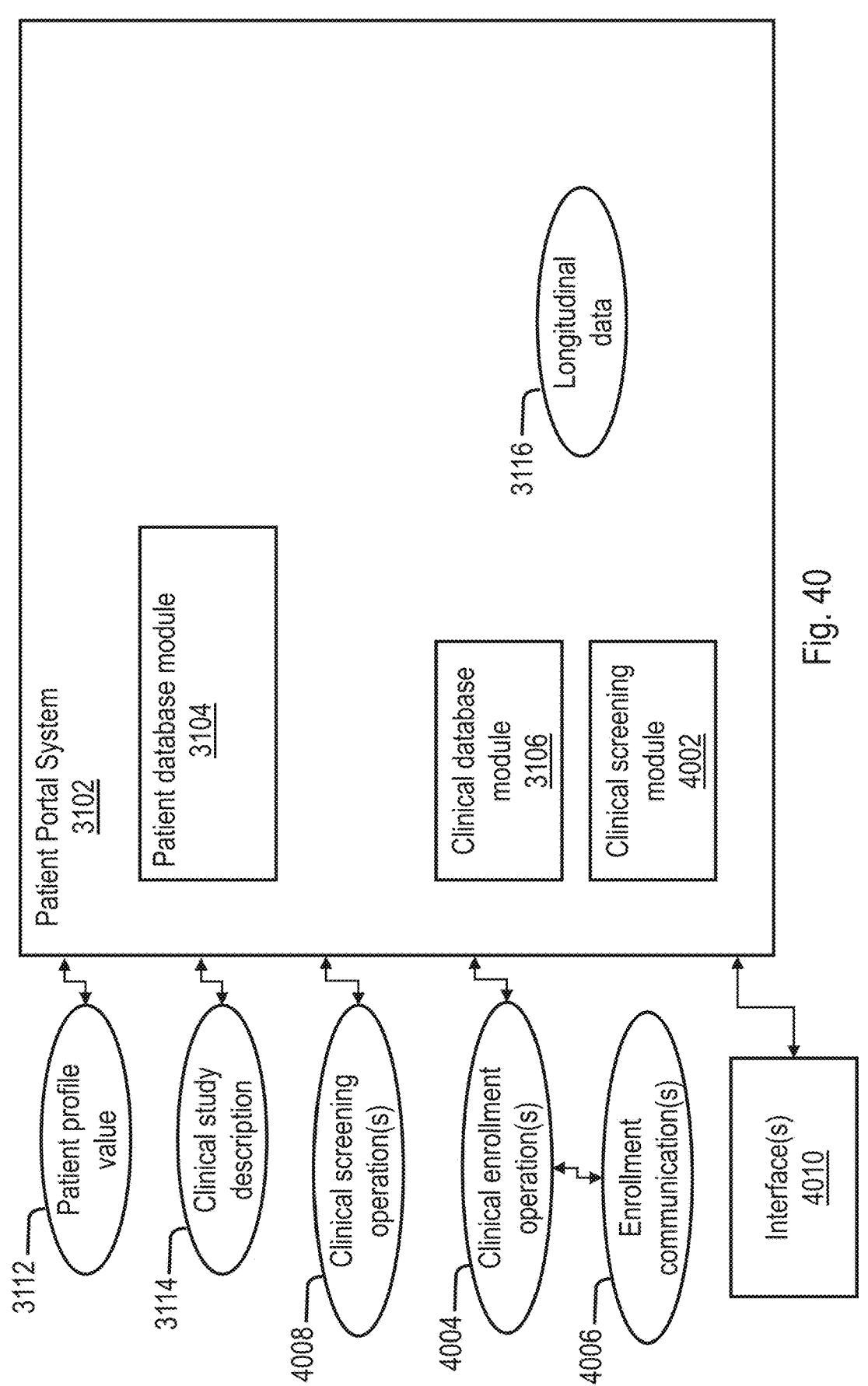
FIG. 40 depicts an example patient portal system.
Figure 41:
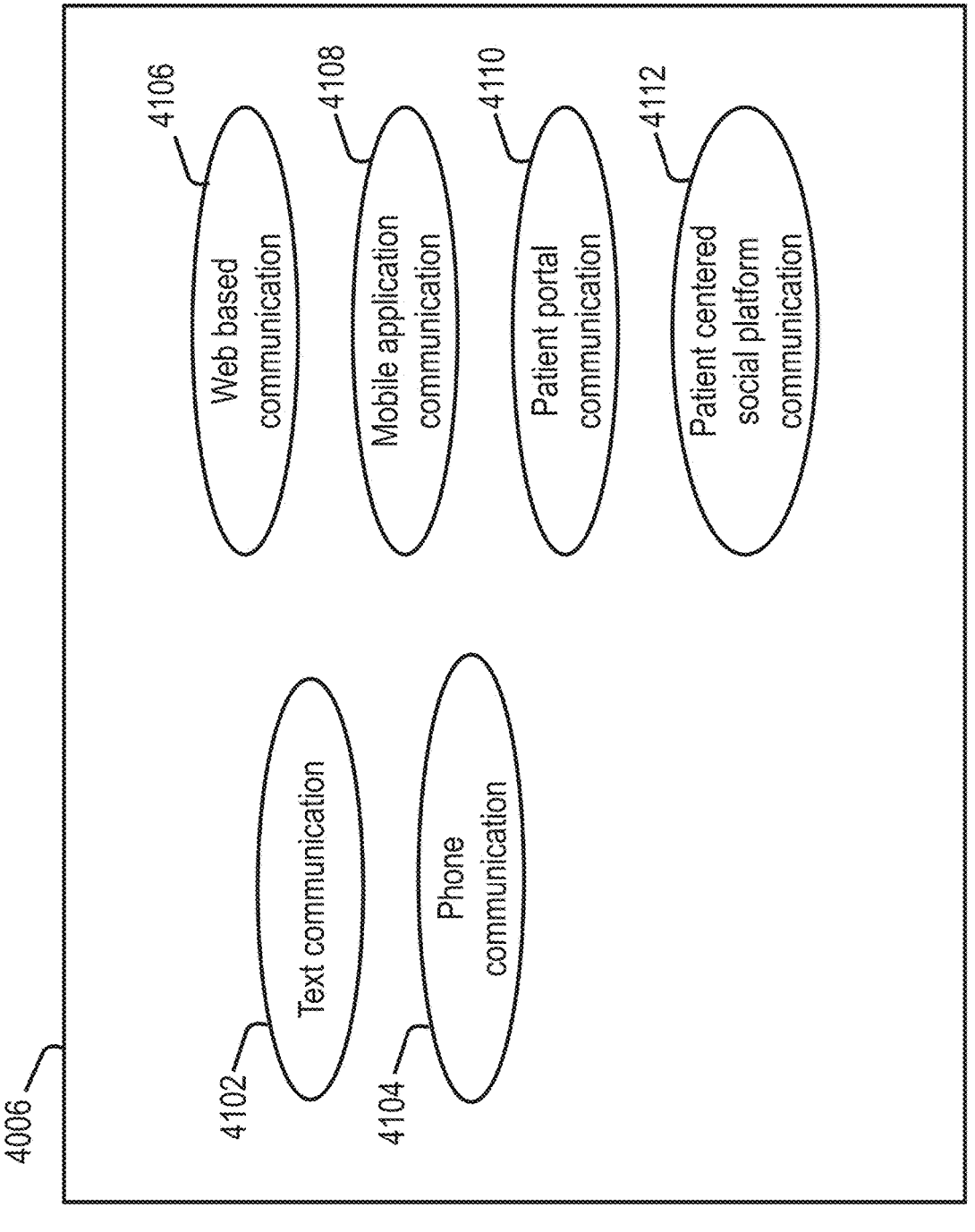
FIG. 41 depicts illustrative enrollment communications.

Referencing FIG. 40, an example system 3102 to engage a patient at any stage of progression through a clinical study is schematically depicted. Without limitation, the example system 3102 of FIG. 40 is particularly useful to ensure that the enrollment process is convenient, screens patients quickly that are not a good fit for the study, and saves computing resources that would otherwise be utilized on ineffective communications with patients and/or an extended enrollment process for patients that are not a good fit for the clinical study, and therefore will not be likely to be able to participate in the study, or succeed in executing operations of the clinical study. The example system 3102 includes a patient database module 3104 configured to interpret a patient profile value 3112 corresponding to a patient, a clinical database module 3106 configured to interpret a plurality of clinical study descriptions 3114, and a clinical screening module 4002 configured to perform a clinical enrollment operation 4004 in response to the patient profile value and at least one of the plurality of clinical study descriptions 3114. The example clinical screening module 4002 is further configured to perform the clinical enrollment operation 4004 by providing enrollment communications 4006 to the patient, for example utilizing any interface 4010 as set forth herein. Referencing FIG. 41, example and non-limiting enrollment communications 4006 are schematically depicted. In certain embodiments, an enrollment communication 4006 may be embodied in more than one form at a time, for example to ensure that certain communications are successful, to provide information that may be utilized to determine the best communication methods to the patient, or the like. The example enrollment communications 4006 include one or more of: a text communication 4102; a phone communication 4104; a web based communication 4106 (e.g., provided on a web portal, web page, or the like); a mobile application communication 4108 (e.g., a communication utilizing a mobile application, for example as an interface, and/or utilized to access any system, portal, and/or platform as set forth herein); a patient portal communication 4110 (e.g., as a message, notification, dashboard item, or the like on any portal as set forth herein); and/or as a patient centered social platform communication 4112 (e.g., to a user feed, to a relevant patient community feed, and/or to a messaging system of the platform).

Figure 42:
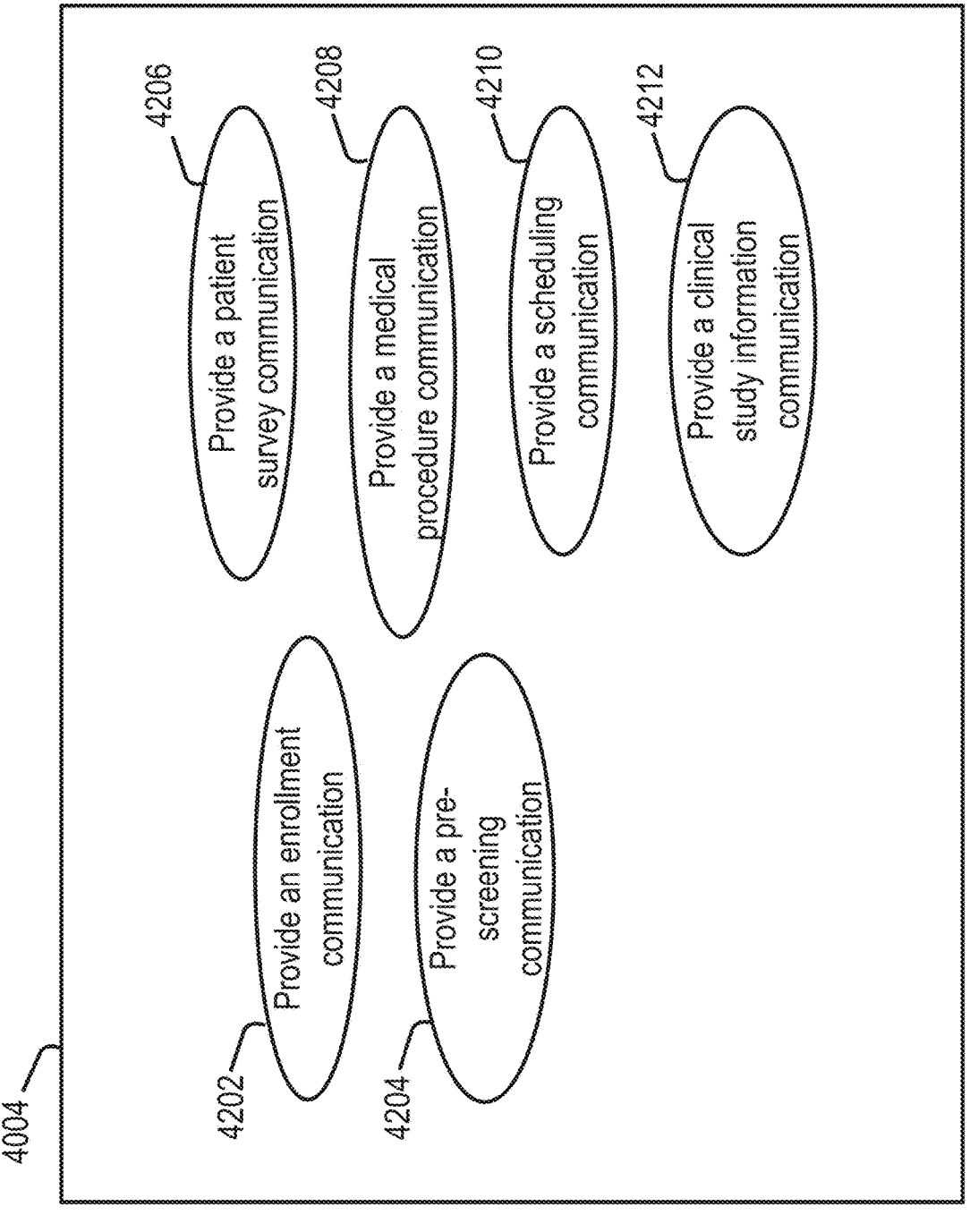
FIG. 42 depicts illustrative clinical enrollment operations.
Figure 43:
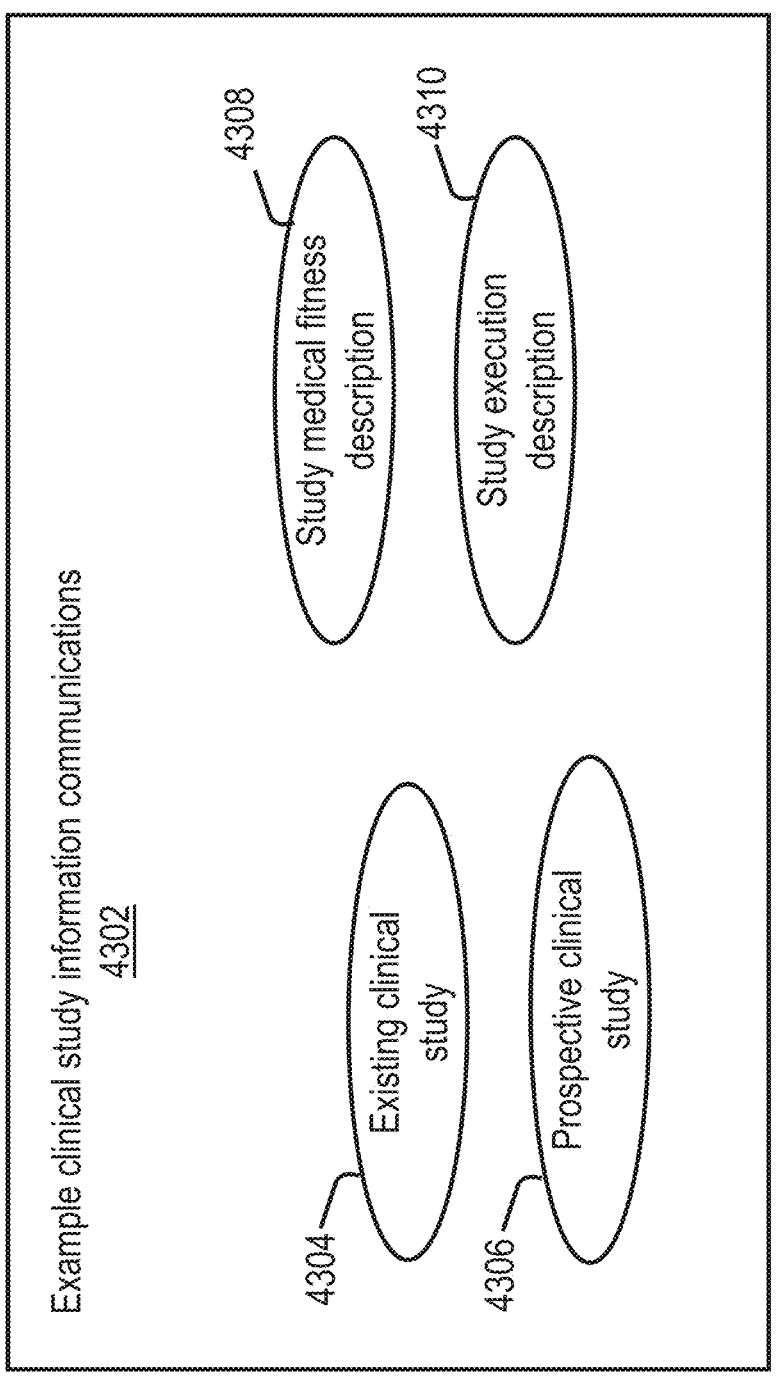
FIG. 43 depicts illustrative clinical study information communications.

Referencing FIG. 42, example and non-limiting clinical enrollment operations 4004 include one or more operations such as: an operation 4202 to provide an enrollment communication; an operation 4204 to provide a pre-screening operation; an operation 4206 to provide a patient survey communication; an operation 4208 to provide a medical procedure communication (e.g., including informing of an upcoming procedure, scheduling a procedure, providing preparatory information for the procedure, providing a question-response dialog about the procedure, etc.); an operation 4210 to provide a scheduling communication (e.g., providing a reminder of any procedure, treatment, communications or information, and/or allowing the user to schedule any one or more of these, for example facilitating communications between the patient and the provider, including potentially interfacing directly with the provider scheduling system); and/or an operation 4212 to provide a clinical study information communication (e.g., providing an information sheet, frequently asked questions, study documentation, and/or an interactive question response dialog about the clinical study). Referencing FIG. 43, example and non-limiting clinical study communications 4302 are schematically depicted, for example which may be utilized with operation 4212 or any other embodiments herein. Example clinical study communications 4302 include one or more of: an existing clinical study 4304 (e.g., describing the study, the goals of the study, relevant patient/participant information, etc.); a prospective clinical study 4306 (e.g., which may be utilized to determine a level of interest in a study, whether a sufficient patient group is available, whether patient locations will be compatible with planned study resources, etc.); a study medical fitness description 4308 (e.g., allowing the patient and/or a clinical study group to determine whether the clinical study is likely to be medically appropriate for the patient); and/or a study execution description 4310 (e.g., allowing the patient and/or a clinical study group to determine whether the clinical study is likely to be operatively appropriate for the patient—for example based on geographic location, patient time commitment, number and/or scheduling of procedures, compatibility with study requirements or activity regimes, or the like).

Figure 44:
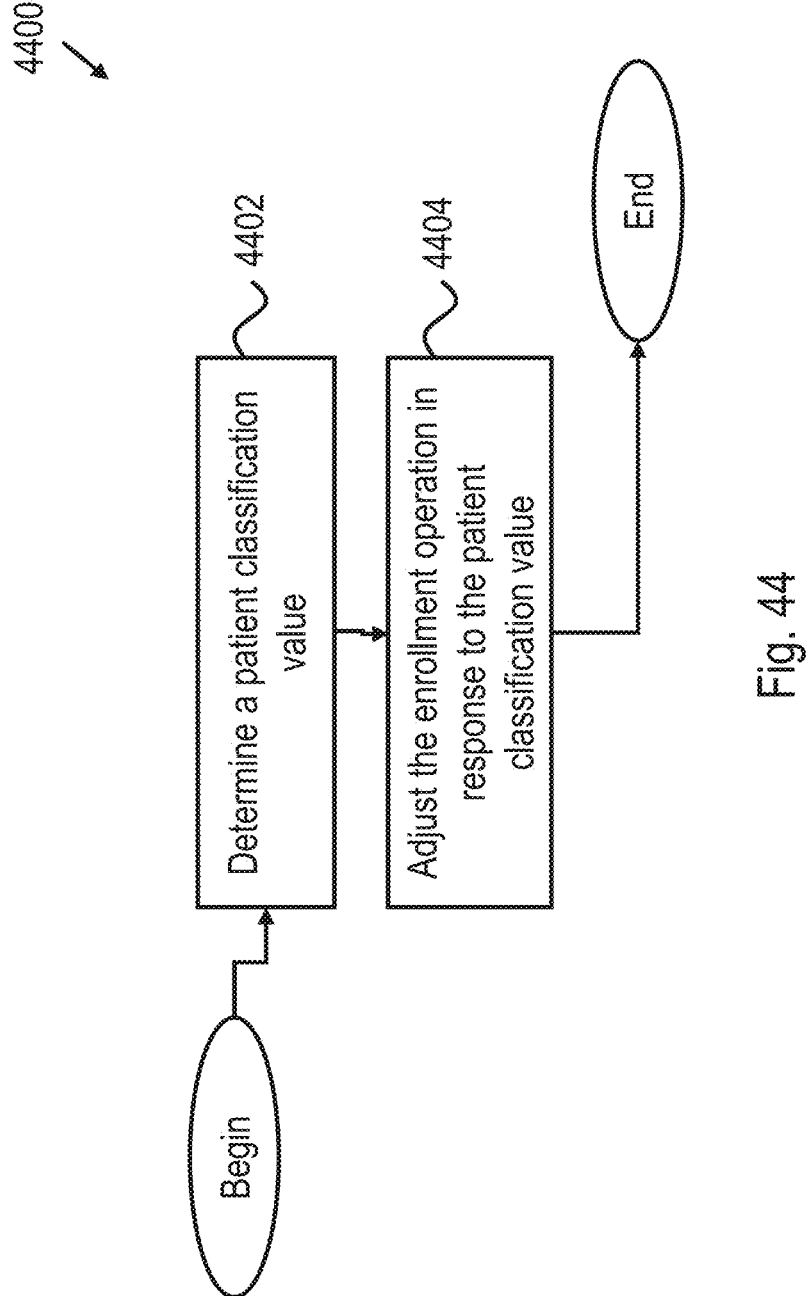
FIG. 44 depicts an example procedure to adjust enrollment operations in response to a patient classification value.

Referencing FIG. 44, an example procedure 4400 to engage a patient at any stage of progression through a clinical study is schematically depicted. The example procedure 4400 includes an operation 4402 to determine a patient classification value, and an operation 4404 to adjust the enrollment operation (e.g., clinical enrollment operation 4004) in response to the patient classification value. In certain embodiments, the patient classification value may be utilized to classify patients into relevant categories, allowing for embodiments herein to more rapidly converge on messaging or communication techniques, to match patients to appropriate studies, to configure touch points with the patient, or the like, while conserving system resources that would otherwise be able to converge on these values over time. Accordingly, the patient classification value may be utilized to determine similarity between various patients along any dimension, for example based on medical conditions (e.g., diagnoses, symptoms, allergies, etc.), geography (e.g., location and/or available locations that would be convenient based on the travel flexibility of the patient), scheduling, demographics (e.g., demographic factors that may be relevant to medical conditions, treatments, clinical studies, or the like), preferred communication methodology, medical treatment preferences, or the like. A given patient may have more than one, or many, associated classification values, for example depending on the purpose of a given classification as utilized by any system, portal, platform, or other embodiments as set forth throughout the present disclosure.

Figure 45:
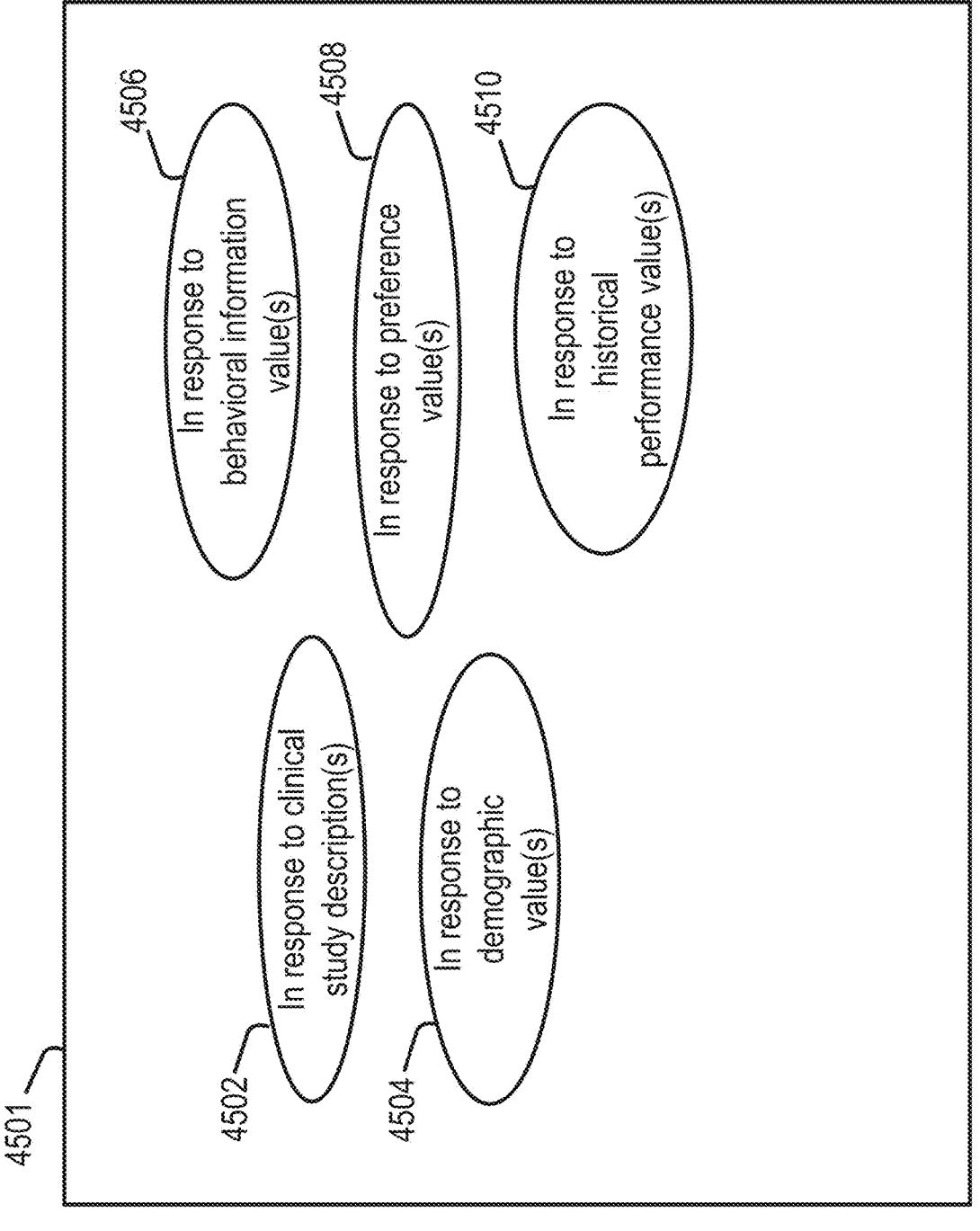
FIG. 45 depicts illustrative considerations for determining a patient classification value.

Referencing FIG. 45, example operations that may be utilized to determine one or classification values 4501 include, without limitation, determining the classification value, at least in part, in response to: the clinical study description 4502 (e.g., description aspects that match or have a relationship to the patient's profile value and/or longitudinal data, and/or that appear to be of interest to the patient based on patient activity); demographic values 4504 (e.g., demographic values, and/or presence within buckets of values (e.g., within an age range), that may indicate compatibility with certain studies, treatments, messaging preferences, etc.); behavioral information values 4506 (e.g., behavioral information that may indicate compatibility or lack thereof with certain treatment regimes, medication regimes, indicate compatibility with characteristics that may indicate long term success for certain treatments, and/or lifestyle behaviors that may indicate that certain procedures and/or studies are likely to be successful or not); preference values 4508 (e.g., classifying the patient based on preferences indicated by the patient in any platform, system, portal, or the like, which preferences may be explicit such as defined values set by the patient, or inferred, for example based on the engagement methods utilized by the patient); and/or historical performance values 4510 (e.g., based on patient interactions with any platform, system, portal, or the like, and/or based on historical scheduling, treatment, medication, compliance with procedures, or the like, for example for medical procedures and/or clinical studies).

Figure 46:
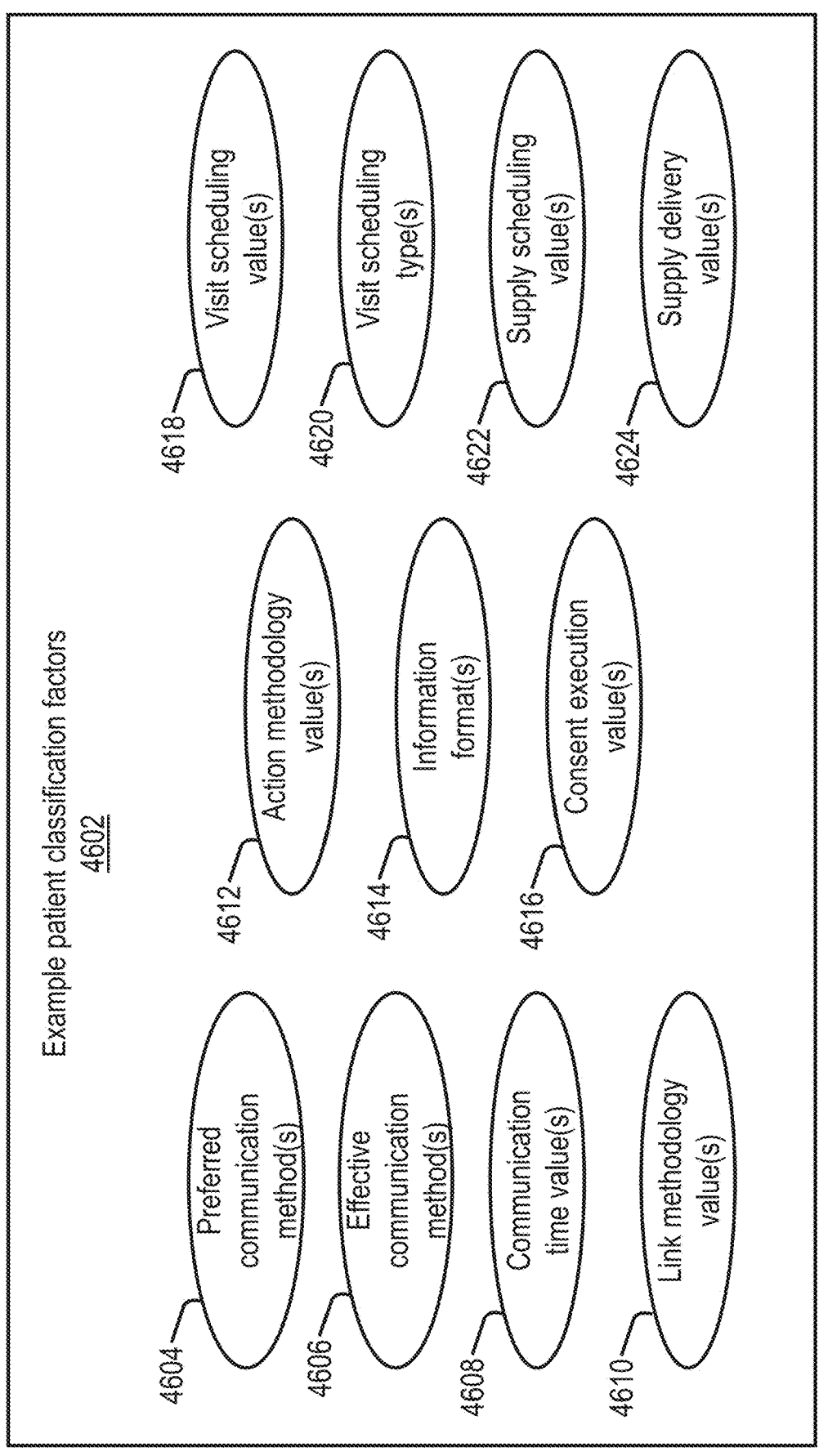
FIG. 46 depicts illustrative patient classification factors.

Referencing FIG. 46, example and non-limiting patient classification factors 4602, for example describing classifying dimensions which embodiments herein may benefit from. Example patient classification factors 4602 include one or more of: preferred communication methods 4604 (e.g., which may be dependent upon the context, including user device access, time of day, calendar time, etc.); effective communication methods 4606 (e.g., communication methods that are likely to reach the patient, and/or that the patient is likely to be responsive to); communication time values 4608 (e.g., communication timing, calendaring, frequency, etc.); link methodology values 4610 (e.g., reference FIG. 5 and the related description, including link formatting, link graphical depictions, links according to communication type or user device, etc.); action methodology values 4612 (e.g., reference FIG. 5 and the related description, including type of action object, graphical depiction, relevant platform/system/portal, communication type or user device, etc.); information formats 4614 (e.g., text flows, tables, graphs, inclusion of FAQs and/or particular types of questions and answers, etc.); consent execution values 4616 (e.g., classifying users according to consent content and/or consent execution); visit scheduling values 4618 (e.g., classifying users according to effective scheduling techniques, touch point methods, scheduling preferences such as time of day, visit frequency and/or clustering preferences, etc.); visit scheduling types 4620 (e.g., how the scheduling is performed, preferred facility types, etc.); supply scheduling values 4622 (e.g., scheduling for supplies for medical treatments, clinical studies, treatment regimes, etc.); and/or supply delivery values 4624 (e.g., supply delivery frequency, time of day, receiving considerations such as mailing, shipping, PO Box utilization, etc.).

Again referencing FIG. 40, an example clinical screening module 4002 is configured to perform a clinical screening operation 4008 in response to the patient profile value 3112 and at least one of the plurality of clinical study descriptions 3114. An example clinical screening operation 4008 includes providing a digital screening questionnaire, for example including selective screening information such as medical conditions, demographic suitability, geographic suitability, and/or allergy information, that is likely to exclude the patient from a clinical study, saving the patient time and system resources utilized further in the enrollment process. An example clinical screening module 4002 performs the clinical enrollment operation 4004 in response to communications from the patient responsive to the digital screening questionnaire. An example clinical screening module 4002 is further configured to perform the clinical screening operation 4008 by pre-completing at least one value of a digital screening questionnaire for the patient, by pre-completing at least one value of a clinical study survey, and/or by pre-completing at least one value of an enrollment document.

Figure 47:
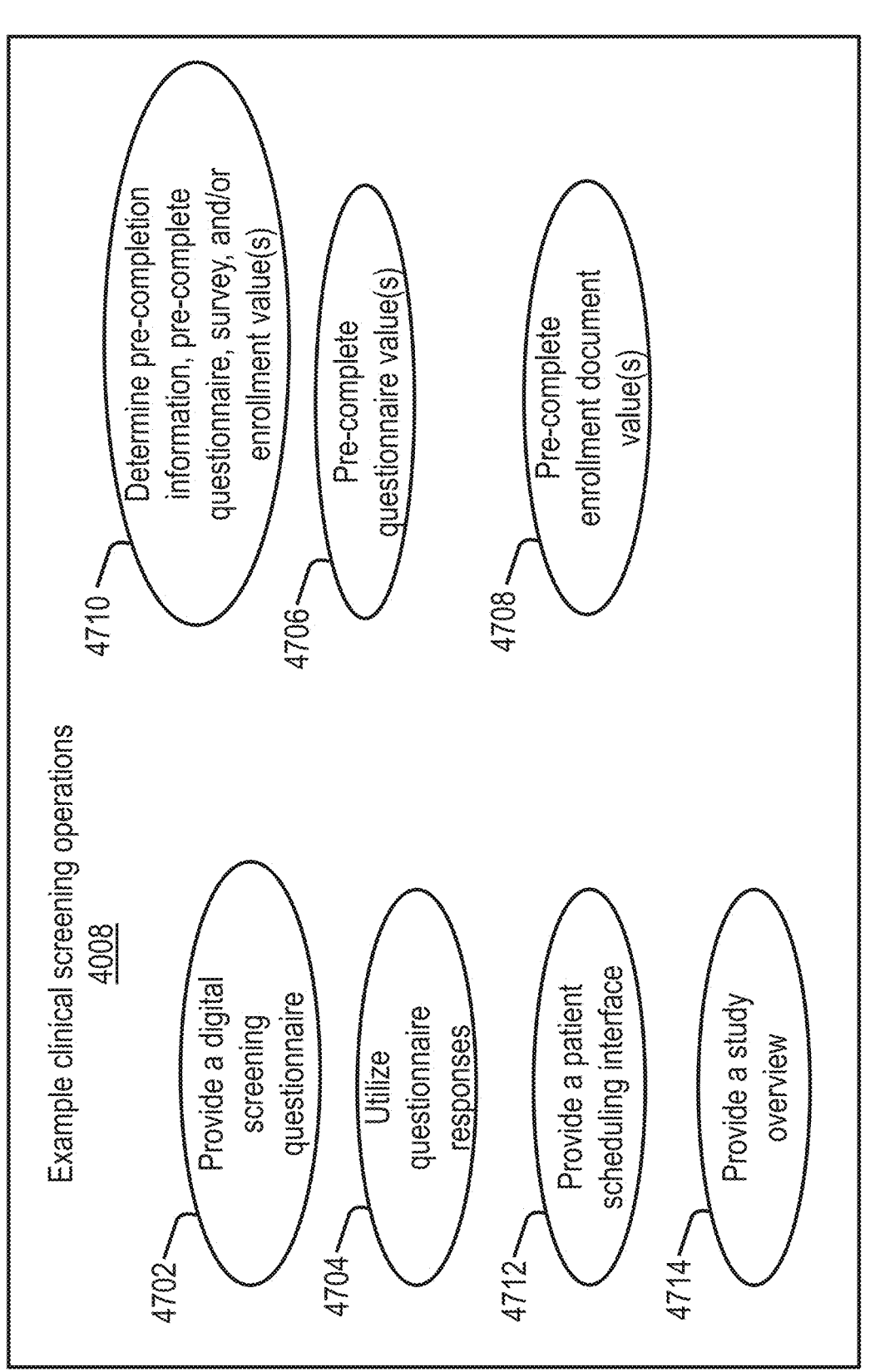
FIG. 47 depicts example clinical screening operations.

Referencing FIG. 47, example and non-limiting clinical screening operations 4008 are schematically depicted, and include one or more operations such as: an operation 4702 to provide a digital screening questionnaire; an operation 4704 to utilize questionnaire responses (e.g., to classify the patient, to determine compatibility with a clinical study, medical treatment, medication, etc., and/or to update patient longitudinal data); an operation 4706 to pre-complete questionnaire value (e.g., providing a questionnaire with one or more questions completed based on information known, estimated, or inferred about the patient, which may for example further prompt the user to confirm the information); an operation 4708 to pre-complete enrollment document values; an operation 4710 to determine pre-completion information (e.g., utilizing patient profile values, longitudinal data, historic performance data, classification values, or the like) and to pre-complete any patient communication or interaction (e.g., a questionnaire, survey, and/or value on an enrollment document); an operation 4712 to provide a patient scheduling interface; and/or an operation 4714 to provide a study overview.

Figure 48:
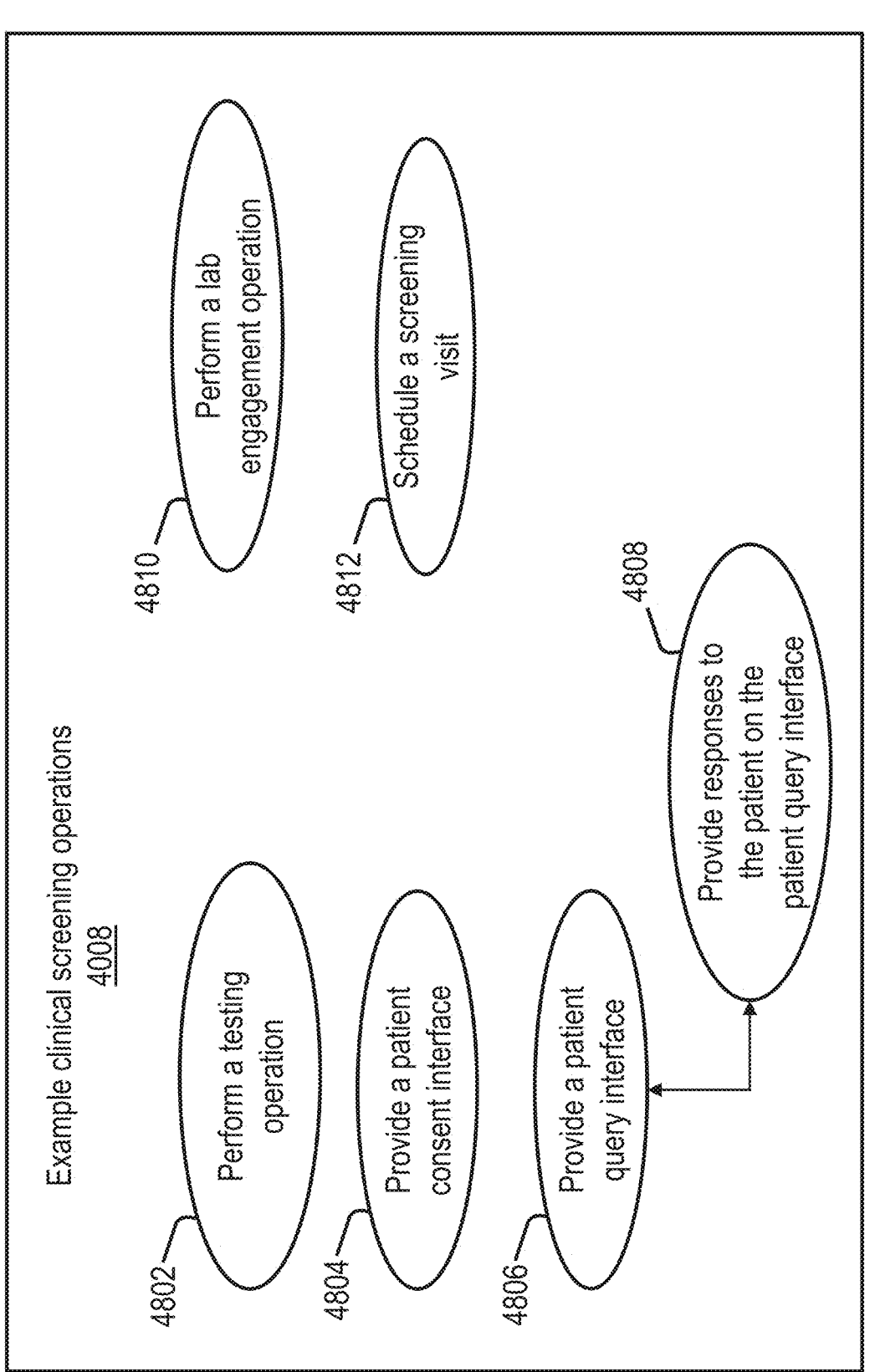
FIG. 48 depicts example clinical screening operations.

Referencing FIG. 48, additional or alternative example clinical screening operations 4008 are schematically depicted, and include one or more operations such as: an operation 4802 to perform a testing operation (e.g., scheduling a test and/or shipping a test to the patient, for example a test to confirm suitability for a clinical trial and/or compatibility with treatments and/or medications utilized in the clinical trial); an operation 4804 to provide a patient consent interface (e.g., to facilitate implementation of appropriate consents for the clinical study, and/or to provide clear consent information to the patient); an operation 4806 to provide a patient query interface (e.g., to allow the patient to request information about the clinical study); an operation 4808 to provide responses to the patient on the patient query interface (e.g., utilizing an automated query response operation, such as answers from a large language model, answers from a database responsive to text recognized and classified questions from the patient, and/or utilizing a human interface such as a chat interface); an operation 4810 to perform a lab engagement operation (e.g., scheduling lab procedures, providing instructions and/or preparations to the patient, and/or providing lab results to the patient and/or a stakeholder such as a clinical study group and/or medical provider); and/or an operation 4812 to schedule a screening visit (e.g., whether at a medical provider location, administrative office, and/or at a patient location such as the patient's home or workplace).

Figure 49:
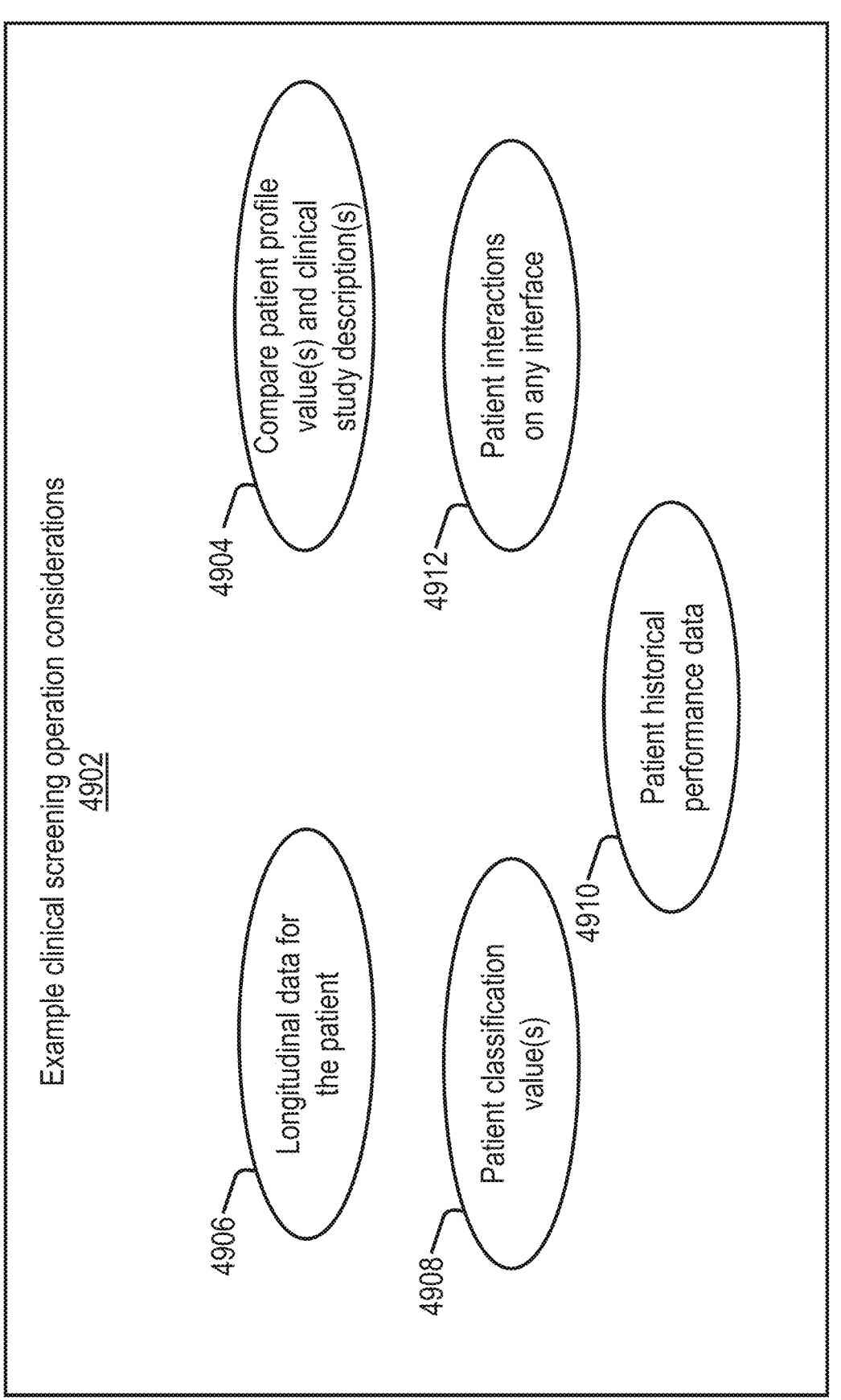
FIG. 49 depicts illustrative considerations for performing a clinical screening operation.

Referencing FIG. 49, example and non-limiting considerations 4902 utilized to perform clinical screening operation 4008 are schematically depicted. Example considerations 4902 include performing the clinical screening operations in response to one or more of: longitudinal data for the patient 4906; patient classification values 4908; a comparison between the patient profile value(s) (and/or longitudinal data for the patient) and relevant clinical study descriptions 4904; patient historical performance data 4910 (e.g., with regard to any platform, system, portal, or other embodiments as set forth throughout the present disclosure); and/or patient interactions on any interface 4912 as set forth throughout the present disclosure.

Figure 50:
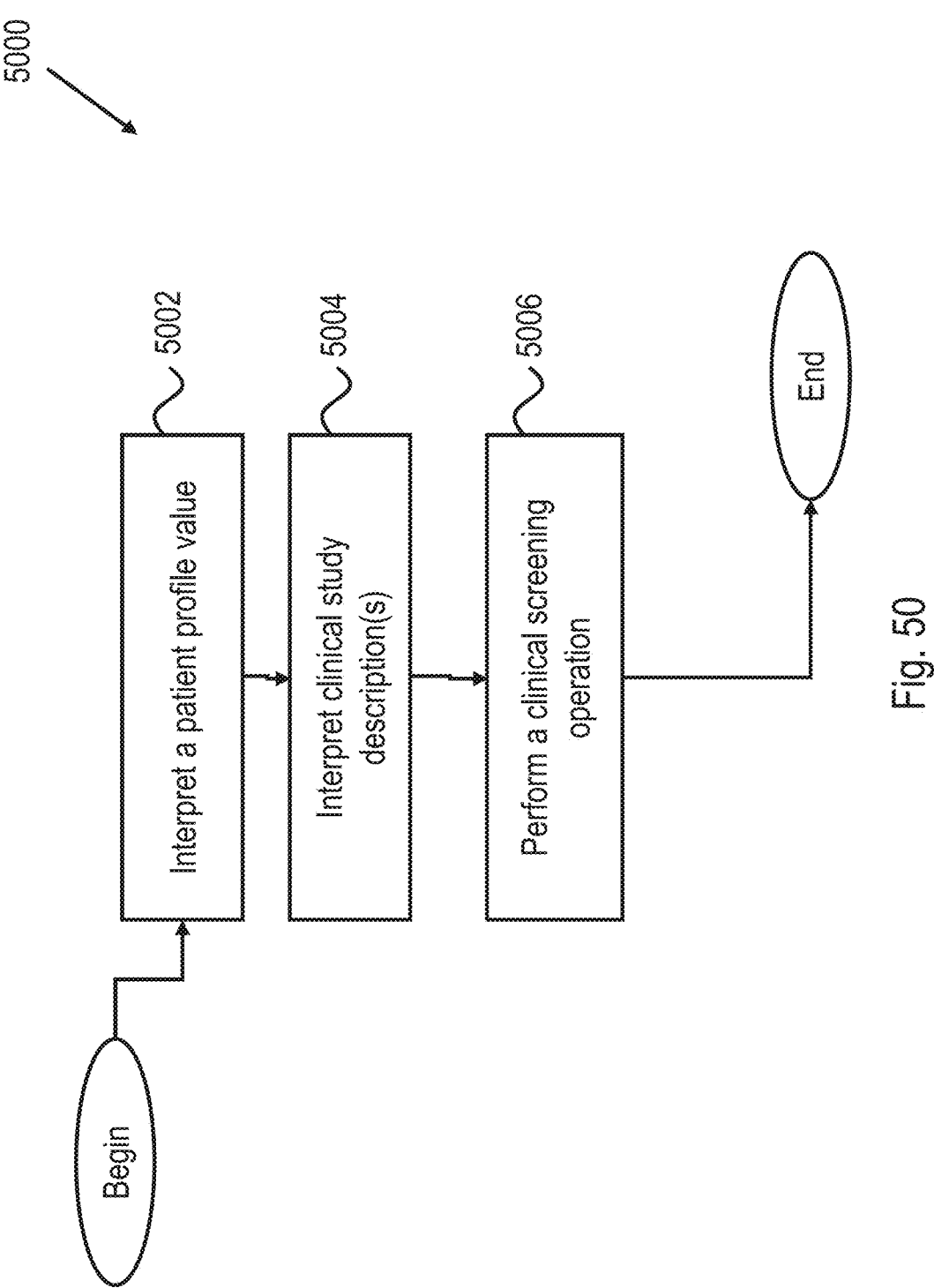
FIG. 50 depicts an example procedure to perform a clinical screening operation.
Figure 51:
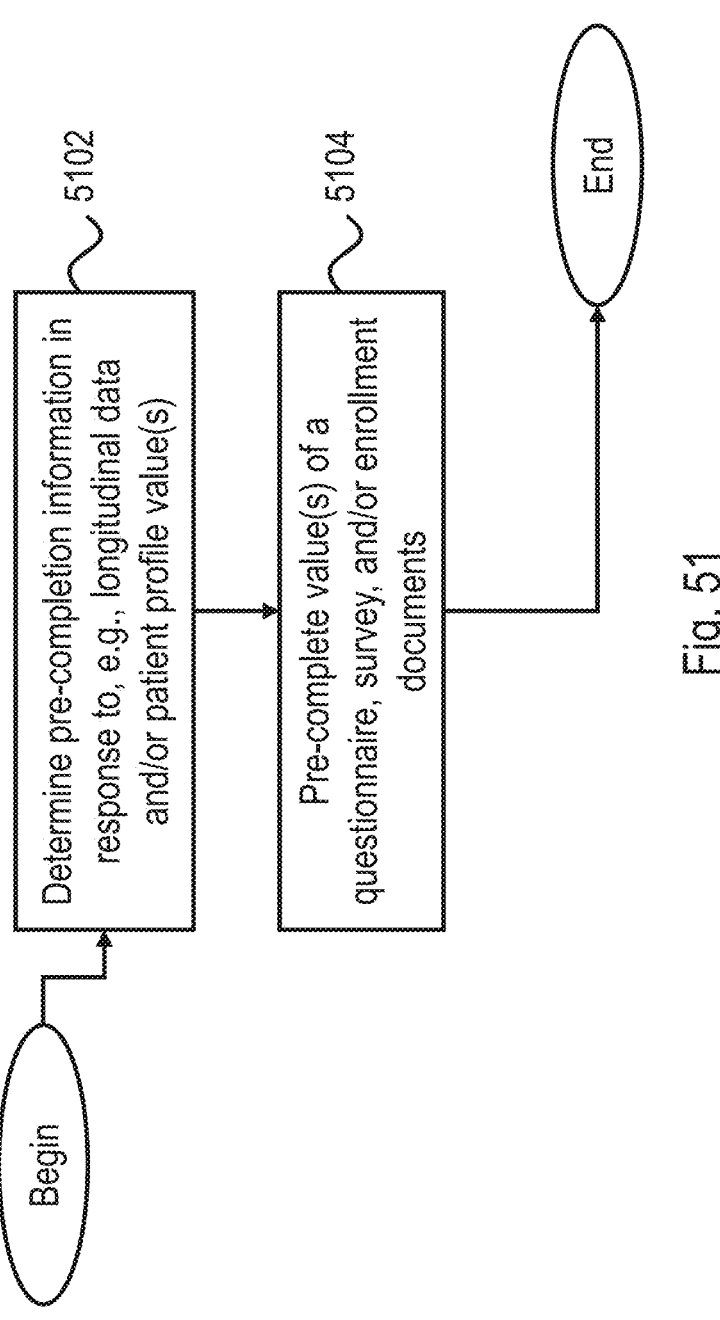
FIG. 51 depicts an example procedure for pre-completing values of a questionnaire, survey, or enrollment document.

Referencing FIG. 50, an example procedure 5000 for performing clinical screening operations is schematically depicted. The example procedure 5000 includes an operation 5002 to interpret a patient profile value, an operation 5004 to interpret clinical study description(s), and an operation 5006 to perform a clinical screening operation in response to the patient profile value and the clinical study description(s). Referencing FIG. 51, an example operation 5006 to perform a clinical screening operation includes an operation 5102 to determine pre-completion information in response to the patient profile value, longitudinal data for the patient, and/or patient historical performance data, and an operation 5104 to pre-complete one or more values of a questionnaire, survey, and/or enrollment document in response to the pre-completion information.

Figure 52:
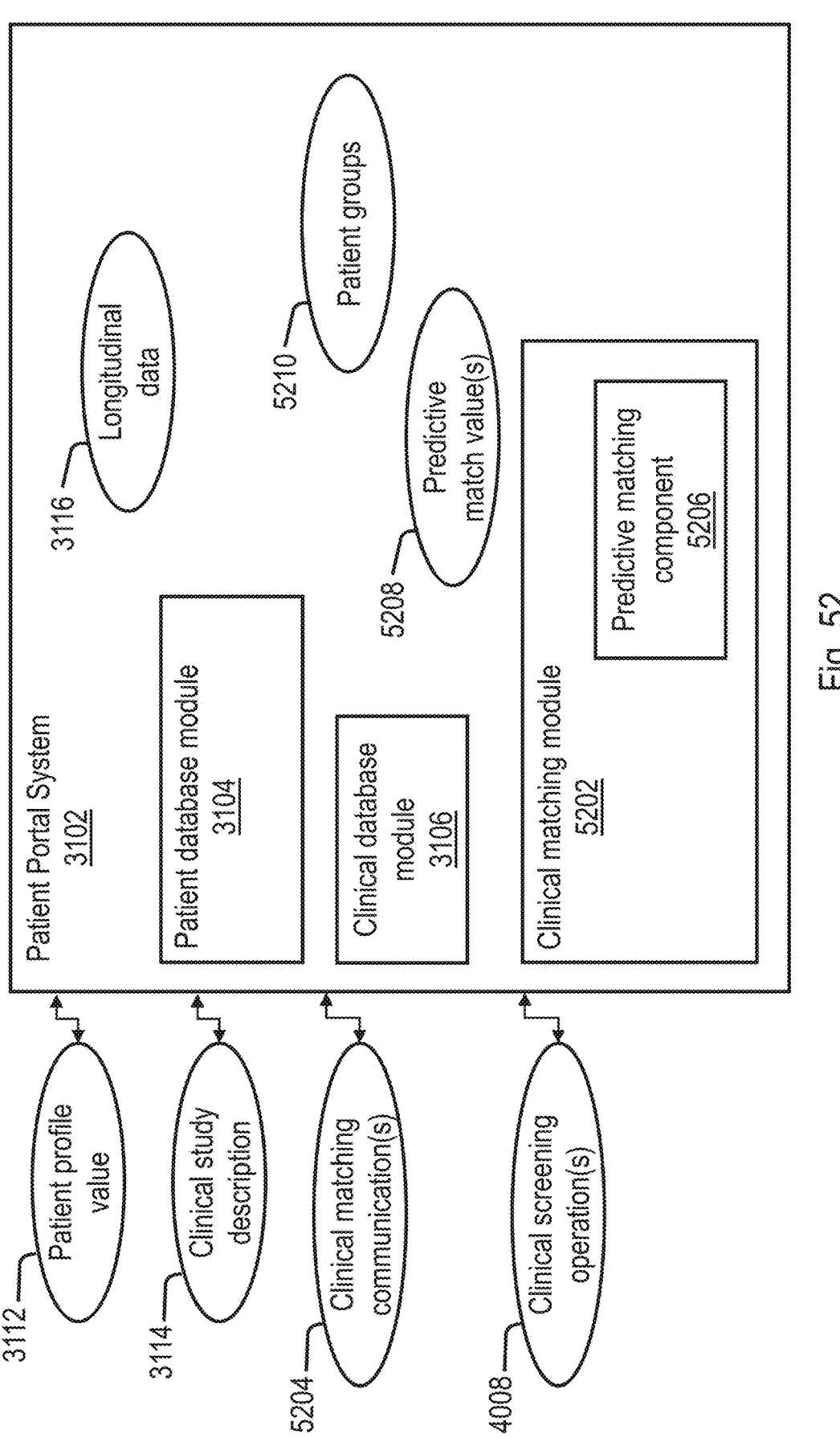
FIG. 52 depicts an example patient portal system.
Figure 53:
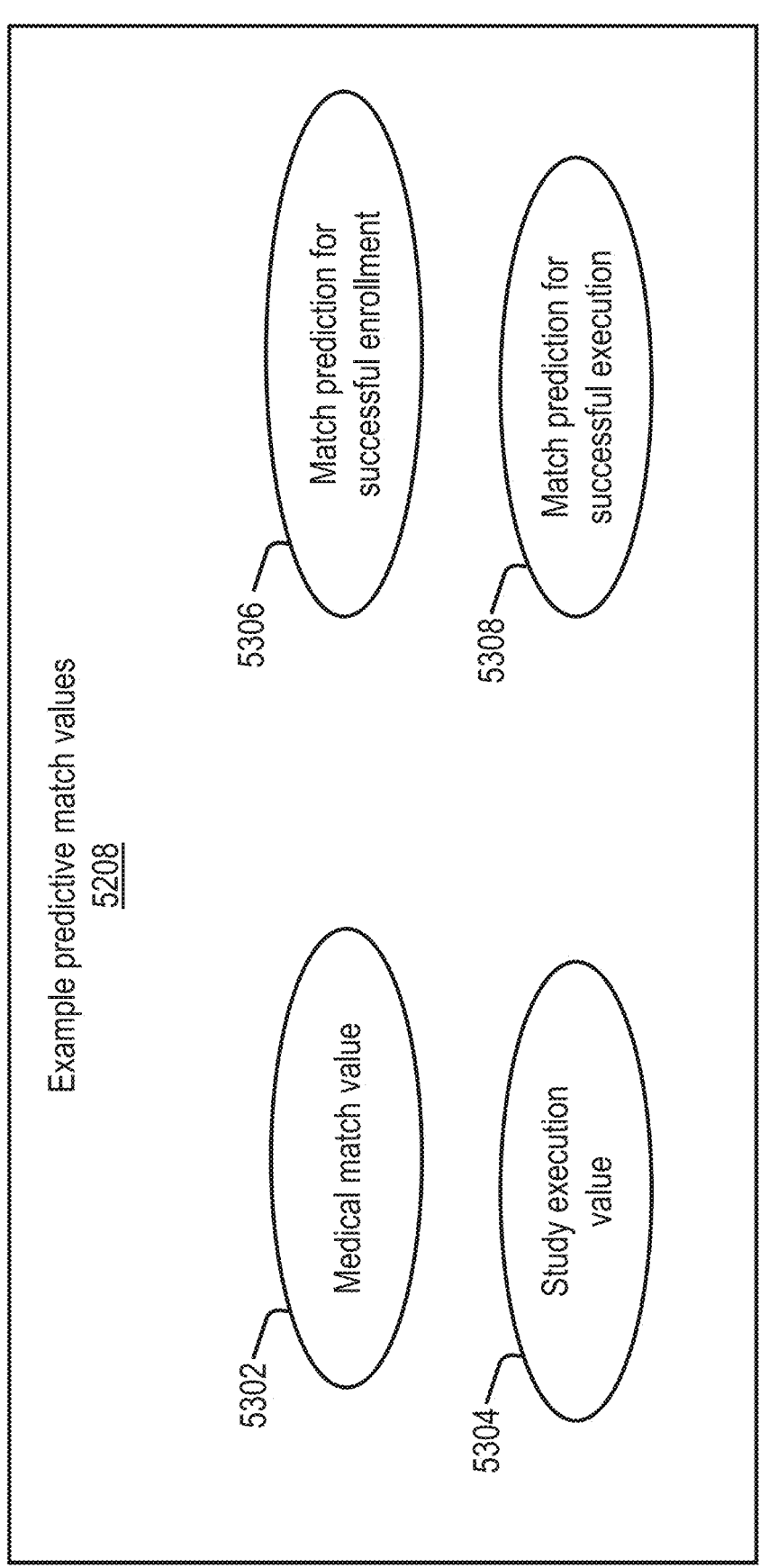
FIG. 53 depicts example predictive match values.
Figure 54:
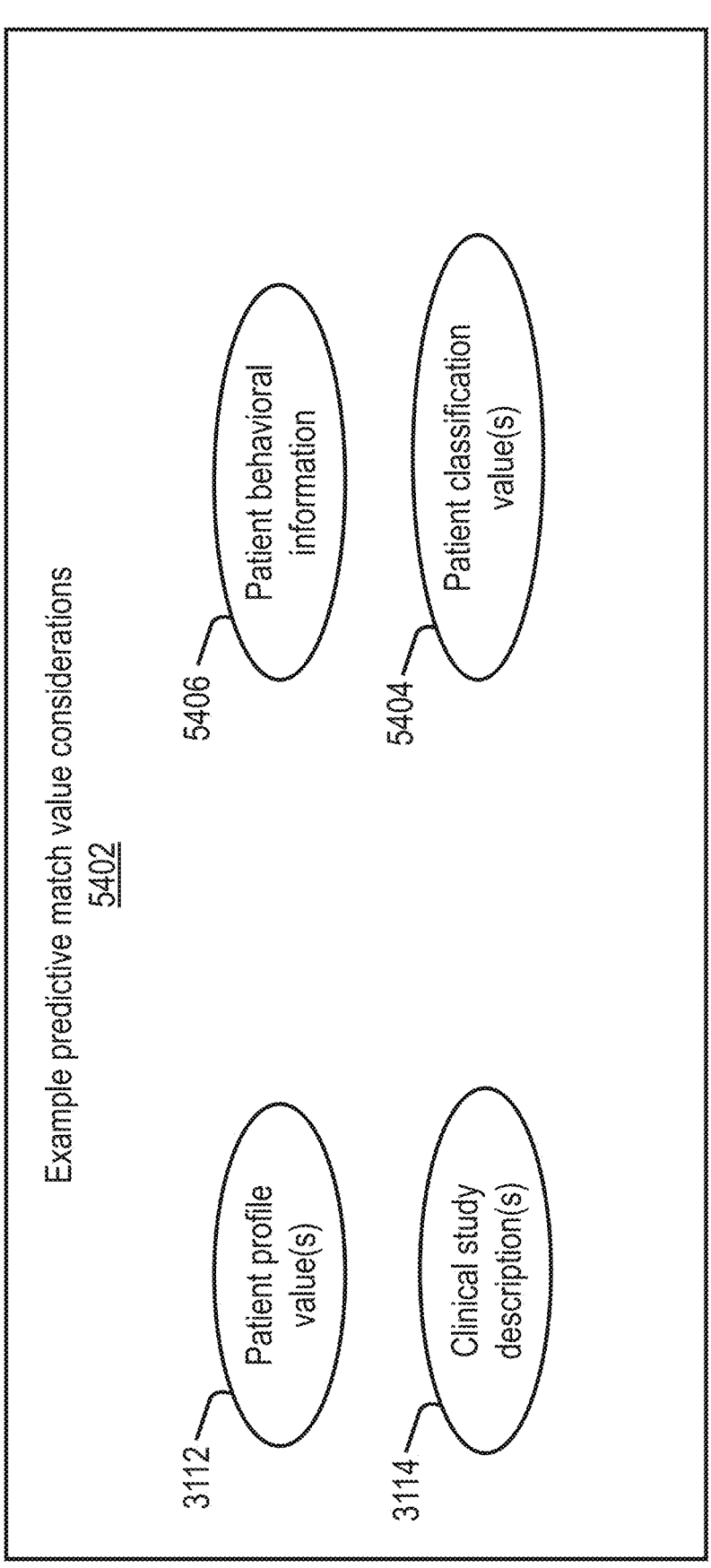
FIG. 54 depicts illustrative considerations for determining a predictive match value.

Referencing FIG. 52, an example system 3102 to match patients to clinical studies, which may be existing clinical studies and/or prospective clinical studies, is schematically depicted. The example system of FIG. 52, in addition to any operations described in relation to FIGS. 52-58, may provide matching information, for example including predictive match values 5208, clinical matching communications 5204, and/or patient groups 5210, to any systems, portals, platforms, or other embodiments, as set forth throughout the present disclosure. The example system 3102 includes a patient database module 3104 configured to interpret a patient profile value 3112 corresponding to a patient, a clinical database module 3106 configured to interpret a plurality of clinical study descriptions 3114, and a clinical matching module 5202 configured to provide a clinical matching communication 5204 in response to the patient profile value 3112 and at least one of the plurality of clinical study descriptions 3114. An example clinical matching module 5202 is further configured to provide the clinical matching communication 5204 in response to a comparison of the patient profile value 3112 and at least one of the plurality of clinical study descriptions 3114.

An example clinical matching module 5202 includes a predictive matching component 5206 that determines a predictive match value 5208 for the patient to at least one clinical study corresponding to at least one of the plurality of clinical study descriptions 3114, and the clinical matching module 5202 provides the clinical matching communication 5204 further in response to the predictive match value 5208. In certain embodiments, the predictive match value 5208 includes a likelihood that the patient will be medically compatible with the clinical study, and operationally compatible with the clinical study. The predictive match value 5208 may further include a confidence of the match, for example based on the source or certainty of selecting criteria, the utilization of correlated data rather than direct data, the utilization of aging data within the matching data utilized, and/or based on data values that are missing or unknown and that may potentially indicate that a given clinical study may end up being medically or operationally incompatible. Referencing FIG. 53, example and non-limiting predictive match values 5208 include one or more of: a medical match value 5302 (e.g., whether the patient is likely to have a relevant medical condition, symptom, or diagnosis, is likely to be able to tolerate the treatments and/or procedures of the clinical study, has completed surveys or other screening operations, has correlating conditions that tend to indicate compatibility or lack thereof, etc.); a study execution value 5304 (e.g., whether the patient is likely to be able to meet time commitments; travel requirements; provide timely attendance to procedures, treatments, or tests; and/or properly conform to therapies, medication regiments, data reporting requirements, or the like); a match prediction for successful enrollment 5306 (e.g., whether the patient is likely to successfully complete enrollment actions, including submission of documents, completion of tests, etc.); and/or a match prediction for successful execution 5308 of the relevant clinical study. Referencing FIG. 54, example and non-limiting predictive match value considerations 5402 include, without limitation, determining the predictive match value 5208 in response to one or more of: the patient profile value 3112; the clinical study description 3114; patient behavioral information 5406 (e.g., from the longitudinal data 3116, and/or tracking via interactions on any platform, system, portal, or other embodiments as set forth throughout the present disclosure); and/or patient classification values 5404 (e.g., as determined by any platform, system, portal, module, component, or other embodiments as set forth throughout the present disclosure).

Figure 55:
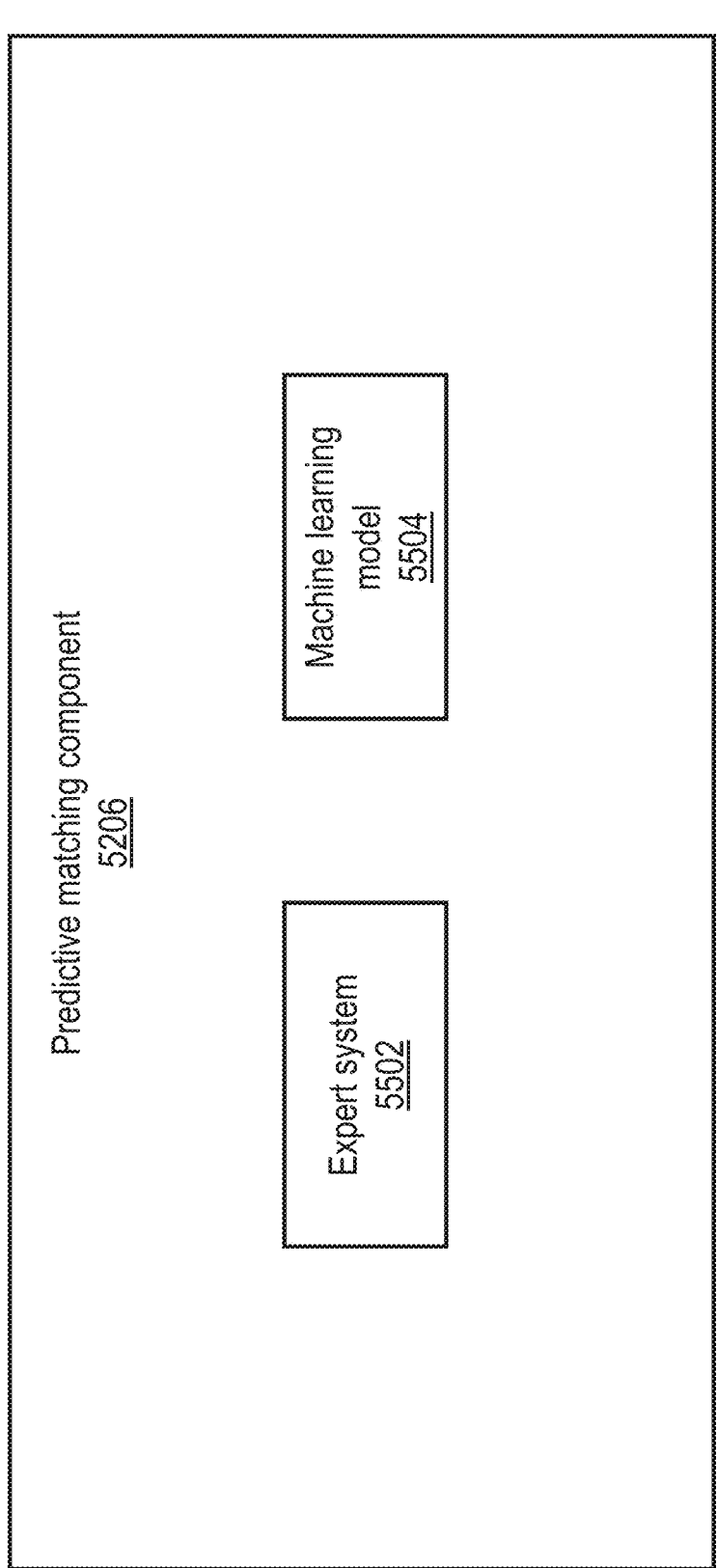
FIG. 55 depicts illustrative elements of an example predictive matching component.
Figure 56:
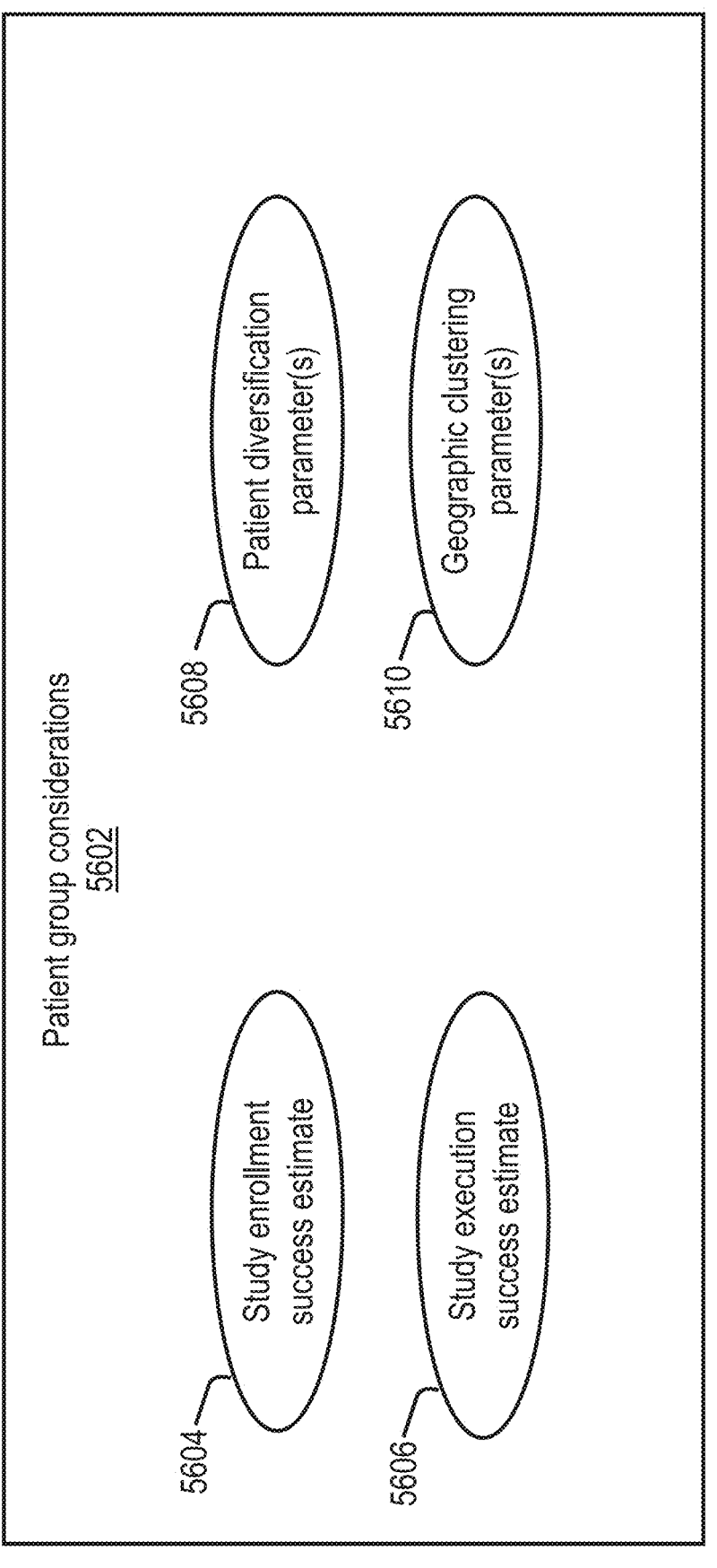
FIG. 56 depicts illustrative considerations for determining patient groups.

Referencing FIG. 55, example and non-limiting aspects of a predictive matching component 5206 are schematically depicted. The example predictive matching component 5206 includes an expert system 5502, for example utilizing a rules-based logic or algorithm to determine the predictive match value 5208 based on the available considerations 5402, including the source of such considerations 5402, and/or weighting the importance of any considerations 5402 (and/or including consideration of missing, high confidence, and/or low confidence values for one or more considerations 5402). The example predictive matching component 5206 additionally or alternatively includes a machine learning model 5504, for example that operates to explore the space of the considerations 5402 to determine considerations 5402 that have effective predictive value to determine the predictive match values 5208, which may converge on and/or iteratively improve the model based on a success metric (e.g., patient success in enrollment in and/or completion of clinical studies).

Again referencing FIG. 52, an example patient database module 3104 interprets a plurality of patient profile values 3112, where the clinical matching module 5202 further determines a number of patient groups 5210 of at least a portion of the plurality of patient profile values 3112, and provides the clinical matching communication 5204 in response to the number of patient groups 5210. In certain embodiments, the patient groups 5210 allow the system 3102 to stratify patients in groups, and create groups of patients that are likely to provide a sufficient number of patients appropriate to constraints of the clinical study, for example according to geographically located clusters of patients, to facilitate success in providing a sufficient group of patients for the study, as well as reducing resources utilized to locate and enroll patients for the study. In certain embodiments, the predictive matching component 5206 operates to iteratively improve the determination of patient groups 5210. Referencing FIG. 56, example and non-limiting considerations 5602 to determine the patient groups 5210 include one or more of: a study enrollment success estimate 5604 (e.g., whether one or more, or a select, number of the groups 5210 are likely to succeed in enrollment operations in sufficient numbers to support the clinical study); a study execution success estimate 5606 (e.g., whether one or more, or a select, number of the groups 5210 are likely to succeed in execution operations in sufficient numbers to support the clinical study); a patient diversification parameter 5608 (e.g., whether one or more, or a select, number of the groups 5210 are likely to succeed in enrollment and/or execution operations, with a sufficient mix of relevant diversity, such as medical diversity, demographic diversity, control parameters, or the like, to support the clinical study); and/or a geographic clustering parameter 5610 (e.g., whether one or more, or a select, number of the groups 5210 are likely to succeed in enrollment and/or execution operations, with a sufficient clustering geographically to meet the needs of the clinical study, for example to be within range of appropriate facilities, and/or sufficiently dispersed to meet the needs of the clinical study, for example not exceeding the capacity of one or more facilities).

Figure 57:
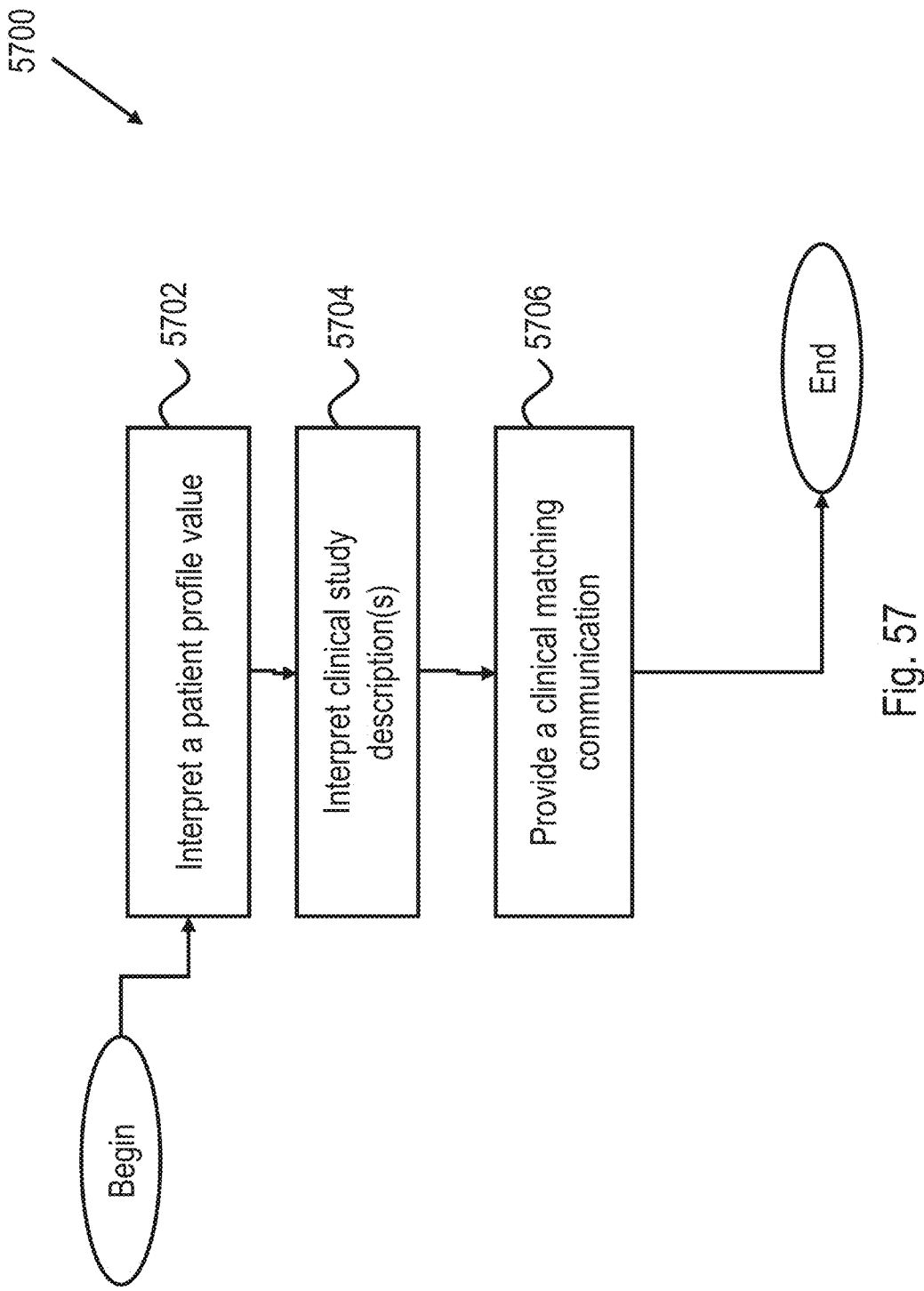
FIG. 57 depicts an example procedure for providing a clinical matching communication.
Figure 58:
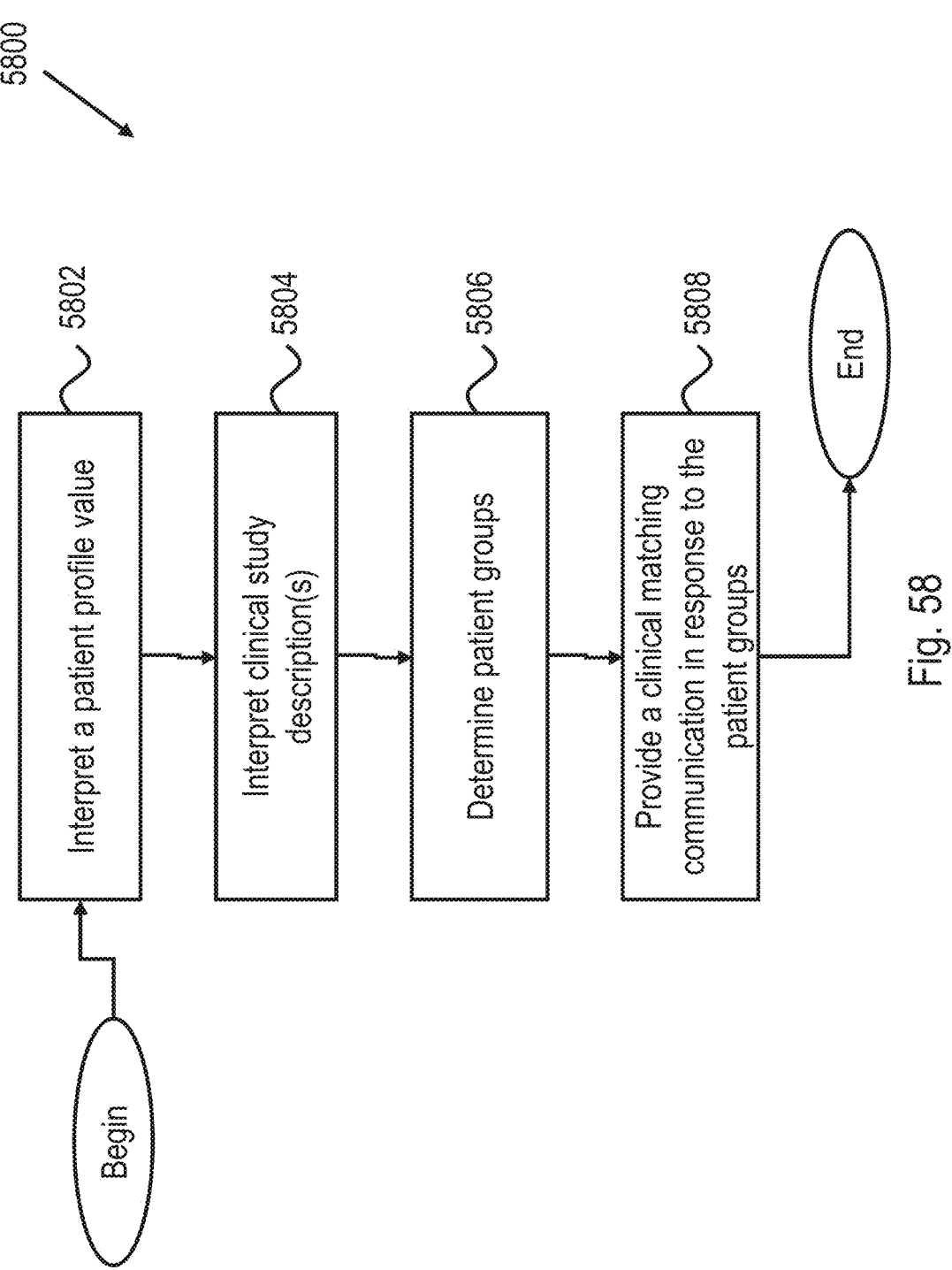
FIG. 58 depicts an example procedure for providing a clinical matching communication.

Referencing FIG. 57, an example procedure 5700 for providing a clinical matching communication is schematically depicted. The example procedure 5700 includes an operation 5702 to interpret a patient profile value, an operation 5704 to interpret a clinical study description, and an operation 5706 to provide a clinical matching communication. Referencing FIG. 58, an example procedure 5800 for providing a clinical matching communication in response to patient groups is schematically depicted. The example procedure 5800 includes an operation 5802 to interpret patient profile values, an operation 5804 to interpret a clinical study description, an operation 5806 to determine patient groups in response to the patient profile values and the clinical study description, and an operation 5808 to provide a clinical matching communication in response to the patient groups.

Figure 59:
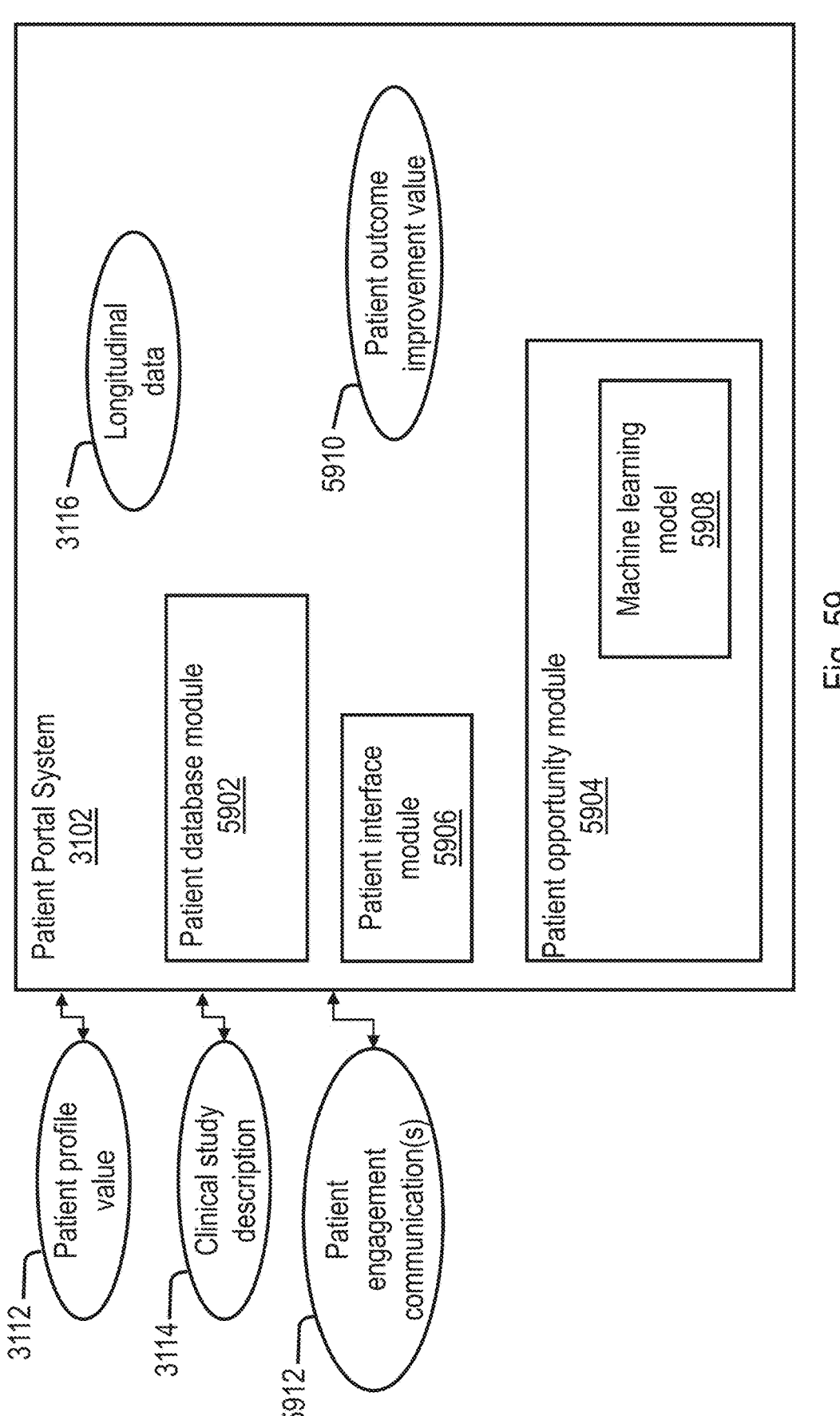
FIG. 59 depicts an example patient portal system.

Referencing FIG. 59, an example system 3102 for providing patient engagement communications, facilitating a number of patient actions with any systems, portals, platforms, or other embodiments as set forth throughout the present disclosure, is schematically depicted. In certain embodiments, operations of the example system 3102 improve patient outcomes, including for individual actions performed utilizing the system, and over time by facilitating touch points with the patient, ensuring the patient has relevant medical information, is aware of clinical study opportunities, and schedules relevant medical procedures and treatments in a timely manner and with high confidence that the correct procedures and treatments are performed. In certain embodiments, aspects of the system 3102, including for example the patient engagement communications 5912 and patient outcome improvement values 5910, may be provided, in whole or part, to any other system, portal, platform, module, component, and/or other embodiments as set forth throughout the present disclosure. The example system 3102 includes a patient database module 5902 configured to interpret a patient profile value 3112 corresponding to a patient, a patient opportunity module 5904 that determines a patient outcome improvement value 5910 in response to the patient profile value 3112, and a patient interface module 5906 configured to provide a patient engagement communication 5912 in response to the patient outcome improvement value 5910.

Figure 60:
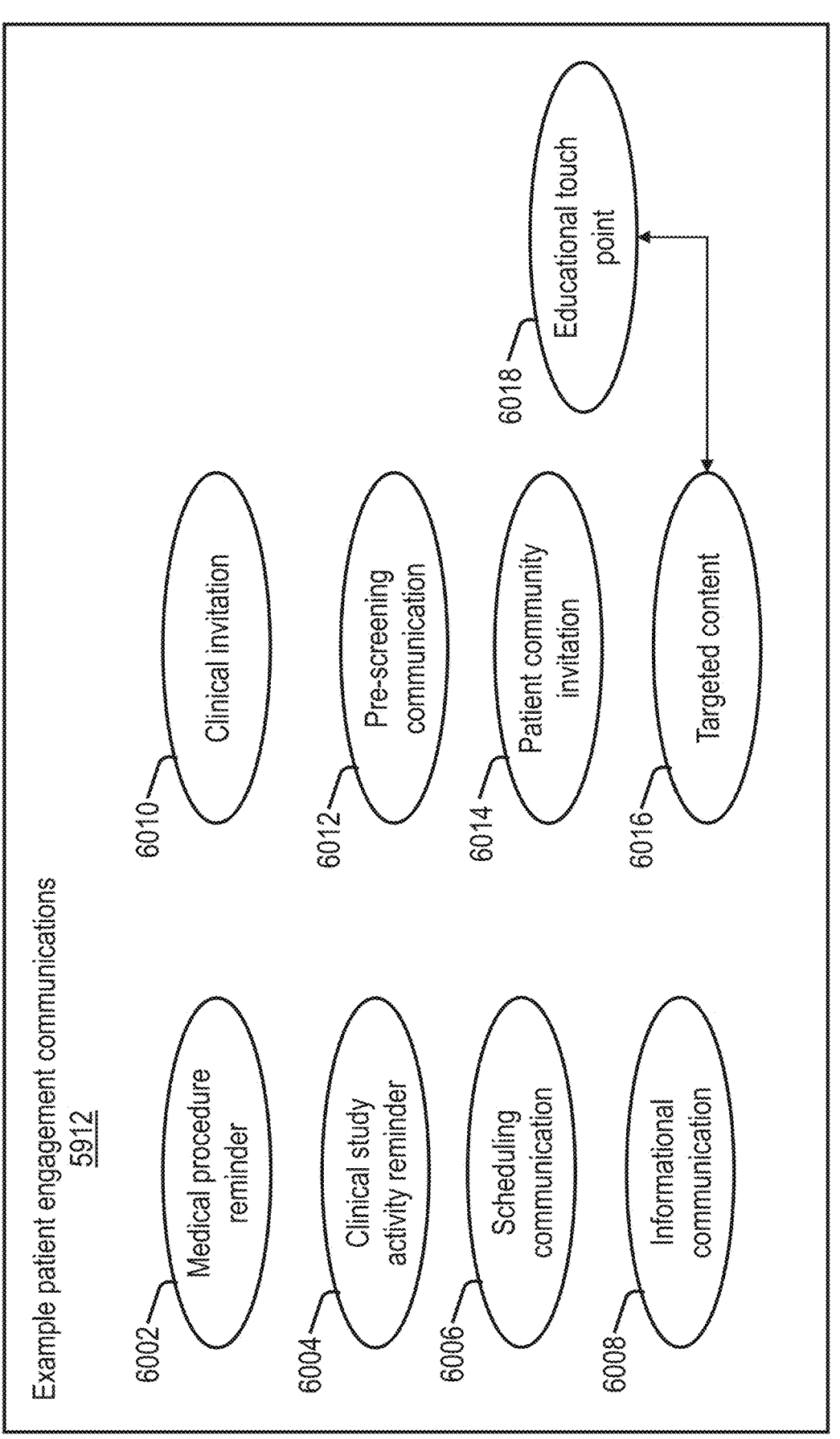
FIG. 60 depicts illustrative patient engagement communications.

Referencing FIG. 60, example and non-limiting patient engagement communications 5912 are schematically depicted, including one or more of: a medical procedure reminder 6002 (e.g., any medical procedure, including a lab test, a treatment, a therapy, and/or a medication reminder); a clinical study activity reminder 6004 (e.g., any activity related to a clinical study, including a screening activity, enrollment activity, treatment, test, visit, reporting, or the like); a scheduling communication 6006 (e.g., any scheduling communication, including communications to a relevant provider, to the patient, requesting schedule availability, and/or actively scheduling an event, where the scheduling may relate to any medical procedure and/or clinical study activity); an informational communication 6008 (e.g., a communication about any treatment, medical condition, medical procedure, clinical study, or the like, that is available to the system 3102 including from any platform, portal, system, or other embodiment herein); a clinical invitation 6010 (e.g., an invitation to screen for, enroll in, and/or participate in a clinical study that may be relevant to the patient); a pre-screening communication 6012; a patient community invitation 6014 (e.g., an invitation to join and/or create a patient community, for example and without limitation, on a patient centered social platform such as set forth in FIGS. 66-68, 24-25, and 28-29 and the related description); and/or targeted content 6016 determined to be relevant to the patient and/or of interest to the patient. In certain embodiments, the targeted content 6016, communicated as a patient engagement communication 5912, may be provided as an educational touch point 6018 (e.g., reference FIG. 27 and the related description), which may include information about a diagnosis, treatment, medication, procedure, therapy, and/or clinical study that is relevant to the patient, that the patient has expressed an interest in, and/or that a system, platform, portal, module, component, or other embodiment of the present disclosure has inferred that the patient has an interest in.

Figure 61:
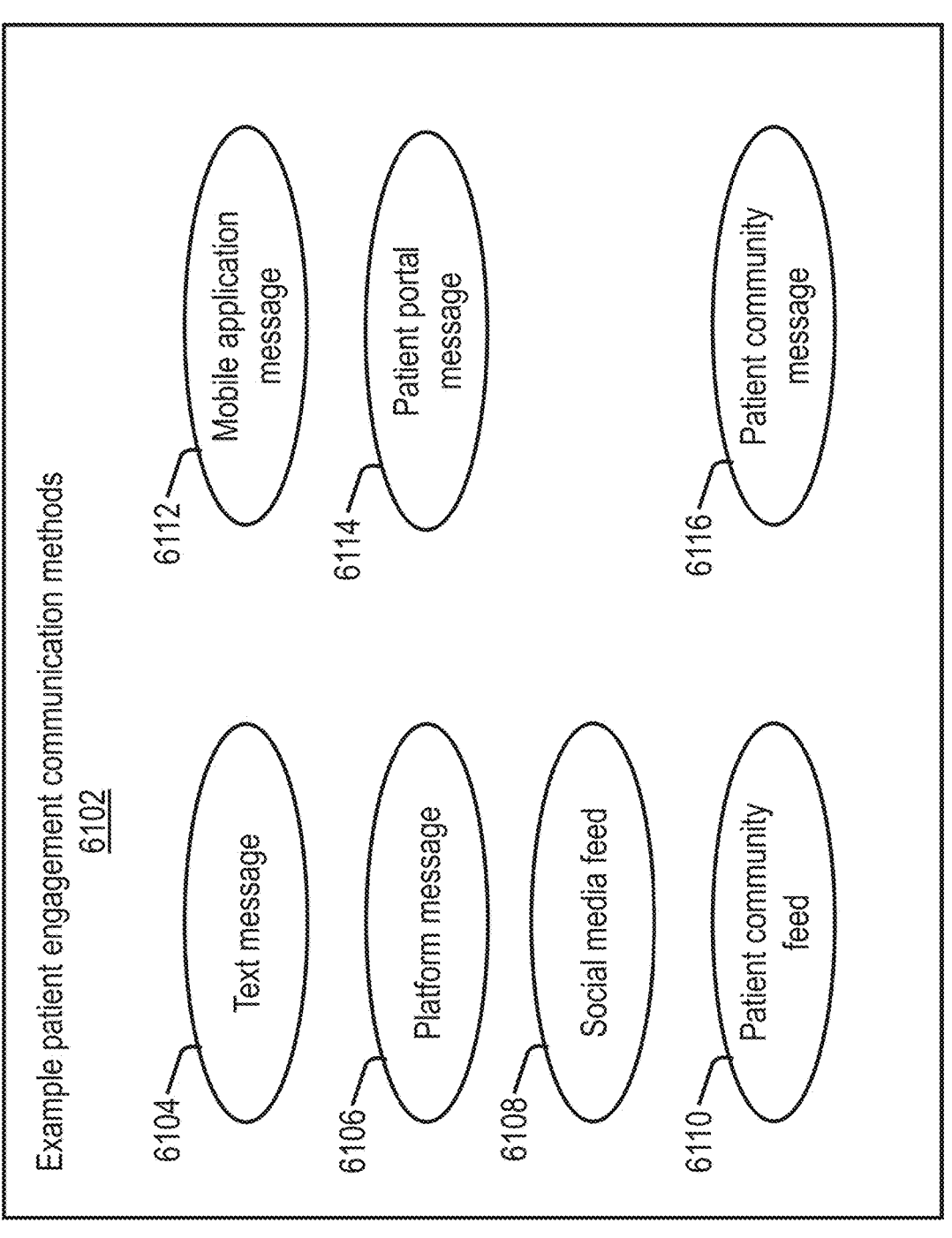
FIG. 61 depicts illustrative patent engagement communication methods.
Figure 62:
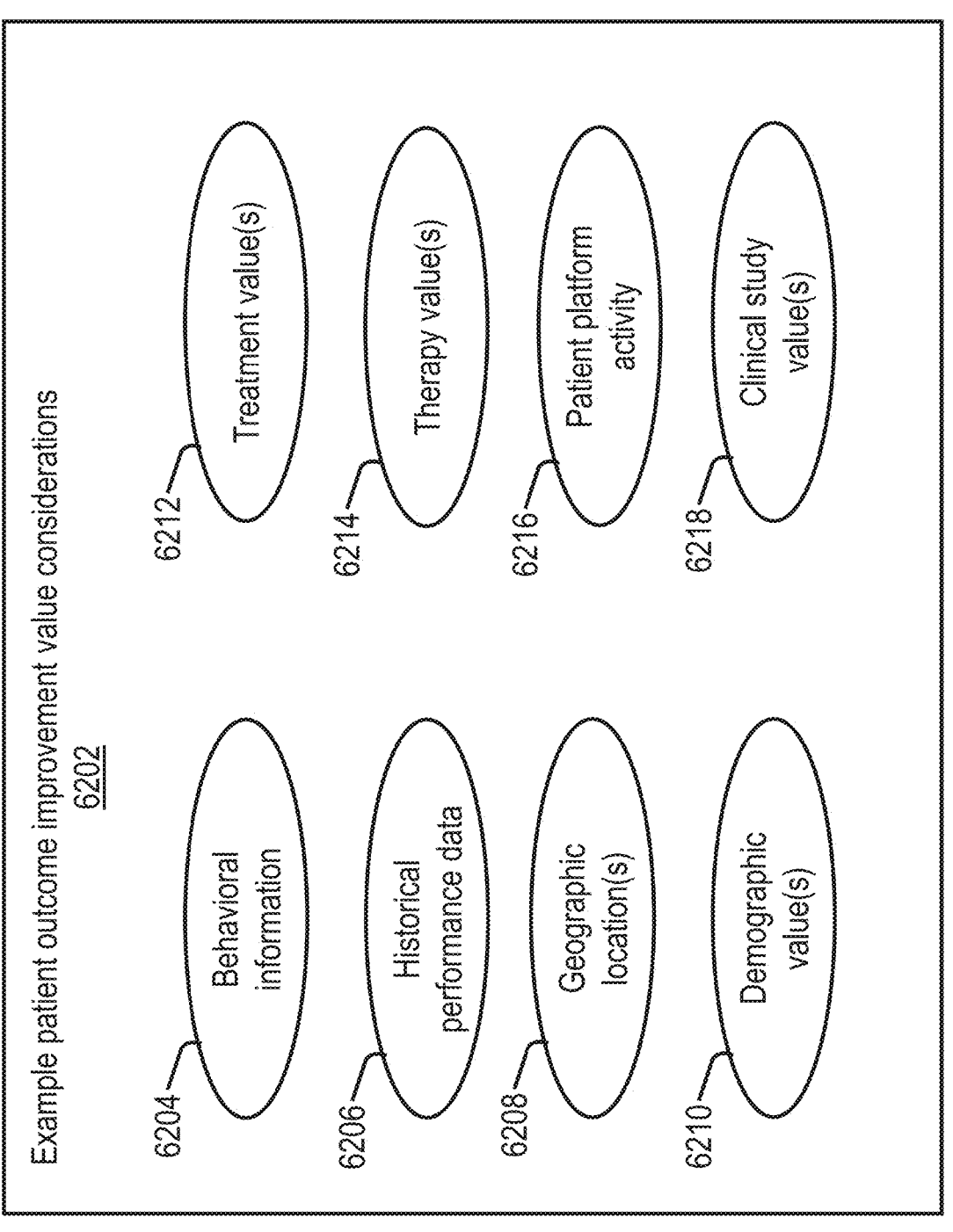
FIG. 62 depicts illustrative considerations for determining a patient outcome improvement value.

Referencing FIG. 61, example and non-limiting patient engagement communication methods 6102 include, without limitation to any other aspect of the present disclosure, one or more of: a text message 6104; a platform message 6106; a social media feed 6108; a patient community feed 6110; a mobile application message 6112; a patient portal message 6114; and/or a patient community message 6116. Referencing FIG. 62, example and non-limiting considerations 6202 utilized by the patient opportunity module 5904 to determine the patient outcome improvement value 5910 include one or more of: behavioral information 6204 (e.g., lifestyle behaviors that may be relevant to the patient long-term health, relevant to specific conditions of the patient, compliance with treatment regimes, testing, medication regimes, etc.); historical performance data 6206 (e.g., based on activity with any platform, system, portal, or other embodiment as set forth throughout the present disclosure, for example responding to new information about the patient, evolving patient communication preferences, etc.); geographic locations 6208 (e.g., which may make new or different facilities available, make the patient eligible for a clinical study, etc.); demographic values 6210 (e.g., which may affect recommended procedures, dosing, testing, availability of clinical studies, etc.); treatment values 6212; therapy values 6214; patient platform activity 6216; and/or clinical study values 6218 (e.g., communicating the availability of a new clinical study, or a newly applicable clinical study based on updated patient information).

Figure 63:
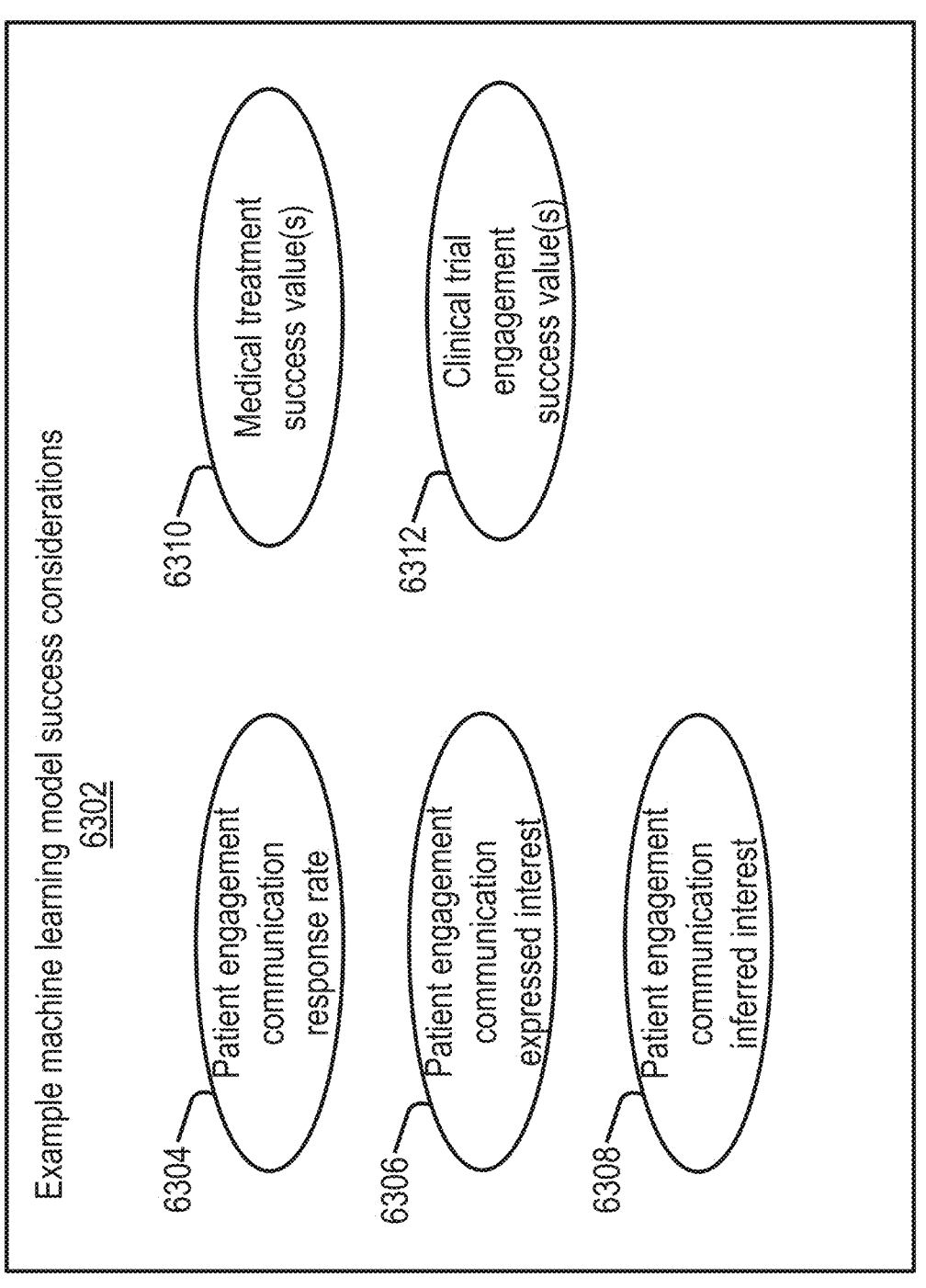
FIG. 63 depicts illustrative success considerations for operating a machine learning model.

An example patient opportunity module 5904 includes a machine learning model 5908 that iteratively improves operations to determine the patient outcome improvement value 5910, for example allowing the patient opportunity module 5904 to continuously improve patient communications to achiever improved results for scheduling, notifications, education of the patient, matching for clinical studies, improve compliance with treatment and/or medication regimes, or the like. In certain embodiments, the machine learning model 5908 searches the input space including patient longitudinal data, patient profile values, clinical study descriptions, and/or historical performance data, to determine effective outputs (e.g., communications of FIG. 61 and/or improvement values of FIG. 62) to iteratively improve a success metric. Referencing FIG. 63, example and non-limiting success metrics, and/or success considerations 6302, are schematically depicted, including one or more of: patient engagement communication response rate 6304 (e.g., the patient receives and response to the communication); patient engagement communication expressed interest 6306 (e.g., the patient expresses an interest in the communication); patient engagement inferred interest 6308 (e.g., interest in the communication is inferred, for example the patient reads the message, requests further related information, and/or responds to the message in a meaningful manner); medical treatment success values 6310 (e.g., medical treatments appear to be appropriate, and/or appear to be achieving the desired effect); and/or a clinical trail engagement success value 6312 (e.g., the patient successfully screens for, enrolls in, and/or participates in relevant clinical studies).

Figure 64:
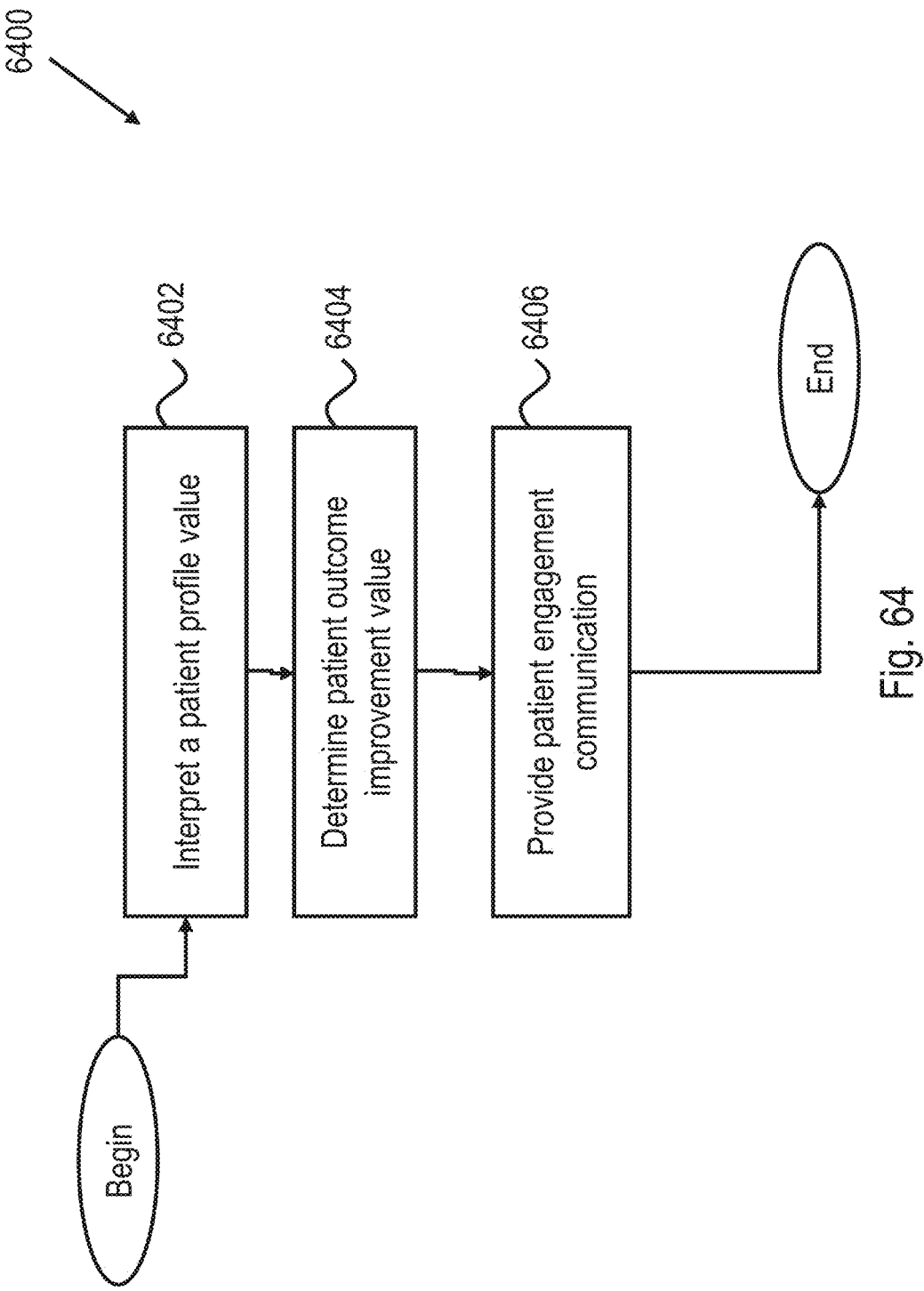
FIG. 64 depicts an example procedure for providing patient engagement communications.
Figure 65:
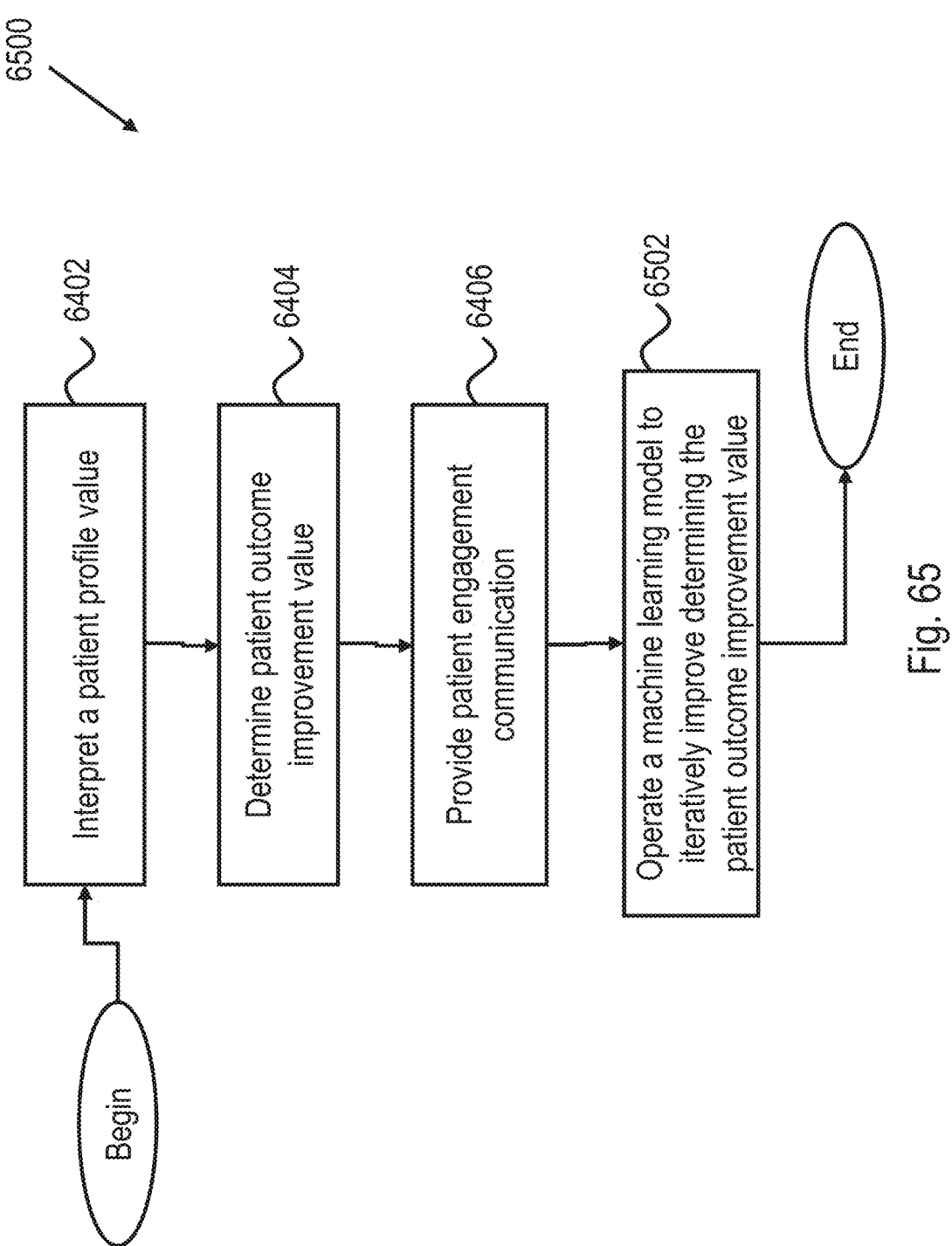
FIG. 65 depicts an example procedure for operating a machine learning model to iteratively improve determining a patient outcome improvement value.

Referencing FIG. 64, an example procedure 6400 for providing a patient engagement communication 6406 is schematically depicted. The example procedure 6400 includes an operation 6402 to interpret a patient profile value, an operation 6404 to determine a patient outcome improvement value, and an operation 6406 to provide a patient engagement communication. Referencing FIG. 65, an example procedure 6500 further includes an operation 6502 to operate a machine learning model to iteratively improve determining the patient outcome improvement value.

Figure 66:
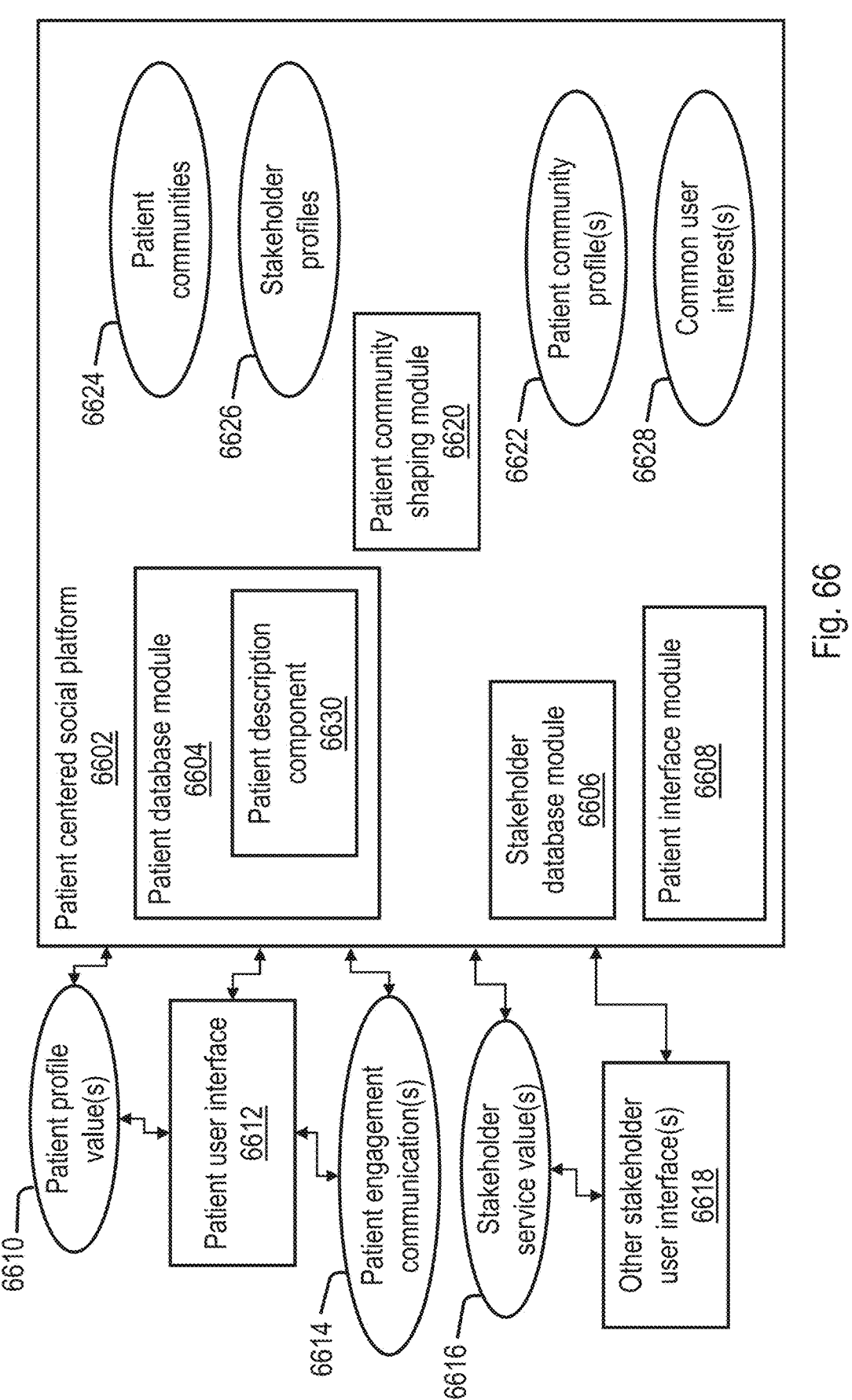
FIG. 66 depicts an example patient centered social platform.

Referencing FIG. 66, an example patient centered social platform 6602 that supports a centralized patient communication platform, facilitates patient communities of interest for knowledge sharing and support, and for engaging various stakeholders for education of patients, connections with advocacy groups, and connecting patients with relevant treatments, medications, and clinical studies, is schematically depicted. The example platform 6602 includes a patient database module 6604 configured to interpret at least one of a plurality of patient profile values 6610 corresponding to a user of the patient centered social platform 6602, a stakeholder database module 6606 configured to interpret a plurality of stakeholder service values 6616, and a patient interface module 6608 configured to implement a user social interface (e.g., as a patient user interface 6612 in the example of FIG. 66), and to provide a patient engagement communication 6614 to the user on the user social interface 6612 in response to the corresponding at least one of the patient profile values 6610 and the plurality of stakeholder service values 6616 (e.g., from other stakeholder user interface(s) 6618). The example platform 6602 may be in communication with any other system, platform, portal, or other embodiments as set forth throughout the present disclosure. For example, the platform 6602 may have access, subject to patient permissions and consent, to longitudinal data, patient profile values, historical performance data, matching values, and/or any other aspects of other systems, platforms, portals, or other embodiments as set forth throughout the present disclosure. In certain embodiments, the platform 6602 and/ or portions thereof may form a part of a system, platform, or the like, in combination with any other system, platform, portal, or other embodiments or portions thereof. In certain embodiments, all or a portion of any other system, platform, portal, module, component, or the like may be included as a part of the platform 6602, and/or be communicatively coupled to the platform 6602. The example patient engagement communications 6614 may, additionally or alternatively, be provided to the user by any communication method set forth herein, for example including utilizing a text message, e-mail, phone call, web portal, mobile application, etc.

Figure 67:
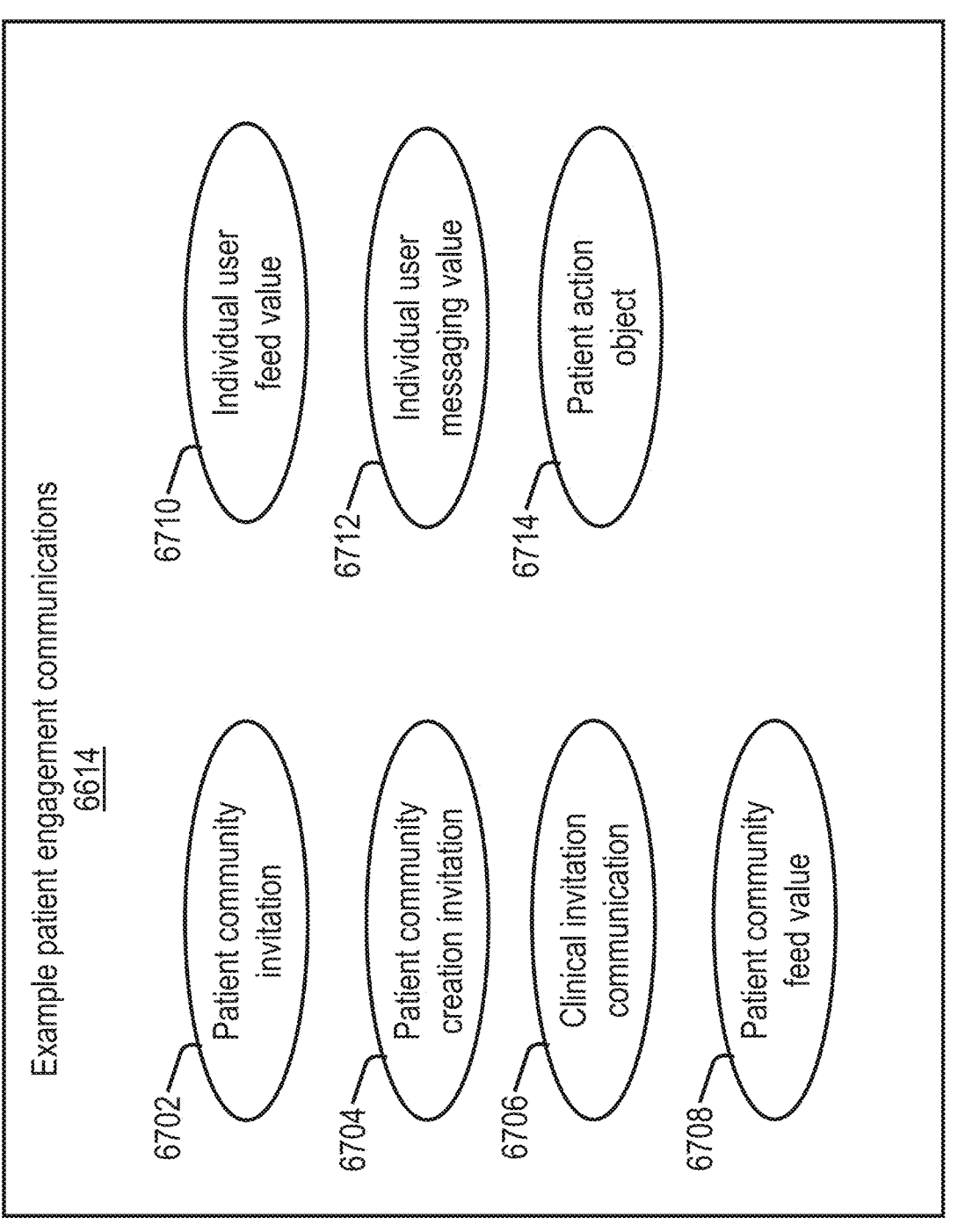
FIG. 67 depicts illustrative patient engagement communications.

Referencing FIG. 67, example and non-limiting patient engagement communications 6614 are schematically depicted, including one or more of: a patient community invitation 6702 (e.g., an invitation to the user to join an existing patient community 6624); a patient community creation invitation 6704 (e.g., an invitation to the user to create a new patient community 6624, including potentially in a group with other relevant users); a clinical invitation communication 6706 (e.g., an invitation to get information about, to screen or pre-screen for, and/or to enroll in a clinical study, e.g., provided as a stakeholder service value 6616 to the platform 6602); a patient community feed value 6708 (e.g., a communication provided as a feed message to one or more selected patient communities 6624); an individual user feed value 6710 (e.g., a communication provided as a feed message to one or more selected patients); an individual user messaging value 6712 (e.g., a communication provided using a message function or application of the platform 6602 to one or more selected users); and/or a patient action object 6714 (e.g., reference FIG. 5 and the related description, which may be provided on a platform GUI and/or as a part of another message).

Figure 68:
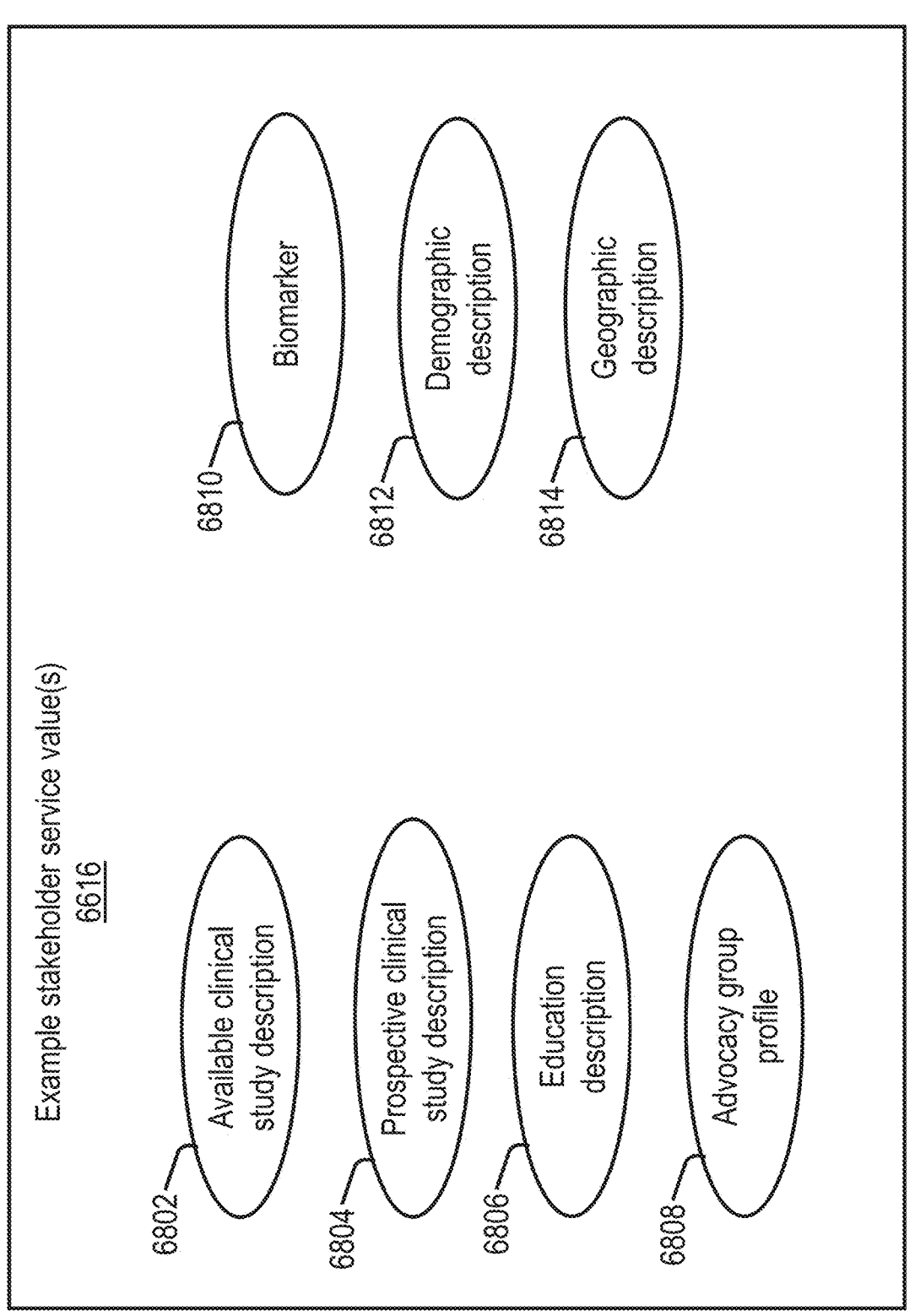
FIG. 68 depicts illustrative stakeholder service values.

Referencing FIG. 68, example and non-limiting stakeholder service values 6616 are schematically depicted. The example stakeholder service values 6616 include any values that provide the platform 6602 with information about any stakeholders that participate on the platform 6602, including information about the stakeholder (which may additionally or alternatively be provide in a stakeholder profile 6626), services offered, educational materials, clinical study descriptions, treatment descriptions, and the like, and may further include information about relevant and/or authorized users to whom the stakeholder service value 6616 should be communicated to, the content of communications, and the like. The example stakeholder service values 6616 include one or more of: an available clinical study description 6802; a prospective clinical study description 6804; an education description 6806 (e.g., information about any medical condition, treatment, medication, lifestyle recommendation, and/or any other health related educational content); and/or an advocacy group profile 6808 (e.g., information about an advocacy group, including for example a related entity if any, profit or non-profit status, purpose of the organization, aspects of users that may be interested the advocacy group such as relevant medical conditions, treatments, medications, keywords or topics of interest or concern, etc.). In certain embodiments, an example education description 6806 includes one or more of: a medical research description; a medical study description; a clinical study description; a medical best practice description; a medical information description; a medical product description; a medical treatment description; and/or a medical condition description.

In certain embodiments, an example stakeholder service value 6616 includes one or more of: a biomarker 6810 (e.g., a biomarker of a patient that provides an indicator of relevance and/or interest in the remainder of the stakeholder service value 6616, for example attached to a clinical study description, education description, etc.); a demographic description 6812 (e.g., one or more demographic values of a user that may indicate the relevance and/or interest of the user in the remainder of the stakeholder service value 6616); and/or a geographic description 6814 (e.g., one or more geographic values or regions, where a user having a connection to that geographic value or region may have an interest in the remainder of the stakeholder service value 6616).

In certain embodiments, aspects of the platform 6602 and/or modules or components thereof may utilize behavioral information about users on the platform to perform various operations set forth herein. An example patient database module 6604 includes a patient description component 6630 that determines behavioral information for users on the platform. The behavioral information may include any behavioral information as set forth throughout the present disclosure. In certain embodiments, referencing FIG. 24, example and not-limiting operations to determine the behavioral information 6902 include one or more of: information determined from patient profile value(s) 6610 and/or longitudinal data corresponding to users 2402; explicit behavioral information 2404 (e.g., behaviors indicated by the user, for example sleep schedules, dietary information, time spent on the platform 6602, medical treatment and/or medication compliance descriptions, etc.); inferred behavioral information 2406 (e.g., behaviors inferred according to user interactions with the platform 6602, and/or with any other portal, system, or platform as set forth herein, inferred from language utilization, word selection, and/or social content from the user on the platform 6602, time of day of engagement, detection of inactive periods, etc.); and/or historical performance data 2408 (e.g., historical communications, interactions, treatments, medical or medication regime compliance, etc., from the platform 6602 and/or with any other portal, system, or platform as set forth herein, and/or historical performance data as set forth otherwise herein).

Figure 25:
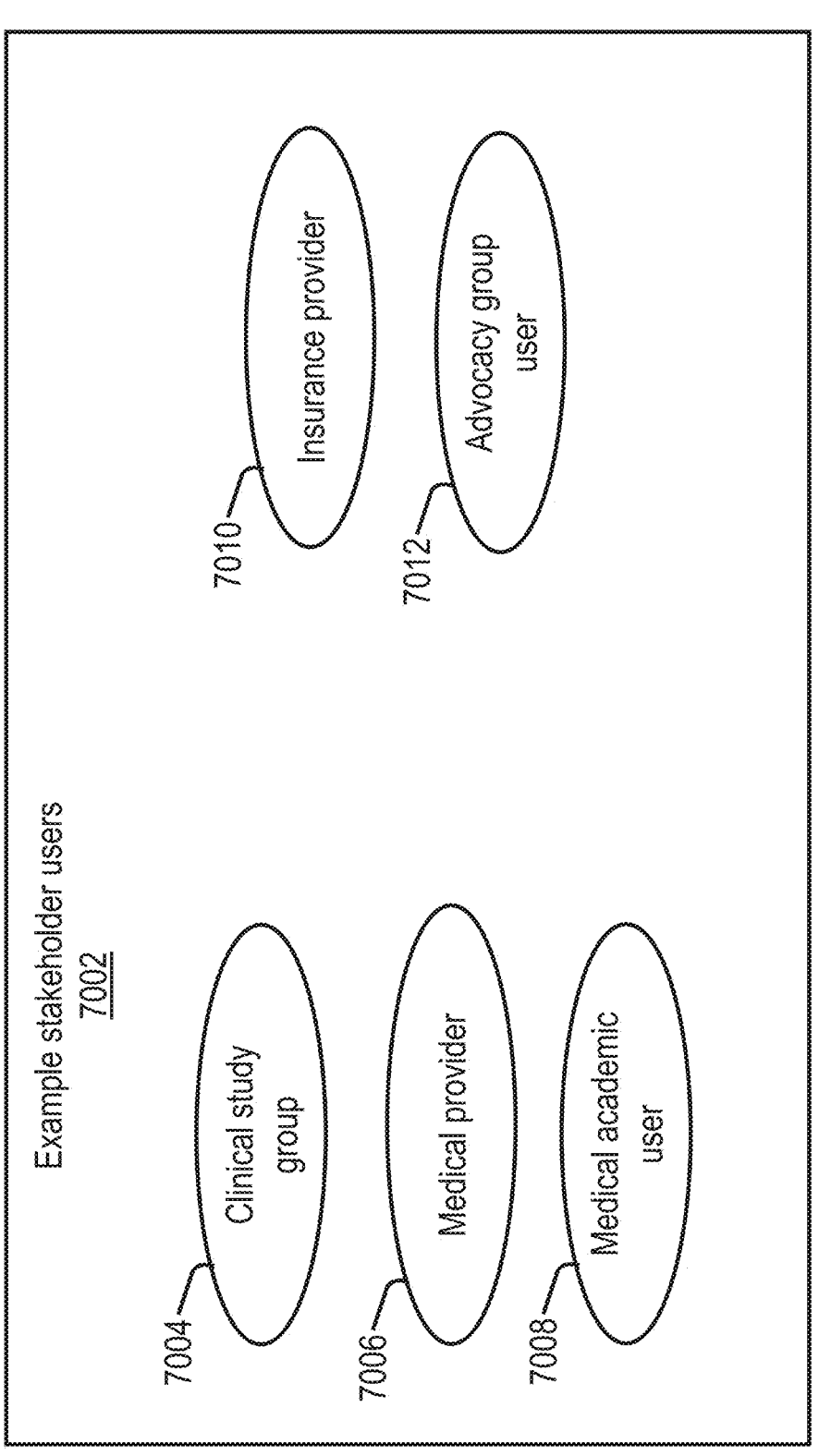
FIG. 25 depicts example stakeholder users of a patient centered social platform.

Referencing FIG. 25, example and non-limiting stakeholder users 7002 are schematically depicted, including one or more of: a clinical study group 7004 (e.g., allowing a clinical study group to educate users about available clinical studies, and/or facilitate enrollment operations from users of the platform 6602); a medical provider 7006 (e.g., allowing a medical provider to educate users about available treatments, medications, therapies, and/or medical conditions); a medical academic user 7008 (e.g., allowing universities, teaching hospitals, governmental organizations, and/or any other academically oriented medical organization to educate users, publish papers or studies, interface with advocacy groups and/or patient communities 6624, understand the concerns of users, etc.); an insurance provider 7010 (e.g., allowing insurance providers to educate users, medical providers, and/or other stakeholders, about evolving insurance changes, regulations, navigation of the complex insurance system, understand concerns of users or any other stakeholders, etc.); and/or an advocacy group user 7012 (e.g., allowing advocacy groups to connect with other stakeholders, develop connections with users and patient communities 6624, provide educational content, or the like).

An example platform 6602 includes a patient community shaping module 6620 that interprets the patient profile values for users of the platform 6602, interprets patient community profiles 6622 on the platform 6602 (e.g., a listing of patient communities 6624, the purpose of the communities, historical messages of the communities, user members of the communities, etc.), and determines a common user interest 6628 in response to the plurality of patient profile values. The common user interest 6628 may include any aspect of the users relevant to the platform 6602, including for example interests related to particular medical conditions, biomarkers, demographic values or ranges, common expressed concerns about any aspect of individual health or a health care system, regulatory interests, or the like. An example patient interface module 6608 is further configured to provide the patient community creation invitation 6704 in response to the plurality of patient community profiles 6622 and the common user interest 6628—for example where the community shaping module 6620 determines that a group of users have a common user interest 6628 that is not being met by one of the available patient communities 6624, and/or determines that additional patient communities 6624 for a particular common user interest 6628 should be created (e.g., due to a number of user members within the presently available patient communities 6624). In certain embodiments, the common user interest 6628 determination may be utilized to provide a patient community invitation 6702, for example to connect a user with an existing patient community 6624 that is likely to be of interest to the user. In certain embodiments, the patient community shaping module 6620 is configured to create a new patient community 6624 in response to interactions with the user on the user social interface, for example in response to a confirmation from the user, in response to a patient action object 6714 selected by the user and provided in the patient engagement communication 6614 including the patient community creation invitation 6704, or the like. In certain embodiments, the patient community shaping module 6620 determines a patient community profile 6622 for the new patient community 6624 (e.g., pre-populating the profile, which may be completed and/or amended by the user) in response to creating the new patient community 6624. In certain embodiments, the patient community shaping module 6620 utilizes the aspects of the common user interest 6628 and/or of the user's patient profile value 6610 to determine the patient community profile 6622.

Figure 28:
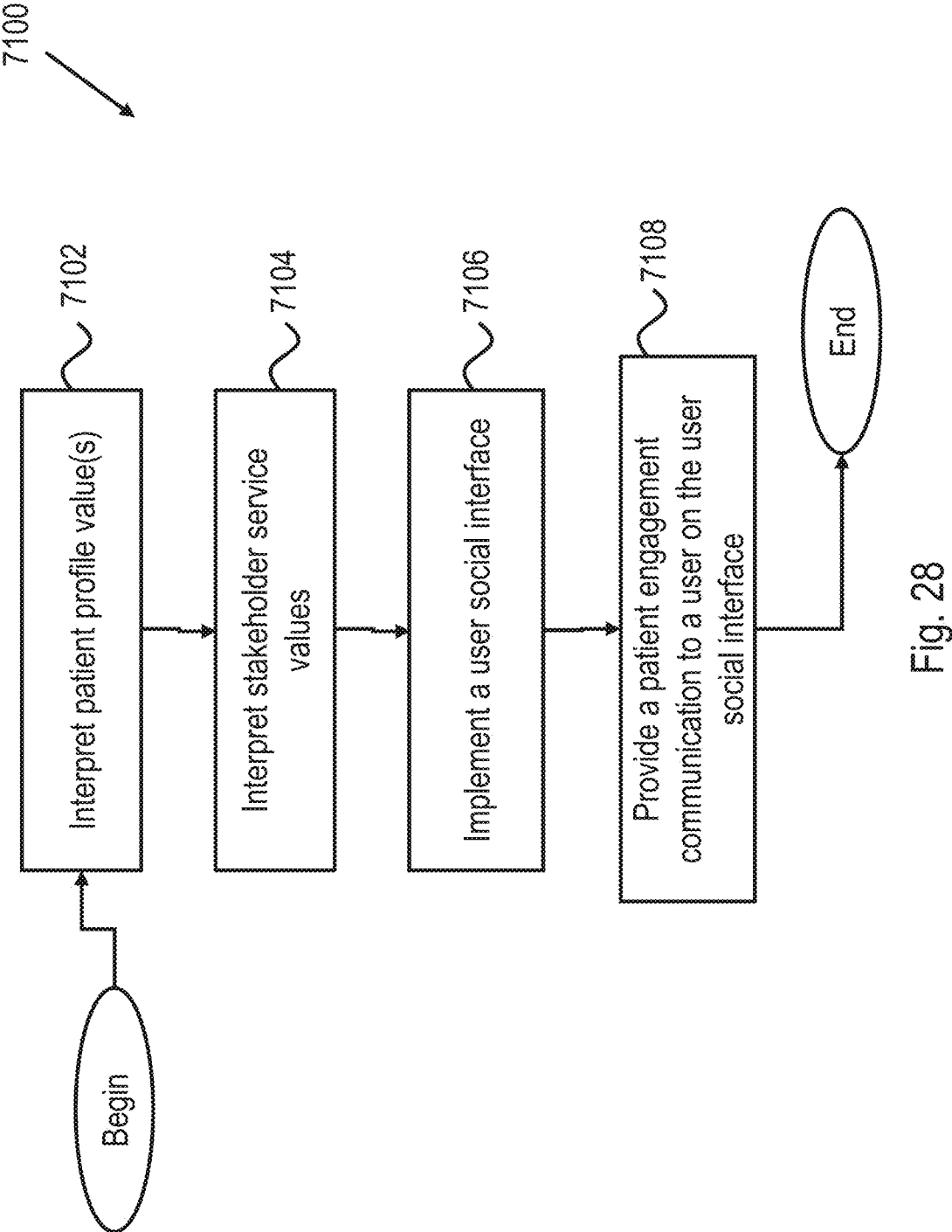
FIG. 28 depicts an example procedure for providing a patient engagement communication.

Referencing FIG. 28, an example procedure 7100 for providing a patient engagement communication to a user is schematically depicted. The example procedure 7100 includes an operation 7102 to interpret a patient profile value, an operation 7104 to interpret stakeholder service values, an operation 7106 to implement a user social interface, and an operation 7108 to provide a patient engagement communication to a user on the user social interface.

Figure 29:
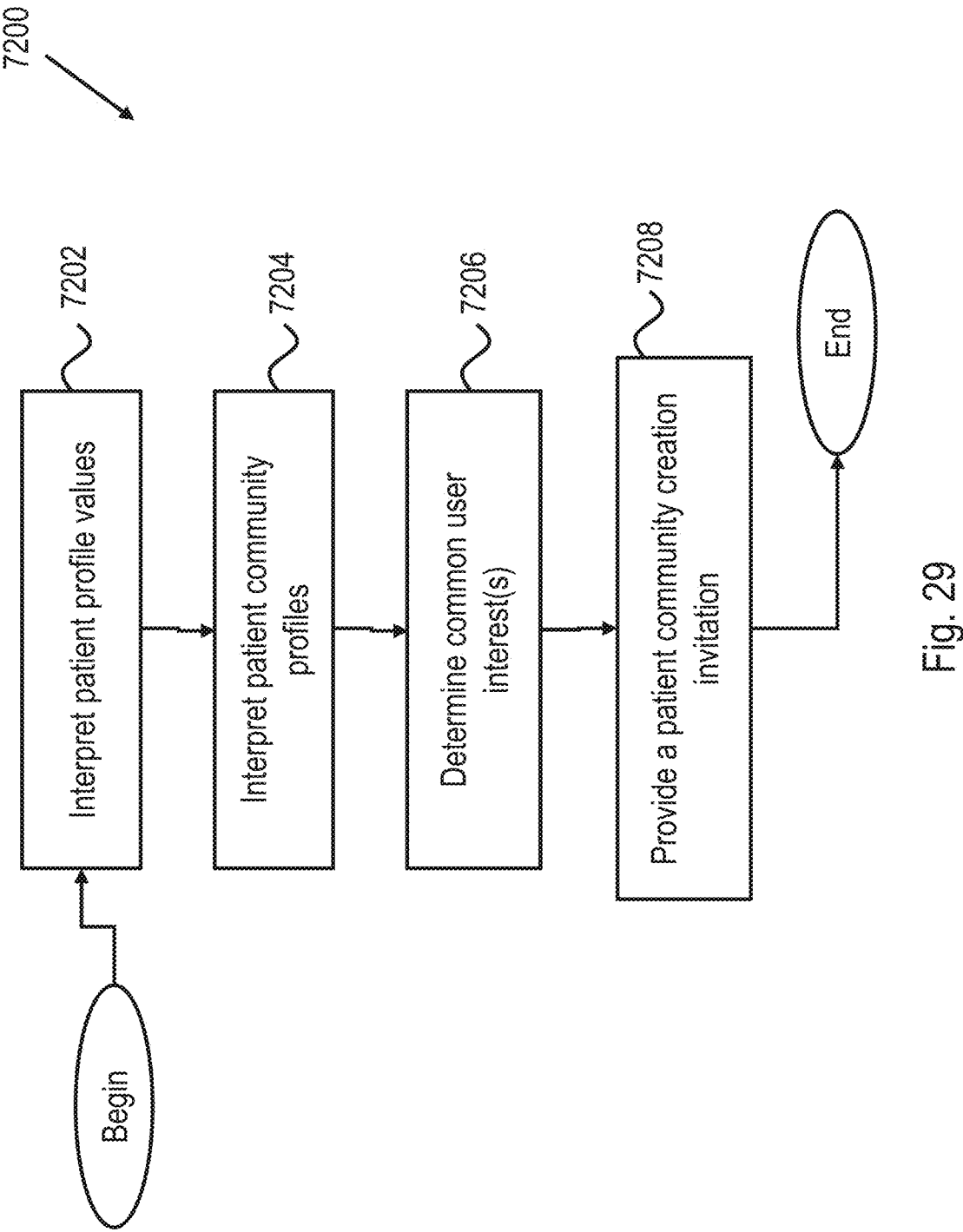
FIG. 29 depicts an example procedure for providing a patient community creation invitation.

Referencing FIG. 29, an example procedure 7200 for providing a patient community creation invitation is schematically depicted. The example procedure 7200 includes an operation 7202 to interpret patient profile values, an operation 7204 to interpret patient community profiles, an operation 7206 to determine common user interests, and an operation 7208 to provide a patient community creation invitation to a user.

As described herein, machine learning models may be trained using supervised learning or unsupervised learning. In supervised learning, a model is generated using a set of labeled examples, where each example has corresponding target label(s). In unsupervised learning, the model is generated using unlabeled examples. The collection of examples constructs a dataset, usually referred to as a training dataset. During training, a model is generated using this training data to learn the relationship between examples in the dataset. The training process may include various phases such as: data collection, preprocessing, feature extraction, model training, model evaluation, and model fine-tuning. The data collection phase may include collecting a representative dataset, typically from multiple users, that covers the range of possible scenarios and positions. The preprocessing phase may include cleaning and preparing the examples in the dataset and may include filtering, normalization, and segmentation. The feature extraction phase may include extracting relevant features from examples to capture relevant information for the task. The model training phase may include training a machine learning model on the preprocessed and feature-extracted data. Models may include support vector machines (SVMs), artificial neural networks (ANNs), decision trees, and the like for supervised learning, or autoencoders, Hopfield, restricted Boltzmann machine (RBM), deep belief, Generative Adversarial Networks (GAN), or other networks, or clustering for unsupervised learning. The model evaluation phase may include evaluating the performance of the trained model on a separate validation dataset to ensure that it generalizes well to new and unseen examples. The model fine-tuning may include refining a model by adjusting its parameters, changing the features used, or using a different machine-learning algorithm, based on the results of the evaluation. The process may be iterated until the performance of the model on the validation dataset is satisfactory and the trained model can then be used to make predictions.

In embodiments, trained models may be periodically fine-tuned for specific user groups, applications, and/or tasks. Fine-tuning of an existing model may improve the performance of the model for an application while avoiding completely retraining the model for the application.

In embodiments, fine-tuning a machine learning model may involve adjusting its hyperparameters or architecture to improve its performance for a particular user group or application. The process of fine-tuning may be performed after initial training and evaluation of the model, and it can involve one or more hyperparameter tuning and architectural methods.

Hyperparameter tuning includes adjusting the values of the model's hyperparameters, such as learning rate, regularization strength, or the number of hidden units. This can be done using methods such as grid search, random search, or Bayesian optimization. Architecture modification may include modifying the structure of the model, such as adding or removing layers, changing the activation functions, or altering the connections between neurons, to improve its performance.

Online training of machine learning models includes a process of updating the model as new examples become available, allowing it to adapt to changes in the data distribution over time. In online training, the model is trained incrementally as new data becomes available, allowing it to adapt to changes in the data distribution over time. Online training can also be useful for user groups that have changing usage habits of the stimulation device, allowing the models to be updated in almost real-time.

In embodiments, online training may include adaptive filtering. In adaptive filtering, a machine learning model is trained online to learn the underlying structure of the new examples and remove noise or artifacts from the examples.

The methods and systems described herein may be deployed in part or in whole through a machine having a computer, computing device, processor, circuit, and/or server that executes computer readable instructions, program codes, instructions, and/or includes hardware configured to functionally execute one or more operations of the methods and systems herein. The terms computer, computing device, processor, circuit, and/or server, ("computing device") as utilized herein, should be understood broadly.

An example computing device includes a computer of any type, capable to access instructions stored in communication thereto such as upon a non-transient computer readable medium, whereupon the computer performs operations of the computing device upon executing the instructions. In certain embodiments, such instructions themselves comprise a computing device. Additionally or alternatively, a computing device may be a separate hardware device, one or more computing resources distributed across hardware devices, and/or may include such aspects as logical circuits, embedded circuits, sensors, actuators, input and/or output devices, network and/or communication resources, memory resources of any type, processing resources of any type, and/or hardware devices configured to be responsive to determined conditions to functionally execute one or more operations of systems and methods herein.

Network and/or communication resources include, without limitation, local area network, wide area network, wireless, internet, or any other known communication resources and protocols. Example and non-limiting hardware and/or computing devices include, without limitation, a general-purpose computer, a server, an embedded computer, a mobile device, a virtual machine, and/or an emulated computing device. A computing device may be a distributed resource included as an aspect of several devices, included as an interoperable set of resources to perform described functions of the computing device, such that the distributed resources function together to perform the operations of the computing device. In certain embodiments, each computing device may be on separate hardware, and/or one or more hardware devices may include aspects of more than one computing device, for example as separately executable instructions stored on the device, and/or as logically partitioned aspects of a set of executable instructions, with some aspects comprising a part of one of a first computing device, and some aspects comprising a part of another of the computing devices.

A computing device may be part of a server, client, network infrastructure, mobile computing platform, stationary computing platform, or other computing platform. A processor may be any kind of computational or processing device capable of executing program instructions, codes, binary instructions and the like. The processor may be or include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more threads. The thread may spawn other threads that may have assigned priorities associated with them; the processor may execute these threads based on priority or any other order based on instructions provided in the program code. The processor may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like.

A processor may include one or more cores that may enhance speed and performance of a multiprocessor. In embodiments, the process may be a dual core processor, quad core processors, other chip-level multiprocessor and the like that combine two or more independent cores (called a die).

The methods and systems described herein may be deployed in part or in whole through a machine that executes computer readable instructions on a server, client, firewall, gateway, hub, router, or other such computer and/or networking hardware. The computer readable instructions may be associated with a server that may include a file server, print server, domain server, internet server, intranet server and other variants such as secondary server, host server, distributed server and the like. The server may include one or more of memories, processors, computer readable transitory and/or non-transitory media, storage media, ports (physical and virtual), communication devices, and interfaces capable of accessing other servers, clients, machines, and devices through a wired or a wireless medium, and the like. The methods, programs, or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers, and the like. Additionally, this coupling and/or connection may facilitate remote execution of instructions across the network. The networking of some or all of these devices may facilitate parallel processing of program code, instructions, and/or programs at one or more locations without deviating from the scope of the disclosure. In addition, all the devices attached to the server through an interface may include at least one storage medium capable of storing methods, program code, instructions, and/or programs. A central repository may provide program instructions to be executed on different devices. In this implementation, the remote repository may act as a storage medium for methods, program code, instructions, and/or programs.

The methods, program code, instructions, and/or programs may be associated with a client that may include a file client, print client, domain client, internet client, intranet client and other variants such as secondary client, host client, distributed client and the like. The client may include one or more of memories, processors, computer readable transitory and/or non-transitory media, storage media, ports (physical and virtual), communication devices, and interfaces capable of accessing other clients, servers, machines, and devices through a wired or a wireless medium, and the like. The methods, program code, instructions, and/or programs as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers, and the like. Additionally, this coupling and/or connection may facilitate remote execution of methods, program code, instructions, and/or programs across the network. The networking of some or all of these devices may facilitate parallel processing of methods, program code, instructions, and/or programs at one or more locations without deviating from the scope of the disclosure. In addition, all the devices attached to the client through an interface may include at least one storage medium capable of storing methods, program code, instructions, and/or programs. A central repository may provide program instructions to be executed on different devices. In this implementation, the remote repository may act as a storage medium for methods, program code, instructions, and/or programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules, and/or components as known in the art. The computing and/or non-computing device(s) associated with the network infrastructure may include, apart from other components, a storage medium such as flash memory, buffer, stack, RAM, ROM and the like. The methods, program code, instructions, and/or programs described herein and elsewhere may be executed by one or more of the network infrastructural elements.

The methods, program code, instructions, and/or programs described herein and elsewhere may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like.

The methods, program code, instructions, and/or programs described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute methods, program code, instructions, and/or programs stored thereon. Alternatively, the mobile devices may be configured to execute instructions in collaboration with other devices. The mobile devices may communicate with base stations interfaced with servers and configured to execute methods, program code, instructions, and/or programs. The mobile devices may communicate on a peer-to-peer network, mesh network, or other communications network. The methods, program code, instructions, and/or programs may be stored on the storage medium associated with the server and executed by a computing device embedded within the server. The base station may include a computing device and a storage medium. The storage device may store methods, program code, instructions, and/or programs executed by the computing devices associated with the base station.

The methods, program code, instructions, and/or programs may be stored and/or accessed on machine readable transitory and/or non-transitory media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

Certain operations described herein include interpreting, receiving, and/or determining one or more values, parameters, inputs, data, or other information ("receiving data"). Operations to receive data include, without limitation: receiving data via a user input; receiving data over a network of any type; reading a data value from a memory location in communication with the receiving device; utilizing a default value as a received data value; estimating, calculating, or deriving a data value based on other information available to the receiving device; and/or updating any of these in response to a later received data value. In certain embodiments, a data value may be received by a first operation, and later updated by a second operation, as part of the receiving a data value. For example, when communications are down, intermittent, or interrupted, a first receiving operation may be performed, and when communications are restored an updated receiving operation may be performed.

Certain logical groupings of operations herein, for example methods or procedures of the current disclosure, are provided to illustrate aspects of the present disclosure. Operations described herein are schematically described and/or depicted, and operations may be combined, divided, re-ordered, added, or removed in a manner consistent with the disclosure herein. It is understood that the context of an operational description may require an ordering for one or more operations, and/or an order for one or more operations may be explicitly disclosed, but the order of operations should be understood broadly, where any equivalent grouping of operations to provide an equivalent outcome of operations is specifically contemplated herein. For example, if a value is used in one operational step, the determining of the value may be required before that operational step in certain contexts (e.g., where the time delay of data for an operation to achieve a certain effect is important), but may not be required before that operation step in other contexts (e.g. where usage of the value from a previous execution cycle of the operations would be sufficient for those purposes). Accordingly, in certain embodiments an order of operations and grouping of operations as described is explicitly contemplated herein, and in certain embodiments re-ordering, subdivision, and/or different grouping of operations is explicitly contemplated herein.

The methods and systems described herein may transform physical and/or or intangible items from one state to another. The methods and systems described herein may also transform data representing physical and/or intangible items from one state to another.

The methods and/or processes described above, and steps thereof, may be realized in hardware, program code, instructions, and/or programs or any combination of hardware and methods, program code, instructions, and/or programs suitable for a particular application. The hardware may include a dedicated computing device or specific computing device, a particular aspect or component of a specific computing device, and/or an arrangement of hardware components and/or logical circuits to perform one or more of the operations of a method and/or system. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and computer readable instructions, or any other machine capable of executing program instructions.

Thus, in one aspect, each method described above, and combinations thereof, may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or computer readable instructions described above. All such permutations and combinations are intended to fall within the scope of the present disclosure.

While the disclosure has been disclosed in connection with certain embodiments shown and described in detail, various modifications and improvements thereon will become readily apparent to those skilled in the art. Accordingly, the spirit and scope of the present disclosure is not to be limited by the foregoing examples but is to be understood in the broadest sense allowable by law.

What is claimed is:

1. A patient portal system, comprising:

at least one processor; and a non-transitory computer readable storage medium storing instructions that, when executed by the at least one processor, comprise:

interpreting a patient profile value, wherein the patient profile value includes information about a patient, and the interpreting the patient profile value includes receiving the information about the patient via at least one application programming interface (API);

interpreting a clinical study description, wherein the clinical study description includes information about a plurality of clinical studies, and the interpreting the clinical study description includes receiving the information about the plurality of clinical studies via the at least one API;

interpreting patient clinical data in response to the patient profile value and the clinical study description, wherein the patient clinical data includes information about a candidacy of the patient for at least one of the plurality of clinical studies, and the interpreting the patient clinical data includes comparing the patient profile to the clinical study description to determine the candidacy of the patient for the at least one of the plurality of clinical studies;

including at least a portion of the patient clinical data as longitudinal data of the patient corresponding to the patient profile value, wherein the longitudinal data of the patient is stored in a patient database;

providing a patient engagement interface;

receiving a patient medical event value in response to patient interactions with the patient engagement interface, wherein the patient medical event value includes a value related to at least one of: communications of the at least one of the plurality of clinical studies, enrollment of the at least one of the plurality of clinical studies, pre-screening of the at least one of the plurality of clinical studies, execution of the at least one of the plurality of clinical studies, or tracking of the at least one of the plurality of clinical studies;

adjusting the longitudinal data of the patient to include a representation of the patient medical event value; and performing a longitudinal data action on the longitudinal data of the patient, the longitudinal data action including indexing the longitudinal data of the patient in a patient database together with longitudinal data of other patients of the plurality of clinical studies according to types of patient data, whereby the longitudinal data of the patient is searchable without regard to the at least one of the plurality of clinical studies.

2. The system of claim 1, wherein the longitudinal data comprises behavioral information data for the patient.

3. The system of claim 1, wherein the longitudinal data comprises historical performance data for the patient.

4. The system of claim 3, wherein the historical performance data comprises data corresponding to at least one of:

activity of the patient on at least one of: a patient engagement platform, the patient portal system, or a patient centered social platform;

activity corresponding to the patient on a patient data system;

medical procedure execution activity;

medical treatment compliance activity;

clinical study execution activity; or clinical study participation activity.

5. The system of claim 1, wherein the longitudinal data comprises patient profile data from at least one of a patient engagement platform, the patient portal system, or a patient centered social platform.

6. The system of claim 1, wherein the longitudinal data comprises enrollment communications of the patient.

7. The system of claim 1, wherein the longitudinal data comprise patient preference information from at least one of a patient engagement platform, the patient portal system, or a patient centered social platform.

8. The system of claim 1, wherein the longitudinal data comprises study intake communications of the patient.

9. The system of claim 1, wherein the longitudinal data comprises screening communications of the patient.

10. The system of claim 1, wherein the longitudinal data comprises medical event data of the patient.

11. The system of claim 1, wherein the longitudinal data comprises at least a portion of a medical record of the patient.

12. The patient portal system of claim 1, wherein interpreting the patient clinical data includes:

comparing the patient profile value with the clinical study description including the information about the plurality of clinical studies to determine the candidacy of the patient for the at least one of the plurality of clinical studies.

13. A method for providing a patient portal, comprising:

interpreting, by at least one computer system, a patient profile value, wherein the patient profile value includes information about a patient, and the interpreting the patient profile value includes receiving the information about the patient via at least one application programming interface (API);

interpreting, by the at least one computer system, a clinical study description, wherein the clinical study description includes information about a plurality of clinical studies, and the interpreting the clinical study description includes receiving the information about the plurality of clinical studies via the at least one API;

interpreting, by the at least one computer system, patient clinical data in response to the patient profile value and the clinical study description, wherein the patient clinical data includes information about a candidacy of the patient for at least one of the plurality of clinical studies, and the interpreting the patient clinical data includes comparing the patient profile to the clinical study description to determine the candidacy of the patient for the at least one of the plurality of clinical studies;

including, by the at least one computer system, at least a portion of the patient clinical data as longitudinal data of the patient corresponding to the patient profile value, wherein the longitudinal data of the patient is stored in a patient database;

providing, by the at least one computer system, a patient engagement interface;

receiving, by the at least one computer system, a patient medical event value in response to patient interactions with the patient engagement interface, wherein the patient medical event value includes a value related to at least one of: communications of the at least one of the plurality of clinical studies, enrollment of the at least one of the plurality of clinical studies, pre-screening of the at least one of the plurality of clinical studies, execution of the at least one of the plurality of clinical studies, or tracking of the at least one of the plurality of clinical studies;

adjusting, by the at least one computer system, the longitudinal data of the patient to include a representation of the patient medical event value; and performing, by the at least one computer system, a longitudinal data action on the longitudinal data of the patient, the longitudinal data action including indexing the longitudinal data of the patient in a patient database together with longitudinal data of other patients of the plurality of clinical studies according to types of patient data, whereby the longitudinal data of the patient is searchable without regard to the at least one of the plurality of clinical studies.

14. The method of claim 13, wherein the longitudinal data comprises at least one of:

behavioral information data for the patient;

historical performance data for the patient;

patient profile data from at least one of a patient engagement platform, a patient portal system, or a patient centered social platform;

enrollment communications of the patient;

patient preference information from at least one of the patient engagement platform, the patient portal system, or the patient centered social platform;

study intake communications of the patient;

screening communications of the patient;

medical event data of the patient; or at least a portion of a medical record of the patient.

15. The method of claim 14, wherein the longitudinal data comprises the historical performance data and the historical performance data comprises data corresponding to at least one of:

activity of the patient on at least one of: the patient engagement platform, the patient portal system, or the patient centered social platform;

activity corresponding to the patient on a patient data system;

medical procedure execution activity;

medical treatment compliance activity;

clinical study execution activity; or clinical study participation activity.

16. The method of claim 13, further comprising:

performing, by the at least one computer system, a longitudinal data action on the longitudinal data of the patient.

17. The method of claim 16, wherein the longitudinal data action includes:

storing patient data values that are relevant to matching a patient to the plurality of clinical studies in a higher-speed memory.

18. The method of claim 17, wherein the patient data values that are relevant include a geographic location of the patient.

19. The method of claim 16, wherein the longitudinal data action includes:

tracking, from longitudinal data of a plurality of patients, which types of patient data values are more likely to be used for matching patients to clinical studies; and storing the types of patient data values more likely to be used in a higher-speed memory.

20. The method of claim 16, wherein the longitudinal data action includes:

using a machine learning model to recognize a pattern in the at least a portion of the patient clinical data in longitudinal data of the patient; and comparing the recognized pattern to the clinical study description to determine a match of the patient to a clinical study corresponding to the clinical study description.

* * * * *